United States Patent
Palmer et al.

(10) Patent No.: US 6,704,749 B2
(45) Date of Patent: *Mar. 9, 2004

(54) INTEGRATED HANGTAG PRODUCTION SYSTEM

(75) Inventors: Trang S. Palmer, Houston, TX (US); Wai C. Ricky Chan, Sugarland, TX (US)

(73) Assignee: AW Printing, Inc., Houston, TX (US)

( * ) Notice: Subject to any disclaimer, the term of this patent is extended or adjusted under 35 U.S.C. 154(b) by 343 days.

This patent is subject to a terminal disclaimer.

(21) Appl. No.: 09/734,414

(22) Filed: Dec. 11, 2000

(65) Prior Publication Data

US 2002/0010693 A1 Jan. 24, 2002

(Under 37 CFR 1.47)

Related U.S. Application Data

(63) Continuation-in-part of application No. 09/408,740, filed on Sep. 29, 1999, now Pat. No. 6,197,823, which is a continuation-in-part of application No. 09/133,103, filed on Aug. 12, 1998, now Pat. No. 6,363,358.

(51) Int. Cl.$^7$ ............................................. G06F 17/30
(52) U.S. Cl. ....................... 707/104.1; 707/10; 705/28
(58) Field of Search ........................... 705/28, 21, 29; 707/104, 10

(56) References Cited

U.S. PATENT DOCUMENTS

| | | | |
|---|---|---|---|
| 4,972,318 A | 11/1990 | Brown et al. | 705/26 |
| 5,425,823 A | 6/1995 | Woodside, III | 156/64 |
| 5,808,894 A | 9/1998 | Wiens et al. | 700/231 |
| 5,860,068 A | 1/1999 | Cook | 705/26 |
| 5,937,393 A | 8/1999 | O'Leary et al. | 705/26 |
| 5,973,711 A | 10/1999 | Schartner et al. | 347/173 |
| 5,983,195 A | 11/1999 | Fierro | 705/10 |
| 6,363,358 B1 * | 3/2002 | Palmer et al. | 705/21 |

* cited by examiner

Primary Examiner—Diane D. Mizrahi
(74) Attorney, Agent, or Firm—Wendy Buskop; Buskop Law Group, P.C.

(57) ABSTRACT

An integrated hangtag production system with an order analysis program for receiving an electronic order file from a customer and outputting an analyzed customer data file in which the order analysis program including means for generating a first plurality of documents from the electronic order file which are useful for evaluating the integrity of the customer order; and a hangtag automation program for receiving the analyzed customer data file in which the hangtag automation program file including means for generating a second plurality of documents from analyzed customer data file which are useful for coordinating the production of hangtags ordered by the customer.

14 Claims, 235 Drawing Sheets

```
FILE CONFIG
  RERUN WORKING FILE                                          [_][☐][x]

[OPEN WORKING FILE]  WORKING DIRECTORY
                       WORKING FILE  [            ]

☑ PRINT QTY DISTRIBUTION LIST     ☑ PRINT PACKING LIST
    ☐ PRINT SUMMARY DISTRIB LIST      ☑ PRINT PACKING SUMMARY LIST        [GENERATE]
    ☑ PRINT PLATE DETAIL LIST         ☑ PRINT OVERALL PACKING SUMMARY LIST
    ☑ PRINT PLATE LAYOUT LIST         ☑ PRINT BOX LABEL                   [EXIT]
    ☑ PRINT PLATE LABEL               ☑ PRINT CARTON LABEL
    ☑ PRINT PLATE SUMMARY LIST        ☐ PRINT BOX LABEL REPORT            USE LEGAL PAPER ☐
    ☑ CREATE ARTWORK ASCII FILE       ☑ PRINT SHIPPING SUMMARY LIST
    ☑ CREATE CUTTING LABEL ASCII FILE ☐ PRINT DELIVERY NOTE
    ☑ CREATE ARTWORK CHECKING FILE    ☑ CREATE BOX CHECKING FILE

CHECK BOX OUTPUT FILE EXTENSION          NO. OF COPIES FOR PACKING DETAIL LIST  [  ]
  [            ]                           NO. OF COPIES FOR PACKING SUMMARY LIST [  ]
  CHECK ARTWORK OUTPUT FILE NAME           NO. OF COPIES FOR SHIPPING SUMMARY LIST [  ]
  [            ]                           NO. OF COPIES FOR DELIVERY NOTES       [  ]
```

| ORDERDATE | YEAR1 | DISTRI | COUNTRY | CHG_CNTRY | CNTYNAME | SEASON | DIV | STYLEHEAD | STYLE | STYLEDESC |
|---|---|---|---|---|---|---|---|---|---|---|
| 19980507 | 1998 | COL | CHN | N | CHINA | E | 15 | STYLE | E15019 | ANKE MEDBACKPAC |
| 19980507 | 1998 | COL | CHN | N | CHINA | E | 15 | STYLE | E15019 | ANKE MEDBACKPAC |
| 19980507 | 1998 | COL | CHN | N | CHINA | E | 15 | STYLE | E15019 | ANKE MEDBACKPAC |
| 19980507 | 1998 | COL | CHN | N | CHINA | E | 15 | STYLE | E15019 | ANKE MEDBACKPAC |
| 19980507 | 1998 | COL | CHN | N | CHINA | E | 15 | STYLE | E15019 | ANKE MEDBACKPAC |
| 19980507 | 1998 | COL | CHN | N | CHINA | E | 15 | STYLE | E15019 | ANKE MEDBACKPAC |
| 19980507 | 1998 | COL | CHN | N | CHINA | E | 15 | STYLE | E15019 | ANKE MEDBACKPAC |
| 19980507 | 1998 | COL | CHN | N | CHINA | E | 15 | STYLE | E15031 | ANKE MIRRORCASE |
| 19980507 | 1998 | COL | CHN | N | CHINA | E | 15 | STYLE | E15031 | ANKE MIRRORCASE |
| 19980507 | 1998 | COL | CHN | N | CHINA | E | 15 | STYLE | E15031 | ANKE MIRRORCASE |
| 19980507 | 1998 | COL | CHN | N | CHINA | E | 15 | STYLE | E15031 | ANKE MIRRORCASE |
| 19980507 | 1998 | COL | CHN | N | CHINA | E | 15 | STYLE | E15031 | ANKE MIRRORCAES |
| 19980507 | 1998 | COL | CHN | N | CHINA | E | 15 | STYLE | E15031 | ANKE MIRRORCASE |
| 19980507 | 1998 | COL | CHN | N | CHINA | E | 15 | STYLE | E15017 | ANKE WALLET |
| 19980507 | 1998 | COL | CHN | N | CHINA | E | 15 | STYLE | E15017 | ANKE WALLET |
| 19980507 | 1998 | COL | CHN | N | CHINA | E | 15 | STYLE | E15017 | ANKE WALLET |
| 19980507 | 1998 | COL | CHN | N | CHINA | E | 15 | STYLE | E15017 | ANKE WALLET |
| 19980507 | 1998 | COL | CHN | N | CHINA | E | 15 | STYLE | E15017 | ANKE WALLET |
| 19980507 | 1998 | COL | CHN | N | CHINA | E | 15 | STYLE | E15023 | ANKE PENCASE |
| 19980507 | 1998 | COL | CHN | N | CHINA | E | 15 | STYLE | E15023 | ANKE PENCASE |
| 19980507 | 1998 | COL | CHN | N | CHINA | E | 15 | STYLE | E15023 | ANKE PENCASE |
| 19980507 | 1998 | COL | CHN | N | CHINA | E | 15 | STYLE | E15023 | ANKE PENCASE |
| 19980507 | 1998 | COL | CHN | N | CHINA | E | 15 | STYLE | E15023 | ANKE PENCASE |
| 19980507 | 1998 | COL | CHN | N | CHINA | E | 15 | STYLE | E15024 | ANKE BACKPACK |
| 19980507 | 1998 | COL | CHN | N | CHINA | E | 15 | STYLE | E15024 | ANKE BACKPACK |

*FIG. 3.1A*

| | | | | | | |
|---|---|---|---|---|---|---|
| 19980507 | 1998 | COL | CHN | N | CHINA | E | 15 | STYLE | E15024 | ANKE BACKPACK |
| 19980507 | 1998 | COL | CHN | N | CHINA | E | 15 | STYLE | E15024 | ANKE BACKPACK |
| 19980507 | 1998 | COL | CHN | N | CHINA | E | 15 | STYLE | E15024 | ANKE BACKPACK |
| 19980507 | 1998 | COL | CHN | N | CHINA | E | 15 | STYLE | E15024 | ANKE BACKPACK |
| 19980507 | 1998 | COL | CHN | N | CHINA | E | 15 | STYLE | E15024 | ANKE BACKPACK |
| 19980507 | 1998 | COL | CHN | N | CHINA | E | 15 | STYLE | E15026 | ANKE WEEKENDER |
| 19980507 | 1998 | COL | CHN | N | CHINA | E | 15 | STYLE | E15026 | ANKE WEEKENDER |
| 19980507 | 1998 | COL | CHN | N | CHINA | E | 15 | STYLE | E15026 | ANKE WEEKENDER |
| 19980507 | 1998 | COL | CHN |   | CHINA | E | 15 | STYLE | E15026 | ANKE WEEKENDER |

*FIG. 3.1B*

| COLORHEAD | CLRCODE | CLRNAME | SIZEHEAD | SIZE | RETAILTXT | RETAIL | RETAILCODE | CODE | SPO | OLD_QTY |
|---|---|---|---|---|---|---|---|---|---|---|
| COLOR | 141 | | | SORT# | | | | 20118129664475 | 450006 | 0 |
| COLOR | 141 | | | 1 SIZE | | | | 40118184838899 | 450006 | 0 |
| COLOR | 258 | | | SORT# | | | | 20118129664482 | 450006 | 0 |
| COLOR | 258 | | | 1 SIZE | | | | 40118184838912 | 450006 | 0 |
| COLOR | 543 | | | SORT# | | | | 20118129664499 | 450006 | 0 |
| COLOR | 543 | | | 1 SIZE | | | | 40118184838936 | 450006 | 0 |
| COLOR | 141 | | | SORT# | | | | 20118129770564 | 450007 | 0 |
| COLOR | 141 | | | 1 SIZE | | | | 40118157657776 | 450007 | 0 |
| COLOR | 258 | | | SORT# | | | | 20118129770571 | 450007 | 0 |
| COLOR | 258 | | | 1 SIZE | | | | 40118157657790 | 450007 | 0 |
| COLOR | 543 | | | SORT# | | | | 20118129770588 | 450007 | 0 |
| COLOR | 543 | | | 1 SIZE | | | | 40118157657813 | 450007 | 0 |
| COLOR | 141 | | | SORT# | | | | 20118129664413 | 450008 | 0 |
| COLOR | 141 | | | 1 SIZE | | | | 40118184837769 | 450008 | 0 |
| COLOR | 258 | | | SORT# | | | | 20118129664420 | 450008 | 0 |
| COLOR | 258 | | | 1 SIZE | | | | 40118184837790 | 450008 | 0 |
| COLOR | 543 | | | SORT# | | | | 20118129664437 | 450008 | 0 |
| COLOR | 543 | | | 1 SIZE | | | | 40118184838133 | 450008 | 0 |
| COLOR | 141 | | | SORT# | | | | 20118129770199 | 450009 | 0 |
| COLOR | 141 | | | 1 SIZE | | | | 40118157660225 | 450009 | 0 |
| COLOR | 258 | | | SORT# | | | | 20118129770205 | 450009 | 0 |
| COLOR | 258 | | | 1 SIZE | | | | 40118157660249 | 450009 | 0 |
| COLOR | 543 | | | SORT# | | | | 20118129770212 | 450009 | 0 |
| COLOR | 543 | | | 1 SIZE | | | | 40118157660263 | 450009 | 0 |
| COLOR | 141 | | | SORT# | | | | 20118129770229 | 450010 | 0 |

*FIG. 3.2A*

| COLOR | 141 | 1 SIZE | 4011815766087 | 450010 | o |
| COLOR | 258 | SORT# | 2011812970236 | 450010 | o |
| COLOR | 258 | 1 SIZE | 4011815766100 | 450010 | o |
| COLOR | 543 | SORT# | 2011812970243 | 450010 | o |
| COLOR | 543 | 1 SIZE | 4011815766124 | 450010 | o |
| COLOR | 141 | SORT# | 2011812970250 | 450011 | o |
| COLOR | 141 | 1 SIZE | 4011815766148 | 450011 | o |
| COLOR | 258 | SORT# | 2011812970267 | 450011 | o |
| COLOR | 258 | 1 SIZE | 4011815766162 | 450011 | o |

*FIG. 3.2B*

| NEW_QTY | QTY | CHG_QTY | AGENT | CHG_AGNT | AGENTNAME | HANGTAGTYP | CHG_HT | FACTORY |
|---|---|---|---|---|---|---|---|---|
| 30 | 30 | N | HK9 | N | ESPRIT FAR EAST LTD | PP | N | JSN |
| 50 | 50 | N | HK9 | N | ESPRIT FAR EAST LTD | AA | N | JSN |
| 30 | 30 | N | HK9 | N | ESPRIT FAR EAST LTD | PP | N | JSN |
| 50 | 50 | N | HK9 | N | ESPRIT FAR EAST LTD | AA | N | JSN |
| 30 | 30 | N | HK9 | N | ESPRIT FAR EAST LTD | PP | N | JSN |
| 50 | 50 | N | HK9 | N | ESPRIT FAR EAST LTD | AA | N | JSN |
| 15 | 15 | N | HK9 | N | ESPRIT FAR EAST LTD | PP | N | JSN |
| 50 | 50 | N | HK9 | N | ESPRIT FAR EAST LTD | AA | N | JSN |
| 15 | 15 | N | HK9 | N | ESPRIT FAR EAST LTD | PP | N | JSN |
| 50 | 50 | N | HK9 | N | ESPRIT FAR EAST LTD | AA | N | JSN |
| 15 | 15 | N | HK9 | N | ESPRIT FAR EAST LTD | PP | N | JSN |
| 50 | 50 | N | HK9 | N | ESPRIT FAR EAST LTD | AA | N | JSN |
| 15 | 15 | N | HK9 | N | ESPRIT FAR EAST LTD | PP | N | JSN4 |
| 50 | 50 | N | HK9 | N | ESPRIT FAR EAST LTD | AA | N | JSN4 |
| 15 | 15 | N | HK9 | N | ESPRIT FAR EAST LTD | PP | N | JSN4 |
| 50 | 50 | N | HK9 | N | ESPRIT FAR EAST LTD | AA | N | JSN4 |
| 15 | 15 | N | HK9 | N | ESPRIT FAR EAST LTD | PP | N | JSN |
| 50 | 50 | N | HK9 | N | ESPRIT FAR EAST LTD | AA | N | JSN |

*FIG. 3.3A*

| | | | | |
|---|---|---|---|---|
| 15 | 15 N | HK9 | N | ESPRIT FAR EAST LTD | PP | | JSN |
| 50 | 50 N | HK9 | N | ESPRIT FAR EAST LTD | AA | N | JSN |
| 30 | 30 N | HK9 | N | ESPRIT FAR EAST LTD | PP | N | JSN |
| 50 | 50 N | HK9 | N | ESPRIT FAR EAST LTD | AU | N | JSN |
| 30 | 30 N | HK9 | N | ESPRIT FAR EAST LTD | PP | N | JSN |
| 50 | 50 N | HK9 | N | ESPRIT FAR EAST LTD | AU | N | JSN |
| 30 | 30 N | HK9 | N | ESPRIT FAR EAST LTD | PP | N | JSN |
| 50 | 50 N | HK9 | N | ESPRIT FAR EAST LTD | AU | N | JSN |
| 30 | 30 N | HK9 | N | ESPRIT FAR EAST LTD | PP | N | JSN |
| 50 | 50 N | HK9 | N | ESPRIT FAR EAST LTD | AA | N | JSN |
| 30 | 30 N | HK9 | N | ESPRIT FAR EAST LTD | PP | N | JSN |
| 50 | 50 N | HK9 | N | ESPRIT FAR EAST LTD | AA | N | JSN |

*FIG. 3.3B*

| SUPP_NAME | SUPP_ADR | SUPP_ZIP | SUPP_CITY | SUPP_CNTRY | SUPP_PHONE |
|---|---|---|---|---|---|
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T. CHANTAL INTERNATIONAL | YIP STREET, KWUN TONG, KO | HONG KONG | | HKG | 0085227630093 |
| T. CHANTAL INTERNATIONAL | YIP STREET, KWUN TONG, KO | HONG KONG | | HKG | 0085227630093 |
| T. CHANTAL INTERNATIONAL | YIP STREET, KWUN TONG, KO | HONG KONG | | HKG | 0085227630093 |
| T. CHANTAL INTERNATIONAL | YIP STREET, KWUN TONG, KO | HONG KONG | | HKG | 0085227630093 |
| T. CHANTAL INTERNATIONAL | YIP STREET, KWUN TONG, KO | HONG KONG | | HKG | 0085227630093 |
| T. CHANTAL INTERNATIONAL | YIP STREET, KWUN TONG, KO | HONG KONG | | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |
| T.CHANTAL INT. LTD., JOHN | 27 SHING YIP STREET KWUN | | HONG KONG | HKG | 0085227630093 |

*FIG. 3.4A*

| | | | |
|---|---|---|---|
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T.CHANTAL INT. LTD., JOHN | 27 SHING YIP STREET KWUN | HONG KONG | HKG | 0085227630093 |
| T. CHANTAL INTERNATIONAL | YIP STREET, KWUN TONG, KO | HONG KONG | HKG | 0085227630093 |
| T. CHANTAL INTERNATIONAL | YIP STREET, KWUN TONG, KO | HONG KONG | HKG | 0085227630093 |

FIG. 3.4B

| SUPP_FAX | SUPP-TELEX | CHG_SUPP | EX_OR_DATE | CHG_EX_OR | CTY_SZ1 | CTY_SZ2 | CTY_SZ3 | CTY_SZ4 | CTY_SZ5 | SIZE1 |
|---|---|---|---|---|---|---|---|---|---|---|
| 00852223426204 | Y | | 19980504 | N | | | | | | |
| 00852223426204 | Y | | 19980504 | N | | | | | | |
| 00852223426204 | Y | | 19980504 | N | | | | | | |
| 00852223426204 | Y | | 19980504 | N | D | F | I | UK | USA | 1 SIZE |
| 00852223426204 | Y | | 19980504 | N | | | | | | |
| 00852223426204 | Y | | 19980504 | N | D | F | I | UK | USA | 1 SIZE |
| 00852223426204 | Y | | 19980409 | Y | | | | | | |
| 00852223426204 | Y | | 19980409 | Y | D | F | I | UK | USA | 1 SIZE |
| 00852223426204 | Y | | 19980409 | Y | | | | | | |
| 00852223426204 | Y | | 19980409 | Y | D | F | I | UK | USA | 1 SIZE |
| 00852223426204 | Y | | 19980409 | Y | | | | | | |
| 00852223426204 | Y | | 19980504 | N | D | F | I | UK | USA | 1 SIZE |
| 00852223426204 | Y | | 19980504 | N | | | | | | |
| 00852223426204 | Y | | 19980504 | N | D | F | I | UK | USA | 1 SIZE |
| 00852223426204 | Y | | 19980504 | N | | | | | | |
| 00852223426204 | Y | | 19980504 | N | D | F | I | UK | USA | 1 SIZE |
| 00852223426204 | Y | | 19980504 | N | | | | | | |
| 00852223426204 | Y | | 19980504 | N | D | F | I | UK | USA | 1 SIZE |
| 00852223426204 | Y | | 19980504 | N | | | | | | |
| 00852223426204 | Y | | 19980504 | N | D | F | | UK | USA | 1 SIZE |
| 00852223426204 | Y | | 19980504 | N | | | | | | |

FIG. 3.5A

| 0085223426204 | Y | 19980504 | N | D | F | — | UK | USA | 1 SIZE |
|---|---|---|---|---|---|---|---|---|---|
| 0085223426204 | Y | 19980409 | Y | D | F | — | UK | USA | 1 SIZE |
| 0085223426204 | Y | 19980409 | Y | D | F | — | UK | USA | 1 SIZE |
| 0085223426204 | Y | 19980409 | Y | D | F | — | UK | USA | 1 SIZE |
| 0085223426204 | Y | 19980409 | Y | D | F | — | UK | USA | 1 SIZE |
| 0085223426204 | Y | 19980409 | Y | D | F | — | UK | USA | 1 SIZE |
| 0085223426204 | Y | 19980409 | Y |   |   |   |   |   |   |
| 0085223426204 | Y | 19980409 | Y |   |   |   |   |   |   |
| 0085223426204 | Y | 19980409 | Y |   |   |   |   |   |   |
| 0085223426204 | Y | 19980409 | Y |   |   |   |   |   |   |
| 0085223426204 | Y | 19980409 | Y |   |   |   |   |   |   |

| SIZE2 | SIZE3 | SIZE4 | SIZE5 | CTY_M1 | CTY_M2 | CTY_M3 | CTY_M4 | CTY_M5 | CTY_M6 | CTY_M7 | CTY_M8 | CTY_M9 | RETDESC11 |
|---|---|---|---|---|---|---|---|---|---|---|---|---|---|
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | | | | | | | | | | |
| 1 SIZE | 1 SIZE | 1 SIZE | 1 SIZE | NL | B | UK | DK | A | S | F | I | | D |

|  | NL | B | UK | DK | A | S | F | I |
|---|---|---|---|---|---|---|---|---|
| 1 SIZE 1 SIZE 1 SIZE D | NL | B | UK | DK | A | S | F | I |
| 1 SIZE 1 SIZE 1 SIZE D | NL | B | UK | DK | A | S | F |  |
| 1 SIZE 1 SIZE 1 SIZE |  |  |  |  |  |  |  |  |
| 1 SIZE 1 SIZE 1 SIZE |  |  |  |  |  |  |  |  |

FIG. 3.6B

| RETDESC12 | RETDESC21 | RETDESC22 | RETDESC31 | RETDESC32 | RETDESC41 |
|---|---|---|---|---|---|
| unverbindliche Preisempfehl | | aanbevolen detailhandelsp | aanbevolen detailhandelsp | prix detail sugg | |
| unverbindliche Preisempfehl | | aanbevolen detailhandelsp | aanbevolen detailhandelsp | prix detail sugg | |
| unverbindliche Preisempfehl | | aanbevolen detailhandelsp | aanbevolen detailhandelsp | prix detail sugg | |

FIG. 3.7

| RETDESC42 | RETDESC51 | RETDESC52 | RETDESC61 | RETDESC62 | RETDESC71 |
|---|---|---|---|---|---|
| recommended retail pri | | vejledende udsalgsp | unverbindlich empfohle | Verkaufsprei | |
| recommended retail pri | | vejledende udsalgsp | unverbindlich empfohle | Verkaufsprei | |
| recommended retail pri | | vejledende udsalgsp | unverbindlich empfohle | Verkaufsprei | |

FIG. 3.8

| RETDESC72 | RETDESC81 | RETDESC82 | RETDESC91 | RETDESC92 | RETCODE1 | RETCODE2 | RETCODE3 |
|---|---|---|---|---|---|---|---|
| rekomenderat cirkapr | | prix detail sugg | | prezzo consiglia | DM | HFL | BFR |
| rekomenderat cirkapr | | prix detail sugg | | prezzo consiglia | DM | HFL | BFR |
| rekomenderat cirkapr | | prix detail sugg | | prezzo consiglia | DM | HFL | BFR |

FIG. 3.9

| RETCODE4 | RETCODE5 | RETCODE6 | RETCODE7 | RETCODE8 | RETCODE9 | RETAIL1 | RETAIL2 | RETAIL3 | RETAIL4 | RETAIL5 | RETAIL6 | RETAIL7 | RETAIL8 |
|---|---|---|---|---|---|---|---|---|---|---|---|---|---|
| ₠ | DKR | OS | SKR | FF | | 79,90 | 89,95 | 1799,00 | 29,00 | 349,00 | 599,00 | 399,00 | 295,00 |
| ₠ | DKR | OS | SKR | FF | | 79,90 | 89,95 | 1799,00 | 29,00 | 349,00 | 599,00 | 399,00 | 295,00 |
| ₠ | DKR | OS | SKR | FF | | 79,90 | 89,95 | 1799,00 | 29,00 | 349,00 | 599,00 | 399,00 | 295,00 |

FIG. 3.10

| SEASON | HT_REF | COUNTRY | FACTORY | SPO | STYLE | DISTRI | DISTNAME | YEAR | CODE | QTY | THERM | CARTON_ID |
|---|---|---|---|---|---|---|---|---|---|---|---|---|
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |
| E | AU | CHN | YTX | 609261 | E15251 | UKI | GERMANY | 98 | 270000 | 60 | Y | |

*FIG. 4A*

| | | | | | | | | | |
|---|---|---|---|---|---|---|---|---|---|
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |
| E | AU | CHN | YTX | 609261 E15251 | UKI | GERMANY | 98 | 270000 | 60 | Y |

FIG. 4B

SPO # 608450 CARTON # 1

| FILENAME | YEAR | COUNTRY | SEASON | DIV | STYLEHEAD | STYLE | STYLEDESC | COLORHEAD | CLRCODE | CLRNAME | SIZE |
|---|---|---|---|---|---|---|---|---|---|---|---|
| G9819005 | 98 | CHN | E | 15 | STYLE | E15042 | SHEILA SHOPPER | COLOR | 070 | | SORT#10 |
| G9819005 | 98 | CHN | E | 15 | STYLE | E15042 | SHEILA SHOPPER | COLOR | 141 | | SORT#10 |
| G9819005 | 98 | CHN | E | 15 | STYLE | E15050 | SHEILA MIRRORCS | COLOR | 070 | | SORT#10 |
| G9819005 | 98 | CHN | E | 15 | STYLE | E15050 | SHEILA MIRRORCS | COLOR | 141 | | SORT#10 |
| G9819005 | 98 | CHN | E | 15 | STYLE | E15047 | SHEILA PENCASE | COLOR | 070 | | SORT#10 |
| G9819005 | 98 | CHN | E | 15 | STYLE | E15047 | SHEILA PENCASE | COLOR | 141 | | SORT#10 |
| G9819005 | 98 | CHN | E | 15 | STYLE | E15044 | SHEILACITYWKND | COLOR | 141 | | SORT#10 |
| G9819005 | 98 | CHN | E | 15 | STYLE | E15044 | SHEILA CITYWKND | COLOR | 258 | | SORT#10 |
| G9819005 | 98 | CHN | E | 15 | STYLE | E15019 | ANKE MEDBACKPAC | COLOR | 543 | | SORT#10 |
| G9819005 | 98 | CHN | E | 15 | STYLE | E15019 | ANKE MADBACKPAC | COLOR | 141 | | SORT#10 |
| G9819005 | 98 | CHN | E | 15 | STYLE | E15031 | ANKE MIRRIRCASE | COLOR | 258 | | SORT#14 |
| G9819005 | 98 | CHN | E | 15 | STYLE | E15031 | ANKE MIRRIRCASE | COLOR | 543 | | SORT#14 |
| G9819005 | 98 | CHN | E | 15 | STYLE | E15017 | ANKE WALLET | COLOR | 141 | | SORT#14 |
| G9819005 | 98 | CHN | E | 15 | STYLE | E15017 | ANKE WALLET | COLOR | 258 | | SORT#14 |
| G9819005 | 98 | CHN | E | 15 | STYLE | E15017 | ANKE WALLET | COLOR | 543 | | SORT#14 |
| G9819005 | 98 | CHN | E | 15 | STYLE | E15023 | ANKE PENCASE | COLOR | 258 | | SORT#14 |

*FIG. 6.1A*

| | | | | | | |
|---|---|---|---|---|---|---|
| G9819005 | 98 | CHN | E | 15 STYLE | E15023 ANKE PENCASE | COLOR | 543 | SORT#14 |
| G9819005 | 98 | CHN | E | 15 STYLE | E15023 ANKE PENCASE | COLOR | 141 | SORT#14 |
| G9819005 | 98 | CHN | E | 15 STYLE | E15024 ANKE BACKPACK | COLOR | 258 | SORT#10 |
| G9819005 | 98 | CHN | E | 15 STYLE | E15024 ANKE BACKPACK | COLOR | 543 | SORT#10 |
| G9819005 | 98 | CHN | E | 15 STYLE | E15042 ANKE BACKPACK | COLOR | 543 | SORT#10 |
| G9819005 | 98 | CHN | E | 15 STYLE | E15026 ANKE WEEKENDER | COLOR | 141 | SORT#10 |
| G9819005 | 98 | CHN | E | 15 STYLE | E15026 ANKE WEEKENDER | COLOR | 258 | SORT#10 |
| G9819005 | 98 | CHN | E | 15 STYLE | E15026 ANKE WEEKENDER | COLOR | 543 | SORT#10 |
| G9819005 | 98 | CHN | E | 15 STYLE | E15068 AFRA MEDBACKPCK | COLOR | 141 | SORT#10 |
| G9819005 | 98 | CHN | E | 15 STYLE | E26000 ALBATROS BACKPC | COLOR | 141 | SORT#10 |
| G9819005 | 98 | CHN | E | 15 STYLE | E26000 ALBATROS BACKPC | COLOR | 543 | SORT#10 |
| G9819005 | 98 | CHN | E | 15 STYLE | E26009 ALBATROS WALLET | COLOR | 141 | SORT#14 |
| G9819005 | 98 | CHN | E | 15 STYLE | E26009 ALBATROS WALLET | COLOR | 543 | SORT#14 |
| G9819005 | 98 | CHN | E | 15 STYLE | E26005 ALBATROS WEEKND | COLOR | 141 | SORT#10 |
| G9819005 | 98 | CHN | E | 15 STYLE | E26005 ALBATROS WEEKND | COLOR | 543 | SORT#10 |
| G9819005 | 98 | CHN | E | 15 STYLE | E15033 ALBATROS MEDBACKP | COLOR | 141 | SORT#10 |

*FIG. 6.1B*

| RETAILTXT | RETAILCODE | RETAIL CODE | SPO | QTY | FACTORY | ORDERDATE | RQTY | SHPQTY | REPEAT | HANGTAGTYP |
|---|---|---|---|---|---|---|---|---|---|---|
| | | 20118129709840 | 450002 | 15 | JF2 | | 0 | 15 | 15 | 15 PP |
| | | 20118129709910 | 450002 | 15 | JF2 | | 0 | 15 | 15 | 15 PP |
| | | 20118129711410 | 450003 | 15 | JF2 | | 0 | 15 | 15 | 15 PP |
| | | 20118129711580 | 450003 | 15 | JF2 | | 0 | 15 | 15 | 15 PP |
| | | 20118133041910 | 450004 | 15 | JF2 | | 0 | 15 | 15 | 15 PP |
| | | 20118133042070 | 450004 | 15 | JF2 | | 0 | 15 | 15 | 15 PP |
| | | 20118129710280 | 450005 | 15 | JF2 | | 0 | 15 | 15 | 15 PP |
| | | 20118129710350 | 450005 | 15 | JF2 | | 0 | 15 | 15 | 15 PP |
| | | 20118129664750 | 450006 | 30 | JSN | | 0 | 30 | 30 | 30 PP |
| | | 20118129664820 | 450006 | 30 | JSN | | 0 | 30 | 30 | 30 PP |
| | | 20118129664990 | 450006 | 30 | JSN | | 0 | 30 | 30 | 30 PP |
| | | 20118129705640 | 450007 | 15 | JSN | | 0 | 15 | 15 | 15 PP |
| | | 20118129705710 | 450007 | 15 | JSN | | 0 | 15 | 15 | 15 PP |
| | | 20118129705880 | 450007 | 15 | JSN | | 0 | 15 | 15 | 15 PP |
| | | 20118129664130 | 450008 | 15 | JSN4 | | 0 | 15 | 15 | 15 PP |
| | | 20118129664200 | 450008 | 15 | JSN4 | | 0 | 15 | 15 | 15 PP |

FIG. 6.2A

| | | | | | |
|---|---|---|---|---|---|
| 20118129664370 | 450008 | 15 JSN4 | 0 | 15 | 15 | 15 PP |
| 20118129701990 | 450009 | 15 JSN | 0 | 15 | 15 | 15 PP |
| 20118129702050 | 450009 | 15 JSN | 0 | 15 | 15 | 15 PP |
| 20118129702120 | 450009 | 15 JSN | 0 | 15 | 15 | 15 PP |
| 20118129702290 | 450010 | 30 JSN | 0 | 30 | 30 | 30 PP |
| 20118129702360 | 450010 | 30 JSN | 0 | 30 | 30 | 30 PP |
| 20118129702430 | 450010 | 30 JSN | 0 | 30 | 30 | 30 PP |
| 20118129702500 | 450011 | 30 JSN | 0 | 30 | 30 | 30 PP |
| 20118129702670 | 450011 | 30 JSN | 0 | 30 | 30 | 30 PP |
| 20118129702740 | 450011 | 30 JSN | 0 | 30 | 30 | 30 PP |
| 20118129716910 | 450012 | 45 JSN | 0 | 45 | 45 | 45 PP |
| 20118129748830 | 450013 | 15 SFL2 | 0 | 15 | 15 | 15 PP |
| 20118129748900 | 450013 | 15 SFL2 | 0 | 15 | 15 | 15 PP |
| 20118129753540 | 450014 | 15 SFL2 | 0 | 15 | 15 | 15 PP |
| 20118129753610 | 450014 | 15 SFL2 | 0 | 15 | 15 | 15 PP |
| 20118129749820 | 450015 | 15 SFL2 | 0 | 15 | 15 | 15 PP |
| 20118129749990 | 450015 | 15 SFL2 | 0 | 15 | 15 | 15 PP |
| 20118129707550 | 450016 | 45 SFL2 | 0 | 45 | 45 | 45 PP |

FIG. 6.2B

| HT_REF | DISTRI | THERM | INVOIC |
|---|---|---|---|
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AA | COL | | EDI |
| AU | COL | | EDI |
| AU | COL | | EDI |
| AU | COL | | EDI |
| AA | COL | | EDI |
| AA | COL | | EDI |
| AA | COL | | EDI |
| AA | COL | | EDI |

FIG. 6.3A

AA COL EDI
AA COL EDI
AA COL EDI
AA COL EDI
AA COL EDI

*FIG. 6.3B*

| ORDATE TEAR1 | DISTRI | COUNTRY | CHG_DNTRY | CNTYNAME | SEASON | DIV | STYLEHEAD | STYLE | STYLEDESC |
|---|---|---|---|---|---|---|---|---|---|
| 1998 | COL | CHN | N | CHINA | E | 15 | STYLE | E15019 | ANKE MEDBACKPAC |
| 1998 | COL | CHN | N | CHINA | E | 15 | STYLE | E15019 | ANKE MEDBACKPAC |
| 1998 | COL | CHN | N | CHINA | E | 15 | STYLE | E15019 | ANKE MEDBACKPAC |
| 1998 | COL | CHN | N | CHINA | E | 15 | STYLE | E15019 | ANKE MEDBACKPAC |
| 1998 | COL | CHN | N | CHINA | E | 15 | STYLE | E15019 | ANKE MEDBACKPAC |
| 1998 | COL | CHN | N | CHINA | E | 15 | STYLE | E15019 | ANKE MEDBACKPAC |
| 1998 | COL | CHN | N | CHINA | E | 15 | STYLE | E15031 | ANKE MIRRORCASE |
| 1998 | COL | CHN | N | CHINA | E | 15 | STYLE | E15031 | ANKE MIRRORCASE |
| 1998 | COL | CHN | N | CHINA | E | 15 | STYLE | E15031 | ANKE MIRRORCASE |
| 1998 | COL | CHN | N | CHINA | E | 15 | STYLE | E15031 | ANKE MIRRORCASE |
| 1998 | COL | CHN | N | CHINA | E | 15 | STYLE | E15031 | ANKE MIRRORCASE |
| 1998 | COL | CHN | N | CHINA | E | 15 | STYLE | E15017 | ANKE WALLET |
| 1998 | COL | CHN | N | CHINA | E | 15 | STYLE | E15017 | ANKE WALLET |
| 1998 | COL | CHN | N | CHINA | E | 15 | STYLE | E15017 | ANKE WALLET |
| 1998 | COL | CHN | N | CHINA | E | 15 | STYLE | E15017 | ANKE WALLET |
| 1998 | COL | CHN | N | CHINA | E | 15 | STYLE | E15017 | ANKE WALLET |
| 1998 | COL | CHN | N | CHINA | E | 15 | STYLE | E15017 | ANKE WALLET |

*FIG. 8.1A*

| | | | | | | | |
|---|---|---|---|---|---|---|---|
| 1998 | COL | CHN | N | CHINA | E | 15 | STYLE | E15023 | ANKE PENCASE |
| 1998 | COL | CHN | N | CHINA | E | 15 | STYLE | E15023 | ANKE PENCASE |
| 1998 | COL | CHN | N | CHINA | E | 15 | STYLE | E15023 | ANKE PENCASE |
| 1998 | COL | CHN | N | CHINA | E | 15 | STYLE | E15023 | ANKE PENCASE |
| 1998 | COL | CHN | N | CHINA | E | 15 | STYLE | E15023 | ANKE PENCASE |
| 1998 | COL | CHN | N | CHINA | E | 15 | STYLE | E15023 | ANKE PENCASE |
| 1998 | COL | CHN | N | CHINA | E | 15 | STYLE | E15024 | ANKE BACKPACK |
| 1998 | COL | CHN | N | CHINA | E | 15 | STYLE | E15024 | ANKE BACKPACK |
| 1998 | COL | CHN | N | CHINA | E | 15 | STYLE | E15024 | ANKE BACKPACK |
| 1998 | COL | CHN | N | CHINA | E | 15 | STYLE | E15024 | ANKE BACKPACK |
| 1998 | COL | CHN | N | CHINA | E | 15 | STYLE | E15024 | ANKE BACKPACK |
| 1998 | COL | CHN | N | CHINA | E | 15 | STYLE | E15024 | ANKE BACKPACK |
| 1998 | COL | CHN | N | CHINA | E | 15 | STYLE | E15026 | ANKE WEEKENDER |
| 1998 | COL | CHN | N | CHINA | E | 15 | STYLE | E15026 | ANKE WEEKENDER |
| 1998 | COL | CHN | N | CHINA | E | 15 | STYLE | E15026 | ANKE WEEKENDER |
| 1998 | COL | CHN | N | CHINA | E | | | E15026 | ANKE WEEKENDER |

*FIG. 8.1B*

| COLORHEAD | CLRCODE | CLRNAME | SIZEHEAD | SIZE | RETAILTXT | RETAIL | RETAILCODE CODE | SPR | OLD_QTY |
|---|---|---|---|---|---|---|---|---|---|
| COLOR | 141 | | | SORT#10 | | | 2011812966475 | 450006 | 0 |
| COLOR | 141 | | | 1 SIZE | | | 4011818483899 | 450006 | 0 |
| COLOR | 258 | | | SORT#10 | | | 2011812966482 | 450006 | 0 |
| COLOR | 258 | | | 1 SIZE | | | 4011818483912 | 450006 | 0 |
| COLOR | 543 | | | SORT#10 | | | 2011812966499 | 450006 | 0 |
| COLOR | 543 | | | 1 SIZE | | | 4011818483936 | 450006 | 0 |
| COLOR | 141 | | | SORT#14 | | | 2011812970564 | 450007 | 0 |
| COLOR | 141 | | | 1 SIZE | | | 4011815765776 | 450007 | 0 |
| COLOR | 258 | | | SORT#14 | | | 2011812970571 | 450007 | 0 |
| COLOR | 258 | | | 1 SIZE | | | 4011815765790 | 450007 | 0 |
| COLOR | 543 | | | SORT#14 | | | 2011815765813 | 450007 | 0 |
| COLOR | 543 | | | 1 SIZE | | | 2011812966413 | 450007 | 0 |
| COLOR | 141 | | | SORT#14 | | | 4011818483769 | 450008 | 0 |
| COLOR | 141 | | | 1 SIZE | | | 2011812966420 | 450008 | 0 |
| COLOR | 258 | | | SORT#14 | | | 4011818483790 | 450008 | 0 |
| COLOR | 258 | | | 1 SIZE | | | 2011812966437 | 450008 | 0 |
| COLOR | 543 | | | SORT#14 | | | | | |

*FIG. 8.2A*

| color | 543 | 1 SIZE | 4011818483813 | 450008 | 0 |
| color | 141 | SORT#14 | 2011812970199 | 450009 | 0 |
| color | 141 | 1 SIZE | 4011815766025 | 450009 | 0 |
| color | 258 | SORT#14 | 2011812970205 | 450009 | 0 |
| color | 258 | 1 SIZE | 4011815766049 | 450009 | 0 |
| color | 543 | SORT#14 | 2011812970212 | 450009 | 0 |
| color | 543 | 1 SIZE | 4011815766063 | 450009 | 0 |
| color | 141 | SORT#10 | 2011812970229 | 450010 | 0 |
| color | 141 | 1 SIZE | 4011815766087 | 450010 | 0 |
| color | 258 | SORT#10 | 2011812970236 | 450010 | 0 |
| color | 258 | 1 SIZE | 4011815766100 | 450010 | 0 |
| color | 543 | SORT#10 | 2011812970243 | 450010 | 0 |
| color | 543 | 1 SIZE | 4011815766124 | 450010 | 0 |
| color | 141 | SORT#10 | 2011812970250 | 450011 | 0 |
| color | 141 | 1 SIZE | 4011815766148 | 450011 | 0 |
| color | 258 | SORT#10 | 2011812970267 | 450011 | 0 |
| color | 258 | 1 SIZE | 4011815766162 | 450011 | 0 |

*FIG. 8.2B*

| NEW_QTY | QTY | CHG_QTY | AGENT | CHG_AGNT | AGENTNAME | HANGTAGTYP | CHG_HT | FACTORY |
|---|---|---|---|---|---|---|---|---|
| 30 | 30 | N | HK9 | N | ESPRIT FAR EAST LTD | PP | N | JSN |
| 50 | 50 | N | HK9 | N | ESPRIT FAR EAST LTD | AA | N | JSN |
| 30 | 30 | N | HK9 | N | ESPRIT FAR EAST LTD | PP | N | JSN |
| 50 | 50 | N | HK9 | N | ESPRIT FAR EAST LTD | AA | N | JSN |
| 30 | 30 | N | HK9 | N | ESPRIT FAR EAST LTD | PP | N | JSN |
| 50 | 50 | N | HK9 | N | ESPRIT FAR EAST LTD | AA | N | JSN |
| 15 | 15 | N | HK9 | N | ESPRIT FAR EAST LTD | PP | N | JSN |
| 50 | 50 | N | HK9 | N | ESPRIT FAR EAST LTD | AA | N | JSN |
| 15 | 15 | N | HK9 | N | ESPRIT FAR EAST LTD | PP | N | JSN |
| 50 | 50 | N | HK9 | N | ESPRIT FAR EAST LTD | AA | N | JSN |
| 15 | 15 | N | HK9 | N | ESPRIT FAR EAST LTD | PP | N | JSN |
| 50 | 50 | N | HK9 | N | ESPRIT FAR EAST LTD | AA | N | JSN |
| 15 | 15 | N | HK9 | N | ESPRIT FAR EAST LTD | PP | N | JSN4 |
| 50 | 50 | N | HK9 | N | ESPRIT FAR EAST LTD | AA | N | JSN4 |
| 15 | 15 | N | HK9 | N | ESPRIT FAR EAST LTD | PP | N | JSN4 |
| 50 | 50 | N | HK9 | N | ESPRIT FAR EAST LTD | AA | N | JSN4 |
| 15 | 15 | N | HK9 | N | ESPRIT FAR EAST LTD | PP | N | JSN |
| 50 | 50 | N | HK9 | N | ESPRIT FAR EAST LTD | AA | N | JSN |

*FIG. 8.3A*

| | | | | | | | | | | | |
|---|---|---|---|---|---|---|---|---|---|---|---|
| 15 | 50 | 30 | 50 | 30 | 50 | 30 | 50 | 30 | 50 | 30 | 50 |
| 15 | 50 | 30 | 50 | 30 | 50 | 30 | 50 | 30 | 50 | 30 | 50 |
| N | N | N | N | N | N | N | N | N | N | N | N |
| HK9 | HK9 | HK9 | HK9 | HK9 | HK9 | HK9 | HK9 | HK9 | HK9 | HK9 | HK9 |
| | N | N | N | N | N | N | N | N | N | N | N |
| ESPRIT FAR EAST LTD | ESPRIT FAR EAST LTD | ESPRIT FAR EAST LTD | ESPRIT FAR EAST LTD | ESPRIT FAR EAST LTD | ESPRIT FAR EAST LTD | ESPRIT FAR EAST LTD | ESPRIT FAR EAST LTD | ESPRIT FAR EAST LTD | ESPRIT FAR EAST LTD | ESPRIT FAR EAST LTD | ESPRIT FAR EAST LTD |
| PP | AA | PP | AU | PP | AU | PP | AU | PP | AA | PP | AA |
| N | N | N | N | N | N | N | N | N | N | N | N |
| JSN | JSN | JSN | JSN | JSN | JSN | JSN | JSN | JSN | JSN | JSN | JSN |

*FIG. 8.3B*

| SUPP_NAME | SUPP_ADR | SUPP_CITY | SUPP_CNTRY | SUPP_PHONE | SUPP_FAX |
|---|---|---|---|---|---|
| T.CHANTAL INT. LTD., JOHN | 27 SHING YIP STREET KWUN | HONG KONG | HKG | 0085227630093 | 0085222342262043 |
| T.CHANTAL INT. LTD., JOHN | 27 SHING YIP STREET KWUN | HONG KONG | HKG | 0085227630093 | 0085222342262043 |
| T.CHANTAL INT. LTD., JOHN | 27 SHING YIP STREET KWUN | HONG KONG | HKG | 0085227630093 | 0085222342262043 |
| T.CHANTAL INT. LTD., JOHN | 27 SHING YIP STREET KWUN | HONG KONG | HKG | 0085227630093 | 0085222342262043 |
| T.CHANTAL INT. LTD., JOHN | 27 SHING YIP STREET KWUN | HONG KONG | HKG | 0085227630093 | 0085222342262043 |
| T.CHANTAL INT. LTD., JOHN | 27 SHING YIP STREET KWUN | HONG KONG | HKG | 0085227630093 | 0085222342262043 |
| T.CHANTAL INT. LTD., JOHN | 27 SHING YIP STREET KWUN | HONG KONG | HKG | 0085227630093 | 0085222342262043 |
| T.CHANTAL INT. LTD., JOHN | 27 SHING YIP STREET KWUN | HONG KONG | HKG | 0085227630093 | 0085222342262043 |
| T.CHANTAL INT. LTD., JOHN | 27 SHING YIP STREET KWUN | HONG KONG | HKG | 0085227630093 | 0085222342262043 |
| T.CHANTAL INT. LTD., JOHN | 27 SHING YIP STREET KWUN | HONG KONG | HKG | 0085227630093 | 0085222342262043 |
| T.CHANTAL INTERNATIONAL | YIP STREET, KWUN TONG, KO | HONG KONG | | 0085227630093 | 0085222342262043 |
| T. CHANTAL INTERNATIONAL | YIP STREET, KWUN TONG, KO | HONG KONG | HKG | 0085227630093 | 0085222342262043 |
| T. CHANTAL INTERNATIONAL | YIP STREET, KWUN TONG, KO | HONG KONG | HKG | 0085227630093 | 0085222342262043 |
| T. CHANTAL INTERNATIONAL | YIP STREET, KWUN TONG, KO | HONG KONG | HKG | 0085227630093 | 0085222342262043 |
| T. CHANTAL INTERNATIONAL | YIP STREET, KWUN TONG, KO | HONG KONG | HKG | 0085227630093 | 0085222342262043 |

FIG. 8.4A

| | | | | |
|---|---|---|---|---|
| T. CHANTAL INTERNATIONAL | YIP STREET, KWUN TONG, KO | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |
| T.CHANTAL INT. LTD., JOHN | 27 SHING YIP STREET KWUN | HONG KONG | HKG | 00852276300093 | 008522342620243 |

*FIG. 8.4B*

| SUPP_TELEX | CHG_SUPP | EX_OR_DATE | CHG_EX_OR | CTY_SZ1 | CTY_SZ2 | CTY_SZ3 | CTY_SZ4 | CTY_SZ5 | SIZE 1 | SIZE2 | SIZE3 | SIZE4 |
|---|---|---|---|---|---|---|---|---|---|---|---|---|
| Y | Y | N | | | | | | | | | | |
| Y | Y | N | | | | | | | | | | |
| Y | Y | N | | | | | | | | | | |
| Y | Y | N | D | F | I | UK | USA | 1 SIZE | 1 SIZE | 1 SIZE | 1 SIZE |
| Y | Y | N | D | F | I | UK | USA | 1 SIZE | 1 SIZE | 1 SIZE | 1 SIZE |
| Y | Y | Y | D | F | I | UK | USA | 1 SIZE | 1 SIZE | 1 SIZE | 1 SIZE |
| Y | Y | Y | D | F | I | UK | USA | 1 SIZE | 1 SIZE | 1 SIZE | 1 SIZE |
| Y | Y | Y | D | F | I | UK | USA | 1 SIZE | 1 SIZE | 1 SIZE | 1 SIZE |
| Y | Y | Y | D | F | I | UK | USA | 1 SIZE | 1 SIZE | 1 SIZE | 1 SIZE |
| Y | Y | N | D | F | I | UK | USA | 1 SIZE | 1 SIZE | 1 SIZE | 1 SIZE |
| Y | Y | N | D | F | I | UK | USA | 1 SIZE | 1 SIZE | 1 SIZE | 1 SIZE |
| Y | Y | N | | | | | | | | | | |
| Y | Y | N | | | | | | | | | | |
| Y | Y | N | | | | | | | | | | |
| Y | Y | N | | | | | | | | | | |
| Y | Y | N | | | | | | | | | | |
| Y | Y | N | | | | | | | | | | |
| Y | Y | N | | | | | | | | | | |

FIG. 8.5A

| | | | | | |
|---|---|---|---|---|---|
| N | D | F | — | UK | USA |
| N | D | F | — | UK | USA | 1 SIZE 1 SIZE 1 SIZE 1 SIZE 1 SIZE 1 SIZE 1 SIZE 1 SIZE |
| N | D | F | — | UK | USA | 1 SIZE 1 SIZE 1 SIZE 1 SIZE 1 SIZE 1 SIZE 1 SIZE 1 SIZE |
| Y | D | F | — | UK | USA | 1 SIZE 1 SIZE 1 SIZE 1 SIZE 1 SIZE 1 SIZE 1 SIZE 1 SIZE |
| Y | D | F | — | UK | USA | 1 SIZE 1 SIZE 1 SIZE 1 SIZE 1 SIZE 1 SIZE 1 SIZE 1 SIZE |
| Y | D | F | — | UK | USA | 1 SIZE 1 SIZE 1 SIZE 1 SIZE 1 SIZE 1 SIZE 1 SIZE 1 SIZE |
| Y | D | F | — | UK | USA | 1 SIZE 1 SIZE 1 SIZE 1 SIZE 1 SIZE 1 SIZE 1 SIZE 1 SIZE |
| Y | D | F | — | UK | USA | 1 SIZE 1 SIZE 1 SIZE 1 SIZE 1 SIZE 1 SIZE 1 SIZE 1 SIZE |
| Y | | | | | |
| Y | | | | | |
| Y | | | | | |
| Y | | | | | |

| SIZE5 | CTY_M1 | CTY_M2 | CTY_M3 | CTY_M4 | CTY_M5 | CTY_M6 | CTY_M7 | CTY_M8 | CTY_M9 | RETDESC11 | RETDESC12 |
|---|---|---|---|---|---|---|---|---|---|---|---|
| 1 SIZE | | | | | | | | | | | |
| 1 SIZE | | | | | | | | | | | |
| 1 SIZE | | | | | | | | | | | |
| 1 SIZE | | | | | | | | | | | |
| 1 SIZE | | | | | | | | | | | |
| 1 SIZE | | | | | | | | | | | |
| 1 SIZE | | | | | | | | | | | |
| 1 SIZE | | | | | | | | | | | |
| 1 SIZE | | | | | | | | | | | |
| 1 SIZE | | | | | | | | | | | |
| 1 SIZE | D | NL | B | UK | DK | A | S | F | — | unverbindliche Preisempfehlung | |
| 1 SIZE | D | NL | B | UK | DK | A | S | F | — | unverbindliche Preisempfehlung | |
| 1 SIZE | D | NL | B | UK | DK | A | S | F | — | unverbindliche Preisempfehlung | |
| 1 SIZE | | | | | | | | | | | |
| 1 SIZE | | | | | | | | | | | |

FIG. 8.6

| RETDESC21 | RETDESC22 | RETDESC31 | RETDESC32 | RETDESC41 | RETDESC42 |
|---|---|---|---|---|---|
| aanbvolen detailhandelsprijs | aanbevolen detailhandelsprijs | aanbevolen detailhandelsprijs | prix detail suppÄrÄ̈ | | recommended retail price |
| | aanbvolen detailhandelsprijs | aanbevolen detailhandelsprijs | prix detail suppÄrÄ̈ | | recommended retail price |
| | aanbvolen detailhandelsprijs | aanbevolen detailhandelsprijs | prix detail suppÄrÄ̈ | | recommended retail price |

*FIG. 8.7*

| RETDESC51 | RETDESC52 | RETDESC61 | RETDESC62 | RETDESC71 | RETDESC72 | RETDESC81K |
|---|---|---|---|---|---|---|
| vejledende udsalgspris | | unverbindlich empfohlener | Verkaufspreis | | rekommenderat cirkapris | |
| vejledende udsalgspris | | unverbindlich empfohlener | Verkaufspreis | | rekommenderat cirkapris | |
| vejledende udsalgspris | | unverbindlich empfohlener | Verkaufspreis | | rekommenderat cirkapris | |

*FIG. 8.8*

| RETDESC82 | RETDESC91 | RETDESC92 | RETCODE1 | RETCODE2 | RETCODE3 | RETCODE4 | RETCODE5 | RETCODE6 | RETCODF |
|---|---|---|---|---|---|---|---|---|---|
| prix detail suggÄrÄ | | prezzo consigliato | DM | HFL | BFR | ù | DKR | àS | SKR |
| prix detail suggÄrÄ | | prezzo consigliato | DM | HFL | BFR | ù | DKR | àS | SKR |
| prix detail suggÄrÄ | | prezzo consigliato | DM | HFL | BFR | ù | DKR | àS | SKR |

FIG. 8.9

| RETCODE8 | RETCODE9 | RETAIL1 | RETAIL2 | RETAIL3 | RETAIL4 | RETAIL5 | RETAIL6 | RETAIL7 | RETAIL8 | RETAIL9 | HT_REF | DISTNAME |
|---|---|---|---|---|---|---|---|---|---|---|---|---|
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |
| | | | | | | | | | | | AA | NEW |

*FIG. 8.10A*

| | | | | | |
|---|---|---|---|---|---|
| 79,90 | 89,95 | 1799,00 | 29,00 | 349,00 | |
| 79,90 | 89,95 | 1799,00 | 29,00 | 349,00 | 599,00 |
| 79,90 | 89,95 | 1799,00 | 29,00 | 349,00 | 599,00 |
| | | | | | 599,00 |

| | | |
|---|---|---|
| | AA | NEW |
| | AA | NEW |
| | AA | NEW |
| | AA | NEW |
| | AU | NEW |
| | AU | NEW |
| | AU | NEW |
| | AU | NEW |
| 399,00 | AU | NEW |
| 399,00 | AU | NEW |
| 399,00 | AA | NEW |
| | AA | NEW |
| | AA | NEW |
| | AA | NEW |

*FIG. 8.10B*

| ERR_HTG | RQTY | ERR_RET | ERR_FTY | LENGTH | AWJOBNO | CODE1 | ERR_CODE | SHPQTY | REPEAT | CARTON_NO | FCARNO | YEAR |
|---|---|---|---|---|---|---|---|---|---|---|---|---|
| N | 30 | | | | | | NOMATCH | 30 | 30 | | | 98 |
| N | 30 | | | | | | NOMATCH | | | | | 98 |
| N | 30 | | | | | | NOMATCH | 30 | 30 | | | 98 |
| N | 15 | | | | | | NOMATCH | 30 | 30 | | | 98 |
| N | 15 | | | | | | NOMATCH | 15 | 15 | | | 98 |
| N | 15 | | | | | | NOMATCH | | | | | 98 |
| N | 15 | | | | | | NOMATCH | 15 | 15 | | | 98 |
| N | 15 | | | | | | NOMATCH | | | | | 98 |
| N | 15 | | | | | | NOMATCH | 15 | 15 | | | 98 |
| N | 15 | | | | | | NOMATCH | 15 | 15 | | | 98 |
| N | 15 | | | | | | NOMATCH | | | | | 98 |
| N | 15 | | | | | | NOMATCH | 15 | 15 | | | 98 |
| N | 15 | | | | | | NOMATCH | | | | | 98 |
| N | | | | | | | NOMATCH | | | | | 98 |
| N | | | | | | | NOMATCH | | | | | 98 |

FIG. 8.11A

| | | | |
|---|---|---|---|
| N | | 15 | NOMATCH | 15 | 98 |
| N | | 15 | NOMATCH | 15 | 98 |
| N | | 30 | NOMATCH | 30 | 98 |
| N | | 30 | NOMATCH | 30 | 98 |
| N | | 30 | NOMATCH | 30 | 98 |
| N | | 30 | NOMATCH | 30 | 98 |
| N | | 30 | NOMATCH | 30 | 98 |
| N | | | NOMATCH | | 98 |
| N | | | NOMATCH | | 98 |
| N | | | NOMATCH | | 98 |
| N | | | NOMATCH | | 98 |
| N | | | NOMATCH | | 98 |
| N | | | NOMATCH | | 98 |
| N | | | NOMATCH | | 98 |

FIG. 8.11B

| BUCKLE | MULTI | ERR_MC | ERR_MS | SPEED | DIS_RET | VALIDCTY | ERR_MUKI | THERM | INVOIC | PRINT | C4 | PP | ILLUS | MISS_ILLUS |
|---|---|---|---|---|---|---|---|---|---|---|---|---|---|---|
| T | | | N | N | N | | | EDI | Y | | | PP | N | |
| S | Y | | N | N | N | | | EDI | N | | | PP | N | |
| T | | | N | N | N | | | EDI | Y | | | PP | N | |
| S | | | N | N | N | | | EDI | Y | | | PP | N | |
| T | | | N | N | N | | | EDI | Y | | | PP | N | |
| S | | | N | N | N | | | EDI | Y | | | PP | N | |
| T | | | N | N | N | | | EDI | Y | | | PP | N | |
| S | | | N | N | N | | | EDI | Y | | | PP | N | |
| T | | | N | N | N | | | EDI | Y | | | PP | N | |
| S | | | N | N | N | | | EDI | Y | | | PP | N | |
| T | | | N | N | N | | | EDI | Y | | | PP | N | |
| S | | | N | N | N | | | EDI | Y | | | PP | N | |
| T | | | N | N | N | | | EDI | Y | | | PP | N | |
| S | | | N | N | N | | | EDI | Y | | | PP | N | |

*FIG. 8.12A*

| | | | | | | | | | | | | | | | | | |
|---|---|---|---|---|---|---|---|---|---|---|---|---|---|---|---|---|---|
| PP | PP | PP | PP | PP | PP | PP | PP | PP | PP | PP | PP | PP | PP | PP | PP | PP | PP |
| N | N | N | N | N | N | N | N | N | N | N | N | N | N | N | N | N | N |

| Y | Y | Y | Y | Y | Y | Y | Y | Y | Y | Y | Y | Y | Y | Y | Y | Y | Y |
|---|---|---|---|---|---|---|---|---|---|---|---|---|---|---|---|---|---|

| EDI | EDI | EDI | EDI | EDI | EDI | EDI | EDI | EDI | EDI | EDI | EDI | EDI | EDI | EDI | EDI | EDI | EDI |
|---|---|---|---|---|---|---|---|---|---|---|---|---|---|---|---|---|---|

| N | N | N | N | N | N | N | N | N | N | N | N | N | N | N | N | N | N |
|---|---|---|---|---|---|---|---|---|---|---|---|---|---|---|---|---|---|
| N | N | N | N | N | N | N | N | N | Y | N | Y | N | Y | N | N | N | N |

| | | | | | | | | N | | N | | N | | | | | |
|---|---|---|---|---|---|---|---|---|---|---|---|---|---|---|---|---|---|
| T | S | T | S | T | S | T | S | T | M | T | M | T | M | T | S | T | S |

*FIG. 8.12B*

| OUTFILE | FILENAME | ERRCODE | REPCODE | CUSTOMER | MODULE |
|---|---|---|---|---|---|
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |
| | G9819005 | | | NEWGERM | MULTI |

FIG. 8.13A

| G9819005 | NEWGERM | MULTI |
|---|---|---|
| G9819005 | NEWGERM | MULTI |
| G9819005 | NEWGERM | MULTI |
| G9819005 | NEWGERM | MULTI |
| G9819005 | NEWGERM | MULTI |
| G9819005 | NEWGERM | MULTI |
| G9819005 | NEWGERM | MULTI |
| G9819005 | NEWGERM | MULTI |
| G9819005 | NEWGERM | MULTI |
| G9819005 | NEWGERM | MULTI |
| G9819005 | NEWGERM | MULTI |
| G9819005 | NEWGERM | MULTI |
| G9819005 | NEWGERM | MULTI |
| G9819005 | NEWGERM | MULTI |
| G9819005 | NEWGERM | MULTI |

FIG. 8.13B

D21522,543,ESPRIT
D21522,543,ESPRIT
D21522,543,ESPRIT
D21522,543,ESPRIT
D21522,543,ESPRIT
D21521,543,ESPRIT
D21521,543,ESPRIT
D21521,543,ESPRIT
D21521,543,ESPRIT
D21521,543,ESPRIT
123456-EU P. 1,,,
D21521,543,ESPRIT
D21521,543,ESPRIT
D21521,543,ESPRIT
D21521,543,ESPRIT
D21521,543,ESPRIT
D21521,543,ESPRIT
D21521,543,ESPRIT
D21521,543,ESPRIT

FIG. 9.1A

D21521,543,ESPRIT
D21521,543,ESPRIT
123456-EU P. 2,,,
D21522,543,ESPRIT
D21522,543,ESPRIT
D21522,543,ESPRIT
D21522,543,ESPRIT
D21522,543,ESPRIT
D21521,543,ESPRIT
D21521,543,ESPRIT
D21521,543,ESPRIT
D21521,543,ESPRIT
D21521,543,ESPRIT
123456-EU P. 3,,,

FIG. 9.1B

PANTY,y<!l")|p=jaecdg<,D,NL,B,UK,DK,A,S,FI,,unverbindliche Preisempfehlung,,aanbevolen detailhandelsprifs,aanbevolen detailhandelsprijs,prixdetail
PANTY,y<!l")|p=jaecdg<,D,NL,B,UK,DK,A,S,FI,,unverbindliche Preisempfehlung,,aanbevolen detailhandelsprifs,aanbevolen detailhandelsprijs,prixdetail
PANTY,y<!l")|p=jaecdg<,D,NL,B,UK,DK,A,S,FI,,unverbindliche Preisempfehlung,,aanbevolen detailhandelsprifs,aanbevolen detailhandelsprijs,prixdetail
PANTY,y<!l")|p=jaecdg<,D,NL,B,UK,DK,A,S,FI,,unverbindliche Preisempfehlung,,aanbevolen detailhandelsprifs,aanbevolen detailhandelsprijs,prixdetail
PANTY,y<!l")|p=jaecdg<,D,NL,B,UK,DK,A,S,FI,,unverbindliche Preisempfehlung,,aanbevolen detailhandelsprifs,aanbevolen detailhandelsprijs,prixdetail
BUSTIER,y<!l")|p=jaeccj<,D,NL,B,UK,DK,A,S,FI,,unverbindliche Preisempfehlung,,aanbevolen detailandelsprijs,aanbevolen detailhandelsprijs,prix deta
BUSTIER,y<!l")|p=jaeccj<,D,NL,B,UK,DK,A,S,FI,,unverbindliche Preisempfehlung,,aanbevolen detailhandelsprijs,aanbevolen detailhandelsprijs,prix deta
BUSTIER,y<!l")|p=jaeccj<,D,NL,B,UK,DK,A,S,FI,,unverbindliche Preisempfehlung,,aanbevolen detailhandelsprijs,aanbevolen detailhandelsprijs,prix deta
BUSTIER,y<!l")|p=jaeccj<,D,NL,B,UK,DK,A,S,FI,,unverbindliche Preisempfehlung,,aanbevolen detailhandelsprijs,aanbevolen detailhandelsprijs,prix deta
BUSTIER,y<!l")|p=jaeccj<,D,NL,B,UK,DK,A,S,FI,,unverbindliche Preisempfehlung,,aanbevolen detailhandelsprijs,aanbevolen detailhandelsprijs,prix deta
BUSTIER,y<!l")|p=jaeccj<,D,NL,B,UK,DK,A,S,FI,,unverbindliche Preisempfehlung,,aanbevolen detailhandelsprijs,aanbevolen detailhandelsprijs,prix deta
PQTY. 50
BUSTIER,y<!l")|p=jaecaf<,D,NL,B,UK,DK,A,S,FI,,unverbindliche Preisempfehlung,aanbevolen detailhandelsprijs,aanbevolen detailhandelsprijs,prix deta
BUSTIER,y<!l")|p=jaecaf<,D,NL,B,UK,DK,A,S,FI,,unverbindliche Preisempfehlung,aanbevolen detailhandelsprijs,aanbevolen detailhandelsprijs,prix deta
BUSTIER,y<!l")|p=jaecaf<,D,NL,B,UK,DK,A,S,FI,,unverbindliche Preisempfehlung,aanbevolen detailhadelsprijs,aanbevolen detailhandelsprijs,prix deta
BUSTIER,y<!l")|p=jaecaf<,D,NL,B,UK,DK,A,S,FI,,unverbindliche Preisempfehlung,aanbevolen detailhandelsprijs,aanbevolen detailhandelsprijs,prix deta
BUSTIER,y<!l")|p=jaecaf<,D,NL,B,UK,DK,A,S,FI,,unverbindliche Preisempfehlung,aanbevolen detailhandelsprijs,aanbevolen detailhandelsprijs,prix deta
BUSTIER,y<!l")|p=jaecaf<,D,NL,B,UK,DK,A,S,FI,,unverbindliche Preisempfehlung,aanbevolen detailhandelsprijs,aanbevolen detailhandelsprijs,prix deta
BUSTIER,y<!l")|p=jaecaf<,D,NL,B,UK,DK,A,S,FI,,unverbindliche Preisempfehlung,aanbevolen detailhandelsprijs,aanbevolen detailhandelsprijs,prix deta
BUSTIER,y<!l")|p=jaecaf<,D,NL,B,UK,DK,A,S,FI,,unverbindliche Preisempfehlung,aanbevolen detailhandelsprijs,aanbevolen detailhandelsprijs,prix deta

*FIG. 9.2A*

BUSTIER,y<!!")|p=jaecaf<,D,NL,B,UK,DK,A,S,FI,,unverbindliche Preisempfehlung,aanbevolen detailhandelsprijs,aanbevolen detailhandelsprijs,prix deta
BUSTIER,y<!!")|p=jaecaf<,D,NL,B,UK,DK,A,S,FI,,unverbindliche Preisempfehlung,aanbevolen detailhandelsprijs,aanbevolen detailhandelsprijs,prix deta
PQTY.25
PANTY,y<!!")|p=jaeced<,D,NL,B,UK,DK,A,S,FI,,unverbindliche Preisempfehlung,aanbevolen detailhandelsprifs,aanbevolen detailhandelsprijs,prixdetail
PANTY,y<!!")|p=jaeced<,D,NL,B,UK,DK,A,S,FI,,unverbindliche Preisempfehlung,aanbevolen detailhandelsprifs,aanbevolen detailhandelsprijs,prix detail
PANTY,y<!!")|p=jaeced<,D,NL,B,UK,DK,A,S,FI,,unverbindliche Preisempfehlung,aanbevolen detailhandelsprifs,aanbevolen detailhandelsprijs,prix detail
PANTY,y<!!")|p=jaeced<,D,NL,B,UK,DK,A,S,FI,,unverbindliche Preisempfehlung,aanbevolen detailhandelsprijs,aanbevolen detailhandelsprijs,prix detail
PANTY,y<!!")|p=jaeced<,D,NL,B,UK,DK,A,S,FI,,unverbindliche Preisempfehlung,aanbevolen detailhandelsprijs,aanbevolen detailhandelsprijs,prix detail
BUSTIER,y<!!")|p=jaecbc<,D,NL,B,UK,DK,A,S,FI,,unverbindliche Preisempfehlung,aanbevolen detailhandelsprijs,aanbevolen detailhandelsprijs,prix data
BUSTIER,y<!!")|p=jaecbc<,D,NL,B,UK,DK,A,S,FI,,unverbindliche Preisempfehlung,aanbevolen detailhandelsprijs,aanbevolen detailhandelsprijs,prix data
BUSTIER,y<!!")|p=jaecbc<,D,NL,B,UK,DK,A,S,FI,,unverbindliche Preisempfehlung,aanbevolen detailhandelsprijs,aanbevolen detailhandelsprijs,prix data
BUSTIER,y<!!")|p=jaecbc<,D,NL,B,UK,DK,A,S,FI,,unverbindliche Preisempfehlung,aanbevolen detailhandelsprijs,aanbevolen detailhandelsprijs,prix data
BUSTIER,y<!!")|p=jaecbc<,D,NL,B,UK,DK,A,S,FI,,unverbindliche Preisempfehlung,aanbevolen detailhandelsprijs,aanbevolen detailhandelsprijs,prix datal
PQTY.75

*FIG. 9.2B*

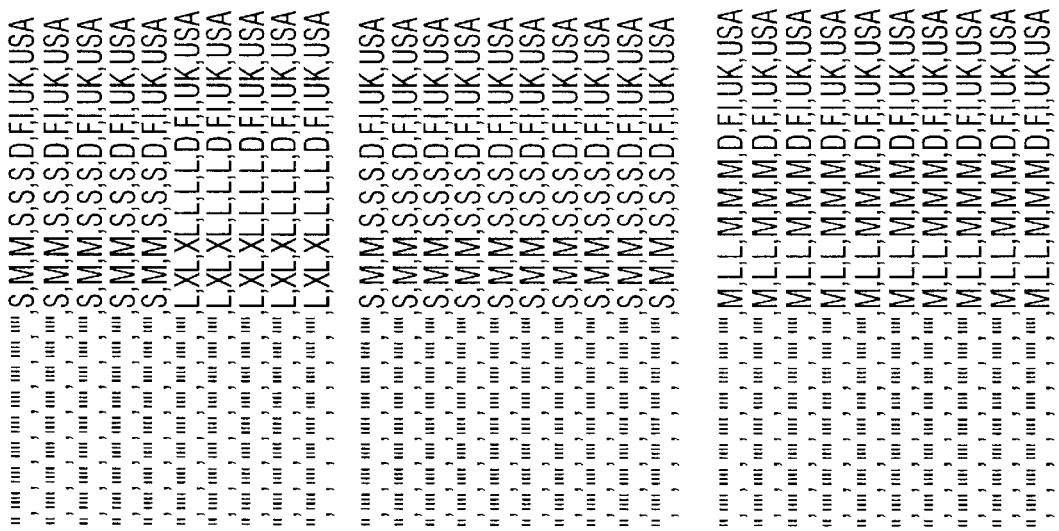
FIG. 9.3

STYLE COLOR SIZE
D21522 543
| D | S |
ESPRIT PANTY
| F | M |
| I | M |
| UK | S |
| USA | S |

4011815 904236

D UNVERBINDLICHE PREISEMPFEHLUNG DM 24,90
NL AANBEVOLEN DETAILHANDELSPRIJS
B AANBEVOLEN DETAILHANDELSPRIJS
  PRIX DETAIL SUGGERE

UK RECOMMENDED RETAIL PRICE
DK VEJLEDENDE UDSALGSPRIS
A UNVERBINDLICH EMPFOHLENER
  VERKAUFSPREIS
S REKOMMENDERAT CIRKAPRIS
F PRIX DETAIL SUGGERE
I PREZZO CONSIGLIATO
S

STYLE COLOR SIZE
D21521 543
| D | L |
ESPRIT BUSTIER
| F | XL |
| I | XL |
| UK | L |
| USA | L |

4011815 904229

D UNVERBINDLICHE PREISEMPFEHLUNG DM 24,90
NL AANBEVOLEN DETAILHANDELSPRIJS
B AANBEVOLEN DETAILHANDELSPRIJS
  PRIX DETAIL SUGGERE

UK RECOMMENDED RETAIL PRICE
DK VEJLEDENDE UDSALGSPRIS
A UNVERBINDLICH EMPFOHLENER
  VERKAUFSPREIS
S REKOMMENDERAT CIRKAPRIS
F PRIX DETAIL SUGGERE
I PREZZO CONSIGLIATO
L

STYLE  COLOR  SIZE
123456-EUP1   EH,EU
              CF,CD,WM,MG,VA,VE,DA,DE,KJ,KG,MM,BE

*FIG. 10.1A*

STYLE   COLOR    SIZE
D21522  543      [D____] S
ESPRIT PANTY     [F____] M
                 [I____] M
                 [UK___] S
                 [USA__] S
4011815 904236

D   UNVERBINDLICHE PREISEMPFEHLUNG    DM    24,90
NL  AANBEVOLEN DETAILHANDELSPRIJS
B   AANBEVOLEN DETAILHANDELSPRIJS
    PRIX DETAIL SUGGERE

UK  RECOMMENDED RETAIL PRICE
DK  VEJLEDENDE UDSALGSPRIS
A   UNVERBINDLICH EMPFOHLENER
    VERKAUFSPREIS
S   REKOMMENDERAT CIRKAPRIS
F   PRIX DETAIL SUGGERE
I   PREZZO CONSIGLIATO
S

STYLE   COLOR    SIZE
D21521  543      [D____] L
ESPRIT BUSTIER   [F____] XL
                 [I____] XL
                 [UK___] L
                 [USA__] L
4011815 904229

D   UNVERBINDLICHE PREISEMPFEHLUNG    DM    24,90
NL  AANBEVOLEN DETAILHANDELSPRIJS
B   AANBEVOLEN DETAILHANDELSPRIJS
    PRIX DETAIL SUGGERE

UK  RECOMMENDED RETAIL PRICE
DK  VEJLEDENDE UDSALGSPRIS
A   UNVERBINDLICH EMPFOHLENER
    VERKAUFSPREIS
S   REKOMMENDERAT CIRKAPRIS
F   PRIX DETAIL SUGGERE
I   PREZZO CONSIGLIATO
L

 STYLE 123456-EU.P1   COLOR   SIZE    EH,EU
                                                 CF,CD,WM,MG,VA,VE,DA,DE,KJ,KG,MM,BE

FIG. 10.1B

| STYLE | COLOR | SIZE | |
|---|---|---|---|
| D21522 | 543 | D | S |
| ESPRIT PANTY | | F | M |
| | | I | M |
| | | UK | S |
| | | USA | S |

D  UNVERBINDLICHE PREISEMPFEHLUNG    DM    24,90
NL AANBEVOLEN DETAILHANDELSPRIJS
B  AANBEVOLEN DETAILHANDELSPRIJS
   PRIX DETAIL SUGGERE
UK RECOMMENDED RETAIL PRICE
DK VEJLEDENDE UDSALGSPRIS
A  UNVERBINDLICH EMPFOHLENER
   VERKAUFSPREIS
S  REKOMMENDERAT CIRKAPRIS
F  PRIX DETAIL SUGGERE
I  PREZZO CONSIGLIATO
S

| STYLE | COLOR | SIZE | |
|---|---|---|---|
| D21521 | 543 | D | L |
| ESPRIT BUSTIER | | F | XL |
| | | I | XL |
| | | UK | L |
| | | USA | L |

D  UNVERBINDLICHE PREISEMPFEHLUNG    DM    24,90
NL AANBEVOLEN DETAILHANDELSPRIJS
B  AANBEVOLEN DETAILHANDELSPRIJS
   PRIX DETAIL SUGGERE
UK RECOMMENDED RETAIL PRICE
DK VEJLEDENDE UDSALGSPRIS
A  UNVERBINDLICH EMPFOHLENER
   VERKAUFSPREIS
S  REKOMMENDERAT CIRKAPRIS
F  PRIX DETAIL SUGGERE
I  PREZZO CONSIGLIATO
L

STYLE  EH,EU
123456-EU.P1
COLOR  CF,CD,WM,MG,VA,VE,DA,DE,KJ,KG,MM,BE
SIZE

FIG. 10.1C

STYLE   COLOR   SIZE
D21522  543
 D  S
ESPRIT PANTY
 F  M
 I  M
 UK  S
 USA  S

D   UNVERBINDLICHE PREISEMPFEHLUNG   DM   24,90
NL  AANBEVOLEN DETAILHANDELSPRIJS
B   AANBEVOLEN DETAILHANDELSPRIJS
    PRIX DETAIL SUGGERE

UK  RECOMMENDED RETAIL PRICE
DK  VEJLEDENDE UDSALGSPRIS
A   UNVERBINDLICH EMPFOHLENER
    VERKAUFSPREIS
S   REKOMMENDERAT CIRKAPRIS
F   PRIX DETAIL SUGGERE
I   PREZZO CONSIGLIATO
S

STYLE   COLOR   SIZE
D21521  543
 D  L
ESPRIT BUSTIER
 F  XL
 I  XL
 UK  L
 USA  L

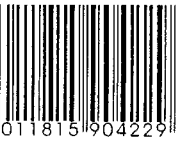

D   UNVERBINDLICHE PREISEMPFEHLUNG   DM   24,90
NL  AANBEVOLEN DETAILHANDELSPRIJS
B   AANBEVOLEN DETAILHANDELSPRIJS
    PRIX DETAIL SUGGERE

UK  RECOMMENDED RETAIL PRICE
DK  VEJLEDENDE UDSALGSPRIS
A   UNVERBINDLICH EMPFOHLENER
    VERKAUFSPREIS
S   REKOMMENDERAT CIRKAPRIS
F   PRIX DETAIL SUGGERE
I   PREZZO CONSIGLIATO
L

STYLE   EH,EU
123456-EUP1
COLOR   CF,CD,WM,MG,VA,VE,DA,DE,KJ,KG,MM,BE
SIZE

*FIG. 10.1D*

STYLE   COLOR   SIZE
D21522  543     [D]    S
ESPRIT PANTY    [F]    M
                [I]    M
                [UK]   S
                [USA]  S D   UNVERBINDLICHE  PREISEMPFEHLUNG    DM    24,90
NL  AANBEVOLEN DETAILHANDELSPRIJS
B   AANBEVOLEN DETAILHANDELSPRIJS
    PRIX DETAIL SUGGERE
UK  RECOMMENDED RETAIL PRICE
DK  VEJLEDENDE UDSALGSPRIS
A   UNVERBINDLICH EMPFOHLENER
    VERKAUFSPREIS
S   REKOMMENDERAT CIRKAPRIS
F   PRIX DETAIL SUGGERE
I   PREZZO CONSIGLIATO
S STYLE   COLOR   SIZE
D21521  543     [D]    L
ESPRIT BUSTIER  [F]    XL
                [I]    XL
                [UK]   L
                [USA]  L D   UNVERBINDLICHE  PREISEMPFEHLUNG    DM    24,90
NL  AANBEVOLEN DETAILHANDELSPRIJS
B   AANBEVOLEN DETAILHANDELSPRIJS
    PRIX DETAIL SUGGERE
UK  RECOMMENDED RETAIL PRICE
DK  VEJLEDENDE UDSALGSPRIS
A   UNVERBINDLICH EMPFOHLENER
    VERKAUFSPREIS
S   REKOMMENDERAT CIRKAPRIS
F   PRIX DETAIL SUGGERE
I   PREZZO CONSIGLIATO
L

 STYLE 123456-EUP1  EH,EU
   COLOR           CF,CD,WM,MG,VA,VE,DA,DE,KJ,KG,MM,BE
   SIZE

FIG. 10.1E

```
STYLE    COLOR      SIZE
D21522   543       [D   ]  M
ESPRIT PANTY       [F   ]  L
                   [I   ]  L
                   [UK  ]  M
                   [USA ]  M
```

D   UNVERBINDLICHE PREISEMPFEHLUNG    DM    24,90
NL  AANBEVOLEN DETAILHANDELSPRIJS
B   AANBEVOLEN DETAILHANDELSPRIJS
    PRIX DETAIL SUGGERE
UK  RECOMMENDED RETAIL PRICE
DK  VEJLEDENDE UDSALGSPRIS
A   UNVERBINDLICH EMPFOHLENER
    VERKAUFSPREIS
S   REKOMMENDERAT CIRKAPRIS
F   PRIX DETAIL SUGGERE
I   PREZZO CONSIGLIATO
M

```
STYLE    COLOR      SIZE
D21521   543       [D   ]  M
ESPRIT BUSTIER     [F   ]  L
                   [I   ]  L
                   [UK  ]  M
                   [USA ]  M
```

D   UNVERBINDLICHE PREISEMPFEHLUNG    DM    24,90
NL  AANBEVOLEN DETAILHANDELSPRIJS
B   AANBEVOLEN DETAILHANDELSPRIJS
    PRIX DETAIL SUGGERE
UK  RECOMMENDED RETAIL PRICE
DK  VEJLEDENDE UDSALGSPRIS
A   UNVERBINDLICH EMPFOHLENER
    VERKAUFSPREIS
S   REKOMMENDERAT CIRKAPRIS
F   PRIX DETAIL SUGGERE
I   PREZZO CONSIGLIATO
M

STYLE    COLOR      SIZE
D21522   543        [D]      M
ESPRIT PANTY        [F]      L
                    [I]      L
                    [UK]     M
                    [USA]    M D   UNVERBINDLICHE PREISEMPFEHLUNG    DM    24,90
NL  AANBEVOLEN DETAILHANDELSPRIJS
B   AANBEVOLEN DETAILHANDELSPRIJS
    PRIX DETAIL SUGGERE UK  RECOMMENDED RETAIL PRICE
DK  VEJLEDENDE UDSALGSPRIS
A   UNVERBINDLICH EMPFOHLENER
    VERKAUFSPREIS
S   REKOMMENDERAT CIRKAPRIS
F   PRIX DETAIL SUGGERE
I   PREZZO CONSIGLIATO
M STYLE    COLOR      SIZE
D21521   543        [D]      M
ESPRIT BUSTIER      [F]      L
                    [I]      L
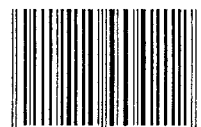
                    [UK]     M
                    [USA]    M D   UNVERBINDLICHE PREISEMPFEHLUNG    DM    24,90
NL  AANBEVOLEN DETAILHANDELSPRIJS
B   AANBEVOLEN DETAILHANDELSPRIJS
    PRIX DETAIL SUGGERE UK  RECOMMENDED RETAIL PRICE
DK  VEJLEDENDE UDSALGSPRIS
A   UNVERBINDLICH EMPFOHLENER
    VERKAUFSPREIS
S   REKOMMENDERAT CIRKAPRIS
F   PRIX DETAIL SUGGERE
I   PREZZO CONSIGLIATO
M STYLE  123456-EUP3   EH,EU
COLOR                CF,CD,WM,MG,VA,VE,DA,DE,KJ,KG,MM,BE
SIZE

*FIG. 10.2B*

| STYLE | COLOR | SIZE | |
|---|---|---|---|
| D21522 | 543 | D | M |
| ESPRIT PANTY | | F | L |
| | | I | L |
| | | UK | M |
| | | USA | M |

D UNVERBINDLICHE PREISEMPFEHLUNG   DM   24,90
NL AANBEVOLEN DETAILHANDELSPRIJS
B  AANBEVOLEN DETAILHANDELSPRIJS
   PRIX DETAIL SUGGERE

UK RECOMMENDED RETAIL PRICE
DK VEJLEDENDE UDSALGSPRIS
A  UNVERBINDLICH EMPFOHLENER
   VERKAUFSPREIS
S  REKOMMENDERAT CIRKAPRIS
F  PRIX DETAIL SUGGERE
I  PREZZO CONSIGLIATO
M

| STYLE | COLOR | SIZE | |
|---|---|---|---|
| D21521 | 543 | D | M |
| ESPRIT BUSTIER | | F | L |
| | | I | L |
| | | UK | M |
| | | USA | M |

D UNVERBINDLICHE PREISEMPFEHLUNG   DM   24,90
NL AANBEVOLEN DETAILHANDELSPRIJS
B  AANBEVOLEN DETAILHANDELSPRIJS
   PRIX DETAIL SUGGERE

UK RECOMMENDED RETAIL PRICE
DK VEJLEDENDE UDSALGSPRIS
A  UNVERBINDLICH EMPFOHLENER
   VERKAUFSPREIS
S  REKOMMENDERAT CIRKAPRIS
F  PRIX DETAIL SUGGERE
I  PREZZO CONSIGLIATO
M

| STYLE | COLOR | SIZE | |
|---|---|---|---|
| D21522 | 543 | D | M |
| ESPRIT PANTY | | F | L |
| | | I | L |
| | | UK | M |
| | | USA | M |

| | | | |
|---|---|---|---|
| D | UNVERBINDLICHE PREISEMPFEHLUNG | DM | 24,90 |
| NL | AANBEVOLEN DETAILHANDELSPRIJS | | |
| B | AANBEVOLEN DETAILHANDELSPRIJS PRIX DETAIL SUGGERE | | |

UK RECOMMENDED RETAIL PRICE
DK VEJLEDENDE UDSALGSPRIS
A  UNVERBINDLICH EMPFOHLENER VERKAUFSPREIS
S  REKOMMENDERAT CIRKAPRIS
F  PRIX DETAIL SUGGERE
I  PREZZO CONSIGLIATO
M

| STYLE | COLOR | SIZE | |
|---|---|---|---|
| D21521 | 543 | D | M |
| ESPRIT BUSTIER | | F | L |
| | | I | L |
| | | UK | M |
| | | USA | M |

| | | | |
|---|---|---|---|
| D | UNVERBINDLICHE PREISEMPFEHLUNG | DM | 24,90 |
| NL | AANBEVOLEN DETAILHANDELSPRIJS | | |
| B | AANBEVOLEN DETAILHANDELSPRIJS PRIX DETAIL SUGGERE | | |

UK RECOMMENDED RETAIL PRICE
DK VEJLEDENDE UDSALGSPRIS
A  UNVERBINDLICH EMPFOHLENER VERKAUFSPREIS
S  REKOMMENDERAT CIRKAPRIS
F  PRIX DETAIL SUGGERE
I  PREZZO CONSIGLIATO
M

 EH,EU
CF,CD,WM,MG,VA,VE,DA,DE,KJ,KG,MM,BE

FIG. 10.2D

STYLE  COLOR    SIZE
D21522  543     [D____] M
ESPRIT PANTY    [F____] L
                [I____] L
                [UK___] M
                [USA__] M

D  UNVERBINDLICHE PREISEMPFEHLUNG   DM   24,90
NL AANBEVOLEN DETAILHANDELSPRIJS
B  AANBEVOLEN DETAILHANDELSPRIJS
   PRIX DETAIL SUGGERE

UK RECOMMENDED RETAIL PRICE
DK VEJLEDENDE UDSALGSPRIS
A  UNVERBINDLICH EMPFOHLENER
   VERKAUFSPREIS
S  REKOMMENDERAT CIRKAPRIS
F  PRIX DETAIL SUGGERE
I  PREZZO CONSIGLIATO
M

STYLE  COLOR    SIZE
D21521  543     [D____] M
ESPRIT BUSTIER  [F____] L
                [I____] L
                [UK___] M
                [USA__] M

D  UNVERBINDLICHE PREISEMPFEHLUNG   DM   24,90
NL AANBEVOLEN DETAILHANDELSPRIJS
B  AANBEVOLEN DETAILHANDELSPRIJS
   PRIX DETAIL SUGGERE

UK RECOMMENDED RETAIL PRICE
DK VEJLEDENDE UDSALGSPRIS
A  UNVERBINDLICH EMPFOHLENER
   VERKAUFSPREIS
S  REKOMMENDERAT CIRKAPRIS
F  PRIX DETAIL SUGGERE
I  PREZZO CONSIGLIATO
M

STYLE 123456-EUR3    EH,EU
COLOR                CF,CD,WM,MG,VA,VE,DA,DE,KJ,KG,MM,BE
SIZE

FIG. 10.2E

STYLE    COLOR    SIZE
D21521  543

ESPRIT BUSTIER

| | |
|---|---|
| D | S |
| F | M |
| I | M |
| UK | S |
| USA | S |

4 011815 904205

D  UNVERBINDLICHE PREISEMPFEHLUNG  DM
NL  AANBEVOLEN DETAILHANDELSPRIJS             24,90
B  AANBEVOLEN DETAILHANDELSPRIJS
    PRIX DETAIL SUGGERE
UK  RECOMMENDED RETAIL PRICE
DK  VEJLEDENDE UDSALGSPRIS
A  UNVERBINDLICH EMPFOHLENER
    VERKAUFSPREIS
S  REKOMMENDERAT CIRKAPRIS
F  PRIX DETAIL SUGGERE
I  PREZZO CONSIGLIATO
S

STYLE    COLOR    SIZE
D21521  543

ESPRIT BUSTIER

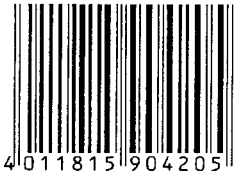

| | |
|---|---|
| D | S |
| F | M |
| I | M |
| UK | S |
| USA | S |

4 011815 904205

D  UNVERBINDLICHE PREISEMPFEHLUNG  DM    24,90
NL  AANBEVOLEN DETAILHANDELSPRIJS
B  AANBEVOLEN DETAILHANDELSPRIJS
    PRIX DETAIL SUGGERE
UK  RECOMMENDED RETAIL PRICE
DK  VEJLEDENDE UDSALGSPRIS
A  UNVERBINDLICH EMPFOHLENER
    VERKAUFSPREIS
S  REKOMMENDERAT CIRKAPRIS
F  PRIX DETAIL SUGGERE
I  PREZZO CONSIGLIATO
S

STYLE  COLOR  SIZE
123456-EUP2

```
STYLE    COLOR    SIZE
D21521   543      [D  ]  S
ESPRIT BUSTIER    [F  ]  M
```
```
                  [I  ]  M
                  [UK ]  S
                  [USA]  S
4 011815 904205
```

D  UNVERBINDLICHE PREISEMPFEHLUNG         DM    24,90
NL AANBEVOLEN DETAILHANDELSPRIJS
B  AANBEVOLEN DETAILHANDELSPRIJS
   PRIX DETAIL SUGGERE

UK RECOMMENDED RETAIL PRICE
DK VEJLEDENDE UDSALGSPRIS
A  UNVERBINDLICH EMPFOHLENER
   VERKAUFSPREIS
S  REKOMMENDERAT CIRKAPRIS
F  PRIX DETAIL SUGGERE
I  PREZZO CONSIGLIATO
S

```
STYLE    COLOR    SIZE
D21521   543      [D  ]  S
ESPRIT BUSTIER    [F  ]  M
```
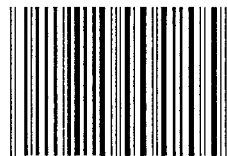
```
                  [I  ]  M
                  [UK ]  S
                  [USA]  S
4 011815 904205
```

D  UNVERBINDLICHE PREISEMPFEHLUNG         DM    24,90
NL AANBEVOLEN DETAILHANDELSPRIJS
B  AANBEVOLEN DETAILHANDELSPRIJS
   PRIX DETAIL SUGGERE

UK RECOMMENDED RETAIL PRICE
DK VEJLEDENDE UDSALGSPRIS
A  UNVERBINDLICH EMPFOHLENER
   VERKAUFSPREIS
S  REKOMMENDERAT CIRKAPRIS
F  PRIX DETAIL SUGGERE
I  PREZZO CONSIGLIATO
S

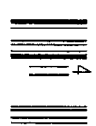  STYLE  123456-EU P2    EH,EU
       COLOR                  CF,CD,WM,MG,VA,VE,DA,DE,KJ,KG,MM,BE
       SIZE

FIG. 10.3B

| STYLE | COLOR | SIZE | |
|---|---|---|---|
| D21521 | 543 | D | S |
| ESPRIT BUSTIER | | F | M |
| | | I | M |
| | | UK | S |
| | | USA | S |

4 011815 904205

| | | | |
|---|---|---|---|
| D | UNVERBINDLICHE PREISEMPFEHLUNG | DM | 24,90 |
| NL | AANBEVOLEN DETAILHANDELSPRIJS | | |
| B | AANBEVOLEN DETAILHANDELSPRIJS PRIX DETAIL SUGGERE | | |
| UK | RECOMMENDED RETAIL PRICE | | |
| DK | VEJLEDENDE UDSALGSPRIS | | |
| A | UNVERBINDLICH EMPFOHLENER VERKAUFSPREIS | | |
| S | REKOMMENDERAT CIRKAPRIS | | |
| F | PRIX DETAIL SUGGERE | | |
| I | PREZZO CONSIGLIATO | | |
| S | | | |

| STYLE | COLOR | SIZE | |
|---|---|---|---|
| D21521 | 543 | D | S |
| ESPRIT BUSTIER | | F | M |
| | | I | M |
| | | UK | S |
| | | USA | S |

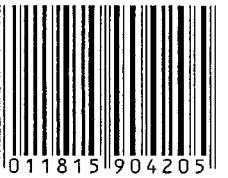

4 011815 904205

| | | | |
|---|---|---|---|
| D | UNVERBINDLICHE PREISEMPFEHLUNG | DM | 24,90 |
| NL | AANBEVOLEN DETAILHANDELSPRIJS | | |
| B | AANBEVOLEN DETAILHANDELSPRIJS PRIX DETAIL SUGGERE | | |
| UK | RECOMMENDED RETAIL PRICE | | |
| DK | VEJLEDENDE UDSALGSPRIS | | |
| A | UNVERBINDLICH EMPFOHLENER VERKAUFSPREIS | | |
| S | REKOMMENDERAT CIRKAPRIS | | |
| F | PRIX DETAIL SUGGERE | | |
| I | PREZZO CONSIGLIATO | | |
| S | | | |

STYLE 123456-EU P2    EH,EU
COLOR    CF,CD,WM,MG,VA,VE,DA,DE,KJ,KG,MM,BE
SIZE

*FIG. 10.3C*

| STYLE | COLOR | SIZE | |
|---|---|---|---|
| D21521 | 543 | D | S |
| ESPRIT BUSTIER | | F | M |
| | | I | M |
| | | UK | S |
| | | USA | S |

4 011815 904205

| | | | |
|---|---|---|---|
| D | UNVERBINDLICHE PREISEMPFEHLUNG | DM | |
| NL | AANBEVOLEN DETAILHANDELSPRIJS | | 24,90 |
| B | AANBEVOLEN DETAILHANDELSPRIJS PRIX DETAIL SUGGERE | | |
| UK | RECOMMENDED RETAIL PRICE | | |
| DK | VEJLEDENDE UDSALGSPRIS | | |
| A | UNVERBINDLICH EMPFOHLENER VERKAUFSPREIS | | |
| S | REKOMMENDERAT CIRKAPRIS | | |
| F | PRIX DETAIL SUGGERE | | |
| I | PREZZO CONSIGLIATO | | |
| S | | | |

| STYLE | COLOR | SIZE | |
|---|---|---|---|
| D21521 | 543 | D | S |
| ESPRIT BUSTIER | | F | M |
| | | I | M |
| | | UK | S |
| | | USA | S |

4 011815 904205

| | | | |
|---|---|---|---|
| D | UNVERBINDLICHE PREISEMPFEHLUNG | DM | 24,90 |
| NL | AANBEVOLEN DETAILHANDELSPRIJS | | |
| B | AANBEVOLEN DETAILHANDELSPRIJS PRIX DETAIL SUGGERE | | |
| UK | RECOMMENDED RETAIL PRICE | | |
| DK | VEJLEDENDE UDSALGSPRIS | | |
| A | UNVERBINDLICH EMPFOHLENER VERKAUFSPREIS | | |
| S | REKOMMENDERAT CIRKAPRIS | | |
| F | PRIX DETAIL SUGGERE | | |
| I | PREZZO CONSIGLIATO | | |
| S | | | |

STYLE 123456-EUP2
COLOR
SIZE

STYLE   COLOR   SIZE
D21521  543     D     S
ESPRIT BUSTIER  F     M
                I     M
                UK    S
                USA   S
4 011815 904205

D  UNVERBINDLICHE PREISEMPFEHLUNG    DM
NL AANBEVOLEN DETAILHANDELSPRIJS              24,90
B  AANBEVOLEN DETAILHANDELSPRIJS
   PRIX DETAIL SUGGERE
UK RECOMMENDED RETAIL PRICE
DK VEJLEDENDE UDSALGSPRIS
A  UNVERBINDLICH EMPFOHLENER
   VERKAUFSPREIS
S  REKOMMENDERAT CIRKAPRIS
F  PRIX DETAIL SUGGERE
I  PREZZO CONSIGLIATO
S

STYLE   COLOR   SIZE
D21521  543     D     S
ESPRIT BUSTIER  F     M
                I     M
                UK    S
                USA   S
4 011815 904205

D  UNVERBINDLICHE PREISEMPFEHLUNG    DM    24,90
NL AANBEVOLEN DETAILHANDELSPRIJS
B  AANBEVOLEN DETAILHANDELSPRIJS
   PRIX DETAIL SUGGERE
UK RECOMMENDED RETAIL PRICE
DK VEJLEDENDE UDSALGSPRIS
A  UNVERBINDLICH EMPFOHLENER
   VERKAUFSPREIS
S  REKOMMENDERAT CIRKAPRIS
F  PRIX DETAIL SUGGERE
I  PREZZO CONSIGLIATO
S

 STYLE  EH,EU
123456-EUP2 COLOR  CF,CD,WM,MG,VA,VE,DA,DE,KJ,KG,MM,BE
           SIZE

*FIG. 10.3E*

FIELDS,A,B,C,D,E,F,G,H,I,J,K,L,M,N,O,P,Q,R,S,T,U,V,W,X,Y,Z,AA,AB,AC,AD,AE,AF,AG,AH,AI,AJ,AK,AL,AM,AN,AO,AP,AQ,AR,AS,AT,AU,AV,AW,AX,AY,AZ,BA,BB,BC,BD,BE,BF,BG

| Style | Color |
|---|---|
| a | b |
| c | |
| | =3 |
| e | |
| f | |
| g | af |
| h | ag |
| i | BFR |
| j | FRB |
| k | ah |
| l | ai |
| m | aj |
| | ak |
| | al |
| | am |
| n | |
| o | |
| p | |
| q | |
| r | |
| s | |
| t | |
| u | |
| v | |
| w | aw |
| x | ax |
| y | ay |
| z | az |
| aa | ba |
| ab | an |
| ac | ao |
| ad | ap |
| ae | aq |
| bb | ar |
| | as |
| | at |
| | au |
| | av |

FIG. 11

| REC_ID | AWWJOBNO | CODE | PLATEUP |
|---|---|---|---|
| 1 | 123456 | 4011815904236 | 10 |
| 1 | 123456 | 4011815904236 | 10 |
| 1 | 123456 | 4011815904236 | 10 |
| 1 | 123456 | 4011815904236 | 10 |
| 1 | 123456 | 4011815904236 | 10 |
| 2 | 123456 | 4011815904229 | 10 |
| 2 | 123456 | 4011815904229 | 10 |
| 2 | 123456 | 4011815904229 | 10 |
| 2 | 123456 | 4011815904229 | 10 |
| 2 | 123456 | 4011815904229 | 10 |
| 3 | 123456 | 4011815904205 | 10 |
| 3 | 123456 | 4011815904205 | 10 |
| 3 | 123456 | 4011815904205 | 10 |
| 3 | 123456 | 4011815904205 | 10 |
| 3 | 123456 | 4011815904205 | 10 |
| 3 | 123456 | 4011815904205 | 10 |
| 3 | 123456 | 4011815904205 | 10 |
| 4 | 123456 | 4011815904243 | 10 |
| 4 | 123456 | 4011815904243 | 10 |
| 4 | 123456 | 4011815904243 | 10 |
| 4 | 123456 | 4011815904243 | 10 |
| 5 | 123456 | 4011815904212 | 10 |
| 5 | 123456 | 4011815904212 | 10 |
| 5 | 123456 | 4011815904212 | 10 |
| 5 | 123456 | 4011815904212 | 10 |
| 5 | 123456 | 4011815904212 | 10 |

*FIG. 12*

| | | |
|---|---|---|
| 4011815904229 | 4011815904212 | 4011815904205 |
| 4011815904243 | 4011815904236 | |

*FIG. 13*

```
SORT: 2-2,JOB: 123456 - HTAG: EU,SPO: 609097 STYLE: D21522,CTY: T FTY: M|SIR,y<|!")|p=jaecdg<,PLATE: 1,PRINT QTY:
SORT: 2-2,JOB: 123456 - HTAG: EU,SPO: 609097 STYLE: D21522,CTY: T FTY: M|SIR,y<|!")|p=jaecdg<,PLATE: 1,PRINT QTY:
SORT: 2-2,JOB: 123456 - HTAG: EU,SPO: 609097 STYLE: D21522,CTY: T FTY: M|SIR,y<|!")|p=jaecdg<,PLATE: 1,PRINT QTY:
SORT: 2-2,JOB: 123456 - HTAG: EU,SPO: 609097 STYLE: D21522,CTY: T FTY: M|SIR,y<|!")|p=jaecdg<,PLATE: 1,PRINT QTY:
SORT: 2-2,JOB: 123456 - HTAG: EU,SPO: 609097 STYLE: D21522,CTY: T FTY: M|SIR,y<|!")|p=jaecdg<,PLATE: 1,PRINT QTY:
SORT: 1-1,JOB: 123456 - HTAG: EU,SPO: 609096 STYLE: D21521,CTY: T FTY: M|SIR,y<|!")|p=jaeccj<,PLATE: 1,PRINT QTY:
SORT: 1-1,JOB: 123456 - HTAG: EU,SPO: 609096 STYLE: D21521,CTY: T FTY: M|SIR,y<|!")|p=jaeccj<,PLATE: 1,PRINT QTY:
SORT: 1-1,JOB: 123456 - HTAG: EU,SPO: 609096 STYLE: D21521,CTY: T FTY: M|SIR,y<|!")|p=jaeccj<,PLATE: 1,PRINT QTY:
SORT: 1-1,JOB: 123456 - HTAG: EU,SPO: 609096 STYLE: D21521,CTY: T FTY: M|SIR,y<|!")|p=jaeccj<,PLATE: 1,PRINT QTY:
SORT: 1-1,JOB: 123456 - HTAG: EU,SPO: 609096 STYLE: D21521,CTY: T FTY: M|SIR,y<|!")|p=jaeccj<,PLATE: 1,PRINT QTY:
123456,P.
SORT: 1-1,JOB: 123456 - HTAG: EU,SPO: 609096 STYLE: D21521,CTY: T FTY: M|SIR,y<|!")|p=jaecaf<,PLATE: 2,PRINT QTY:
SORT: 1-1,JOB: 123456 - HTAG: EU,SPO: 609096 STYLE: D21521,CTY: T FTY: M|SIR,y<|!")|p=jaecaf<,PLATE: 2,PRINT QTY:
SORT: 1-1,JOB: 123456 - HTAG: EU,SPO: 609096 STYLE: D21521,CTY: T FTY: M|SIR,y<|!")|p=jaecaf<,PLATE: 2,PRINT QTY:
SORT: 1-1,JOB: 123456 - HTAG: EU,SPO: 609096 STYLE: D21521,CTY: T FTY: M|SIR,y<|!")|p=jaecaf<,PLATE: 2,PRINT QTY:
SORT: 1-1,JOB: 123456 - HTAG: EU,SPO: 609096 STYLE: D21521,CTY: T FTY: M|SIR,y<|!")|p=jaecaf<,PLATE: 2,PRINT QTY:
SORT: 1-1,JOB: 123456 - HTAG: EU,SPO: 609096 STYLE: D21521,CTY: T FTY: M|SIR,y<|!")|p=jaecaf<,PLATE: 2,PRINT QTY:
SORT: 1-1,JOB: 123456 - HTAG: EU,SPO: 609096 STYLE: D21521,CTY: T FTY: M|SIR,y<|!")|p=jaecaf<,PLATE: 2,PRINT QTY:
SORT: 1-1,JOB: 123456 - HTAG: EU,SPO: 609096 STYLE: D21521,CTY: T FTY: M|SIR,y<|!")|p=jaecaf<,PLATE: 2,PRINT QTY:
```

*FIG. 14.1A*

```
SORT:   1- 1,JOB:  123456 - HTAG:  EU,SPO:  609096 STYLE:  D21521,CTY:  T FTY:  MISIR,y<!!")lp=jaecaf<,PLATE:  2,PRINT QTY:
SORT:   1- 1,JOB:  123456 - HTAG:  EU,SPO:  609096 STYLE:  D21521,CTY:  T FTY:  MISIR,y<!!")lp=jaecaf<,PLATE:  2,PRINT QTY:
123456,P. 2
SORT:   2- 2,JOB:  123456 - HTAG:  EU,SPO:  609097 STYLE:  D21522,CTY:  T FTY:  MISIR,y<!!")lp=jaeced<,PLATE:  3,PRINT QTY:
SORT:   2- 2,JOB:  123456 - HTAG:  EU,SPO:  609097 STYLE:  D21522,CTY:  T FTY:  MISIR,y<!!")lp=jaeced<,PLATE:  3,PRINT QTY:
SORT:   2- 2,JOB:  123456 - HTAG:  EU,SPO:  609097 STYLE:  D21522,CTY:  T FTY:  MISIR,y<!!")lp=jaeced<,PLATE:  3,PRINT QTY:
SORT:   2- 2,JOB:  123456 - HTAG:  EU,SPO:  609097 STYLE:  D21522,CTY:  T FTY:  MISIR,y<!!")lp=jaeced<,PLATE:  3,PRINT QTY:
SORT:   2- 2,JOB:  123456 - HTAG:  EU,SPO:  609096 STYLE:  D21522,CTY:  T FTY:  MISIR,y<!!")lp=jaeced<,PLATE:  3,PRINT QTY:
SORT:   1- 1,JOB:  123456 - HTAG:  EU,SPO:  609096 STYLE:  D21521,CTY:  T FTY:  MISIR,y<!!")lp=jaecbc<,PLATE:  3,PRINT QTY:
SORT:   1- 1,JOB:  123456 - HTAG:  EU,SPO:  609096 STYLE:  D21521,CTY:  T FTY:  MISIR,y<!!")lp=jaecbc<,PLATE:  3,PRINT QTY:
SORT:   1- 1,JOB:  123456 - HTAG:  EU,SPO:  609096 STYLE:  D21521,CTY:  T FTY:  MISIR,y<!!")lp=jaecbc<,PLATE:  3,PRINT QTY:
SORT:   1- 1,JOB:  123456 - HTAG:  EU,SPO:  609096 STYLE:  D21521,CTY:  T FTY:  MISIR,y<!!")lp=jaecbc<,PLATE:  3,PRINT QTY:
123456,P. 3
```

*FIG. 14.1B*

50,MULTI-SIZE; MULTI-CURRENCY
50,MULTI-SIZE; MULTI-CURRENCY
50,MULTI-SIZE; MULTI-CURRENCY
50,MULTI-SIZE; MULTI-CURRENCY
50,MULTI-SIZE; MULTI-CURRENCY
50,MULTI-SIZE; MULTI-CURRENCY
50,MULTI-SIZE; MULTI-CURRENCY
50,MULTI-SIZE; MULTI-CURRENCY
50,MULTI-SIZE; MULTI-CURRENCY
50,MULTI-SIZE; MULTI-CURRENCY
25,MULTI-SIZE; MULTI-CURRENCY
25,MULTI-SIZE; MULTI-CURRENCY
25,MULTI-SIZE; MULTI-CURRENCY
25,MULTI-SIZE; MULTI-CURRENCY
25,MULTI-SIZE; MULTI-CURRENCY
25,MULTI-SIZE; MULTI-CURRENCY
25,MULTI-SIZE; MULTI-CURRENCY
25,MULTI-SIZE; MULTI-CURRENCY
25,MULTI-SIZE; MULTI-CURRENCY

*FIG. 14.2A*

75,MULTI-SIZE; MULTI-CURRENCY
75,MULTI-SIZE; MULTI-CURRENCY
75,MULTI-SIZE; MULTI-CURRENCY
75,MULTI-SIZE; MULTI-CURRENCY
75,MULTI-SIZE; MULTI-CURRENCY
75,MULTI-SIZE; MULTI-CURRENCY
75,MULTI-SIZE; MULTI-CURRENCY
75,MULTI-SIZE; MULTI-CURRENCY
75,MULTI-SIZE; MULTI-CURRENCY
75,MULTI-SIZE; MULTI-CURRENCY

*FIG. 14.2B*

SORT: 2- 2
JOB: 123456 - HTAG: EU
SPO: 609097 STYLE: D21522
CTY: T FTY: MISIR
4 011815 904236
PLATE: 1
PRINT QTY: 50
MULTI-SIZE; MULTI-CURRENCY
SORT: 2- 2
JOB: 123456 - HTAG: EU
SPO: 609097 STYLE: D21522
CTY: T FTY: MISIR
4 011815 904236
PLATE: 1
PRINT QTY: 50
MULTI-SIZE; MULTI-CURRENCY
SORT: 1- 1
JOB: 123456 - HTAG: EU
SPO: 609096 STYLE: D21521
CTY: T FTY: MISIR
4 011815 904229
PLATE: 1
PRINT QTY: 50
MULTI-SIZE; MULTI-CURRENCY
SORT: 1- 1
JOB: 123456 - HTAG: EU
SPO: 609096 STYLE: D21521
CTY: T FTY: MISIR
4 011815 904229
PLATE: 1
PRINT QTY: 50
MULTI-SIZE; MULTI-CURRENCY
*FIG. 15.1A*

SORT: 2- 2
JOB: 123456 - HTAG: EU
SPO: 609097 STYLE: D21522
CTY: T FTY: MISIR

PLATE: 1
PRINT QTY: 50

MULTI-SIZE; MULTI-CURRENCY

SORT: 2- 2
JOB: 123456 - HTAG: EU
SPO: 609097 STYLE: D21522
CTY: T FTY: MISIR

PLATE: 1
PRINT QTY: 50

MULTI-SIZE; MULTI-CURRENCY

SORT: 1- 1
JOB: 123456 - HTAG: EU
SPO: 609096 STYLE: D21521
CTY: T FTY: MISIR

PLATE: 1
PRINT QTY: 50

MULTI-SIZE; MULTI-CURRENCY

SORT: 1- 1
JOB: 123456 - HTAG: EU
SPO: 609096 STYLE: D21521
CTY: T FTY: MISIR

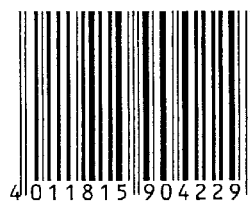

PLATE: 1
PRINT QTY: 50

MULTI-SIZE; MULTI-CURRENCY

FIG. 15.1B

123456 P.1     EH,EU AND MANY OTHERS CUT

SORT: 2- 2
JOB: 123456 - HTAG: EU
SPO: 609097 STYLE: D21522
CTY: T FTY: MISIR
4 011815 904236
PLATE: 1
PRINT QTY: 50
MULTI-SIZE; MULTI-CURRENCY
SORT: 1- 1
JOB: 123456 - HTAG: EU
SPO: 609096 STYLE: D21521
CTY: T FTY: MISIR
4 011815 904229
PLATE: 1
PRINT QTY: 50
MULTI-SIZE; MULTI-CURRENCY
*FIG. 15.1C*

SORT: 1- 1
JOB: 123456 - HTAG: EU
SPO: 609096 STYLE: D21521
CTY: T FTY: MISIR
PLATE: 2
PRINT QTY: 25
MULTI-SIZE; MULTI-CURRENCY
SORT: 1- 1
JOB: 123456 - HTAG: EU
SPO: 609096 STYLE: D21521
CTY: T FTY: MISIR
PLATE: 2
PRINT QTY: 25
MULTI-SIZE; MULTI-CURRENCY
SORT: 1- 1
JOB: 123456 - HTAG: EU
SPO: 609096 STYLE: D21521
CTY: T FTY: MISIR
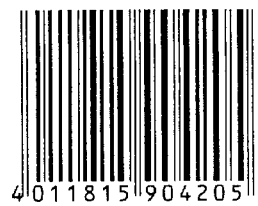
PLATE: 2
PRINT QTY: 25
MULTI-SIZE; MULTI-CURRENCY
SORT: 1- 1
JOB: 123456 - HTAG: EU
SPO: 609096 STYLE: D21521
CTY: T FTY: MISIR
PLATE: 2
PRINT QTY: 25
MULTI-SIZE; MULTI-CURRENCY
*FIG. 15.2A*

SORT: 1- 1
JOB: 123456 - HTAG: EU
SPO: 609096 STYLE: D21521
CTY: T FTY: MISIR

4 011815 904205

PLATE: 2
PRINT QTY: 25

MULTI-SIZE; MULTI-CURRENCY

SORT: 1- 1
JOB: 123456 - HTAG: EU
SPO: 609096 STYLE: D21521
CTY: T FTY: MISIR

4 011815 904205

PLATE: 2
PRINT QTY: 25

MULTI-SIZE; MULTI-CURRENCY

SORT: 1- 1
JOB: 123456 - HTAG: EU
SPO: 609096 STYLE: D21521
CTY: T FTY: MISIR

4 011815 904205

PLATE: 2
PRINT QTY: 25

MULTI-SIZE; MULTI-CURRENCY

SORT: 1- 1
JOB: 123456 - HTAG: EU
SPO: 609096 STYLE: D21521
CTY: T FTY: MISIR

4 011815 904205

PLATE: 2
PRINT QTY: 25

MULTI-SIZE; MULTI-CURRENCY

EH,EU AND MANY OTHERS CUT

SORT: 1- 1
JOB: 123456 - HTAG: EU
SPO: 609096 STYLE: D21521
CTY: T FTY: MISIR
4 011815 904205
PLATE: 2
PRINT QTY: 25
MULTI-SIZE; MULTI-CURRENCY
SORT: 1- 1
JOB: 123456 - HTAG: EU
SPO: 609096 STYLE: D21521
CTY: T FTY: MISIR
4 011815 904205
PLATE: 2
PRINT QTY: 25
MULTI-SIZE; MULTI-CURRENCY
FIG. 15.2C

SORT: 2- 2
JOB: 123456 - HTAG: EU
SPO: 609097 STYLE: D21522
CTY: T FTY: MISIR
4 011815 904243
PLATE: 3
PRINT QTY: 75
MULTI-SIZE; MULTI-CURRENCY
SORT: 2- 2
JOB: 123456 - HTAG: EU
SPO: 609097 STYLE: D21522
CTY: T FTY: MISIR
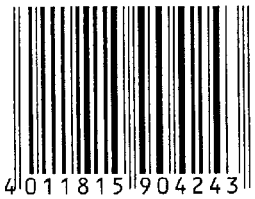
4 011815 904243
PLATE: 3
PRINT QTY: 75
MULTI-SIZE; MULTI-CURRENCY
SORT: 1- 1
JOB: 123456 - HTAG: EU
SPO: 609096 STYLE: D21521
CTY: T FTY: MISIR
4 011815 904212
PLATE: 3
PRINT QTY: 75
MULTI-SIZE; MULTI-CURRENCY
SORT: 1- 1
JOB: 123456 - HTAG: EU
SPO: 609096 STYLE: D21521
CTY: T FTY: MISIR
4 011815 904212
PLATE: 3
PRINT QTY: 75
MULTI-SIZE; MULTI-CURRENCY
*FIG. 15.3A*

SORT: 2- 2
JOB: 123456 - HTAG: EU
SPO: 609097 STYLE: D21522
CTY: T FTY: MISIR

4 011815 904243

PLATE: 3
PRINT QTY: 75

MULTI-SIZE; MULTI-CURRENCY

SORT: 2- 2
JOB: 123456 - HTAG: EU
SPO: 609097 STYLE: D21522
CTY: T FTY: MISIR

4 011815 904243

PLATE: 3
PRINT QTY: 75

MULTI-SIZE; MULTI-CURRENCY

SORT: 1- 1
JOB: 123456 - HTAG: EU
SPO: 609096 STYLE: D21521
CTY: T FTY: MISIR

4 011815 904212

PLATE: 3
PRINT QTY: 75

MULTI-SIZE; MULTI-CURRENCY

SORT: 1- 1
JOB: 123456 - HTAG: EU
SPO: 609096 STYLE: D21521
CTY: T FTY: MISIR

4 011815 904212

PLATE: 3
PRINT QTY: 75

MULTI-SIZE; MULTI-CURRENCY

123456 P3   EH,EU AND MANY OTHERS CUT

FIG. 15.3B

SORT: 2- 2
JOB: 123456 - HTAG: EU
SPO: 609097 STYLE: D21522
CTY: T FTY: MISIR
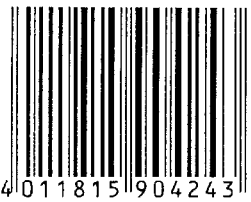
4 011815 904243
PLATE: 3
PRINT QTY: 75
MULTI-SIZE; MULTI-CURRENCY
SORT: 1- 1
JOB: 123456 - HTAG: EU
SPO: 609096 STYLE: D21521
CTY: T FTY: MISIR
4 011815 904212
PLATE: 3
PRINT QTY: 75
MULTI-SIZE; MULTI-CURRENCY
*FIG. 15.3C*

| AWJOBNO | YEAR | ORDERDATE | DISTRI | COUNTRY | SEASON | DIV | STYLEHEAD | STYLE | STYLEDESC | COLORHEAD | CLRCODE |
|---|---|---|---|---|---|---|---|---|---|---|---|
| 123456 | 98 | | 0 | UKI | D | 21 | STYLE | D21521 | ESPRIT BUSTIER | COLOR | 543 |
| 123456 | 98 | | 0 | UKI | D | 21 | STYLE | D21521 | ESPRIT BUSTIER | COLOR | 543 |
| 123456 | 98 | | 0 | UKI | D | 21 | STYLE | D21521 | ESPRIT BUSTIER | COLOR | 543 |
| 123456 | 98 | | 0 | UKI | D | 21 | STYLE | D21522 | ESPRIT PANTY | COLOR | 543 |
| 123456 | 98 | | 0 | UKI | D | 21 | STYLE | D21522 | ESPRIT PANTY | COLOR | 543 |

*FIG. 16.1*

| CLRNAME | SIZEHEAD | SIZE | RETAILTXT | RETAILCODE | RETAIL CODE | CODE1 | SPO | QTY | AGENT | HANGTAGTYP |
|---|---|---|---|---|---|---|---|---|---|---|
| | | L | | ü | 4011815904229 | NO MATCH | 609096 | 250 | G | EU |
| | | M | | ü | 4011815904212 | NO MATCH | 609096 | 375 | G | EU |
| | | S | | ü | 4011815904205 | NO MATCH | 609096 | 250 | G | EU |
| | | M | | ü | 4011815904243 | NO MATCH | 609097 | 375 | G | EU |
| | | S | | ü | 4011815904236 | NO MATCH | 609097 | 250 | G | EU |

*FIG. 16.2*

| FACTORY | EX_OR_DATE | CTY_SZ1 | CTY_SZ2 | CTY_SZ3 | CTY-SZ4 | CTY_SZ5 | SIZE1 | SIZE2 | SIZE3 | SIZE4 | SIZE5 | CTY_M1 | CTY_M2 | CTY_M3 |
|---|---|---|---|---|---|---|---|---|---|---|---|---|---|---|
| MISIR | OD | F | I | UK | USA | | L | XL | L | L | D | NL | B |
| MISIR | OD | F | I | UK | USA | | M | L | M | M | D | NL | B |
| MISIR | OD | F | I | UK | USA | | S | M | S | S | D | NL | B |
| MISIR | OD | F | I | UK | USA | | M | L | M | M | D | NL | B |
| MISIR | OD | F | I | UK | USA | | S | M | S | S | D | NL | B |

*FIG. 16.3*

| CTY_M4 | CTY_M5 | CTY_M6 | CTY_M7 | CTY_M8 | CTY_M9 | RETDESC11 | RETDEC12 | RETDESC21 |
|---|---|---|---|---|---|---|---|---|
| UK | DK | A | S | F | I | | unverbindliche Preisempfehlung | |
| UK | DK | A | S | F | I | | unverbindliche Preisempfehlung | |
| UK | DK | A | S | F | I | | unverbindliche Preisempfehlung | |
| UK | DK | A | S | F | I | | unverbindliche Preisempfehlung | |
| UK | DK | A | S | F | I | | unverbindliche Preisempfehlung | |

*FIG. 16.4*

| RETDESC22 | RETDESC31 | RETDESC32 | RETDESC41 | RETDESC42 | RETDESC51 |
|---|---|---|---|---|---|
| aanbevolen detailhandelsprijs | aanbevolen detailhandelsprijs | prix detail suggÄrÄ | | recommended retail price | |
| aanbevolen detailhandelsprijs | aanbevolen detailhandelsprijs | prix detail suggÄrÄ | | recommended retail price | |
| aanbevolen detailhandelsprijs | aanbevolen detailhandelsprijs | prix detail suggÄrÄ | | recommended retail price | |
| aanbevolen detailhandelsprijs | aanbevolen detailhandelsprijs | prix detail suggÄrÄ | | recommended retail price | |
| aanbevolen detailhandelsprijs | aanbevolen detailhandelsprijs | prix detail suggÄrÄ | | recommended retail price | |

*FIG. 16.5*

| RETDESC52 | RETDESC61 | RETDESC62 | RETDESC71 | RETDESC72 | RETDESC81 | RETDESC82 |
|---|---|---|---|---|---|---|
| vejledende udsalgspris | unverbindlich empfohlener Verkaufspreis | | rekommenderat cirkapris | rekommenderat cirkapris | | prix detail suggÄrÄ |
| vejledende udsalgspris | unverbindlich empfohlener Verkaufspreis | | rekommenderat cirkapris | rekommenderat cirkapris | | prix detail suggÄrÄ |
| vejledende udsalgspris | unverbindlich empfohlener Verkaufspreis | | rekommenderat cirkapris | rekommenderat cirkapris | | prix detail suggÄrÄ |
| vejledende udsalgspris | unverbindlich empfohlener Verkaufspreis | | rekommenderat cirkapris | rekommenderat cirkapris | | prix detail suggÄrÄ |
| vejledende udsalgspris | unverbindlich empfohlener Verkaufspreis | | rekommenderat cirkapris | rekommenderat cirkapris | | prix detail suggÄrÄ |

*FIG. 16.6*

| RETDESC91 | RETDESC92 | RETCODE1 | RETCODE2 | RETCODE3 | RETCODE4 | RETCODE5 | RETCODE6 | RETCODE7 | RETCPDE8 |
|---|---|---|---|---|---|---|---|---|---|
| | prezzo consigliato | DM | | | | | | | |
| | prezzo consigliato | DM | | | | | | | |
| | prezzo consigliato | DM | | | | | | | |
| | prezzo consigliato | DM | | | | | | | |
| | prezzo consigliato | DM | | | | | | | |

*FIG. 16.7*

| RETCODE9 | RETAIL1 | RETAIL2 | RETAIL3 | RETAIL4 | RETAIL5 | RETAIL6 | RETAIL7 | RETAIL8 | RETAIL9 | LENGTH | FILENAME | THERM | INVOIC |
|---|---|---|---|---|---|---|---|---|---|---|---|---|---|
| | 24,90 | | | | | | | | | | G9819005 | | UKI |
| | 24,90 | | | | | | | | | | G9819005 | | UKI |
| | 24,90 | | | | | | | | | | G9819005 | | UKI |
| | 24,90 | | | | | | | | | | G9819005 | | UKI |
| | 24,90 | | | | | | | | | | G9819005 | | UKI |

*FIG. 16.8*

| CARTON_ID | PLATENO | RQTY | SHPQTY | REPEAT | PLATEQTY | REC_ID | SORTNUM | SORT | FSORTNUM | LSORTNUM | PLATEUP | TOTPLATE |
|---|---|---|---|---|---|---|---|---|---|---|---|---|
| 3 | 1 | 250 | 250 | 5 | 50 | 1 | S0001 | 1 | | | 10 | 3 |
| 2 | 3 | 375 | 375 | 5 | 75 | 2 | S0001 | 1 | | | 10 | 3 |
| 1 | 2 | 250 | 250 | 10 | 25 | 3 | S0001 | 1 | | | 10 | 3 |
| 5 | 3 | 375 | 375 | 5 | 75 | 4 | S0002 | 2 | | | 10 | 3 |
| 4 | 1 | 250 | 250 | 5 | 50 | 5 | S0002 | 2 | | | 10 | 3 |

FIG. 16.9

| PACKID | FBOXNO1 | LBOXNO1 | CAPACITY1 | FBOXNO2 | LBOXNO2 | CAPCITY2 | CODEASC | CODETYPE | REMAINDER | CHKSUM |
|---|---|---|---|---|---|---|---|---|---|---|
| 1 | 1 | 1 | | | | 1 | | | | |
| 2 | 1 | 1 | | | | 1 | | | | |
| 3 | 1 | 1 | | | | 1 | | | | |
| 4 | 2 | 2 | | | | 1 | | | | |
| 5 | 2 | 2 | | | | 1 | | | | |

FIG. 16.10

| STRUCODE | PRODCODE | WTUNIT | FBOXNO | LBOXNO | FCARNO | LCARNO | BCAPACITY | CCAPACITY | INFILE | PLTPAGE | PLTLABEL |
|---|---|---|---|---|---|---|---|---|---|---|---|
| EDCGM-MULTI | EU | 0.0000 | | | | | | | EU456 | | |
| EDCGM-MULTI | EU | 0.0000 | | | | | | | EU456 | | |
| EDCGM-MULTI | EU | 0.0000 | | | | | | | EU456 | 1 | |
| EDCGM-MULTI | EU | 0.0000 | | | | | | | EU456 | 1 | 2 |
| EDCGM-MULTI | EU | 0.0000 | | | | | | | EU456 | 1 | 3 |

FIG. 16.11

| AWJOBNO | YEAR | ORDERDATE | DISTI | COUNTRY | SEASON | DIV | STYLEHEAD | STYLE | STYLEDESC | COLORHEAD |
|---|---|---|---|---|---|---|---|---|---|---|
| 123456 | 98 | 0 | UKI | T | D | 21 | STYLE | D21521 | ESPRIT BUSTIER | COLOR |
| 123456 | 98 | 0 | UKI | T | D | 21 | STYLE | D21521 | ESPRIT BUSTIER | COLOR |
| 123456 | 98 | 0 | UKI | T | D | 21 | STYLE | D21521 | ESPRIT BUSTIER | COLOR |
| 123456 | 98 | 0 | UKI | T | D | 21 | STYLE | D21522 | ESPRIT PANTY | COLOR |
| 123456 | 98 | 0 | UKI | T | D | 21 | STYLE | D21522 | ESPRIT PANTY | COLOR |

FIG. 17.1

| CLRCODE | CLRNAME | SIZEHEAD | SIZE | RETAILTXT | RETAILCODE | RETAIL CODE | CODE1 | SPO | QTY | AGENT |
|---|---|---|---|---|---|---|---|---|---|---|
| 543 | | | S | ú | | 4011815904205 | NO MATCH | 609096 | 250 | G |
| 543 | | | M | ú | | 4011815904212 | NO MATCH | 609096 | 375 | G |
| 543 | | | L | ú | | 4011815904229 | NO MATCH | 609096 | 250 | G |
| 543 | | | S | ú | | 4011815904236 | NO MATCH | 609097 | 250 | G |
| 543 | | | M | ú | | 4011815904243 | NO MATCH | 609097 | 375 | G |

*FIG. 17.2*

| HANGTAGTYP | FACTORY | EX_OR_DATE | CTY_SZ1 | CTY_SZ2 | CTY_SZ3 | CTY_SZ4 | CTY_SZ5 | SIZE1 | SIZE2 | SIZE3 | SIZE4 | SIZE5 |
|---|---|---|---|---|---|---|---|---|---|---|---|---|
| EU | MISIR | O D | F | I | UK | USA | | S | M | M | S | S |
| EU | MISIR | O D | F | I | UK | USA | | M | L | L | M | M |
| EU | MISIR | O D | F | I | UK | USA | | L | XL | XL | L | L |
| EU | MISIR | O D | F | I | UK | USA | | S | M | M | S | S |
| EU | MISIR | O D | F | I | UK | USA | | M | L | L | M | M |

| CTY_M1 | CTY_M2 | CTY_M3 | CTY_M4 | CTY_M5 | CTY_M6 | CTY_M7 | CTY_M8 | CTY_M9 | RETDESC11 | RETDESC12 |
|---|---|---|---|---|---|---|---|---|---|---|
| D | NL | B | UK | DK | A | S | F | — | | unverbindliche Preisempfehl |
| D | NL | B | UK | DK | A | S | F | — | | unverbindliche Preisempfehl |
| D | NL | B | UK | DK | A | S | F | — | | unverbindliche Preisempfehl |
| D | NL | B | UK | DK | A | S | F | — | | unverbindliche Preisempfehl |
| D | NL | B | UK | DK | A | S | F | — | | |

FIG. 17.5

| RETDESC21 | RETDESC22 | RETDESC31 | RETDESC32 | RETDESC41 | RETDESC42 |
|---|---|---|---|---|---|
| | aanbevolen detailhandelsp | aanbevolen detailhandelsp | prix detail sugg | | recommended retail pri |
| | aanbevolen detailhandelsp | aanbevolen detailhandelsp | prix detail sugg | | recommended retail pri |
| | aanbevolen detailhandelsp | aanbevolen detailhandelsp | prix detail sugg | | recommended retail pri |
| | aanbevolen detailhandelsp | aanbevolen detailhandelsp | prix detail sugg | | recommended retail pri |
| | aanbevolen detailhandelsp | aanbevolen detailhandelsp | prix detail sugg | | recommended retail pri |

| RETDESC51 | RETDESC52 | RETDESC61 | RETDESC62 | RETDESC71 | RETDESC72 | RETDESC81 |
|---|---|---|---|---|---|---|
| | vejledende udsalgsp | unverbindlich empfohle | Verkaufsprei | | rekommenderat cirkapr | |
| | vejledende udsalgsp | unverbindlich empfohle | Verkaufsprei | | rekommenderat cirkapr | |
| | vejledende udsalgsp | unverbindlich empfohle | Verkaufsprei | | rekommenderat cirkapr | |
| | vejledende udsalgsp | unverbindlich empfohle | Verkaufsprei | | rekommenderat cirkapr | |
| | vejledende udsalgsp | unverbindlich empfohle | Verkaufsprei | | rekommenderat cirkapr | |

*FIG. 17.6*

| RETDESC62 | RETDESC91 | RETDESC92 | RETCODE1 | RETCODE2 | RETCODE3 | RETCODE4 | RETCODE5 | RETCODE6 |
|---|---|---|---|---|---|---|---|---|
| prix detail sugg | | prezzo consiglia | DM | | | | | |
| prix detail sugg | | prezzo consiglia | DM | | | | | |
| prix detail sugg | | prezzo consiglia | DM | | | | | |
| prix detail sugg | | prezzo consiglia | DM | | | | | |
| prix detail sugg | | prezzo consiglia | DM | | | | | |

*FIG. 17.7*

| RETCODE7 | RETCODE8 | RETCODE9 | RETAIL1 | RETAIL2 | RETAIL3 | RETAIL4 | RETAIL5 | RETAIL6 | RETAIL7 | RETAIL8 | RETAIL9 |
|---|---|---|---|---|---|---|---|---|---|---|---|
| | | | 24,90 | | | | | | | | |
| | | | 24,90 | | | | | | | | |
| | | | 24,90 | | | | | | | | |
| | | | 24,90 | | | | | | | | |
| | | | 24,90 | | | | | | | | |

*FIG. 17.8*

| LENGTH | FILENAME | THERM | INVOIC | CARTON_ID |
|---|---|---|---|---|
| | G9819005 | | UKI | 1 |
| | G9819005 | | UKI | 2 |
| | G9819005 | | UKI | 3 |
| | G9819005 | | UKI | 4 |
| | G9819005 | | UKI | 5 |

*FIG. 17.9*

| AWJOBNO | YEAR | ORDERDATE | DISTRI | COUNTRY | SEASON | DIV | STYLEHEAD | STYLE | STYLEDESC | COLORHEAD | CLRCODE |
|---|---|---|---|---|---|---|---|---|---|---|---|
| 123456 | 98 | 0 | UKI | T | D | 21 | STYLE | D21521 | ESPRIT BUSTIER | COLOR | 543 |
| 123456 | 98 | 0 | UKI | T | D | 21 | STYLE | D21521 | ESPRIT BUSTIER | COLOR | 543 |
| 123456 | 98 | 0 | UKI | T | D | 21 | STYLE | D21521 | ESPRIT BUSTIER | COLOR | 543 |
| 123456 | 98 | 0 | UKI | T | D | 21 | STYLE | D21522 | ESPRIT PANTY | COLOR | 543 |
| 123456 | 98 | 0 | UKI | T | D | 21 | STYLE | D21522 | ESPRIT PANTY | COLOR | 543 |

| CLRNAME | SIZEHEAD SIZE | RETAILTXT | RETAILCODE RETAIL CODE | CODE1 | SP0 | QTY | AGENT | HANGTAGTYP |
|---|---|---|---|---|---|---|---|---|
| | S | ü | 4011815904205 | NO MATCH | 609096 | 250 | G | EU |
| | M | ü | 4011815904212 | NO MATCH | 609096 | 375 | G | EU |
| | L | ü | 4011815904229 | NO MATCH | 609096 | 250 | G | EU |
| | S | ü | 4011815904236 | NO MATCH | 609097 | 250 | G | EU |
| | M | ü | 4011815904243 | NO MATCH | 609097 | 375 | G | EU |

FIG. 18.3

| FACTORY | EX_OR_DATE | CTY_SZ1 | CTY_SZ2 | CTY_SZ3 | CTY_SZ4 | CTY_SZ5 | SIZE1 | AIZE2 | SIZE3 | SIZE4 | SIZE5 | CTY_M1 | CTY_M2 | CTY_M3 |
|---|---|---|---|---|---|---|---|---|---|---|---|---|---|---|
| MISIR | O D | F | — | UK | USA | S | M | M | S | S | D | NL | B |
| MISIR | O D | F | — | UK | USA | M | L | L | M | M | D | NL | B |
| MISIR | O D | F | — | UK | USA | L | XL | XL | L | L | D | NL | B |
| MISIR | O D | F | — | UK | USA | S | M | M | S | S | D | NL | B |
| MISIR | O D | F | — | UK | USA | M | L | L | M | M | D | NL | B |

FIG. 18.4

| CTY_M4 | CTY_M5 | CTY_M6 | CTY_M7 | CTY_M8 | CTY_M9 | RETDESC11 | RETDESC12 | RETDESC21 |
|---|---|---|---|---|---|---|---|---|
| UK | DK | A | S | F | — | | unverbindliche Preisempfehlung | |
| UK | DK | A | S | F | — | | unverbindliche Preisempfehlung | |
| UK | DK | A | S | F | — | | unverbindliche Preisempfehlung | |
| UK | DK | A | S | F | — | | unverbindliche Preisempfehlung | |
| UK | DK | A | S | F | — | | unverbindliche Preisempfehlung | |

FIG. 18.5

| RETDESC22 | RETDESC31 | RETDESC32 | RETDESC41 | RETDESC42 | RETDESC551 |
|---|---|---|---|---|---|
| aanbevolen detailhandelsprijs | aanbevolen detailhandelsprijs | prix detail suggÄrÄ | | recommended retail price | |
| aanbevolen detailhandelsprijs | aanbevolen detailhandelsprijs | prix detail suggÄrÄ | | recommended retail price | |
| aanbevolen detailhandelsprijs | aanbevolen detailhandelsprijs | prix detail suggÄrÄ | | recommended retail price | |
| aanbevolen detailhandelsprijs | aanbevolen detailhandelsprijs | prix detail suggÄrÄ | | recommended retail price | |
| aanbevolen detailhandelsprijs | aanbevolen detailhandelsprijs | prix detail suggÄrÄ | | recommended retail price | |

FIG. 18.6

| RETDESC52 | RETDESC61 | RETDESC62 | RETDESC71 | RETDESC72 | RETDESC81 | RETDESC82 |
|---|---|---|---|---|---|---|
| vejledende udsalgspris | unverbindlich empfohlener | Verkaufspreis | | rekommenderat cirkapris | | prix detail suggÄrÄ |
| vejledende udsalgspris | unverbindlich empfohlener | Verkaufspreis | | rekommenderat cirkapris | | prix detail suggÄrÄ |
| vejledende udsalgspris | unverbindlich empfohlener | Verkaufspreis | | rekommenderat cirkapris | | prix detail suggÄrÄ |
| vejledende udsalgspris | unverbindlich empfohlener | Verkaufspreis | | rekommenderat cirkapris | | prix detail suggÄrÄ |
| vejledende udsalgspris | unverbindlich empfohlener | Verkaufspreis | | rekommenderat cirkapris | | prix detail suggÄrÄ |

FIG. 18.7

| RETDESC91 | RETDESC92 | RETCODE1 | RETCODE2 | RETCODE3 | RETCODE4 | RETCODE5 | RETCODE6 | RETCODE7 | RETCODE8 |
|---|---|---|---|---|---|---|---|---|---|
| | prezzo consigliato | DM | | | | | | | |
| | prezzo consigliato | DM | | | | | | | |
| | prezzo consigliato | DM | | | | | | | |
| | prezzo consigliato | DM | | | | | | | |
| | prezzo consigliato | DM | | | | | | | |

| RETCODE9 | RETAIL1 | RETAIL2 | RETAIL3 | RETAIL4 | RETAIL5 | RETAIL6 | RETAIL7 | RETAIL8 | RETAIL9 | LENGTH | FILENAME | THERM | INCOIC |
|---|---|---|---|---|---|---|---|---|---|---|---|---|---|
| | | | | | | | | | 24,90 | | G9819005 | 3 | UKI |
| | | | | | | | | | 24,90 | | G9819005 | 3 | UKI |
| | | | | | | | | | 24,90 | | G9819005 | 3 | UKI |
| | | | | | | | | | 24,90 | | G9819005 | 3 | UKI |
| | | | | | | | | | 24,90 | | G9819005 | 3 | UKI |

*FIG. 18.9*

| CARTON_ID | PLATENO | RQTY | SHPQTY | REPEAT | PLATEQTY | REC_ID | SORTNUM | SORT | FSORTNUM | LSORTNUM | PLATEUP | TOTPLATE |
|---|---|---|---|---|---|---|---|---|---|---|---|---|
| 1 | 2 | 250 | 250 | 10 | 25 | 3 | | | 1 | 1 | 1 | 10 |
| 2 | 3 | 375 | 375 | 5 | 75 | 5 | | | 1 | 1 | 1 | 10 |
| 3 | 1 | 250 | 250 | 5 | 50 | 2 | | | 1 | 1 | 1 | 10 |
| 4 | 1 | 250 | 250 | 5 | 50 | 1 | | | 2 | 2 | 2 | 10 |
| 5 | 3 | 375 | 375 | 5 | 75 | 4 | | | 2 | 2 | 2 | 10 |

*FIG. 18.10*

| PACKID | FBOXNO1 | LBOXNO1 | CAPACITY1 | FBOXNO2 | LBOXNO2 | CAPCITY2 | CODEASC | CODETYPE | REMAINDER | CHKSUM |
|---|---|---|---|---|---|---|---|---|---|---|
| 3 | 1 | 1 | 1 | 1 | 1 | 1 | 4011815904205 | | | |
| 2 | 1 | 1 | 1 | 1 | 1 | 1 | 4011815904212 | | | |
| 1 | 1 | 1 | 1 | 1 | 1 | 1 | 4011815904229 | | | |
| 5 | 2 | 2 | 2 | 1 | 1 | 1 | 4011815904236 | | | |
| 4 | 2 | 2 | 2 | 1 | 1 | 1 | 4011815904243 | | | |

| STRUCODE | PRODCODE | WTUNIT | FBOXNO | LBOXNO | FCARNO | LCARNO | BCAPACITY | CCAPACITY | INFILE | PLTPAGE | PLTLABEL |
|---|---|---|---|---|---|---|---|---|---|---|---|
| EDCGM-MULTI | EU | 0.0000 | 1 | 1 | 1 | 1 | | | EU456 | 1 | 2 |
| EDCGM-MULTI | EU | 0.0000 | 1 | 1 | 1 | 1 | | | EU456 | | |
| EDCGM-MULTI | EU | 0.0000 | 1 | 1 | 1 | 1 | | | EU456 | 1 | 1 |
| EDCGM-MULTI | EU | 0.0000 | 2 | 2 | 1 | 1 | | | EU456 | 1 | |
| EDCGM-MULTI | EU | 0.0000 | 2 | 2 | 1 | 1 | | | EU456 | 1 | 3 |

CUSTOMER     : NEWGERM
MODULE       : MULTI
DESCRIPTION  : MULTI CURRENCY FORMAT
FILE NAME    : GM19005
DATE/TIME    : 06/11/98 / 4:19:12 PM

<< ESPRIT GERMANY HANGTAG SUMMARY >>

PAGE# 1

| SEASON | HANGTAGTYP | QTY | REC # |
|--------|------------|--------|-------|
| D | C4 | 40 | 2 |
| D | EU | 1500 | 5 |
| D | PP | 270 | 2 |
| E | AA | 3525 | 62 |
| E | AU | 206200 | 347 |
| E | BE | 32650 | 230 |
| E | C4 | 8670 | 119 |
| E | KG | 133125 | 794 |
| E | PP | 92085 | 935 |
| N | C4 | 25 | 1 |
|   |    | 478090 |   |

*FIG. 19*

| Customer | : NEWGERM |
|---|---|
| Module | : MULTI |
| Description | : MULTI CURRENCY FORMAT |
| Date/Time | : 03/30/98 / 2:27:26 PM |

<< ESPRIT GERMANY HANGTAG ORDER DETAIL REPORT >>

FILENAME: G9814001  SEASON : C    HANGTAGTYP : BE    DIV : 20

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 30663 | C20993 | ESPRIT STARS TS | 041 | 68 | 4011817019730 | CN | | | 25 | P | M&O |
| 30663 | C20993 | ESPRIT STARS TS | 041 | 74 | 4011817019747 | CN | | | 25 | P | M&O |
| 30663 | C20993 | ESPRIT STARS TS | 041 | 80 | 4011817019754 | CN | | | 25 | P | M&O |
| 30663 | C20993 | ESPRIT STARS TS | 041 | 86 | 4011817019778 | CN | | | 25 | P | M&O |
| 30663 | C20993 | ESPRIT STARS TS | 241 | 68 | 4011817019792 | CN | | | 25 | P | M&O |
| 30663 | C20993 | ESPRIT STARS TS | 241 | 74 | 4011817019808 | CN | | | 25 | P | M&O |
| 30663 | C20993 | ESPRIT STARS TS | 241 | 80 | 4011817019815 | CN | | | 25 | P | M&O |
| 30663 | C20993 | ESPRIT STARS TS | 241 | 86 | 4011817019822 | CN | | | 25 | P | M&O |
| 30663 | C20993 | ESPRIT STARS TS | 543 | 68 | 4011817019853 | CN | | | 25 | P | M&O |
| 30663 | C20993 | ESPRIT STARS TS | 543 | 74 | 4011817019860 | CN | | | 25 | P | M&O |
| 30663 | C20993 | ESPRIT STARS TS | 543 | 80 | 4011817019877 | CN | | | 25 | P | M&O |
| 30663 | C20993 | ESPRIT STARS TS | 543 | 86 | 4011817019884 | CN | | | 25 | P | M&O |

FIG. 20.1

| Customer | : NEWGERM |
|---|---|
| Module | : MULTI |
| Description | : MULTI CURRENCY FORMAT |
| File Name | : GM19005 |
| Date/Time | : 06/11/98  /  4:22:56 PM |

<< ESPRIT GERMANY HANGTAG ORDER DETAIL REPORT >>

FILENAME : G9819005    SEASON : D    HANGTAGTYP : EU    DIV : 21

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 609096 | D21521 | ESPRIT BUSTIER | 543 | L | 4011859042229 | UKI | £ | | 250 | T | MISIR |
| 609096 | D21521 | ESPRIT BUSTIER | 543 | M | 4011859042212 | UKI | £ | | 375 | T | MISIR |
| 609096 | D21521 | ESPRIT BUSTIER | 543 | S | 4011859042205 | UKI | £ | | 250 | T | MISIR |
| 609097 | D21522 | ESPRIT PANTY | 543 | M | 4011859042243 | UKI | £ | | 375 | T | MISIR |
| 609097 | D21522 | ESPRIT PANTY | 543 | S | 4011859042236 | UKI | £ | | 250 | T | MISIR |

FIG. 20.2

<< ESPRIT GERMANY HANGTAG ORDER DETAIL REPORT >>

| Customer | : NEWGERM |
|---|---|
| Module | : MULTI |
| Description | : MULTI CURRENCY FORMAT |
| Date/Time | : 06/11/98 / 4:22:57 PM |

FILENAME: G98109005  SEASON : E   HANGYAGTYP: AA   DIV :15

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 450002 | E15042 | SHEILA SHOPPER | 070 | 1 SIZE | 4011818504730 | COL | | | 25 | CHN | JF2 |
| 450002 | E15042 | SHEILA SHOPPER | 141 | 1 SIZE | 4011818504754 | COL | | | 25 | CHN | JF2 |
| 450003 | E15050 | SHEILA MIRRORCS | 070 | 1 SIZE | 4011818505744 | COL | | | 25 | CHN | JF2 |
| 450003 | E15050 | SHEILA MIRRORCS | 141 | 1 SIZE | 4011818505768 | COL | | | 25 | CHN | JF2 |
| 450004 | E15047 | SHEILA PENCASE | 070 | 1 SIZE | 4011818505171 | COL | | | 25 | CHN | JF2 |
| 450004 | E15047 | SHEILA PENCASE | 141 | 1 SIZE | 4011818505195 | COL | | | 25 | CHN | JF2 |
| 450005 | E15044 | SHEILA CITYWKND | 070 | 1 SIZE | 4011818504815 | COL | | | 25 | CHN | JF2 |
| 450005 | E15044 | SHEILA CITYWKND | 141 | 1 SIZE | 4011818504839 | COL | | | 25 | CHN | JF2 |
| 450006 | E15019 | ANKE MEDBACKPAC | 258 | 1 SIZE | 4011818483912 | COL | | | 50 | CHN | JSN |
| 450006 | E15019 | ANKE MEDBACKPAC | 543 | 1 SIZE | 4011818483936 | COL | | | 50 | CHN | JSN |
| 450007 | E15031 | ANKE MIRRORCASE | 141 | 1 SIZE | 4011815765776 | COL | | | 50 | CHN | JSN |
| 450007 | E15031 | ANKE MIRRORCASE | 258 | 1 SIZE | 4011815765790 | COL | | | 50 | CHN | JSN |
| 450007 | E15031 | ANKE MIRRORCASE | 543 | 1 SIZE | 4011815765813 | COL | | | 50 | CHN | JSN |
| 450008 | E15017 | ANKE WALLET | 141 | 1 SIZE | 4011818483769 | COL | | | 50 | CHN | JSN4 |
| 450008 | E15017 | ANKE WALLET | 258 | 1 SIZE | 4011818483790 | COL | | | 50 | CHN | JSN4 |
| 450008 | E15017 | ANKE WALLET | 543 | 1 SIZE | 4011818483813 | COL | | | 50 | CHN | JSN4 |
| 450009 | E15023 | ANKE PENCASE | 141 | 1 SIZE | 4011815766049 | COL | | | 50 | CHN | JSN |
| 450009 | E15023 | ANKE PENCASE | 258 | 1 SIZE | 4011815766063 | COL | | | 50 | CHN | JSN |
| 450009 | E15023 | ANKE PENCASE | 543 | 1 SIZE | 4011815766063 | COL | | | 50 | CHN | JSN |
| 450011 | E15026 | ANKE WEEKENDER | 141 | 1 SIZE | 4011815766148 | COL | | | 50 | CHN | JSN |

FIG. 20.3A

| | | | | | | | |
|---|---|---|---|---|---|---|---|
| 450011 | E15026 | ANKE WEEKENDER | 258 | 1 SIZE | 4011815576612 | COL | | 50 | CHN | JSN |
| 450011 | E15026 | ANKE WEEKENDER | 543 | 1 SIZE | 4011815766186 | COL | | 75 | CHN | JSN |
| 450012 | E15068 | AFRA MEDBACKPCK | 141 | 1 SIZE | 4011818506765 | COL | | 75 | CHN | JSN |
| 450016 | E15033 | SANDRA MEDBACKP | 141 | 1 SIZE | 4011818504280 | COL | | 75 | CHN | SFL2 |
| 450016 | E15033 | SANDRA MEDBACKP | 161 | 1 SIZE | 4011818504303 | COL | | 75 | CHN | SFL2 |
| 450017 | E15037 | SANDRA LGSHBAG | 141 | 1 SIZE | 4011818504464 | COL | | 75 | CHN | SFL2 |
| 450017 | E15037 | SANDRA LGSHBAG | 161 | 1 SIZE | 4011818504488 | COL | | 75 | CHN | SFL2 |
| 450018 | E15055 | AKIM LGSHLDRBAG | 141 | 1 SIZE | 4011818506000 | COL | | 50 | CHN | SUI2 |
| 450018 | E15055 | AKIM LGSHLDRBAG | 159 | 1 SIZE | 4011818506024 | COL | | 50 | CHN | SUI2 |
| 450019 | E15058 | AKIM MEDBACKPCK | 141 | 1 SIZE | 4011818506185 | COL | | 50 | CHN | SUI2 |
| 450019 | E15058 | AKIM MEDBACKPCK | 159 | 1 SIZE | 4011818506208 | COL | | 50 | CHN | SUI2 |
| 450020 | E15052 | AKIM MEDSHOPPER | 141 | 1 SIZE | 4011818505829 | COL | | 25 | CHN | SUI4 |
| 450020 | E15052 | AKIM MEDSHOPPER | 159 | 1 SIZE | 4011818505843 | COL | | 25 | CHN | SUI4 |
| 450021 | E15064 | AKIM WALLET | 141 | 1 SIZE | 4011818506581 | COL | | 25 | CHN | SUI4 |
| 450021 | E15064 | AKIM WALLET | 159 | 1 SIZE | 4011818506604 | COL | | 25 | CHN | SUI4 |
| 450021 | E15064 | AKIM WALLET | 543 | 1 SIZE | 4011818506628 | COL | | 25 | CHN | SUI4 |
| 450022 | E15000 | ACACIA ZIPSHOPR | 070 | 1 SIZE | 4011818481574 | COL | | 25 | CHN | SUI2 |
| 450022 | E15000 | ACACIA ZIPSHOPR | 141 | 1 SIZE | 4011818481598 | COL | | 25 | CHN | SUI2 |
| 450070 | E15203 | BRAZIL BANDANA | 141 | 1 SIZE | 4011818546730 | T | DM | 32,90 | 50 | CHN | MGR |
| 450070 | E15203 | BRAZIL BANDANA | 166 | 1 SIZE | 4011818546747 | T | DM | 32,90 | 100 | CHN | MGR |

*FIG. 20.3B*

| Customer | : NEWGERM |
|---|---|
| Module | : MULTI |
| Description | : MULTI CURRENCY FORMAT |
| Date/Time | : 06/11/98 / 4:22:57 PM |

<< ESPRIT GERMANY HANGTAG ORDER DETAIL REPORT >>

FILENAME : G98109005  SEASON : E  HANGYAGTYP: AA  HANGYAGTYPE: E  DIV :15

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 8520770 | E15203 | BRAZIL BANDANA | 250 | 1SIZE | 4011818546754 | T | DM | 32,90 | 100 | CHN | MGR |
| 8520770 | E15203 | BRAZIL BANDANA | 444 | 1SIZE | 4011818546761 | T | DM | 32,90 | 50 | CHN | MGR |
| 8520770 | E15203 | BRAZIL BANDANA | 543 | 1SIZE | 4011818546778 | T | DM | 32,90 | 100 | CHN | MGR |
| 8520772 | E15204 | CHILE OBLONG | 141 | 1SIZE | 4011818546785 | T | DM | 55,90 | 75 | CHN | UNN |
| 8520772 | E15204 | CHILE OBLONG | 166 | 1SIZE | 4011818546792 | T | DM | 55,90 | 100 | CHN | UNN |
| 8520772 | E15204 | CHILE OBLONG | 250 | 1SIZE | 4011818546808 | T | DM | 55,90 | 75 | CHN | UNN |
| 8520772 | E15204 | CHILE OBLONG | 444 | 1SIZE | 4011818546815 | T | DM | 55,90 | 75 | CHN | UNN |
| 8520772 | E15204 | CHILE OBLONG | 543 | 1SIZE | 4011818546822 | T | DM | 55,90 | 100 | CHN | UNN |
| 8520773 | E15206 | ORNAMENTS SCARF | 166 | 1SIZE | 4011818546877 | T | DM | 55,90 | 100 | CHN | UNN |
| 8520773 | E15206 | ORNAMENTS SCARF | 174 | 1SIZE | 4011818546884 | T | DM | 55,90 | 100 | CHN | UNN |
| 8520773 | E15206 | ORNAMENTS SCARF | 250 | 1SIZE | 4011818546891 | T | DM | 55,90 | 100 | CHN | UNN |
| 8520773 | E15206 | ORNAMENTS SCARF | 444 | 1SIZE | 4011818546907 | T | DM | 55,90 | 75 | CHN | UNN |
| 8520773 | E15206 | ORNAMENTS SCARF | 557 | 1SIZE | 4011818546914 | T | DM | 55,90 | 75 | CHN | UNN |
| 8520774 | E15192 | GALA OBLONG | 141 | 1SIZE | 4011818539848 | T | DM | 32,90 | 150 | CHN | UNN |
| 8520774 | E15192 | GALA OBLONG | 250 | 1SIZE | 4011818539855 | T | DM | 32,90 | 150 | CHN | UNN |
| 8520774 | E15192 | GALA OBLONG | 557 | 1SIZE | 4011818539862 | T | DM | 32,90 | 150 | CHN | UNN |

FIG. 20.4

| Customer | : NEWGERM |
|---|---|
| Module | : MULTI |
| Description | : MULTI CURRENCY FORMAT |
| Date/Time | : 06/11/98 / 4:22:57 PM |

<< ESPRIT GERMANY HANGTAG ORDER DETAIL REPORT >>

FILENAME: G9819005   SEASON: E   HANGTAGTYP : AU   DIV:15

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 450010 | E15024 | ANKE BACKPACK | 141 | 1 SIZE | 4011815766087 | COL | | | 50 | CHN | JSN |
| 450010 | E15024 | ANKE BACKPACK | 258 | 1 SIZE | 4011815766100 | COL | | | 50 | CHN | JSN |
| 450010 | E15024 | ANKE BACKPACK | 543 | 1 SIZE | 4011815766124 | COL | | | 50 | CHN | JSN |
| 609261 | E15251 | BASIC FLC SCARF | 141 | 1 SIZE | 4011818548109 | UKI | & | | 725 | CHN | YTX |
| 609261 | E15251 | BASIC FLC SCARF | 154 | 1 SIZE | 4011818548116 | UKI | & | | 725 | CHN | YTX |
| 609261 | E15251 | BASIC FLC SCARF | 252 | 1 SIZE | 4011818548123 | UKI | & | | 200 | CHN | YTX |
| 609261 | E15251 | BASIC FLC SCARF | 444 | 1 SIZE | 4011818548130 | UKI | & | | 500 | CHN | YTX |
| 609261 | E15251 | BASIC FLC SCARF | 543 | 1 SIZE | 4011818548147 | UKI | & | | 450 | CHN | YTX |
| 609261 | E15251 | BASIC FLC SCARF | 557 | 1 SIZE | 4011818548154 | UKI | & | | 175 | CHN | YTX |
| 609261 | E15251 | BASIC FLC SCARF | 558 | 1 SIZE | 4011818548161 | UKI | & | | 50 | CHN | YTX |
| 609262 | E15291 | BSC FLEECE GLOV | 141 | L | 4011815770275 | UKI | & | | 550 | CHN | YTX |
| 609262 | E15291 | BSC FLEECE GLOV | 141 | M | 4011815770268 | UKI | & | | 550 | CHN | YTX |
| 609262 | E15291 | BSC FLEECE GLOV | 141 | S | 4011815770251 | UKI | & | | 550 | CHN | YTX |
| 609262 | E15291 | BSC FLEECE GLOV | 154 | L | 4011815770305 | UKI | & | | 450 | CHN | YTX |
| 609262 | E15291 | BSC FLEECE GLOV | 154 | M | 4011815770299 | UKI | & | | 450 | CHN | YTX |
| 609262 | E15291 | BSC FLEECE GLOV | 154 | S | 4011815770282 | UKI | & | | 450 | CHN | YTX |
| 609262 | E15291 | BSC FLEECE GLOV | 252 | L | 4011815770336 | UKI | & | | 50 | CHN | YTX |

*FIG. 20.5A*

| | | | | | | | |
|---|---|---|---|---|---|---|---|
| 609262 | E15291 | BSC FLEECE GLOV | 252 | M | 4011815770329 | UKI | £ | 50 | CHN | YTX |
| 609262 | E15291 | BSC FLEECE GLOV | 252 | S | 4011815770312 | UKI | £ | 50 | CHN | YTX |
| 609262 | E15291 | BSC FLEECE GLOV | 444 | L | 4011815770367 | UKI | £ | 175 | CHN | YTX |
| 609262 | E15291 | BSC FLEECE GLOV | 444 | M | 4011815770350 | UKI | £ | 175 | CHN | YTX |
| 609262 | E15291 | BSC FLEECE GLOV | 444 | S | 4011815770343 | UKI | £ | 175 | CHN | YTX |
| 609262 | E15291 | BSC FLEECE GLOV | 543 | L | 4011815770398 | UKI | £ | 150 | CHN | YTX |
| 609262 | E15291 | BSC FLEECE GLOV | 543 | M | 4011815770381 | UKI | £ | 150 | CHN | YTX |
| 609262 | E15291 | BSC FLEECE GLOV | 543 | S | 4011815770374 | UKI | £ | 150 | CHN | YTX |
| 609262 | E15291 | BSC FLEECE GLOV | 557 | L | 4011815770428 | UKI | £ | 75 | CHN | YTX |
| 609262 | E15291 | BSC FLEECE GLOV | 557 | M | 4011815770411 | UKI | £ | 75 | CHN | YTX |
| 609262 | E15291 | BSC FLEECE GLOV | 557 | S | 4011815770404 | UKI | £ | 75 | CHN | YTX |
| 609262 | E15291 | BSC FLEECE GLOV | 558 | L | 4011815770459 | UKI | £ | 50 | CHN | YTX |
| 609262 | E15291 | BSC FLEECE GLOV | 558 | M | 4011815770442 | UKI | £ | 50 | CHN | YTX |
| 609262 | E15291 | BSC FLEECE GLOV | 558 | S | 4011815770435 | UKI | £ | 50 | CHN | YTX |
| 609264 | E15295 | DAISY GLOVE | 070 | L | 4011818556449 | UKI | £ | 175 | CHN | MWH |
| 609264 | E15295 | DAISY GLOVE | 070 | M | 4011818556432 | UKI | £ | 275 | CHN | MWH |
| 609264 | E15295 | DAISY GLOVE | 070 | S | 4011818556425 | UKI | £ | 100 | CHN | MWH |
| 609264 | E15295 | DAISY GLOVE | 141 | L | 4011818556470 | UKI | £ | 200 | CHN | MWH |
| 609264 | E15295 | DAISY GLOVE | 141 | M | 4011818556463 | UKI | £ | 300 | CHN | MWH |
| 609264 | E15295 | DAISY GLOVE | 141 | S | 4011818556456 | UKI | £ | 100 | CHN | MWH |
| 609264 | E15295 | DAISY GLOVE | 250 | L | 4011815915706 | UKI | £ | 25 | CHN | MWH |
| 609264 | E15295 | DAISY GLOVE | 250 | M | 4011815915690 | UKI | £ | 50 | CHN | MWH |
| 609264 | E15295 | DAISY GLOVE | 250 | S | 4011815915683 | UKI | £ | 25 | CHN | MWH |

FIG. 20.5B

| Customer | : NEWGERM |
|---|---|
| Module | : MULTI |
| Description | : MULTI CURRENCY FORMAT |
| Date/Time | : 06/11/98 / 4:22:57 PM |

<< ESPRIT GERMANY HANGTAG ORDER DETAIL REPORT >>

FILENAME: G9819005  SEASON: E  HANGTAGTYP : AU  DIV:15

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 609264 | E15295 | DAISY GLOVE | 251 | L | 4011818556500 | UKI | £ | | 25 | CHN | MWH |
| 609264 | E15295 | DAISY GLOVE | 251 | M | 4011818556494 | UKI | £ | | 25 | CHN | MWH |
| 609264 | E15295 | DAISY GLOVE | 251 | S | 4011818556487 | UKI | £ | | 25 | CHN | MWH |
| 609264 | E15295 | DAISY GLOVE | 543 | L | 4011818556562 | UKI | £ | | 50 | CHN | MWH |
| 609264 | E15295 | DAISY GLOVE | 543 | M | 4011818556555 | UKI | £ | | 50 | CHN | MWH |
| 609264 | E15295 | DAISY GLOVE | 543 | S | 4011818556548 | UKI | £ | | 25 | CHN | MWH |
| 609265 | E15297 | SALIMA GLOVE | 070 | L | 4011818556784 | UKI | £ | | 50 | CHN | MWH |
| 609265 | E15297 | SALIMA GLOVE | 070 | M | 4011818556777 | UKI | £ | | 50 | CHN | MWH |
| 609265 | E15297 | SALIMA GLOVE | 070 | S | 4011818556760 | UKI | £ | | 25 | CHN | MWH |
| 609265 | E15297 | SALIMA GLOVE | 141 | L | 4011818556814 | UKI | £ | | 100 | CHN | MWH |
| 609265 | E15297 | SALIMA GLOVE | 141 | M | 4011818556807 | UKI | £ | | 150 | CHN | MWH |
| 609265 | E15297 | SALIMA GLOVE | 141 | S | 4011818556791 | UKI | £ | | 50 | CHN | MWH |
| 609270 | E15300 | CTY NAPPA GLOVE | 070 | L | 4011818557101 | UKI | £ | | 100 | CHN | MWH |
| 609270 | E15300 | CTY NAPPA GLOVE | 070 | M | 4011818557095 | UKI | £ | | 150 | CHN | MWH |
| 609270 | E15300 | CTY NAPPA GLOVE | 070 | S | 4011818557088 | UKI | £ | | 50 | CHN | MWH |
| 609270 | E15300 | CTY NAPPA GLOVE | 141 | L | 4011818557132 | UKI | £ | | 125 | CHN | MWH |
| 609270 | E15300 | CTY NAPPA GLOVE | 141 | M | 4011818557125 | UKI | £ | | 200 | CHN | MWH |
| 609270 | E15300 | CTY NAPPA GLOVE | 141 | S | 4011818557118 | UKI | £ | | 75 | CHN | MWH |

FIG. 20.6A

| | | | | | | | | |
|---|---|---|---|---|---|---|---|---|
| 609270 | E15300 | CTY NAPPA GLOVE | 543 | L | 4011818557163 | UKI | G | 25 | CHN | MWH |
| 609270 | E15300 | CTY NAPPA GLOVE | 543 | M | 4011818557156 | UKI | G | 50 | CHN | MWH |
| 609270 | E15300 | CTY NAPPA GLOVE | 543 | S | 4011818557149 | UKI | G | 25 | CHN | MWH |
| 609271 | E15321 | BASIC FLEECE HT | 141 | M | 4011818559649 | UKI | G | 200 | CHN | YTX |
| 609271 | E15321 | BASIC FLEECE HT | 141 | S | 4011818549632 | UKI | G | 200 | CHN | YTX |
| 609271 | E15321 | BASIC FLEECE HT | 154 | M | 4011818549663 | UKI | G | 125 | CHN | YTX |
| 609271 | E15321 | BASIC FLEECE HT | 154 | S | 4011818549656 | UKI | G | 125 | CHN | YTX |
| 609271 | E15321 | BASIC FLEECE HT | 252 | M | 4011818549687 | UKI | G | 50 | CHN | YTX |
| 609271 | E15321 | BASIC FLEECE HT | 252 | S | 4011818549670 | UKI | G | 50 | CHN | YTX |
| 609271 | E15321 | BASIC FLEECE HT | 444 | M | 4011818549700 | UKI | G | 150 | CHN | YTX |
| 609271 | E15321 | BASIC FLEECE HT | 444 | S | 4011818549694 | UKI | G | 150 | CHN | YTX |
| 609271 | E15321 | BASIC FLEECE HT | 543 | M | 4011818549724 | UKI | G | 150 | CHN | YTX |
| 609271 | E15321 | BASIC FLEECE HT | 543 | S | 4011818549717 | UKI | G | 150 | CHN | YTX |
| 609271 | E15321 | BASIC FLEECE HT | 557 | M | 4011818549748 | UKI | G | 50 | CHN | YTX |
| 609271 | E15321 | BASIC FLEECE HT | 557 | S | 4011818549731 | UKI | G | 50 | CHN | YTX |
| 609271 | E15321 | BASIC FLEECE HT | 558 | M | 4011818549762 | UKI | G | 25 | CHN | YTX |
| 609271 | E15321 | BASIC FLEECE HT | 558 | S | 4011818549755 | UKI | G | 25 | CHN | YTX |
| 609273 | E15359 | BSC FLC HEADBND | 141 | M | 4011818550089 | UKI | G | 100 | CHN | YTX |
| 609273 | E15359 | BSC FLC HEADBND | 141 | S | 4011818550072 | UKI | G | 100 | CHN | YTX |
| 609273 | E15359 | BSC FLC HEADBND | 154 | M | 4011818550102 | UKI | G | 100 | CHN | YTX |
| 609273 | E15359 | BSC FLC HEADBND | 154 | S | 4011818550096 | UKI | G | 100 | CHN | YTX |
| 609273 | E15359 | BSC FLC HEADBND | 252 | M | 4011818550126 | UKI | G | 50 | CHN | YTX |

FIG. 20.6B

| Customer | : NEWGERM |
|---|---|
| Module | : MULTI |
| Description | : MULTI CURRENCY FORMAT |
| Date/Time | : 06/11/98 / 4:22:57 PM |

<< ESPRIT GERMANY HANGTAG ORDER DETAIL REPORT >>

FILENAME: G9819005  SEASON: E  HANGTAGTYP : AU  DIV:15

| SPO | STYLE | STYLEDESC | CLRCODE | SIZE | CODE | DISTRI | RETAILCODE | RETAIL QTY | COUNTRY | FACTORY |
|---|---|---|---|---|---|---|---|---|---|---|
| 609273 | E15359 | BSC FLC HEADBND | 252 | S | 4011818550119 | UKI | $ | 50 | CHN | YTX |
| 609273 | E15359 | BSC FLC HEADBND | 444 | M | 4011818550140 | UKI | $ | 50 | CHN | YTX |
| 609273 | E15359 | BSC FLC HEADBND | 444 | S | 4011818550133 | UKI | $ | 50 | CHN | YTX |
| 609273 | E15359 | BSC FLC HEADBND | 543 | M | 4011818550164 | UKI | $ | 75 | CHN | YTX |
| 609273 | E15359 | BSC FLC HEADBND | 543 | S | 4011818550157 | UKI | $ | 75 | CHN | YTX |
| 609273 | E15359 | BSC FLC HEADBND | 557 | M | 4011818550188 | UKI | $ | 50 | CHN | YTX |
| 609273 | E15359 | BSC FLC HEADBND | 557 | S | 4011818550171 | UKI | $ | 50 | CHN | YTX |
| 609273 | E15359 | BSC FLC HEADBND | 558 | M | 4011818550201 | UKI | $ | 75 | CHN | YTX |
| 609273 | E15359 | BSC FLC HEADBND | 558 | S | 4011818550195 | UKI | $ | 75 | CHN | YTX |
| 609525 | E15361 | H.-K. CHECK FOLD | 252 | 1 SIZE | 4011818550170 | UKI | $ | 925 | CHN | HTU2 |
| 609525 | E15361 | H.-K. CHECK FOLD | 543 | 1 SIZE | 4011818550187 | UKI | $ | 1300 | CHN | HTU2 |
| 609526 | E15362 | STOCK UMBERLLA | 141 | 1 SIZE | 4011818550194 | UKI | $ | 1025 | CHN | HTU2 |
| 609526 | E15362 | STOCK UMBERLLA | 543 | 1 SIZE | 4011818550200 | UKI | $ | 600 | CHN | HTU2 |
| 609527 | E15363 | LOGO BUGGY | 141 | 1 SIZE | 4011818550217 | UKI | $ | 2375 | CHN | HTU2 |
| 609527 | E15363 | LOGO BUGGY | 250 | 1 SIZE | 4011818550224 | UKI | $ | 175 | CHN | HTU2 |
| 609527 | E15364 | LOGO BUGGY | 543 | 1 SIZE | 4011818550231 | UKI | $ | 1625 | CHN | HTU2 |

*FIG. 20.7A*

| | | | | | | | | |
|---|---|---|---|---|---|---|---|---|
| 609529 | E15364 | GERA FOLDING | 141 | 1 SIZE | 4011818550248 | UKI | ↵ | | 1775 | CHN | HTU2 |
| 609529 | E15364 | GERA FOLDING | 250 | 1 SIZE | 4011818550255 | UKI | ↵ | | 175 | CHN | HTU2 |
| 609529 | E15364 | GERA FOLDING | 543 | 1 SIZE | 4011818550262 | UKI | ↵ | | 1350 | CHN | HTU2 |
| 609592 | E15295 | DAISY GLOVE | 070 | L | 4011818556449 | UKI | ↵ | | 700 | CHN | MWH |
| 609592 | E15295 | DAISY GLOVE | 070 | M | 4011818556432 | UKI | ↵ | | 1025 | CHN | MWH |
| 609592 | E15295 | DAISY GLOVE | 070 | S | 4011818556425 | UKI | ↵ | | 350 | CHN | MWH |
| 609592 | E15295 | DAISY GLOVE | 141 | L | 4011818556470 | UKI | ↵ | | 975 | CHN | MWH |
| 609592 | E15295 | DAISY GLOVE | 141 | M | 4011818556463 | UKI | ↵ | | 1450 | CHN | MWH |
| 609592 | E15295 | DAISY GLOVE | 141 | S | 4011818556456 | UKI | ↵ | | 500 | CHN | MWH |
| 609592 | E15295 | DAISY GLOVE | 250 | L | 4011815915706 | UKI | ↵ | | 25 | CHN | MWH |
| 609592 | E15295 | DAISY GLOVE | 250 | M | 4011815915690 | UKI | ↵ | | 25 | CHN | MWH |
| 609592 | E15295 | DAISY GLOVE | 250 | S | 4011815915683 | UKI | ↵ | | 25 | CHN | MWH |
| 609592 | E15295 | DAISY GLOVE | 251 | L | 4011818556500 | UKI | ↵ | | 50 | CHN | MWH |
| 609592 | E15295 | DAISY GLOVE | 251 | M | 4011818556494 | UKI | ↵ | | 75 | CHN | MWH |
| 609592 | E15295 | DAISY GLOVE | 251 | S | 4011818556487 | UKI | ↵ | | 25 | CHN | MWH |
| 609592 | E15295 | DAISY GLOVE | 543 | L | 4011818556562 | UKI | ↵ | | 450 | CHN | MWH |
| 609592 | E15295 | DAISY GLOVE | 543 | M | 4011818556555 | UKI | ↵ | | 675 | CHN | MWH |
| 609592 | E15295 | DAISY GLOVE | 25 | S | 4011818556548 | UKI | ↵ | | 225 | CHN | MWH |
| 609593 | E15295 | DAISY GLOVE | 070 | L | 4011818556449 | UKI | ↵ | | 875 | CHN | MWH |
| 609593 | E15295 | DAISY GLOVE | 070 | M | 4011818556432 | UKI | ↵ | | 1300 | CHN | MWH |
| 609593 | E15295 | DAISY GLOVE | 070 | S | 4011818556425 | UKI | ↵ | | 450 | CHN | MWH |
| 609593 | E15295 | DAISY GLOVE | 141 | L | 4011818556470 | UKI | ↵ | | 1575 | CHN | MWH |
| 609593 | E15295 | DAISY GLOVE | 141 | M | 4011818556463 | UKI | ↵ | | 2350 | CHN | MWH |
| 609593 | E15295 | DAISY GLOVE | 141 | S | 4011818556456 | UKI | ↵ | | 775 | CHN | MWH |

*FIG. 20.7B*

| Customer | : NEWGERM |
|---|---|
| Module | : MULTI |
| Description | : MULTI CURRENCY FORMAT |
| Date/Time | : 06/11/98 / 4:22:57 PM |

<< ESPRIT GERMANY HANGTAG ORDER DETAIL REPORT >>

FILENAME: G9819005  SEASON: E  HANGTAGTYP: AU  DIV:15

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 609593 | E15295 | DAISY GLOVE | 250 | L | 4011815915706 | UKI | £ | | 75 | CHN | MWH |
| 609593 | E15295 | DAISY GLOVE | 250 | M | 4011815915690 | UKI | £ | | 100 | CHN | MWH |
| 609593 | E15295 | DAISY GLOVE | 250 | S | 4011815915683 | UKI | £ | | 50 | CHN | MWH |
| 609593 | E15295 | DAISY GLOVE | 251 | L | 4011818556500 | UKI | £ | | 175 | CHN | MWH |
| 609593 | E15295 | DAISY GLOVE | 251 | M | 4011818556494 | UKI | £ | | 250 | CHN | MWH |
| 609593 | E15295 | DAISY GLOVE | 251 | S | 4011818556487 | UKI | £ | | 100 | CHN | MWH |
| 609593 | E15295 | DAISY GLOVE | 543 | L | 4011818556562 | UKI | £ | | 450 | CHN | MWH |
| 609593 | E15295 | DAISY GLOVE | 543 | M | 4011818556555 | UKI | £ | | 650 | CHN | MWH |
| 609593 | E15295 | DAISY GLOVE | 543 | S | 4011818556548 | UKI | £ | | 225 | CHN | MWH |
| 609595 | E15297 | SALIMA GLOVE | 070 | L | 4011818556784 | UKI | £ | | 150 | CHN | MWH |
| 609595 | E15297 | SALIMA GLOVE | 070 | M | 4011818556777 | UKI | £ | | 200 | CHN | MWH |
| 609595 | E15297 | SALIMA GLOVE | 070 | S | 4011818556760 | UKI | £ | | 75 | CHN | MWH |
| 609595 | E15297 | SALIMA GLOVE | 141 | L | 4011818556814 | UKI | £ | | 225 | CHN | MWH |
| 609595 | E15297 | SALIMA GLOVE | 141 | M | 4011818556807 | UKI | £ | | 325 | CHN | MWH |
| 609595 | E15297 | SALIMA GLOVE | 141 | S | 4011818556791 | UKI | £ | | 125 | CHN | MWH |
| 609596 | E15297 | SALIMA GLOVE | 070 | L | 4011818556784 | UKI | £ | | 450 | CHN | MWH |
| 609596 | E15297 | SALIMA GLOVE | 070 | M | 4011818556777 | UKI | £ | | 650 | CHN | MWH |
| 609596 | E15297 | SALIMA GLOVE | 070 | S | 4011818556760 | UKI | £ | | 225 | CHN | MWH |

*FIG. 20.8A*

| | | | | | | | | |
|---|---|---|---|---|---|---|---|---|
| 609596 | E15297 | SALIMA GLOVE | 141 | L | 4011818556814 | UKI | £ | 1050 | CHN | MWH |
| 609596 | E15297 | SALIMA GLOVE | 141 | M | 4011818556807 | UKI | £ | 1575 | CHN | MWH |
| 609596 | E15297 | SALIMA GLOVE | 141 | S | 4011818556791 | UKI | £ | 525 | CHN | MWH |
| 609598 | E15300 | CTY NAPPA GLOVE | 070 | L | 4011818557101 | UKI | £ | 825 | CHN | MWH |
| 609598 | E15300 | CTY NAPPA GLOVE | 070 | M | 4011818557095 | UKI | £ | 1225 | CHN | MWH |
| 609598 | E15300 | CTY NAPPA GLOVE | 070 | S | 4011818557088 | UKI | £ | 425 | CHN | MWH |
| 609598 | E15300 | CTY NAPPA GLOVE | 141 | L | 4011818557132 | UKI | £ | 1625 | CHN | MWH |
| 609598 | E15300 | CTY NAPPA GLOVE | 141 | M | 4011818557125 | UKI | £ | 2425 | CHN | MWH |
| 609598 | E15300 | CTY NAPPA GLOVE | 141 | S | 4011818557118 | UKI | £ | 825 | CHN | MWH |
| 609598 | E15300 | CTY NAPPA GLOVE | 543 | L | 4011818557163 | UKI | £ | 350 | CHN | MWH |
| 609598 | E15300 | CTY NAPPA GLOVE | 543 | M | 4011818557156 | UKI | £ | 525 | CHN | MWH |
| 609598 | E15300 | CTY NAPPA GLOVE | 543 | S | 4011818557149 | UKI | £ | 175 | CHN | MWH |
| 609599 | E15300 | CTY NAPPA GLOVE | 070 | L | 4011818557101 | UKI | £ | 625 | CHN | MWH |
| 609599 | E15300 | CTY NAPPA GLOVE | 070 | M | 4011818557095 | UKI | £ | 925 | CHN | MWH |
| 609599 | E15300 | CTY NAPPA GLOVE | 070 | S | 4011818557088 | UKI | £ | 325 | CHN | MWH |
| 609599 | E15300 | CTY NAPPA GLOVE | 141 | L | 4011818557132 | UKI | £ | 1100 | CHN | MWH |
| 609599 | E15300 | CTY NAPPA GLOVE | 141 | M | 4011818557125 | UKI | £ | 1650 | CHN | MWH |
| 609599 | E15300 | CTY NAPPA GLOVE | 141 | S | 4011818557118 | UKI | £ | 550 | CHN | MWH |
| 609599 | E15300 | CTY NAPPA GLOVE | 543 | L | 4011818557163 | UKI | £ | 200 | CHN | MWH |
| 609599 | E15300 | CTY NAPPA GLOVE | 543 | M | 4011818557156 | UKI | £ | 300 | CHN | MWH |
| 609599 | E15300 | CTY NAPPA GLOVE | 543 | S | 4011818557149 | UKI | £ | 100 | CHN | MWH |
| 609686 | E15300 | TRINIDAD OBLONG | 141 | 1 SIZE | 4011818546600 | UKI | £ | 375 | CHN | MGR |

FIG. 20.8B

| Customer | : NEWGERM |
|---|---|
| Module | : MULTI |
| Description | : MULTI CURRENCY FORMAT |
| Date/Time | : 06/11/98 / 4:22:57 PM |

<< ESPRIT GERMANY HANGTAG ORDER DETAIL REPORT >>

FILENAME: G9819005  SEASON: E  HANGTAGTYP : AU  DIV:15

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 609686 | E15200 | TRINIDAD OBLONG | 166 | 1 SIZE | 4011818546617 | UKI | £ | | 200 | CHN | MGR |
| 609686 | E15200 | TRINIDAD OBLONG | 250 | 1 SIZE | 4011818546624 | UKI | £ | | 100 | CHN | MGR |
| 609686 | E15200 | TRINIDAD OBLONG | 444 | 1 SIZE | 4011818546631 | UKI | £ | | 100 | CHN | MGR |
| 609688 | E15204 | CHILE OBLONG | 141 | 1 SIZE | 4011818546785 | UKI | £ | | 4425 | CHN | UNN |
| 609688 | E15204 | CHILE OBLONG | 166 | 1 SIZE | 4011818546792 | UKI | £ | | 975 | CHN | UNN |
| 609688 | E15204 | CHILE OBLONG | 250 | 1 SIZE | 4011818546808 | UKI | £ | | 4775 | CHN | UNN |
| 609688 | E15204 | CHILE OBLONG | 444 | 1 SIZE | 4011818546815 | UKI | £ | | 800 | CHN | UNN |
| 609688 | E15204 | CHILE OBLONG | 543 | 1 SIZE | 4011818546822 | UKI | £ | | 3500 | CHN | UNN |
| 609716 | E15259 | INDRA TUBULAR | 141 | 1 SIZE | 4011818549304 | UKI | £ | | 2800 | CHN | MGR |
| 609716 | E15259 | INDRA TUBULAR | 173 | 1 SIZE | 4011818549311 | UKI | £ | | 1075 | CHN | MGR |
| 609716 | E15259 | INDRA TUBULAR | 260 | 1 SIZE | 4011815859765 | UKI | £ | | 250 | CHN | MGR |
| 609716 | E15259 | INDRA TUBULAR | 444 | 1 SIZE | 4011818549328 | UKI | £ | | 2150 | CHN | MGR |
| 609716 | E15259 | INDRA TUBULAR | 543 | 1 SIZE | 4011818549335 | UKI | £ | | 950 | CHN | MGR |
| 609718 | E15261 | OMBRE TUBULAR | 558 | 1 SIZE | 4011818549342 | UKI | £ | | 175 | CHN | MGR |
| 609718 | E15261 | OMBRE TUBULAR | 141 | 1 SIZE | 4011818549373 | UKI | £ | | 1250 | CHN | UNN |
| 609718 | E15261 | OMBRE TUBULAR | 250 | 1 SIZE | 4011818549380 | UKI | £ | | 1500 | CHN | UNN |
| 609719 | E15262 | OMBRE TUBULAR | 359 | 1 SIZE | 4011818549397 | UKI | £ | | 2300 | CHN | UNN |
| 609719 | E15262 | OMBRE TUBULAR | 543 | 1 SIZE | 4011818549403 | UKI | £ | | 1675 | CHN | UNN |

*FIG. 20.9A*

| | | | | | | |
|---|---|---|---|---|---|---|
| 609719 | E15262 | BAMBOO LEAF TUB | 070 | 1 SIZE | 4011815902072 | UKI | ¢ | 300 CHN | MGR |
| 609719 | E15262 | BAMBOO LEAF TUB | 141 | 1 SIZE | 4011815902089 | UKI | ¢ | 775 CHN | MGR |
| 609719 | E15262 | BAMBOO LEAF TUB | 444 | 1 SIZE | 4011815902096 | UKI | ¢ | 425 CHN | MGR |
| 610017 | E15196 | BAMBOO LEAF TUB | 543 | 1 SIZE | 4011815902102 | UKI | ¢ | 600 CHN | MGR |
| 610017 | E15196 | GOOFY BANDANA | 141 | 1 SIZE | 4011818546433 | UKI | ¢ | 3050 — | ITALC |
| 610017 | E15196 | GOOFY BANDANA | 445 | 1 SIZE | 4011818546440 | UKI | ¢ | 2500 — | ITALC |
| 610021 | E15197 | GOOFY BANDANA | 543 | 1 SIZE | 4011818546457 | UKI | ¢ | 5375 — | ITALC |
| 610021 | E15197 | CANGIANTE OBLNG | 175 | 1 SIZE | 4011818561191 | UKI | ¢ | 775 — | MASET |
| 610021 | E15197 | CANGIANTE OBLNG | 250 | 1 SIZE | 4011818561207 | UKI | ¢ | 550 — | MASET |
| 610292 | E15203 | BRAZIL BANDANA | 141 | 1 SIZE | 4011818546730 | UKI | ¢ | 1750 CHN | MGR |
| 610292 | E15203 | BRAZIL BANDANA | 166 | 1 SIZE | 4011818546747 | UKI | ¢ | 375 CHN | MGR |
| 610292 | E15203 | BRAZIL BANDANA | 250 | 1 SIZE | 4011818546754 | UKI | ¢ | 975 CHN | MGR |
| 610292 | E15203 | BRAZIL BANDANA | 444 | 1 SIZE | 4011818546761 | UKI | ¢ | 800 CHN | MGR |
| 610292 | E15203 | BRAZIL BANDANA | 543 | 1 SIZE | 4011818546778 | UKI | ¢ | 1875 CHN | MGR |
| 610294 | E15205 | PANAMA BANDANA | 141 | 1 SIZE | 4011818546839 | UKI | ¢ | 3050 CHN | UNN |
| 610294 | E15205 | PANAMA BANDANA | 250 | 1 SIZE | 4011818546846 | UKI | ¢ | 1575 CHN | UNN |
| 610294 | E15205 | PANAMA BANDANA | 444 | 1 SIZE | 4011818546853 | UKI | ¢ | 925 CHN | UNN |
| 610294 | E15205 | PANAMA BANDANA | 557 | 1 SIZE | 4011818546860 | UKI | ¢ | 1875 CHN | UNN |
| 610296 | E15206 | ORNAMENTS SCARF | 166 | 1 SIZE | 4011818546877 | UKI | ¢ | 225 CHN | UNN |
| 610296 | E15206 | ORNAMENTS SCARF | 174 | 1 SIZE | 4011818546884 | UKI | ¢ | 175 CHN | UNN |
| 610296 | E15206 | ORNAMENTS SCARF | 250 | 1 SIZE | 4011818546891 | UKI | ¢ | 75 CHN | UNN |
| 610296 | E15206 | ORNAMENTS SCARF | 444 | 1 SIZE | 4011818546907 | UKI | ¢ | 75 CHN | UNN |

*FIG. 20.9B*

| Customer | : NEWGERM |
|---|---|
| Module | : MULTI |
| Description | : MULTI CURRENCY FORMAT |
| Date/Time | : 06/11/98  /  4:22:57 PM |

<< ESPRIT GERMANY HANGTAG ORDER DETAIL REPORT >>

FILENAME: G9819005   SEASON: E   HANGTAGTYP : AU        DIV:15

| SPO | STYLE | STYLEDESC | CLRCODE | SIZE | CODE | DISTRI | RETAILCODE | RETAIL QTY | COUNTRY | FACTORY |
|---|---|---|---|---|---|---|---|---|---|---|
| 610296 | E15206 | ORNAMENTS SCARF | 557 | 1 SIZE | 4011818546914 | UKI | £ | 225 | CHN | UNN |
| 610395 | E15192 | GALA OBLONG | 141 | 1 SIZE | 4011818539848 | UKI | £ | 2400 | CHN | UNN |
| 610395 | E15192 | GALA OBLONG | 250 | 1 SIZE | 4011818539855 | UKI | £ | 2100 | CHN | UNN |
| 610395 | E15192 | GALA OBLONG | 557 | 1 SIZE | 4011818539862 | UKI | £ | 2350 | CHN | UNN |
| 610396 | E15192 | GALA OBLONG | 141 | 1 SIZE | 4011818539848 | UKI | £ | 500 | CHN | UNN |
| 610396 | E15192 | GALA OBLONG | 250 | 1 SIZE | 4011818539855 | UKI | £ | 250 | CHN | UNN |
| 610396 | E15192 | GALA OBLONG | 557 | 1 SIZE | 4011818539862 | UKI | £ | 275 | CHN | UNN |
| 611015 | E15204 | CHILE OBLONG | 141 | 1 SIZE | 4011818546785 | UKI | £ | 1125 | CHN | UNN |
| 611015 | E15204 | CHILE OBLONG | 166 | 1 SIZE | 4011818546792 | UKI | £ | 250 | CHN | UNN |
| 611015 | E15204 | CHILE OBLONG | 250 | 1 SIZE | 4011818546808 | UKI | £ | 725 | CHN | UNN |
| 611015 | E15204 | CHILE OBLONG | 444 | 1 SIZE | 4011818546815 | UKI | £ | 200 | CHN | UNN |
| 611015 | E15204 | CHILE OBLONG | 543 | 1 SIZE | 4011818546822 | UKI | £ | 700 | CHN | UNN |
| 611019 | E15251 | BASIC FLC SCARF | 141 | 1 SIZE | 4011818548109 | UKI | £ | 4750 | CHN | YTX |
| 611019 | E15251 | BASIC FLC SCARF | 154 | 1 SIZE | 4011818548116 | UKI | £ | 3500 | CHN | YTX |
| 611019 | E15251 | BASIC FLC SCARF | 252 | 1 SIZE | 4011818548123 | UKI | £ | 775 | CHN | YTX |
| 611019 | E15251 | BASIC FLC SCARF | 444 | 1 SIZE | 4011818548130 | UKI | £ | 2075 | CHN | YTX |
| 611019 | E15251 | BASIC FLC SCARF | 543 | 1 SIZE | 4011818548147 | UKI | £ | 2425 | CHN | YTX |
| 611019 | E15251 | BASIC FLC SCARF | 557 | 1 SIZE | 4011818548154 | UKI | £ | 900 | CHN | YTX |

FIG. 20.10A

| | | | | | | | |
|---|---|---|---|---|---|---|---|
| 611019 | E15251 | BASIC FLC SCARF | 558 | 1 SIZE | 4011818548161 | UKI | £ | 325 | CHN | YTX |
| 611028 | E15259 | INDRA TUBULAR | 141 | 1 SIZE | 4011818549304 | UKI | £ | 3575 | CHN | MRG |
| 611028 | E15259 | INDRA TUBULAR | 173 | 1 SIZE | 4011818549311 | UKI | £ | 1800 | CHN | MRG |
| 611028 | E15259 | INDRA TUBULAR | 260 | 1 SIZE | 4011818549765 | UKI | £ | 100 | CHN | MRG |
| 611028 | E15259 | INDRA TUBULAR | 444 | 1 SIZE | 4011818549328 | UKI | £ | 1900 | CHN | MRG |
| 611028 | E15259 | INDRA TUBULAR | 543 | 1 SIZE | 4011818549335 | UKI | £ | 375 | CHN | MRG |
| 611028 | E15259 | INDRA TUBULAR | 558 | 1 SIZE | 4011818549342 | UKI | £ | 125 | CHN | MRG |
| 611029 | E15261 | OMBRE TUBULAR | 141 | 1 SIZE | 4011818549373 | UKI | £ | 1675 | CHN | UNN |
| 611029 | E15261 | OMBRE TUBULAR | 250 | 1 SIZE | 4011818549380 | UKI | £ | 225 | CHN | UNN |
| 611029 | E15261 | OMBRE TUBULAR | 359 | 1 SIZE | 4011818549397 | UKI | £ | 250 | CHN | UNN |
| 611029 | E15261 | OMBRE TUBULAR | 543 | 1 SIZE | 4011818549403 | UKI | £ | 425 | CHN | UNN |
| 611030 | E15262 | BAMBOO LEAF TUB | 070 | 1 SIZE | 4011815902072 | UKI | £ | 125 | CHN | MGR |
| 611030 | E15262 | BAMBOO LEAF TUB | 141 | 1 SIZE | 4011815902089 | UKI | £ | 150 | CHN | MGR |
| 611030 | E15262 | BAMBOO LEAF TUB | 444 | 1 SIZE | 4011815902096 | UKI | £ | 75 | CHN | MGR |
| 611030 | E15262 | BAMBOO LEAF TUB | 543 | 1 SIZE | 4011815902102 | UKI | £ | 125 | CHN | MGR |
| 611031 | E15291 | BSC FLEECE GLOV | 141 | L | 4011815770275 | UKI | £ | 1775 | CHN | YTX |
| 611031 | E15291 | BSC FLEECE GLOV | 141 | M | 4011815770268 | UKI | £ | 1775 | CHN | YTX |
| 611031 | E15291 | BSC FLEECE GLOV | 141 | S | 4011815770251 | UKI | £ | 1775 | CHN | YTX |
| 611031 | E15291 | BSC FLEECE GLOV | 154 | L | 4011815770305 | UKI | £ | 1075 | CHN | YTX |
| 611031 | E15291 | BSC FLEECE GLOV | 154 | M | 4011815770299 | UKI | £ | 1075 | CHN | YTX |
| 611031 | E15291 | BSC FLEECE GLOV | 154 | S | 4011815770282 | UKI | £ | 1075 | CHN | YTX |
| 611031 | E15291 | BSC FLEECE GLOV | 252 | L | 4011815770336 | UKI | £ | 300 | CHN | YTX |

*FIG. 20.10B*

| Customer | : NEWGERM |
|---|---|
| Module | : MULTI |
| Description | : MULTI CURRENCY FORMAT |
| Date/Time | : 06/11/98 / 4:22:59 PM |

<< ESPRIT GERMANY HANGTAG ORDER DETAIL REPORT >>

FILENAME: G9819005  SEASON: E     HANGTAGTYP: AU   DIV: 15

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 611031 | E15291 | BSC FLEECE GLOV | 252 | M | 4011815770329 | UKI | | | 300 | CHN | YTX |
| 611031 | E15291 | BSC FLEECE GLOV | 252 | S | 4011815770312 | UKI | | | 300 | CHN | YTX |
| 611031 | E15291 | BSC FLEECE GLOV | 444 | L | 4011815770367 | UKI | | | 525 | CHN | YTX |
| 611031 | E15291 | BSC FLEECE GLOV | 444 | M | 4011815770350 | UKI | | | 525 | CHN | YTX |
| 611031 | E15291 | BSC FLEECE GLOV | 444 | S | 4011815770343 | UKI | | | 525 | CHN | YTX |
| 611031 | E15291 | BSC FLEECE GLOV | 543 | L | 4011815770398 | UKI | | | 1025 | CHN | YTX |
| 611031 | E15291 | BSC FLEECE GLOV | 543 | M | 4011815770381 | UKI | | | 1025 | CHN | YTX |
| 611031 | E15291 | BSC FLEECE GLOV | 543 | S | 4011815770374 | UKI | | | 1025 | CHN | YTX |
| 611031 | E15291 | BSC FLEECE GLOV | 557 | L | 4011815770428 | UKI | | | 375 | CHN | YTX |
| 611031 | E15291 | BSC FLEECE GLOV | 557 | M | 4011815770411 | UKI | | | 375 | CHN | YTX |
| 611031 | E15291 | BSC FLEECE GLOV | 557 | S | 4011815770404 | UKI | | | 375 | CHN | YTX |
| 611031 | E15291 | BSC FLEECE GLOV | 558 | L | 4011815770459 | UKI | | | 75 | CHN | YTX |
| 611031 | E15291 | BSC FLEECE GLOV | 558 | M | 4011815770442 | UKI | | | 75 | CHN | YTX |

FIG. 20.11A

| | | | | | | |
|---|---|---|---|---|---|---|
| 611031 | E15291 BSC FLEECE GLOV | 558 | S | 4011815770435 | UKI | 75 | CHN | YTX |
| 611033 | E15321 BASIC FLEECE HT | 141 | M | 4011818549649 | UKI | 850 | CHN | YTX |
| 611033 | E15321 BASIC FLEECE HT | 141 | S | 4011818549632 | UKI | 850 | CHN | YTX |
| 611033 | E15321 BASIC FLEECE HT | 154 | M | 4011818549663 | UKI | 700 | CHN | YTX |
| 611033 | E15321 BASIC FLEECE HT | 154 | S | 4011818549656 | UKI | 700 | CHN | YTX |
| 611033 | E15321 BASIC FLEECE HT | 252 | M | 4011818549687 | UKI | 100 | CHN | YTX |
| 611033 | E15321 BASIC FLEECE HT | 252 | S | 4011818549670 | UKI | 100 | CHN | YTX |
| 611033 | E15321 BASIC FLEECE HT | 444 | M | 4011818549700 | UKI | 225 | CHN | YTX |
| 611033 | E15321 BASIC FLEECE HT | 444 | S | 4011818549694 | UKI | 225 | CHN | YTX |
| 611033 | E15321 BASIC FLEECE HT | 543 | M | 4011818549724 | UKI | 475 | CHN | YTX |
| 611033 | E15321 BASIC FLEECE HT | 543 | S | 4011818549717 | UKI | 475 | CHN | YTX |
| 611033 | E15321 BASIC FLEECE HT | 557 | M | 4011818549748 | UKI | 150 | CHN | YTX |
| 611033 | E15321 BASIC FLEECE HT | 557 | S | 4011818549731 | UKI | 150 | CHN | YTX |
| 611033 | E15321 BASIC FLEECE HT | 558 | M | 4011818549762 | UKI | 50 | CHN | YTX |
| 611033 | E15321 BASIC FLEECE HT | 558 | S | 4011818549755 | UKI | 50 | CHN | YTX |
| 611035 | E15359 BSC FLC HEADBND | 141 | M | 4011818550089 | UKI | 775 | CHN | YTX |
| 611035 | E15359 BSC FLC HEADBND | 141 | S | 4011818550072 | UKI | 775 | CHN | YTX |
| 611035 | E15359 BSC FLC HEADBND | 154 | M | 4011818550102 | UKI | 575 | CHN | YTX |
| 611035 | E15359 BSC FLC HEADBND | 154 | S | 4011818550096 | UKI | 575 | CHN | YTX |
| 611035 | E15359 BSC FLC HEADBND | 252 | M | 4011818550126 | UKI | 150 | CHN | YTX |
| 611035 | E15359 BSC FLC HEADBND | 252 | S | 4011818550119 | UKI | 150 | CHN | YTX |
| 611035 | E15359 BSC FLC HEADBND | 444 | M | 4011818550140 | UKI | 250 | CHN | YTX |
| 611035 | E15359 BSC FLC HEADBND | 444 | S | 4011818550133 | UKI | 250 | CHN | YTX |
| 611035 | E15359 BSC FLC HEADBND | 543 | M | 4011818550164 | UKI | 475 | CHN | YTX |
| 611035 | E15359 BSC FLC HEADBND | 543 | S | 4011818550157 | UKI | 475 | CHN | YTX |
| 611035 | E15359 BSC FLC HEADBND | 557 | M | 4011818550188 | UKI | 100 | CHN | YTX |
| 611035 | E15359 BSC FLC HEADBND | 557 | S | 4011818550171 | UKI | 100 | CHN | YTX |

FIG. 20.11B

Customer  : NEWGERM
Module    : MULTI
Description : MULTI CURRENCY FORMAT
Date/Time : 06/11/98 / 4:22:59 PM

<< ESPRIT GERMANY HANGTAG ORDER DETAIL REPORT >>

FILENAME: G9819005  SEASON: E  HANGTAGTYP: AU  DIV: 15

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 611036 | E15361 | H.-K.CHECK FOLD | 252 | 1 SIZE | 4011818557170 | UKI | | | 775 | CHN | HTU2 |
| 611036 | E15361 | H.-K.CHECK FOLD | 543 | 1 SIZE | 4011818557187 | UKI | | | 1375 | CHN | HTU2 |
| 611043 | E15362 | STOCK UMBRELLA | 141 | 1 SIZE | 4011818557194 | UKI | | | 200 | CHN | HTU2 |
| 611043 | E15362 | STOCK UMBRELLA | 543 | 1 SIZE | 4011818557200 | UKI | | | 125 | CHN | HTU2 |
| 611044 | E15363 | LOGO BUGGY | 141 | 1 SIZE | 4011818557217 | UKI | | | 1500 | CHN | HTU2 |
| 611044 | E15363 | LOGO BUGGY | 250 | 1 SIZE | 4011818557224 | UKI | | | 75 | CHN | HTU2 |
| 611044 | E15363 | LOGO BUGGY | 543 | 1 SIZE | 4011818557231 | UKI | | | 1175 | CHN | HTU2 |
| 611045 | E15364 | GERA FOLDING | 141 | 1 SIZE | 4011818557248 | UKI | | | 300 | CHN | HTU2 |
| 611045 | E15364 | GERA FOLDING | 250 | 1 SIZE | 4011818557255 | UKI | | | 25 | CHN | HTU2 |
| 611045 | E15364 | GERA FOLDING | 543 | 1 SIZE | 4011818557262 | UKI | | | 350 | CHN | HTU2 |

FIG. 20.12

Customer : NEWGERM
Module : MULTI
Description : MULTI CURRENCY FORMAT
Date/Time : 06/11/98 / 4:22:59 PM

<< ESPRIT GERMANY HANGTAG ORDER DETAIL REPORT >>

FILENAME: G9819005  SEASON: E     HANGTAGTYP: AU   DIV: 26

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 609779 | E26003 | ALBATROS BIGSHB | 141 | 1 SIZE | 4011818514890 | UKI | & | | 875 | CHN | SFL2 |
| 609779 | E26003 | ALBATROS BIGSHB | 543 | 1 SIZE | 4011818514913 | UKI | & | | 75 | CHN | SFL2 |
| 609781 | E26004 | ALBATROS POSTBG | 141 | 1 SIZE | 4011818514937 | UKI | & | | 725 | CHN | SFL2 |
| 609781 | E26004 | ALBATROS POSTBG | 543 | 1 SIZE | 4011818514951 | UKI | & | | 100 | CHN | SFL2 |
| 609782 | E26005 | ALBATROS WEEKND | 141 | 1 SIZE | 4011818514975 | UKI | & | | 575 | CHN | SFL2 |
| 609782 | E26005 | ALBATROS WEEKND | 543 | 1 SIZE | 4011818514999 | UKI | & | | 50 | CHN | SFL2 |
| 609784 | E26009 | ALBATROS WALLET | 141 | 1 SIZE | 4011818515149 | UKI | & | | 1100 | CHN | SFL2 |
| 609784 | E26009 | ALBATROS WALLET | 543 | 1 SIZE | 4011818515163 | UKI | & | | 50 | CHN | SFL2 |
| 609981 | E26453 | JOCHEM PASSPURS | 141 | 1 SIZE | 4011818517457 | UKI | & | | 425 | CHN | MAXY |
| 610042 | E26022 | APOLLO SCHOOLBG | 070 | 1 SIZE | 4011818517006 | UKI | & | | 50 | CHN | JF2 |
| 610042 | E26022 | APOLLO SCHOOLBG | 141 | 1 SIZE | 4011818517020 | UKI | & | | 675 | CHN | JF2 |
| 610048 | E26023 | APOLLO OFFICEBG | 070 | 1 SIZE | 4011818517051 | UKI | & | | 25 | CHN | JF2 |
| 610048 | E26023 | APOLLO OFFICEBG | 141 | 1 SIZE | 4011818517075 | UKI | & | | 550 | CHN | JF2 |

FIG. 20.14A

| | | | | | | |
|---|---|---|---|---|---|---|
| 610057 | E26024 APOLLO PORTFLIO | 070 | 1 SIZE | 4011818517099 | UKI | 50 CHN | JF2 |
| 610057 | E26024 APOLLO PORTFLIO | 141 | 1 SIZE | 4011818517112 | UKI | 750 CHN | JF2 |
| 610067 | E26026 APOLLO COSMBAG | 070 | 1 SIZE | 4011818517174 | UKI | 100 CHN | JF2 |
| 610067 | E26026 APOLLO COSMBAG | 141 | 1 SIZE | 4011818517198 | UKI | 1125 CHN | JF2 |
| 610094 | E26027 APOLLO KEYHOLDR | 070 | 1 SIZE | 4011818517211 | UKI | 50 CHN | JF4 |
| 610094 | E26027 APOLLO KEYHOLDR | 141 | 1 SIZE | 4011818517235 | UKI | 1200 CHN | JF4 |
| 610099 | E26028 APOLLO ZIPWALET | 070 | 1 SIZE | 4011818517259 | UKI | 125 CHN | JF4 |
| 610099 | E26028 APOLLO ZIPWALET | 141 | 1 SIZE | 4011818517273 | UKI | 1600 CHN | JF4 |
| 611046 | E26290 BASIC RIB GLOVE | 141 | L | 4011818558061 | UKI | 675 CHN | HD |
| 611046 | E26290 BASIC RIB GLOVE | 141 | M | 4011818558054 | UKI | 350 CHN | HD |
| 611046 | E26290 BASIC RIB GLOVE | 141 | XL | 4011818558078 | UKI | 675 CHN | HD |
| 611046 | E26290 BASIC RIB GLOVE | 141 | XXL | 4011818558085 | UKI | 350 CHN | HD |
| 611046 | E26290 BASIC RIB GLOVE | 152 | L | 4011818558092 | UKI | 50 CHN | HD |
| 611046 | E26290 BASIC RIB GLOVE | 152 | M | 4011818558108 | UKI | 25 CHN | HD |
| 611046 | E26290 BASIC RIB GLOVE | 152 | XL | 4011818558115 | UKI | 50 CHN | HD |
| 611046 | E26290 BASIC RIB GLOVE | 152 | XXL | 4011818558122 | UKI | 25 CHN | HD |
| 611046 | E26290 BASIC RIB GLOVE | 154 | L | 4011818558146 | UKI | 675 CHN | HD |
| 611046 | E26290 BASIC RIB GLOVE | 154 | M | 4011818558139 | UKI | 350 CHN | HD |
| 611046 | E26290 BASIC RIB GLOVE | 154 | XL | 4011818558153 | UKI | 675 CHN | HD |
| 611046 | E26290 BASIC RIB GLOVE | 154 | XXL | 4011818558160 | UKI | 350 CHN | HD |
| 611046 | E26290 BASIC RIB GLOVE | 571 | L | 4011818558184 | UKI | 350 CHN | HD |
| 611046 | E26290 BASIC RIB GLOVE | 571 | M | 4011818558177 | UKI | 175 CHN | HD |
| 611046 | E26290 BASIC RIB GLOVE | 571 | XL | 4011818558207 | UKI | 350 CHN | HD |
| 611046 | E26290 BASIC RIB GLOVE | 571 | XXL | 4011818558191 | UKI | 175 CHN | HD |
| 611047 | E26293 COUNTRY GLOVE | 070 | L | 4011818558528 | UKI | 50 CHN | MWH |
| 611047 | E26293 COUNTRY GLOVE | 070 | M | 4011818558511 | UKI | 25 CHN | MWH |
| 611047 | E26293 COUNTRY GLOVE | 070 | XL | 4011818558535 | UKI | 50 CHN | MWH |

FIG. 20.14B

Customer : NEWGERM
Module : MULTI
Description : MULTI CURRENCY FORMAT
Date/Time : 06/11/98 / 4:22:59 PM

<< ESPRIT GERMANY HANGTAG ORDER DETAIL REPORT>>

FILENAME: G9819005 SEASON: E     HANGTAGTYP: AU    DIV: 26

| SPO | STYLE | STYLEDESC | CLRCODE | SIZE | CODE | DISTRI | RETAILCODE | RETAIL | QTY | COUNTRY | FACTORY |
|---|---|---|---|---|---|---|---|---|---|---|---|
| 611047 | E26293 | COUNTRY GLOVE | 070 | XXL | 4011818558542 | UKI | £ | | 25 | CHN | MWH |
| 611047 | E26293 | COUNTRY GLOVE | 141 | L | 4011818558566 | UKI | £ | | 100 | CHN | MWH |
| 611047 | E26293 | COUNTRY GLOVE | 141 | M | 4011818558559 | UKI | £ | | 50 | CHN | MWH |
| 611047 | E26293 | COUNTRY GLOVE | 141 | XL | 4011818558573 | UKI | £ | | 100 | CHN | MWH |
| 611047 | E26293 | COUNTRY GLOVE | 141 | XXL | 4011818558580 | UKI | £ | | 50 | CHN | MWH |
| 611048 | E26293 | COUNTRY GLOVE | 070 | L | 4011818558528 | UKI | £ | | 400 | CHN | MWH |
| 611048 | E26293 | COUNTRY GLOVE | 070 | M | 4011818558511 | UKI | £ | | 200 | CHN | MWH |
| 611048 | E26293 | COUNTRY GLOVE | 070 | XL | 4011818558535 | UKI | £ | | 400 | CHN | MWH |
| 611048 | E26293 | COUNTRY GLOVE | 070 | XXL | 4011818558542 | UKI | £ | | 200 | CHN | MWH |
| 611048 | E26293 | COUNTRY GLOVE | 141 | L | 4011818558566 | UKI | £ | | 625 | CHN | MWH |
| 611048 | E26293 | COUNTRY GLOVE | 141 | M | 4011818558559 | UKI | £ | | 325 | CHN | MWH |
| 611048 | E26293 | COUNTRY GLOVE | 141 | XL | 4011818558573 | UKI | £ | | 625 | CHN | MWH |
| 611048 | E26293 | COUNTRY GLOVE | 141 | XXL | 4011818558580 | UKI | £ | | 325 | CHN | MWH |

FIG. 20.15

Customer : NEWGERM
Module : MULTI
Description : MULTI CURRENCY FORMAT
File Name : GM19005
Date/Time : 06/11/98 / 4:19:33 PM

<< ESPRIT GERMANY HANGTAG/DIV SUMMARY >>

| SEASON | HANGTAGTYP | DIV | QTY |
|--------|------------|-----|-----|
| D | C4 | 21 | 40 |
| D | EU | 21 | 1500 |
| D | PP | 21 | 270 |
| E | AA | 15 | 3375 |
| E | AA | 26 | 150 |
| E | AU | 15 | 185050 |
| E | AU | 26 | 21150 |
| E | BE | 20 | 32650 |
| E | C4 | 15 | 4055 |
| E | C4 | 2 | 1540 |
| E | C4 | 20 | 650 |
| E | C4 | 26 | 875 |
| E | C4 | 6 | 1180 |
| E | C4 | 8 | 370 |
| E | KG | 2 | 61925 |
| E | KG | 6 | 58100 |
| E | KG | 8 | 13100 |
| E | PP | 15 | 30945 |
| E | PP | 2 | 21255 |
| E | PP | 20 | 7725 |
| E | PP | 26 | 7035 |
| E | PP | 6 | 20655 |
| E | PP | 8 | 4470 |
| N | C4 | 29 | 25 |
| | | | 478090 |

*FIG. 21*

Customer    : NEWGERM
Module      : MULTI
Description : MULTI CURRENCY FORMAT
File Name   : GM19005
Date/Time   : 06/11/98 / 4:21:07 PM

<< ESPRIT GERMANY ERROR REPORT >>

| FILENAME | COUNTRY | FACTORY | SPO | STYLE | CLRCODE | DISTRI | ERR_CODE | ERR_FTY | ERR_HTG | ERR_RET | HANGTAGTYP | DIV | QTY |
|---|---|---|---|---|---|---|---|---|---|---|---|---|---|
| G9819005 | HKG | | 610049 | E02106 | | UKI | Y | N | | | C4 | 2 | 0 |
| G9819005 | HKG | | 610049 | E02106 | 955 | UKI | Y | N | | | KG | 2 | 0 |
| G9819005 | HKG | | 610049 | E02106 | 955 | UKI | Y | N | | | KG | 2 | 0 |
| G9819005 | HKG | | 610049 | E02106 | 955 | UKI | Y | N | | | KG | 2 | 0 |
| G9819005 | HKG | | 610049 | E02106 | 955 | UKI | Y | N | | | KG | 2 | 0 |
| G9819005 | HKG | WGF | 610645 | N29510 | 141 | UKI | | Y | | | EU | 29 | 25 |
| G9819005 | HKG | WGF | 610645 | N29510 | 141 | UKI | | Y | | | EU | 29 | 75 |
| G9819005 | HKG | WGF | 610645 | N29510 | 141 | UKI | | Y | | | EU | 29 | 125 |
| G9819005 | HKG | WGF | 610645 | N29510 | 141 | UKI | | Y | | | EU | 29 | 200 |
| G9819005 | HKG | WGF | 610645 | N29510 | 141 | UKI | | Y | | | EU | 29 | 175 |
| G9819005 | HKG | WGF | 610645 | N29510 | 041 | UKI | | Y | | | EU | 29 | 25 |
| G9819005 | HKG | WGF | 610645 | N29510 | 041 | UKI | | Y | | | EU | 29 | 75 |
| G9819005 | HKG | WGF | 610645 | N29510 | 041 | UKI | | Y | | | EU | 29 | 125 |
| G9819005 | HKG | WGF | 610645 | N29510 | 041 | UKI | | Y | | | EU | 29 | 200 |
| G9819005 | HKG | WGF | 610645 | N29510 | 041 | UKI | | Y | | | EU | 29 | 175 |

FIG. 22

Customer    : NEWGERM
Module      : MULTI
Description : MULTI CURRENCY FORMAT
File Name   : GM19005
Date/Time   : 06/11/98 / 4:20:30 PM

<< ZERO QUANTITY REPORT >>

| SEASON | HANGTAGTYP | SIZE    | DIV | DISTRI | COUNTRY | FACTORY | SPO    | STYLE  | CODE           | CHG_AGNT |
|--------|------------|---------|-----|--------|---------|---------|--------|--------|----------------|----------|
| E      | PP         | SORT#03 | 2   | UKI    | HKG     | DRGT    | 610049 | E02106 | 20118131139328 | N        |
| E      | PP         | SORT#22 | 2   | UKI    | HKG     | DRGT    | 610049 | E02106 | 20118131139335 | N        |
| E      | PP         | SORT#23 | 2   | UKI    | HKG     | DRGT    | 610049 | E02106 | 20118131139342 | N        |
| E      | PP         | SORT#24 | 2   | UKI    | HKG     | DRGT    | 610049 | E02106 | 20118131139359 | N        |
| E      | KG         | 128     | 2   | UKI    | HKG     | DRGT    | 610049 | E02106 | 40118182243790 | N        |
| E      | KG         | 134     | 2   | UKI    | HKG     | DRGT    | 610049 | E02106 | 40118182243806 | N        |
| E      | KG         | 140     | 2   | UKI    | HKG     | DRGT    | 610049 | E02106 | 40118182243813 | N        |
| E      | KG         | 146     | 2   | UKI    | HKG     | DRGT    | 610049 | E02106 | 40118182243820 | N        |
| E      | KG         | 152     | 2   | UKI    | HKG     |         | 610049 | E02106 | 40118182243844 | N        |
| E      | KG         | 158     | 2   | UKI    | HKG     |         | 610049 | E02106 | 40118182243851 | N        |
| E      | KG         | 164     | 2   | UKI    | HKG     |         | 610049 | E02106 | 40118182243868 | N        |
| E      | KG         | 176     | 2   | UKI    | HKG     |         | 610049 | E02106 | 40118182243875 | N        |
| E      | C4         |         | 2   | UKI    | HKG     |         | 610049 | E02106 | 27000006100497 | N        |

*FIG. 23A*

| CHG_CNTRY | CHG_SUPP | CHG_EX_OR | CHG_HT | OLD_QTY | NEW_QTY | CHG_QTY |
|---|---|---|---|---|---|---|
| N | N | N | N | 180 | 180 | 0 |
| N | N | N | N | 105 | 105 | 0 |
| N | N | N | N | 60 | 60 | 0 |
| N | N | N | N | 15 | 15 | 0 |
| N | N | N | N | 175 | 175 | 0 |
| N | N | N | N | 175 | 175 | 0 |
| N | N | N | N | 175 | 175 | 0 |
| N | N | N | N | 225 | 225 | 0 |
| N | N | N | N | 150 | 150 | 0 |
| N | N | N | N | 150 | 150 | 0 |
| N | N | N | N | 100 | 100 | 0 |
| N | N | N | N | 40 | 40 | 0 |

*FIG. 23B*

Customer    : NEWGERM
Module      : MULTI
Description : MULTI CURRENCY FORMAT
File Name   : GM19005
Date/Time   : 06/11/98 / 4:20:48PM

<< DUPLICATE ORDERS >>

| CODE | SPO | STYLE | COUNTRY | FACTORY | CHG_AGNT | CHG_CNTRY | CHG_SUPP | CHG_EX_OR | CHG_HT |
|---|---|---|---|---|---|---|---|---|---|
| 20118129764450 | 610057 | E26024 | CHN | JF2 | | | | | |
| 40118185170599 | 610057 | E26024 | CHN | JF2 | N | N | Y | N | N |
| 20118129764647 | 610057 | E26024 | CHN | JF2 | N | N | Y | N | N |
| 40118185171112 | 610057 | E26024 | CHN | JF2 | N | N | Y | N | N |
| 27000061000572 | 610057 | E26024 | CHN | JF2 | N | N | Y | N | N |
| 20118129764988 | 610057 | E26026 | CHN | JF2 | N | N | Y | N | N |
| 40118185171774 | 610067 | E26026 | CHN | JF2 | N | N | Y | N | N |
| 20118129764504 | 610067 | E26026 | CHN | JF2 | N | N | Y | N | N |
| 40118185171988 | 610067 | E26026 | CHN | JF2 | N | N | Y | N | N |
| 27000061000671 | 610067 | E26026 | CHN | JF2 | N | N | Y | N | N |
| 20118129764450 | 610067 | E26024 | CHN | JF2 | N | N | Y | N | N |
| 40118185170599 | 610067 | E26024 | CHN | JF2 | N | N | Y | N | N |
| 20118129764647 | 610067 | E26024 | CHN | JF2 | N | N | Y | N | N |
| 40118185171112 | 610067 | E26024 | CHN | JF2 | N | N | Y | N | N |
| 27000061000572 | 610067 | E26024 | CHN | JF2 | N | N | Y | N | N |
| 20118129764988 | 610067 | E26026 | CHN | JF2 | N | N | Y | N | N |
| 40118185171774 | 610067 | E26026 | CHN | JF2 | N | N | Y | N | N |
| 20118129764504 | 610067 | E26026 | CHN | JF2 | N | N | Y | N | N |
| 40118185171988 | 610067 | E26026 | CHN | JF2 | N | N | Y | N | N |
| 27000061000671 | 610067 | E26026 | CHN | JF2 | N | N | Y | N | N |

FIG. 24A

| CHG_QTY | OLD_QTY | NEW_QTY | QTY | SEASON | HANGTAGTYP |
|---|---|---|---|---|---|
| N | 0 | 30 | 30 | E | PP |
| N | 0 | 50 | 50 | E | AU |
| N | 0 | 375 | 375 | E | PP |
| N | 0 | 750 | 750 | E | AU |
| N | 0 | 80 | 80 | E | C4 |
| N | 0 | 45 | 45 | E | PP |
| N | 0 | 100 | 100 | E | AU |
| N | 0 | 555 | 555 | E | PP |
| N | 0 | 1125 | 1125 | E | AU |
| N | 0 | 25 | 25 | E | C4 |
| N | 0 | 30 | 30 | E | PP |
| N | 0 | 50 | 50 | E | AU |
| N | 0 | 375 | 375 | E | PP |
| N | 0 | 750 | 750 | E | AU |
| N | 0 | 80 | 80 | E | C4 |
| N | 0 | 45 | 45 | E | PP |
| N | 0 | 100 | 100 | E | AU |
| N | 0 | 555 | 555 | E | PP |
| N | 0 | 1125 | 1125 | E | AU |
| N | 0 | 25 | 25 | E | C4 |

*FIG. 24B*

Customer    : NEWGERM
Module      : MULTI
Description : MULTI CURRENCY FORMAT
File Name   : GM19005
Date/Time   : 06/11/98 / 4:28:16 PM

<< INVOICE DISTRIBUTORS >>

| INVOIC | DISTRI | COUNTRY | #REC |
|--------|--------|---------|------|
| CN     | CN     | P       | 144  |
| EDI    | COL    | CHN     | 96   |
| EDI    | T      | CHN     | 40   |
| EDI    | UKI    | CHN     | 613  |
| EDI    | UKI    | HKG     | 25   |
| UKI    | UKI    | I       | 12   |
| UKI    | UKI    | P       | 1569 |
| UKI    | UKI    | T       | 10   |

*FIG. 25*

Customer : NEWGERM
Module : MULTI
Description : MULTI CURRENCY FORMAT
File Name : GM19005
Date/Time : 06/11/98 / 4:29:21 PM

<< ESPRIT GERMANY'S REJECTED SPO'S >>

FILENAME:G9819005 SEASON:D HANGTAGTYP:EU

| C4 | PP | DISTRI | SPO | STYLE | CLRCODE | ERR_CODE | ERR_MC | ERR_MS | ERR_MUKI | ERR_RET | MISS_ILLUS | QTY |
|----|----|--------|-----|-------|---------|----------|--------|--------|----------|---------|------------|-----|
| C4 | PP | UKI | 609097 | D21522 | 543 | | Y | | | | | 250 |
| | | | | | | | | | | | | 250 |

FILENAME:G9819005 SEASON:E HANGTAGTYP:AA

| C4 | PP | DISTRI | SPO | STYLE | CLRCODE | ERR_CODE | ERR_MC | ERR_MS | ERR_MUKI | ERR_RET | MISS_ILLUS | QTY |
|----|----|--------|-----|-------|---------|----------|--------|--------|----------|---------|------------|-----|
| | PP | COL | 450006 | E15019 | 141 | | | Y | | | | 50 |
| | | | | | | | | | | | | 50 |

FILENAME:G9819005 SEASON:N HANGTAGTYP:EU

| C4 | PP | DISTRI | SPO | STYLE | CLRCODE | ERR_CODE | ERR_MC | ERR_MS | ERR_MUKI | ERR_RET | MISS_ILLUS | QTY |
|----|----|--------|-----|-------|---------|----------|--------|--------|----------|---------|------------|-----|
| C4 | | UKI | 610645 | N29510 | 041 | | N | Y | | | | 600 |
| C4 | | UKI | 610645 | N29510 | 141 | | N | Y | | | | 600 |
| | | | | | | | | | | | | 1200 |

FIG. 26

Customer : NEWGERM
Module : MULTI
Description : MULTI CURRENCY FORMAT
File Name : GM19005
Date/Time : 06/11/98 / 4:21:07 PM

<< MISSING MULTI-SIZE/CURRENCY DATA >>

| FILENAME | SEASON | HANGTAGTYP | SPO | STYLE | ERR_MC | ERR_MS | RETAILCODE | RETAIL |
|---|---|---|---|---|---|---|---|---|
| G9819005 | D | EU | 609097 | D21522 | Y | | £ | |
| G9819005 | E | AA | 450006 | E15019 | N | Y | | |
| G9819005 | N | EU | 610645 | B29510 | N | Y | £ | |

FIG. 27

Customer : NEWGERM
Module : MULTI
Description : MULTI CURRENCY FORMAT
File Name : GM19005
Date/Time : 06/11/98 / 4:21:27 PM

<< ESPRIT GERMANY C4 REPORT FOR THERMAL PRINTING>>

HT_REF: AA   SEASON: E

| SPO | CODE | STYLE | OLD_QTY | NEW_QTY | QTY | STICKER |
|---|---|---|---|---|---|---|
| 850770 | 2700008507706 | E15203 | 0 | 10 | 10 | 40 |
| 850772 | 2700008507720 | E15204 | 0 | 10 | 10 | 40 |
| 850773 | 2700008507737 | E15206 | 0 | 10 | 10 | 40 |
| 850774 | 2700008507744 | E15192 | 0 | 10 | 10 | 40 |
|  |  |  |  |  | 40 | 160 |

HT_REF: AU   SEASON: E

| SPO | CODE | STYLE | OLD_QTY | NEW_QTY | QTY | STICKER |
|---|---|---|---|---|---|---|
| 609261 | 2700006092617 | E15251 | 0 | 60 | 60 | 240 |
| 609262 | 2700006092624 | E15291 | 0 | 95 | 95 | 380 |
| 609264 | 2700006092648 | E15295 | 0 | 30 | 30 | 120 |
| 609265 | 2700006092655 | E15297 | 0 | 10 | 10 | 40 |
| 609270 | 2700006092709 | E15300 | 0 | 15 | 15 | 60 |
| 609271 | 2700006092716 | E15321 | 0 | 30 | 30 | 120 |
| 609273 | 2700006092730 | E15359 | 0 | 20 | 20 | 80 |
| 609525 | 2700006095250 | E15361 | 0 | 55 | 55 | 220 |
| 609526 | 2700006095267 | E15362 | 0 | 40 | 40 | 160 |
| 609527 | 2700006095274 | E15363 | 0 | 105 | 105 | 420 |
| 609529 | 2700006095298 | E15364 | 0 | 80 | 80 | 320 |
| 609592 | 2700006095922 | E15295 | 0 | 140 | 140 | 560 |
| 609593 | 2700006095939 | E15295 | 0 | 200 | 200 | 800 |
| 609595 | 2700006095953 | E15297 | 0 | 20 | 20 | 80 |

*FIG. 28.1A*

| | | | | | | |
|---|---|---|---|---|---|---|
| 609596 | 2700006095960 | E15297 | 0 | 95 | 95 | 380 |
| 609598 | 2700006095984 | E15300 | 0 | 180 | 180 | 720 |
| 609599 | 2700006095991 | E15300 | 0 | 125 | 125 | 500 |
| 609686 | 2700006096868 | E15200 | 0 | 15 | 15 | 60 |
| 609688 | 2700006096882 | E15204 | 0 | 310 | 310 | 1240 |
| 609716 | 2700006097162 | E15259 | 0 | 160 | 160 | 640 |
| 609718 | 2700006097186 | E15261 | 0 | 145 | 145 | 580 |
| 609719 | 2700006097193 | E15262 | 0 | 45 | 45 | 180 |
| 609779 | 2700006097797 | E26003 | 0 | 95 | 95 | 380 |
| 609781 | 2700006097810 | E26004 | 0 | 85 | 85 | 340 |
| 609782 | 2700006097827 | E26005 | 0 | 65 | 65 | 260 |
| 609784 | 2700006097841 | E26009 | 0 | 25 | 25 | 100 |
| 609981 | 2700006099814 | E26453 | 0 | 10 | 10 | 40 |
| 610017 | 2700006100176 | E15196 | 0 | 235 | 235 | 940 |
| 610021 | 2700006100213 | E15197 | 0 | 30 | 30 | 120 |
| 610042 | 2700006100428 | E26022 | 0 | 70 | 70 | 280 |
| 610048 | 2700006100480 | E26023 | 0 | 60 | 60 | 240 |
| 610057 | 2700006100572 | E26024 | 0 | 80 | 160 | 640 |
| 610067 | 2700006100671 | E26026 | 0 | 25 | 50 | 200 |
| 610094 | 2700006100947 | E26027 | 0 | 30 | 30 | 120 |
| 610099 | 2700006100992 | E26028 | 0 | 40 | 40 | 160 |
| 610292 | 2700006102927 | E15203 | 0 | 125 | 125 | 500 |
| 610294 | 2700006102941 | E15205 | 0 | 160 | 160 | 640 |
| 610296 | 2700006102965 | E15206 | 0 | 15 | 15 | 60 |
| 610395 | 2700006103955 | E15192 | 0 | 150 | 150 | 600 |
| 610396 | 2700006103962 | E15192 | 0 | 20 | 20 | 80 |
| 611015 | 2700006110151 | E15204 | 0 | 65 | 65 | 260 |
| 611019 | 2700006110199 | E15251 | 0 | 315 | 315 | 1260 |
| 611028 | 2700006110281 | E15259 | 0 | 170 | 170 | 680 |
| 611029 | 2700006110298 | E15261 | 0 | 55 | 55 | 220 |
| 611030 | 2700006110304 | E15262 | 0 | 10 | 10 | 40 |
| 611031 | 2700006110311 | E15291 | 0 | 330 | 330 | 1320 |
| 611033 | 2700006110335 | E15321 | 0 | 105 | 105 | 420 |

*FIG. 28.1B*

Customer   : NEWGERM
Module     : MULTI
Description : MULTI CURRENCY FORMAT
File Name  : GM19005
Date/Time  : 06/11/98 / 4:21:27 PM

<< ESPRIT  GERMANY  C4 REPORT FOR THERMAL PRINTING >>

| | | | | | | |
|---|---|---|---|---|---|---|
| 611035 | 2700006110359 | E15359 | 0 | 100 | 100 | 400 |
| 611036 | 2700006110366 | E15361 | 0 | 55 | 55 | 220 |
| 611043 | 2700006110434 | E15362 | 0 | 10 | 10 | 40 |
| 611044 | 2700006110441 | E15363 | 0 | 70 | 70 | 280 |
| 611045 | 2700006110458 | E15364 | 0 | 20 | 20 | 80 |
| 611046 | 2700006110465 | E26290 | 0 | 110 | 110 | 440 |
| 611047 | 2700006110472 | E26293 | 0 | 10 | 10 | 40 |
| 611048 | 2700006110489 | E26293 | 0 | 65 | 65 | 260 |
| | | | | | 4890 | 19560 |

HT_REF: BE    SEASON: E

| SPO | CODE | STYLE | OLD_QTY | NEW_QTY | QTY | STICKER |
|---|---|---|---|---|---|---|
| 610951 | 2700006109513 | E20953 | 0 | 90 | 90 | 360 |
| 610952 | 2700006109520 | E20954 | 0 | 60 | 60 | 240 |
| 610953 | 2700006109537 | E20955 | 0 | 45 | 45 | 180 |
| 610956 | 2700006109568 | E20956 | 0 | 25 | 25 | 100 |
| 610957 | 2700006109575 | E20957 | 0 | 70 | 70 | 280 |
| 610958 | 2700006109582 | E20958 | 0 | 95 | 95 | 380 |
| 610959 | 2700006109599 | E20959 | 0 | 75 | 75 | 300 |
| 610963 | 2700006109636 | E20962 | 0 | 80 | 80 | 320 |
| 610967 | 2700006109674 | E20967 | 0 | 80 | 80 | 320 |
| 610976 | 2700006109766 | E20998 | 0 | 30 | 30 | 120 |
| | | | | | 650 | 2600 |

*FIG. 28.2A*

HT_REF: EU    SEASON: D

| SPO | CODE | STYLE | OLD_QTY | NEW_QTY | QTY | STICKER |
|---|---|---|---|---|---|---|
| 609096 | 2700006090965 | D21521 | 0 | 20 | 20 | 80 |
| 609097 | 2700006090972 | D21522 | 0 | 20 | 20 | 80 |
|  |  |  |  |  | 40 | 160 |

HT_REF: EU    SEASON: N

| SPO | CODE | STYLE | OLD_QTY | NEW_QTY | QTY | STICKER |
|---|---|---|---|---|---|---|
| 610645 | 2700006106451 | N29510 | 0 | 25 | 25 | 100 |
|  |  |  |  |  | 25 | 100 |

HT_REF: KG    SEASON: E

| SPO | CODE | STYLE | OLD_QTY | NEW_QTY | QTY | STICKER |
|---|---|---|---|---|---|---|
| 610059 | 2700006100596 | E02132 | 0 | 20 | 20 | 80 |
| 610807 | 2700006108073 | E02930 | 0 | 95 | 95 | 380 |
| 610808 | 2700006108080 | E02931 | 0 | 65 | 65 | 260 |
| 610809 | 2700006108097 | E02932 | 0 | 105 | 105 | 420 |
| 610810 | 2700006108103 | E02933 | 0 | 230 | 230 | 920 |
| 610811 | 2700006108110 | E02934 | 0 | 15 | 15 | 60 |
| 610812 | 2700006108127 | E02936 | 0 | 20 | 20 | 80 |
| 610813 | 2700006108134 | E02937 | 0 | 120 | 120 | 480 |
| 610822 | 2700006108226 | E02945 | 0 | 70 | 70 | 280 |
| 610824 | 2700006108240 | E02946 | 0 | 55 | 55 | 220 |
| 610825 | 2700006108257 | E02948 | 0 | 100 | 100 | 400 |

*FIG. 28.2B*

```
Customer    : NEWGERM
Module      : MULTI
Description : MULTI CURRENCY FORMAT
File Name   : GM19005
Date/Time   : 06/11/98 / 4:21:27 PM
```

<< ESPRIT GERMANY C4 REPORT FOR THERMAL PRINTING >>

| | | | | | | |
|---|---|---|---|---|---|---|
| 610827 | 2700006108271 | E02949 | 0 | 40 | 40 | 160 |
| 610835 | 2700006108356 | E02957 | 0 | 20 | 20 | 80 |
| 610839 | 2700006108394 | E02960 | 0 | 110 | 110 | 440 |
| 610840 | 2700006108400 | E02961 | 0 | 20 | 20 | 80 |
| 610841 | 2700006108417 | E02963 | 0 | 70 | 70 | 280 |
| 610843 | 2700006108431 | E02967 | 0 | 60 | 60 | 240 |
| 610848 | 2700006108486 | E02970 | 0 | 85 | 85 | 340 |
| 610850 | 2700006108509 | E02971 | 0 | 20 | 20 | 80 |
| 610851 | 2700006108516 | E02973 | 0 | 155 | 155 | 620 |
| 610853 | 2700006108530 | E02980 | 0 | 20 | 20 | 80 |
| 610854 | 2700006108547 | E02990 | 0 | 15 | 15 | 60 |
| 610855 | 2700006108554 | E02991 | 0 | 10 | 10 | 40 |
| 610857 | 2700006108578 | E02999 | 0 | 20 | 20 | 80 |
| 610871 | 2700006108714 | E06928 | 0 | 55 | 55 | 220 |
| 610872 | 2700006108721 | E06930 | 0 | 90 | 90 | 360 |
| 610873 | 2700006108738 | E06931 | 0 | 70 | 70 | 280 |
| 610874 | 2700006108745 | E06933 | 0 | 30 | 30 | 120 |
| 610876 | 2700006108769 | E06936 | 0 | 185 | 185 | 740 |
| 610882 | 2700006108820 | E06941 | 0 | 15 | 15 | 60 |
| 610884 | 2700006108844 | E06945 | 0 | 20 | 20 | 80 |
| 610885 | 2700006108851 | E06947 | 0 | 125 | 125 | 500 |
| 610886 | 2700006108868 | E06948 | 0 | 115 | 115 | 460 |
| 610902 | 2700006109025 | E06958 | 0 | 75 | 75 | 300 |
| 610906 | 2700006109063 | E06963 | 0 | 35 | 35 | 140 |
| 610907 | 2700006109070 | E06970 | 0 | 35 | 35 | 140 |
| 610914 | 2700006109148 | E07925 | 0 | 115 | 115 | 460 |
| 610916 | 2700006109162 | E07927 | 0 | 60 | 60 | 240 |
| 610921 | 2700006109216 | E07934 | 0 | 35 | 35 | 140 |
| 610922 | 2700006109223 | E07935 | 0 | 20 | 20 | 80 |
| 610926 | 2700006109261 | E07940 | 0 | 15 | 15 | 60 |
| 610927 | 2700006109278 | E07942 | 0 | 85 | 85 | 340 |
| 610928 | 2700006109285 | E08926 | 0 | 70 | 70 | 280 |

```
Customer     : NEWGERM
Module       : MULTI
Description  : MULTI CURRENCY FORMAT
File Name    : GM19005
Date/Time    : 06/11/98 / 4:22:04 PM
```

<< ESPRIT GERMANY PP REPORT FOR SERVICE BUREAU >>

SEASON: D    HT_REF: EU

```
SPO     STYLE    CODE            OLD_QTY   NEW_QTY   QTY    RQTY
-----   ------   -------------   -------   -------   -----  ------

SEASON: E   HT_REF: AA

| SPO | STYLE | CODE | OLD_QTY | NEW_QTY | QTY | RQTY |
|---|---|---|---|---|---|---|
| 450002 | E15042 | 2011812970984 | 0 | 15 | 15 | 15 |
| 450002 | E15042 | 2011812970991 | 0 | 15 | 15 | 15 |
| 450003 | E15050 | 2011812971141 | 0 | 15 | 15 | 15 |
| 450003 | E15050 | 2011812971158 | 0 | 15 | 15 | 15 |
| 450004 | E15047 | 2011813304191 | 0 | 15 | 15 | 15 |
| 450004 | E15047 | 2011813304207 | 0 | 15 | 15 | 15 |
| 450005 | E15044 | 2011812971028 | 0 | 15 | 15 | 15 |
| 450005 | E15044 | 2011812971035 | 0 | 15 | 15 | 15 |
| 450006 | E15019 | 2011812966475 | 0 | 30 | 30 | 30 |
| 450006 | E15019 | 2011812966482 | 0 | 30 | 30 | 30 |
| 450006 | E15019 | 2011812966499 | 0 | 30 | 30 | 30 |
| 450007 | E15031 | 2011812970564 | 0 | 15 | 15 | 15 |
| 450007 | E15031 | 2011812970571 | 0 | 15 | 15 | 15 |
| 450007 | E15031 | 2011812970588 | 0 | 15 | 15 | 15 |
| 450008 | E15017 | 2011812966413 | 0 | 15 | 15 | 15 |
| 450008 | E15017 | 2011812966420 | 0 | 15 | 15 | 15 |
| 450008 | E15017 | 2011812966437 | 0 | 15 | 15 | 15 |
| 450009 | E15023 | 2011812970199 | 0 | 15 | 15 | 15 |
| 450009 | E15023 | 2011812970205 | 0 | 15 | 15 | 15 |
| 450009 | E15023 | 2011812970212 | 0 | 15 | 15 | 15 |
| 450011 | E15026 | 2011812970250 | 0 | 30 | 30 | 30 |
| 450011 | E15026 | 2011812970267 | 0 | 30 | 30 | 30 |
| 450011 | E15026 | 2011812970274 | 0 | 30 | 30 | 30 |
| 450012 | E15068 | 2011812971691 | 0 | 45 | 45 | 45 |
| 450013 | E26000 | 2011812974883 | 0 | 15 | 15 | 15 |
| 450013 | E26000 | 2011812974890 | 0 | 15 | 15 | 15 |
| 450014 | E26009 | 2011812975354 | 0 | 15 | 15 | 15 |
| 450014 | E26009 | 2011812975361 | 0 | 15 | 15 | 15 |
| 450015 | E26005 | 2011812974982 | 0 | 15 | 15 | 15 |
| 450015 | E26005 | 2011812974999 | 0 | 15 | 15 | 15 |
| 450016 | E15033 | 2011812970755 | 0 | 45 | 45 | 45 |
| 450016 | E15033 | 2011812970762 | 0 | 45 | 45 | 45 |

*FIG. 29.1A*

| | | | | | | |
|---|---|---|---|---|---|---|
| 450017 | E15037 | 2011812970847 | 0 | 45 | 45 | 45 |
| 450017 | E15037 | 2011812970854 | 0 | 45 | 45 | 45 |
| 450018 | E15055 | 2011812971301 | 0 | 30 | 30 | 30 |
| 450018 | E15055 | 2011812971318 | 0 | 30 | 30 | 30 |
| 450019 | E15058 | 2011812971394 | 0 | 30 | 30 | 30 |
| 450019 | E15058 | 2011812971400 | 0 | 30 | 30 | 30 |
| 450020 | E15052 | 2011812971219 | 0 | 15 | 15 | 15 |
| 450020 | E15052 | 2011812971226 | 0 | 15 | 15 | 15 |
| 450021 | E15064 | 2011812971608 | 0 | 15 | 15 | 15 |
| 450021 | E15064 | 2011812971615 | 0 | 15 | 15 | 15 |
| 450021 | E15064 | 2011812971622 | 0 | 15 | 15 | 15 |
| 450022 | E15000 | 2011812965850 | 0 | 15 | 15 | 15 |
| 450022 | E15000 | 2011812965867 | 0 | 15 | 15 | 15 |
| 850770 | E15203 | 2011813008495 | 0 | 15 | 15 | 15 |
| 850770 | E15203 | 2011813008501 | 0 | 30 | 30 | 30 |
| 850770 | E15203 | 2011813008518 | 0 | 30 | 30 | 30 |
| 850770 | E15203 | 2011813008525 | 0 | 15 | 15 | 15 |
| 850770 | E15203 | 2011813008532 | 0 | 30 | 30 | 30 |
| 850772 | E15204 | 2011813008549 | 0 | 15 | 15 | 15 |
| 850772 | E15204 | 2011813008556 | 0 | 30 | 30 | 30 |
| 850772 | E15204 | 2011813008563 | 0 | 15 | 15 | 15 |
| 850772 | E15204 | 2011813008570 | 0 | 15 | 15 | 15 |
| 850772 | E15204 | 2011813008587 | 0 | 15 | 15 | 15 |
| 850773 | E15206 | 2011813008631 | 0 | 15 | 15 | 15 |
| 850773 | E15206 | 2011813008648 | 0 | 15 | 15 | 15 |
| 850773 | E15206 | 2011813008655 | 0 | 15 | 15 | 15 |
| 850773 | E15206 | 2011813008662 | 0 | 15 | 15 | 15 |
| 850773 | E15206 | 2011813008679 | 0 | 15 | 15 | 15 |
| 850774 | E15192 | 2011813005586 | 0 | 30 | 30 | 30 |
| 850774 | E15192 | 2011813005593 | 0 | 30 | 30 | 30 |
| 850774 | E15192 | 2011813005609 | 0 | 30 | 30 | 30 |
| | | | | | ----- | ------ |
| | | | | | 1350 | 1350 |
| | | | | | ===== | ====== |

FIG. 29.1B

Customer : NEWGERM
Module : MULTI
Description : MULTI CURRENCY FORMAT
File Name : GM19005
Date/Time : 06/11/98 / 4:22:04 PM

<< ESPRIT GERMANY PP REPORT FOR SERVICE BUREAU >>

SEASON: E    HT_REF: AU

| SPO | STYLE | CODE | OLD_QTY | NEW_QTY | QTY | RQTY |
|---|---|---|---|---|---|---|
| 450010 | E15024 | 2011812970229 | 0 | 30 | 30 | 30 |
| 450010 | E15024 | 2011812970236 | 0 | 30 | 30 | 30 |
| 450010 | E15024 | 2011812970243 | 0 | 30 | 30 | 30 |
| 609261 | E15251 | 2011813009355 | 0 | 120 | 120 | 120 |
| 609261 | E15251 | 2011813009362 | 0 | 120 | 120 | 120 |
| 609261 | E15251 | 2011813009379 | 0 | 45 | 45 | 45 |
| 609261 | E15251 | 2011813009386 | 0 | 90 | 90 | 90 |
| 609261 | E15251 | 2011813009393 | 0 | 75 | 75 | 75 |
| 609261 | E15251 | 2011813009409 | 0 | 30 | 30 | 30 |
| 609261 | E15251 | 2011813009416 | 0 | 15 | 15 | 15 |
| 609262 | E15291 | 2011813017633 | 0 | 270 | 270 | 270 |
| 609262 | E15291 | 2011813017640 | 0 | 225 | 225 | 225 |
| 609262 | E15291 | 2011813017657 | 0 | 30 | 30 | 30 |
| 609262 | E15291 | 2011813017664 | 0 | 90 | 90 | 90 |
| 609262 | E15291 | 2011813017671 | 0 | 75 | 75 | 75 |
| 609262 | E15291 | 2011813017688 | 0 | 30 | 30 | 30 |
| 609262 | E15291 | 2011813017695 | 0 | 30 | 30 | 30 |
| 609264 | E15295 | 2011813018807 | 0 | 90 | 90 | 90 |
| 609264 | E15295 | 2011813018814 | 0 | 105 | 105 | 105 |
| 609264 | E15295 | 2011813018821 | 0 | 15 | 15 | 15 |
| 609264 | E15295 | 2011813018845 | 0 | 15 | 15 | 15 |
| 609264 | E15295 | 2011813175241 | 0 | 15 | 15 | 15 |
| 609265 | E15297 | 2011813018968 | 0 | 15 | 15 | 15 |
| 609265 | E15297 | 2011813018975 | 0 | 60 | 60 | 60 |
| 609270 | E15300 | 2011813019064 | 0 | 45 | 45 | 45 |
| 609270 | E15300 | 2011813019071 | 0 | 60 | 60 | 60 |
| 609270 | E15300 | 2011813019088 | 0 | 15 | 15 | 15 |
| 609271 | E15321 | 2011813016988 | 0 | 60 | 60 | 60 |

*FIG. 29.2A*

Customer : NEWGERM
Module : MULTI
Description : MULTI CURRENCY FORMAT
File Name : GM19005
Date/Time : 06/11/98 / 4:22:04 PM

<< ESPRIT GERMANY PP REPORT FOR SERVICE BUREAU >>

| | | | | | |
|---|---|---|---|---|---|
| 609271 E15321 | 2011813016995 | 0 | 45 | 45 | 45 |
| 609271 E15321 | 2011813016995 | 0 | 45 | 45 | 45 |
| 609271 E15321 | 2011813017008 | 0 | 30 | 30 | 30 |
| 609271 E15321 | 2011813017015 | 0 | 45 | 45 | 45 |
| 609271 E15321 | 2011813017022 | 0 | 45 | 45 | 45 |
| 609271 E15321 | 2011813017039 | 0 | 15 | 15 | 15 |
| 609271 E15321 | 2011813017046 | 0 | 15 | 15 | 15 |
| 609273 E15359 | 2011813017343 | 0 | 30 | 30 | 30 |
| 609273 E15359 | 2011813017350 | 0 | 45 | 45 | 45 |
| 609273 E15359 | 2011813017367 | 0 | 15 | 15 | 15 |
| 609273 E15359 | 2011813017374 | 0 | 15 | 15 | 15 |
| 609273 E15359 | 2011813017381 | 0 | 30 | 30 | 30 |
| 609273 E15359 | 2011813017398 | 0 | 30 | 30 | 30 |
| 609273 E15359 | 2011813017404 | 0 | 30 | 30 | 30 |
| 609525 E15361 | 2011813019095 | 0 | 165 | 165 | 165 |
| 609525 E15361 | 2011813019101 | 0 | 225 | 225 | 225 |
| 609526 E15362 | 2011813019132 | 0 | 180 | 180 | 180 |
| 609526 E15362 | 2011813019149 | 0 | 105 | 105 | 105 |
| 609527 E15363 | 2011813019170 | 0 | 405 | 405 | 405 |
| 609527 E15363 | 2011813019187 | 0 | 30 | 30 | 30 |
| 609527 E15363 | 2011813019194 | 0 | 270 | 270 | 270 |
| 609529 E15364 | 2011813019231 | 0 | 300 | 300 | 300 |
| 609529 E15364 | 2011813019248 | 0 | 30 | 30 | 30 |
| 609529 E15364 | 2011813019255 | 0 | 225 | 225 | 225 |
| 609592 E15295 | 2011813018807 | 0 | 345 | 345 | 345 |
| 609592 E15295 | 2011813018814 | 0 | 495 | 495 | 495 |
| 609592 E15295 | 2011813018821 | 0 | 30 | 30 | 30 |
| 609592 E15295 | 2011813018845 | 0 | 225 | 225 | 225 |
| 609592 E15295 | 2011813175241 | 0 | 15 | 15 | 15 |
| 609593 E15295 | 2011813018807 | 0 | 435 | 435 | 435 |
| 609593 E15295 | 2011813018814 | 0 | 780 | 780 | 780 |

*FIG. 29.2B*

Customer : NEWGERM
Module : MULTI
Description : MULTI CURRENCY FORMAT
File Name : GM19005
Date/Time : 06/11/98 / 4:22:05 PM

<< ESPRIT GERMANY PP REPORT FOR SERVICE BUREAU >>

| | | | | | |
|---|---|---|---|---|---|
| 609593 E15295 | 2011813018821 | 0 | 90 | 90 | 90 |
| 609593 E15295 | 2011813018845 | 0 | 225 | 225 | 225 |
| 609593 E15295 | 2011813175241 | 0 | 45 | 45 | 45 |
| 609595 E15297 | 2011813018968 | 0 | 75 | 75 | 75 |
| 609595 E15297 | 2011813018975 | 0 | 105 | 105 | 105 |
| 609596 E15297 | 2011813018968 | 0 | 225 | 225 | 225 |
| 609596 E15297 | 2011813018975 | 0 | 525 | 525 | 525 |
| 609598 E15300 | 2011813019064 | 0 | 420 | 420 | 420 |
| 609598 E15300 | 2011813019071 | 0 | 810 | 810 | 810 |
| 609598 E15300 | 2011813019088 | 0 | 180 | 180 | 180 |
| 609599 E15300 | 2011813019064 | 0 | 315 | 315 | 315 |
| 609599 E15300 | 2011813019071 | 0 | 555 | 555 | 555 |
| 609599 E15300 | 2011813019088 | 0 | 105 | 105 | 105 |
| 609686 E15200 | 2011813008365 | 0 | 75 | 75 | 75 |
| 609686 E15200 | 2011813008372 | 0 | 30 | 30 | 30 |
| 609686 E15200 | 2011813008389 | 0 | 15 | 15 | 15 |
| 609686 E15200 | 2011813008396 | 0 | 15 | 15 | 15 |
| 609688 E15204 | 2011813008549 | 0 | 735 | 735 | 735 |
| 609688 E15204 | 2011813008556 | 0 | 165 | 165 | 165 |
| 609688 E15204 | 2011813008563 | 0 | 795 | 795 | 795 |
| 609688 E15204 | 2011813008570 | 0 | 135 | 135 | 135 |
| 609688 E15204 | 2011813008587 | 0 | 585 | 585 | 585 |
| 609716 E15259 | 2011813016360 | 0 | 465 | 465 | 465 |
| 609716 E15259 | 2011813016377 | 0 | 180 | 180 | 180 |
| 609716 E15259 | 2011813016384 | 0 | 360 | 360 | 360 |
| 609716 E15259 | 2011813016391 | 0 | 165 | 165 | 165 |
| 609716 E15259 | 2011813016407 | 0 | 30 | 30 | 30 |
| 609716 E15259 | 2011813141383 | 0 | 45 | 45 | 45 |
| 609718 E15261 | 2011813016636 | 0 | 210 | 210 | 210 |
| 609718 E15261 | 2011813016643 | 0 | 255 | 255 | 255 |
| 609718 E15261 | 2011813016650 | 0 | 390 | 390 | 390 |
| 609718 E15261 | 2011813016667 | 0 | 285 | 285 | 285 |

*FIG. 29.3A*

Customer : NEWGERM
Module : MULTI
Description : MULTI CURRENCY FORMAT
File Name : GM19005
Date/Time : 06/11/98 / 4:22:04 PM

<< ESPRIT GERMANY PP REPORT FOR SERVICE BUREAU >>

| | | | | | |
|---|---|---|---|---|---|
| 609719 E15262 | 2011813172622 | 0 | 60 | 60 | 60 |
| 609719 E15262 | 2011813172639 | 0 | 135 | 135 | 135 |
| 609719 E15262 | 2011813172646 | 0 | 75 | 75 | 75 |
| 609719 E15262 | 2011813172653 | 0 | 105 | 105 | 105 |
| 609779 E26003 | 2011812974951 | 0 | 30 | 30 | 30 |
| 609781 E26004 | 2011812974968 | 0 | 360 | 360 | 360 |
| 609781 E26004 | 2011812974975 | 0 | 60 | 60 | 60 |
| 609782 E26005 | 2011812974982 | 0 | 285 | 285 | 285 |
| 609782 E26005 | 2011812974999 | 0 | 15 | 15 | 15 |
| 609784 E26009 | 2011812975354 | 0 | 180 | 180 | 180 |
| 609784 E26009 | 2011812975361 | 0 | 15 | 15 | 15 |
| 609981 E26453 | 2011812976689 | 0 | 75 | 75 | 75 |
| 610017 E15196 | 2011813019910 | 0 | 255 | 255 | 255 |
| 610017 E15196 | 2011813019927 | 0 | 210 | 210 | 210 |
| 610017 E15196 | 2011813019934 | 0 | 450 | 450 | 450 |
| 610021 E15197 | 2011813021760 | 0 | 135 | 135 | 135 |
| 610021 E15197 | 2011813021777 | 0 | 90 | 90 | 90 |
| 610042 E26022 | 2011812976412 | 0 | 30 | 30 | 30 |
| 610042 E26022 | 2011812976429 | 0 | 330 | 330 | 330 |
| 610048 E26023 | 2011812976436 | 0 | 15 | 15 | 15 |
| 610048 E26023 | 2011812976443 | 0 | 270 | 270 | 270 |
| 610057 E26024 | 2011812976450 | 0 | 30 | 60 | 60 |
| 610057 E26024 | 2011812976467 | 0 | 375 | 750 | 750 |
| 610067 E26026 | 2011812976498 | 0 | 45 | 90 | 90 |
| 610067 E26026 | 2011812976504 | 0 | 555 | 1110 | 1110 |
| 610094 E26027 | 2011813114714 | 0 | 15 | 15 | 15 |
| 610094 E26027 | 2011813114721 | 0 | 210 | 210 | 210 |
| 610099 E26028 | 2011812976535 | 0 | 60 | 60 | 60 |
| 610099 E26028 | 2011812976542 | 0 | 795 | 795 | 795 |
| 610292 E15203 | 2011813008495 | 0 | 300 | 300 | 300 |
| 610292 E15203 | 2011813008501 | 0 | 75 | 75 | 75 |

*FIG. 29.3B*

Customer : NEWGERM
Module : MULTI
Description : MULTI CURRENCY FORMAT
File Name : GM19005
Date/Time : 06/11/98 / 4:22:05 PM

<< ESPRIT GERMANY PP REPORT FOR SERVICE BUREAU >>

| | | | | | |
|---|---|---|---|---|---|
| 610292 E15203 | 2011813008518 | 0 | 165 | 165 | 165 |
| 610292 E15203 | 2011813008525 | 0 | 135 | 135 | 135 |
| 610292 E15203 | 2011813008532 | 0 | 315 | 315 | 315 |
| 610294 E15205 | 2011813008594 | 0 | 360 | 360 | 360 |
| 610294 E15205 | 2011813008600 | 0 | 270 | 270 | 270 |
| 610294 E15205 | 2011813008617 | 0 | 120 | 120 | 120 |
| 610294 E15205 | 2011813008624 | 0 | 195 | 195 | 195 |
| 610296 E15206 | 2011813008631 | 0 | 45 | 45 | 45 |
| 610296 E15206 | 2011813008648 | 0 | 30 | 30 | 30 |
| 610296 E15206 | 2011813008655 | 0 | 15 | 15 | 15 |
| 610296 E15206 | 2011813008662 | 0 | 15 | 15 | 15 |
| 610296 E15206 | 2011813008679 | 0 | 45 | 45 | 45 |
| 610395 E15192 | 2011813005586 | 0 | 45 | 45 | 45 |
| 610395 E15192 | 2011813005593 | 0 | 45 | 45 | 45 |
| 610395 E15192 | 2011813005609 | 0 | 45 | 45 | 45 |
| 610395 E15192 | 2011813138468 | 0 | 180 | 180 | 180 |
| 610395 E15192 | 2011813138475 | 0 | 165 | 165 | 165 |
| 610395 E15192 | 2011813138482 | 0 | 180 | 180 | 180 |
| 610396 E15192 | 2011813005586 | 0 | 30 | 30 | 30 |
| 610396 E15192 | 2011813005593 | 0 | 15 | 15 | 15 |
| 610396 E15192 | 2011813005609 | 0 | 15 | 15 | 15 |
| 610396 E15192 | 2011813138468 | 0 | 45 | 45 | 45 |
| 610396 E15192 | 2011813138475 | 0 | 30 | 30 | 30 |
| 610396 E15192 | 2011813138482 | 0 | 30 | 30 | 30 |
| 611015 E15204 | 2011813008549 | 0 | 195 | 195 | 195 |
| 611015 E15204 | 2011813008556 | 0 | 45 | 45 | 45 |
| 611015 E15204 | 2011813008563 | 0 | 120 | 120 | 120 |
| 611015 E15204 | 2011813008570 | 0 | 45 | 45 | 45 |
| 611015 E15204 | 2011813008587 | 0 | 120 | 120 | 120 |
| 611019 E15251 | 2011813009355 | 0 | 795 | 795 | 795 |
| 611019 E15251 | 2011813009362 | 0 | 585 | 585 | 585 |

*FIG. 29.4A*

Customer : NEWGERM
Module : MULTI
Description : MULTI CURRENCY FORMAT
File Name : GM19005
Date/Time : 06/11/98 / 4:22:04 PM

<< ESPRIT GERMANY PP REPORT FOR SERVICE BUREAU >>

| | | | | | |
|---|---|---|---|---|---|
| 611019 E15251 | 2011813009379 | 0 | 135 | 135 | 135 |
| 611019 E15251 | 2011813009386 | 0 | 345 | 345 | 345 |
| 611019 E15251 | 2011813009393 | 0 | 405 | 405 | 405 |
| 611019 E15251 | 2011813009409 | 0 | 150 | 150 | 150 |
| 611019 E15251 | 2011813009416 | 0 | 60 | 60 | 60 |
| 611028 E15259 | 2011813016360 | 0 | 600 | 600 | 600 |
| 611028 E15259 | 2011813016377 | 0 | 300 | 300 | 300 |
| 611028 E15259 | 2011813016384 | 0 | 315 | 315 | 315 |
| 611028 E15259 | 2011813016391 | 0 | 60 | 60 | 60 |
| 611028 E15259 | 2011813016407 | 0 | 30 | 30 | 30 |
| 611028 E15259 | 2011813141383 | 0 | 30 | 30 | 30 |
| 611029 E15261 | 2011813016636 | 0 | 285 | 285 | 285 |
| 611029 E15261 | 2011813016643 | 0 | 45 | 45 | 45 |
| 611029 E15261 | 2011813016650 | 0 | 45 | 45 | 45 |
| 611029 E15261 | 2011813016667 | 0 | 75 | 75 | 75 |
| 611030 E15262 | 2011813172622 | 0 | 30 | 30 | 30 |
| 611030 E15262 | 2011813172639 | 0 | 30 | 30 | 30 |
| 611030 E15262 | 2011813172646 | 0 | 15 | 15 | 15 |
| 611030 E15262 | 2011813172653 | 0 | 30 | 30 | 30 |
| 611031 E15291 | 2011813017633 | 0 | 900 | 900 | 900 |
| 611031 E15291 | 2011813017640 | 0 | 540 | 540 | 540 |
| 611031 E15291 | 2011813017657 | 0 | 150 | 150 | 150 |
| 611031 E15291 | 2011813017664 | 0 | 255 | 255 | 255 |
| 611031 E15291 | 2011813017671 | 0 | 510 | 510 | 510 |
| 611031 E15291 | 2011813017688 | 0 | 195 | 195 | 195 |
| 611031 E15291 | 2011813017695 | 0 | 30 | 30 | 30 |
| 611033 E15321 | 2011813016988 | 0 | 285 | 285 | 285 |
| 611033 E15321 | 2011813016995 | 0 | 240 | 240 | 240 |
| 611033 E15321 | 2011813017008 | 0 | 30 | 30 | 30 |
| 611033 E15321 | 2011813017015 | 0 | 75 | 75 | 75 |
| 611033 E15321 | 2011813017022 | 0 | 165 | 165 | 165 |

*FIG. 29.4B*

| Customer | : NEWGERM |
|---|---|
| Module | : MULTI |
| Description | : MULTI CURRENCY FORMAT |
| File Name | : GM19005 |
| Date/Time | : 06/11/98 / 4:22:05 PM |

<< ESPRIT GERMANY PP REPORT FOR SERVICE BUREAU>>

| | | | | | |
|---|---|---|---|---|---|
| 611033 E15321 | 2011813017039 | 0 | 45 | 45 | 45 |
| 611033 E15321 | 2011813017046 | 0 | 15 | 15 | 15 |
| 611035 E15359 | 2011813017343 | 0 | 255 | 255 | 255 |
| 611035 E15359 | 2011813017350 | 0 | 195 | 195 | 195 |
| 611035 E15359 | 2011813017367 | 0 | 45 | 45 | 45 |
| 611035 E15359 | 2011813017374 | 0 | 90 | 90 | 90 |
| 611035 E15359 | 2011813017381 | 0 | 165 | 165 | 165 |
| 611035 E15359 | 2011813017398 | 0 | 45 | 45 | 45 |
| 611036 E15361 | 2011813019095 | 0 | 135 | 135 | 135 |
| 611036 E15361 | 2011813019101 | 0 | 240 | 240 | 240 |
| 611043 E15362 | 2011813019132 | 0 | 45 | 45 | 45 |
| 611043 E15362 | 2011813019149 | 0 | 30 | 30 | 30 |
| 611044 E15363 | 2011813019170 | 0 | 255 | 255 | 255 |
| 611044 E15363 | 2011813019187 | 0 | 15 | 15 | 15 |
| 611044 E15363 | 2011813019194 | 0 | 195 | 195 | 195 |
| 611045 E15364 | 2011813019231 | 0 | 60 | 60 | 60 |
| 611045 E15364 | 2011813019248 | 0 | 15 | 15 | 15 |
| 611045 E15364 | 2011813019255 | 0 | 60 | 60 | 60 |
| 611046 E26290 | 2011813019668 | 0 | 345 | 345 | 345 |
| 611046 E26290 | 2011813019675 | 0 | 30 | 30 | 30 |
| 611046 E26290 | 2011813019682 | 0 | 345 | 345 | 345 |
| 611046 E26290 | 2011813019699 | 0 | 165 | 165 | 165 |
| 611047 E26293 | 2011813019767 | 0 | 30 | 30 | 30 |
| 611047 E26293 | 2011813019774 | 0 | 45 | 45 | 45 |
| 611048 E26293 | 2011813019767 | 0 | 195 | 195 | 195 |
| 611048 E26293 | 2011813019774 | 0 | 315 | 315 | 315 |
| | | | | 35910 | 35910 |

*FIG. 29.5A*

Customer : NEWGERM
Module : MULTI
Description : MULTI CURRENCY FORMAT
File Name : GM19005
Date/Time : 06/11/98 / 4:22:05 PM

<<  ESPRIT  GERMANY  PP REPORT FOR SERVICE BUREAU>>

SEASON: E    HT_REF: BE

| SPO | STYLE | CODE | OLD_QTY | NEW_QTY | QTY | RQTY |
|---|---|---|---|---|---|---|
| 610951 | E20953 | 2011812895881 | 0 | 15 | 15 | 15 |
| 610951 | E20953 | 2011812895898 | 0 | 60 | 60 | 60 |
| 610951 | E20953 | 2011812895928 | 0 | 30 | 30 | 30 |
| 610951 | E20953 | 2011812895935 | 0 | 90 | 90 | 90 |
| 610951 | E20953 | 2011812895966 | 0 | 45 | 45 | 45 |
| 610951 | E20953 | 2011812895973 | 0 | 210 | 210 | 210 |
| 610951 | E20953 | 2011812895997 | 0 | 15 | 15 | 15 |
| 610951 | E20953 | 2011812896048 | 0 | 30 | 30 | 30 |
| 610951 | E20953 | 2011812896055 | 0 | 180 | 180 | 180 |
| 610951 | E20953 | 2011812896079 | 0 | 15 | 15 | 15 |
| 610951 | E20953 | 2011812896086 | 0 | 60 | 60 | 60 |
| 610951 | E20953 | 2011812896093 | 0 | 195 | 195 | 195 |
| 610951 | E20953 | 2011812896116 | 0 | 15 | 15 | 15 |
| 610951 | E20953 | 2011812896987 | 0 | 30 | 30 | 30 |
| 610951 | E20953 | 2011812897007 | 0 | 30 | 30 | 30 |
| 610951 | E20953 | 2011812897014 | 0 | 15 | 15 | 15 |
| 610952 | E20954 | 2011812896161 | 0 | 30 | 30 | 30 |
| 610952 | E20954 | 2011812896178 | 0 | 30 | 30 | 30 |
| 610952 | E20954 | 2011812896208 | 0 | 45 | 45 | 45 |
| 610952 | E20954 | 2011812896215 | 0 | 120 | 120 | 120 |
| 610952 | E20954 | 2011812896246 | 0 | 15 | 15 | 15 |
| 610952 | E20954 | 2011812896253 | 0 | 60 | 60 | 60 |
| 610952 | E20954 | 2011812896284 | 0 | 30 | 30 | 30 |
| 610952 | E20954 | 2011812896291 | 0 | 30 | 30 | 30 |
| 610952 | E20954 | 2011812896314 | 0 | 15 | 15 | 15 |
| 610952 | E20954 | 2011812896321 | 0 | 15 | 15 | 15 |
| 610952 | E20954 | 2011812896338 | 0 | 45 | 45 | 45 |

*FIG. 29.5B*

Customer    : NEWGERM
Module      : MULTI
Description : MULTI CURRENCY FORMAT
File Name   : GM19005
Date/Time   : 06/11/98 / 4:22:05 PM

<< ESPRIT GERMANY PP REPORT FOR SERVICE BUREAU >>

| | | | | | |
|---|---|---|---|---|---|
| 610952 E20954 | 2011812896352 | 0 | 30 | 30 | 30 |
| 610952 E20954 | 2011812896369 | 0 | 60 | 60 | 60 |
| 610952 E20954 | 2011812896376 | 0 | 165 | 165 | 165 |
| 610952 E20954 | 2011812896390 | 0 | 15 | 15 | 15 |
| 610952 E20954 | 2011812897083 | 0 | 15 | 15 | 15 |
| 610953 E20955 | 2011812896505 | 0 | 30 | 30 | 30 |
| 610953 E20955 | 2011812896512 | 0 | 90 | 90 | 90 |
| 610953 E20955 | 2011812896529 | 0 | 15 | 15 | 15 |
| 610953 E20955 | 2011812896550 | 0 | 15 | 15 | 15 |
| 610953 E20955 | 2011812896567 | 0 | 45 | 45 | 45 |
| 610953 E20955 | 2011812896598 | 0 | 15 | 15 | 15 |
| 610953 E20955 | 2011812896703 | 0 | 45 | 45 | 45 |
| 610953 E20955 | 2011812896710 | 0 | 135 | 135 | 135 |
| 610953 E20955 | 2011812896727 | 0 | 15 | 15 | 15 |
| 610953 E20955 | 2011812896741 | 0 | 15 | 15 | 15 |
| 610956 E20956 | 2011812897199 | 0 | 15 | 15 | 15 |
| 610956 E20956 | 2011812897205 | 0 | 75 | 75 | 75 |
| 610956 E20956 | 2011812897212 | 0 | 15 | 15 | 15 |
| 610956 E20956 | 2011812897243 | 0 | 45 | 45 | 45 |
| 610956 E20956 | 2011812897250 | 0 | 60 | 60 | 60 |
| 610956 E20956 | 2011812897281 | 0 | 15 | 15 | 15 |
| 610956 E20956 | 2011812897397 | 0 | 45 | 45 | 45 |
| 610956 E20956 | 2011812897403 | 0 | 45 | 45 | 45 |
| 610956 E20956 | 2011812897410 | 0 | 15 | 15 | 15 |
| 610956 E20956 | 2011812897434 | 0 | 30 | 30 | 30 |
| 610957 E20957 | 2011812897441 | 0 | 15 | 15 | 15 |
| 610957 E20957 | 2011812897458 | 0 | 45 | 45 | 45 |
| 610957 E20957 | 2011812897540 | 0 | 240 | 240 | 240 |
| 610957 E20957 | 2011812897557 | 0 | 375 | 375 | 375 |
| 610957 E20957 | 2011812897564 | 0 | 45 | 45 | 45 |

*FIG. 29.6A*

Customer : NEWGERM
Module : MULTI
Description : MULTI CURRENCY FORMAT
File Name : GM19005
Date/Time : 06/11/98 / 4:22:05 PM

<< ESPRIT GERMANY PP REPORT FOR SERVICE BUREAU >>

| | | | | | | |
|---|---|---|---|---|---|---|
| 610957 | E20957 | 2011812897588 | 0 | 30 | 30 | 30 |
| 610957 | E20957 | 2011812897595 | 0 | 15 | 15 | 15 |
| 610957 | E20957 | 2011812897601 | 0 | 15 | 15 | 15 |
| 610958 | E20958 | 2011812897748 | 0 | 15 | 15 | 15 |
| 610958 | E20958 | 2011812897755 | 0 | 45 | 45 | 45 |
| 610958 | E20958 | 2011812897793 | 0 | 30 | 30 | 30 |
| 610958 | E20958 | 2011812897809 | 0 | 45 | 45 | 45 |
| 610958 | E20958 | 2011812897830 | 0 | 15 | 15 | 15 |
| 610958 | E20958 | 2011812897847 | 0 | 30 | 30 | 30 |
| 610958 | E20958 | 2011812897854 | 0 | 60 | 60 | 60 |
| 610958 | E20958 | 2011812897861 | 0 | 15 | 15 | 15 |
| 610958 | E20958 | 2011812897885 | 0 | 15 | 15 | 15 |
| 610958 | E20958 | 2011812897946 | 0 | 165 | 165 | 165 |
| 610958 | E20958 | 2011812897953 | 0 | 360 | 360 | 360 |
| 610958 | E20958 | 2011812897960 | 0 | 30 | 30 | 30 |
| 610958 | E20958 | 2011812897984 | 0 | 30 | 30 | 30 |
| 610958 | E20958 | 2011812897991 | 0 | 90 | 90 | 90 |
| 610958 | E20958 | 2011812898004 | 0 | 165 | 165 | 165 |
| 610958 | E20958 | 2011812898011 | 0 | 15 | 15 | 15 |
| 610958 | E20958 | 2011812898035 | 0 | 15 | 15 | 15 |
| 610959 | E20959 | 2011812898042 | 0 | 15 | 15 | 15 |
| 610959 | E20959 | 2011812898059 | 0 | 30 | 30 | 30 |
| 610959 | E20959 | 2011812898080 | 0 | 15 | 15 | 15 |
| 610959 | E20959 | 2011812898097 | 0 | 15 | 15 | 15 |
| 610959 | E20959 | 2011812898103 | 0 | 30 | 30 | 30 |
| 610959 | E20959 | 2011812898134 | 0 | 15 | 15 | 15 |
| 610959 | E20959 | 2011812898141 | 0 | 30 | 30 | 30 |
| 610959 | E20959 | 2011812898158 | 0 | 30 | 30 | 30 |
| 610959 | E20959 | 2011812898240 | 0 | 150 | 150 | 150 |
| 610959 | E20959 | 2011812898257 | 0 | 315 | 315 | 315 |
| 610959 | E20959 | 2011812898264 | 0 | 15 | 15 | 15 |
| 610959 | E20959 | 2011812898288 | 0 | 30 | 30 | 30 |
| 610959 | E20959 | 2011812898295 | 0 | 75 | 75 | 75 |

*FIG. 29.6B*

| Customer | : NEWGERM |
|---|---|
| Module | : MULTI |
| Description | : MULTI CURRENCY FORMAT |
| File Name | : GM19005 |
| Date/Time | : 06/11/98 / 4:22:06 PM |

<< ESPRIT GERMANY PP REPORT FOR SERVICE BUREAU >>

| | | | | | |
|---|---|---|---|---|---|
| 610959 | E20959 | 2011812898301 | 0 | 75 | 75 | 75 |
| 610959 | E20959 | 2011812898318 | 0 | 15 | 15 | 15 |
| 610959 | E20959 | 2011812898332 | 0 | 45 | 45 | 45 |
| 610963 | E20962 | 2011812898592 | 0 | 30 | 30 | 30 |
| 610963 | E20962 | 2011812898608 | 0 | 60 | 60 | 60 |
| 610963 | E20962 | 2011812898646 | 0 | 270 | 270 | 270 |
| 610963 | E20962 | 2011812898653 | 0 | 345 | 345 | 345 |
| 610963 | E20962 | 2011812898660 | 0 | 75 | 75 | 75 |
| 610963 | E20962 | 2011812898684 | 0 | 30 | 30 | 30 |
| 610963 | E20962 | 2011812898691 | 0 | 15 | 15 | 15 |
| 610963 | E20962 | 2011812898707 | 0 | 15 | 15 | 15 |
| 610967 | E20967 | 2011812900134 | 0 | 60 | 60 | 60 |
| 610967 | E20967 | 2011812900172 | 0 | 30 | 30 | 30 |
| 610967 | E20967 | 2011812900219 | 0 | 270 | 270 | 270 |
| 610967 | E20967 | 2011812900226 | 0 | 15 | 15 | 15 |
| 610967 | E20967 | 2011812900240 | 0 | 30 | 30 | 30 |
| 610967 | E20967 | 2011812900257 | 0 | 240 | 240 | 240 |
| 610967 | E20967 | 2011812900264 | 0 | 30 | 30 | 30 |
| 610967 | E20967 | 2011812900288 | 0 | 30 | 30 | 30 |
| 610967 | E20967 | 2011813029476 | 0 | 15 | 15 | 15 |
| 610967 | E20967 | 2011813029483 | 0 | 30 | 30 | 30 |
| 610967 | E20967 | 2011813029490 | 0 | 90 | 90 | 90 |
| 610967 | E20967 | 2011813029506 | 0 | 75 | 75 | 75 |
| 610976 | E20998 | 2011813182140 | 0 | 45 | 45 | 45 |
| 610976 | E20998 | 2011813182157 | 0 | 45 | 45 | 45 |
| 610976 | E20998 | 2011813182164 | 0 | 45 | 45 | 45 |
| 610976 | E20998 | 2011813182188 | 0 | 60 | 60 | 60 |
| 610976 | E20998 | 2011813182201 | 0 | 60 | 60 | 60 |
| 610977 | E20999 | 2011813174787 | 0 | 45 | 45 | 45 |
| 610977 | E20999 | 2011813174794 | 0 | 60 | 60 | 60 |
| 610977 | E20999 | 2011813174800 | 0 | 15 | 15 | 15 |
| 610977 | E20999 | 2011813174817 | 0 | 15 | 15 | 15 |

*FIG. 29.7A*

Customer    : NEWGERM
Module      : MULTI
Description : MULTI CURRENCY FORMAT
File Name   : GM19005
Date/Time   : 06/11/98 / 4:22:06 PM

<< ESPRIT GERMANY PP REPORT FOR SERVICE BUREAU >>

| | | | | | | |
|---|---|---|---|---|---|---|
| 610977 | E20999 | 2011813174824 | 0 | 30 | 30 | 30 |
| 610977 | E20999 | 2011813174831 | 0 | 15 | 15 | 15 |
| 610977 | E20999 | 2011813174909 | 0 | 75 | 75 | 75 |
| 610977 | E20999 | 2011813174916 | 0 | 105 | 105 | 105 |
| | | | | ----- | ------ | |
| | | | | | 7725 | 7725 |
| | | | | | ===== | ====== |

SEASON: E    HT_REF: KG

| SPO | STYLE | CODE | OLD_QTY | NEW_QTY | QTY | RQTY |
|---|---|---|---|---|---|---|
| 610059 | E02132 | 2011813189026 | 0 | 60 | 60 | 60 |
| 610059 | E02132 | 2011813189033 | 0 | 30 | 30 | 30 |
| 610059 | E02132 | 2011813189040 | 0 | 15 | 15 | 15 |
| 610059 | E02132 | 2011813189057 | 0 | 15 | 15 | 15 |
| 610059 | E02132 | 2011813189071 | 0 | 90 | 90 | 90 |
| 610807 | E02930 | 2011812872806 | 0 | 60 | 60 | 60 |
| 610807 | E02930 | 2011812872813 | 0 | 45 | 45 | 45 |
| 610807 | E02930 | 2011812872837 | 0 | 105 | 105 | 105 |
| 610807 | E02930 | 2011812872851 | 0 | 60 | 60 | 60 |
| 610807 | E02930 | 2011812872868 | 0 | 45 | 45 | 45 |
| 610807 | E02930 | 2011812872875 | 0 | 15 | 15 | 15 |
| 610807 | E02930 | 2011812872882 | 0 | 165 | 165 | 165 |
| 610807 | E02930 | 2011812872905 | 0 | 120 | 120 | 120 |
| 610807 | E02930 | 2011812872912 | 0 | 105 | 105 | 105 |
| 610807 | E02930 | 2011812872929 | 0 | 15 | 15 | 15 |
| 610807 | E02930 | 2011812872936 | 0 | 30 | 30 | 30 |
| 610807 | E02930 | 2011812873001 | 0 | 45 | 45 | 45 |
| 610807 | E02930 | 2011812873018 | 0 | 75 | 75 | 75 |
| 610807 | E02930 | 2011812873032 | 0 | 45 | 45 | 45 |
| 610807 | E02930 | 2011812873049 | 0 | 30 | 30 | 30 |

*FIG. 29.7B*

Customer     : NEWGERM
Module       : MULTI
Description  : MULTI CURRENCY FORMAT
File Name    : GM19005
Date/Time    : 06/11/98 / 4:22:06 PM

<< ESPRIT  GERMANY  PP REPORT FOR SERVICE BUREAU>>

| | | | | |
|---|---|---|---|---|
| 610807 E02930 | 2011812873056 | 0 | 120 | 120 | 120 |
| 610807 E02930 | 2011812873063 | 0 | 150 | 150 | 150 |
| 610807 E02930 | 2011812873070 | 0 | 15 | 15 | 15 |
| 610807 E02930 | 2011812873087 | 0 | 60 | 60 | 60 |
| 610807 E02930 | 2011812873094 | 0 | 30 | 30 | 30 |
| 610808 E02931 | 2011812873100 | 0 | 45 | 45 | 45 |
| 610808 E02931 | 2011812873117 | 0 | 45 | 45 | 45 |
| 610808 E02931 | 2011812873131 | 0 | 15 | 15 | 15 |
| 610808 E02931 | 2011812873148 | 0 | 15 | 15 | 15 |
| 610808 E02931 | 2011812873155 | 0 | 315 | 315 | 315 |
| 610808 E02931 | 2011812873162 | 0 | 315 | 315 | 315 |
| 610808 E02931 | 2011812873186 | 0 | 120 | 120 | 120 |
| 610808 E02931 | 2011812873193 | 0 | 45 | 45 | 45 |
| 610809 E02932 | 2011812873308 | 0 | 105 | 105 | 105 |
| 610809 E02932 | 2011812873315 | 0 | 120 | 120 | 120 |
| 610809 E02932 | 2011812873339 | 0 | 30 | 30 | 30 |
| 610809 E02932 | 2011812873353 | 0 | 270 | 270 | 270 |
| 610809 E02932 | 2011812873360 | 0 | 285 | 285 | 285 |
| 610809 E02932 | 2011812873384 | 0 | 105 | 105 | 105 |
| 610809 E02932 | 2011812873391 | 0 | 60 | 60 | 60 |
| 610809 E02932 | 2011812873407 | 0 | 120 | 120 | 120 |
| 610809 E02932 | 2011812873414 | 0 | 120 | 120 | 120 |
| 610809 E02932 | 2011812873438 | 0 | 60 | 60 | 60 |
| 610809 E02932 | 2011812873445 | 0 | 30 | 30 | 30 |
| 610809 E02932 | 2011812873452 | 0 | 90 | 90 | 90 |
| 610809 E02932 | 2011812873469 | 0 | 90 | 90 | 90 |
| 610809 E02932 | 2011812873483 | 0 | 30 | 30 | 30 |
| 610809 E02932 | 2011812873490 | 0 | 30 | 30 | 30 |
| 610810 E02933 | 2011812873506 | 0 | 660 | 660 | 660 |
| 610810 E02933 | 2011812873513 | 0 | 840 | 840 | 840 |
| 610810 E02933 | 2011812873537 | 0 | 225 | 225 | 225 |
| 610810 E02933 | 2011812873544 | 0 | 180 | 180 | 180 |

*FIG. 29.8A*

Customer    : NEWGERM
Module      : MULTI
Description : MULTI CURRENCY FORMAT
File Name   : GM19005
Date/Time   : 06/11/98 / 4:22:06 PM

<< ESPRIT  GERMANY  PP REPORT FOR SERVICE BUREAU >>

| | | | | |
|---|---|---|---|---|
| 610810 E02933 | 2011812873551 | 0 | 435 | 435 | 435 |
| 610810 E02933 | 2011812873568 | 0 | 495 | 495 | 495 |
| 610810 E02933 | 2011812873575 | 0 | 45 | 45 | 45 |
| 610810 E02933 | 2011812873582 | 0 | 120 | 120 | 120 |
| 610810 E02933 | 2011812873599 | 0 | 75 | 75 | 75 |
| 610810 E02933 | 2011812873605 | 0 | 60 | 60 | 60 |
| 610810 E02933 | 2011812873612 | 0 | 60 | 60 | 60 |
| 610810 E02933 | 2011812873636 | 0 | 30 | 30 | 30 |
| 610810 E02933 | 2011813192354 | 0 | 30 | 30 | 30 |
| 610811 E02934 | 2011812873759 | 0 | 45 | 45 | 45 |
| 610811 E02934 | 2011812873766 | 0 | 30 | 30 | 30 |
| 610811 E02934 | 2011812873780 | 0 | 45 | 45 | 45 |
| 610811 E02934 | 2011812873797 | 0 | 15 | 15 | 15 |
| 610812 E02936 | 2011812874152 | 0 | 30 | 30 | 30 |
| 610812 E02936 | 2011812874169 | 0 | 15 | 15 | 15 |
| 610812 E02936 | 2011812874183 | 0 | 75 | 75 | 75 |
| 610812 E02936 | 2011812874305 | 0 | 15 | 15 | 15 |
| 610812 E02936 | 2011812874329 | 0 | 45 | 45 | 45 |
| 610812 E02936 | 2011812874336 | 0 | 60 | 60 | 60 |
| 610813 E02937 | 2011812874350 | 0 | 375 | 375 | 375 |
| 610813 E02937 | 2011812874367 | 0 | 435 | 435 | 435 |
| 610813 E02937 | 2011812874374 | 0 | 60 | 60 | 60 |
| 610813 E02937 | 2011812874381 | 0 | 240 | 240 | 240 |
| 610813 E02937 | 2011812874398 | 0 | 105 | 105 | 105 |
| 610813 E02937 | 2011812874404 | 0 | 90 | 90 | 90 |
| 610813 E02937 | 2011812874411 | 0 | 90 | 90 | 90 |
| 610813 E02937 | 2011812874435 | 0 | 60 | 60 | 60 |
| 610813 E02937 | 2011812874442 | 0 | 30 | 30 | 30 |
| 610813 E02937 | 2011813192514 | 0 | 30 | 30 | 30 |
| 610822 E02945 | 2011812875807 | 0 | 135 | 135 | 135 |
| 610822 E02945 | 2011812875814 | 0 | 135 | 135 | 135 |
| 610822 E02945 | 2011812875838 | 0 | 45 | 45 | 45 |
| 610822 E02945 | 2011812875852 | 0 | 120 | 120 | 120 |

*FIG. 29.8B*

Customer : NEWGERM
Module : MULTI
Description : MULTI CURRENCY FORMAT
File Name : GM19005
Date/Time : 06/11/98 / 4:22:06 PM

<< ESPRIT GERMANY PP REPORT FOR SERVICE BUREAU >>

| | | | | | | |
|---|---|---|---|---|---|---|
| 610822 | E02945 | 2011812875869 | 0 | 150 | 150 | 150 |
| 610822 | E02945 | 2011812875883 | 0 | 45 | 45 | 45 |
| 610822 | E02945 | 2011812875890 | 0 | 45 | 45 | 45 |
| 610822 | E02945 | 2011812875906 | 0 | 90 | 90 | 90 |
| 610822 | E02945 | 2011812875913 | 0 | 90 | 90 | 90 |
| 610822 | E02945 | 2011812875937 | 0 | 30 | 30 | 30 |
| 610822 | E02945 | 2011812875951 | 0 | 45 | 45 | 45 |
| 610822 | E02945 | 2011812875968 | 0 | 45 | 45 | 45 |
| 610822 | E02945 | 2011812875982 | 0 | 15 | 15 | 15 |
| 610824 | E02946 | 2011812876002 | 0 | 60 | 60 | 60 |
| 610824 | E02946 | 2011812876019 | 0 | 60 | 60 | 60 |
| 610824 | E02946 | 2011812876033 | 0 | 15 | 15 | 15 |
| 610824 | E02946 | 2011812876057 | 0 | 90 | 90 | 90 |
| 610824 | E02946 | 2011812876064 | 0 | 105 | 105 | 105 |
| 610824 | E02946 | 2011812876088 | 0 | 30 | 30 | 30 |
| 610824 | E02946 | 2011812876095 | 0 | 30 | 30 | 30 |
| 610824 | E02946 | 2011812876101 | 0 | 60 | 60 | 60 |
| 610824 | E02946 | 2011812876118 | 0 | 45 | 45 | 45 |
| 610824 | E02946 | 2011812876132 | 0 | 15 | 15 | 15 |
| 610824 | E02946 | 2011812876156 | 0 | 30 | 30 | 30 |
| 610824 | E02946 | 2011812876163 | 0 | 30 | 30 | 30 |
| 610824 | E02946 | 2011812876187 | 0 | 15 | 15 | 15 |
| 610824 | E02946 | 2011813192897 | 0 | 60 | 60 | 60 |
| 610824 | E02946 | 2011813192903 | 0 | 30 | 30 | 30 |
| 610825 | E02948 | 2011812877474 | 0 | 30 | 30 | 30 |
| 610825 | E02948 | 2011812877481 | 0 | 30 | 30 | 30 |
| 610825 | E02948 | 2011812877504 | 0 | 45 | 45 | 45 |
| 610825 | E02948 | 2011812877528 | 0 | 45 | 45 | 45 |
| 610825 | E02948 | 2011812877535 | 0 | 30 | 30 | 30 |
| 610825 | E02948 | 2011812877559 | 0 | 30 | 30 | 30 |
| 610825 | E02948 | 2011812877573 | 0 | 180 | 180 | 180 |
| 610825 | E02948 | 2011812877580 | 0 | 165 | 165 | 165 |

*FIG. 29.9A*

Customer : NEWGERM
Module : MULTI
Description : MULTI CURRENCY FORMAT
File Name : GM19005
Date/Time : 06/11/98 / 4:22:06 PM

<< ESPRIT GERMANY PP REPORT FOR SERVICE BUREAU >>

| | | | | | | |
|---|---|---|---|---|---|---|
| 610825 | E02948 | 2011812877597 | 0 | 15 | 15 | 15 |
| 610825 | E02948 | 2011812877603 | 0 | 90 | 90 | 90 |
| 610825 | E02948 | 2011812877627 | 0 | 165 | 165 | 165 |
| 610825 | E02948 | 2011812877634 | 0 | 135 | 135 | 135 |
| 610825 | E02948 | 2011812877658 | 0 | 90 | 90 | 90 |
| 610825 | E02948 | 2011813180238 | 0 | 75 | 75 | 75 |
| 610825 | E02948 | 2011813180245 | 0 | 75 | 75 | 75 |
| 610825 | E02948 | 2011813180252 | 0 | 15 | 15 | 15 |
| 610825 | E02948 | 2011813180269 | 0 | 15 | 15 | 15 |
| 610825 | E02948 | 2011813193993 | 0 | 30 | 30 | 30 |
| 610825 | E02948 | 2011813194013 | 0 | 30 | 30 | 30 |
| 610827 | E02949 | 2011812877825 | 0 | 135 | 135 | 135 |
| 610827 | E02949 | 2011812877832 | 0 | 135 | 135 | 135 |
| 610827 | E02949 | 2011812877856 | 0 | 60 | 60 | 60 |
| 610827 | E02949 | 2011812877863 | 0 | 30 | 30 | 30 |
| 610827 | E02949 | 2011812877870 | 0 | 75 | 75 | 75 |
| 610827 | E02949 | 2011812877887 | 0 | 60 | 60 | 60 |
| 610827 | E02949 | 2011812877900 | 0 | 30 | 30 | 30 |
| 610827 | E02949 | 2011812877917 | 0 | 15 | 15 | 15 |
| 610835 | E02957 | 2011812880023 | 0 | 45 | 45 | 45 |
| 610835 | E02957 | 2011812880030 | 0 | 45 | 45 | 45 |
| 610835 | E02957 | 2011812880054 | 0 | 15 | 15 | 15 |
| 610835 | E02957 | 2011812880061 | 0 | 15 | 15 | 15 |
| 610835 | E02957 | 2011812880078 | 0 | 120 | 120 | 120 |
| 610835 | E02957 | 2011812880085 | 0 | 120 | 120 | 120 |
| 610835 | E02957 | 2011812880108 | 0 | 30 | 30 | 30 |
| 610835 | E02957 | 2011812880115 | 0 | 30 | 30 | 30 |
| 610839 | E02960 | 2011812880672 | 0 | 45 | 45 | 45 |
| 610839 | E02960 | 2011812880689 | 0 | 60 | 60 | 60 |
| 610839 | E02960 | 2011812880702 | 0 | 30 | 30 | 30 |
| 610839 | E02960 | 2011812880719 | 0 | 30 | 30 | 30 |
| 610839 | E02960 | 2011812880726 | 0 | 195 | 195 | 195 |

*FIG. 29.9B*

Customer : NEWGERM
Module : MULTI
Description : MULTI CURRENCY FORMAT
File Name : GM19005
Date/Time : 06/11/98 / 4:22:07 PM

<< ESPRIT GERMANY PP REPORT FOR SERVICE BUREAU >>

| | | | | | |
|---|---|---|---|---|---|
| 610839 E02960 | 2011812880733 | 0 | 195 | 195 | 195 |
| 610839 E02960 | 2011812880740 | 0 | 60 | 60 | 60 |
| 610839 E02960 | 2011812880757 | 0 | 75 | 75 | 75 |
| 610839 E02960 | 2011812880764 | 0 | 30 | 30 | 30 |
| 610839 E02960 | 2011812880771 | 0 | 135 | 135 | 135 |
| 610839 E02960 | 2011812880788 | 0 | 180 | 180 | 180 |
| 610839 E02960 | 2011812880801 | 0 | 45 | 45 | 45 |
| 610839 E02960 | 2011812880818 | 0 | 60 | 60 | 60 |
| 610839 E02960 | 2011812880825 | 0 | 150 | 150 | 150 |
| 610839 E02960 | 2011812880832 | 0 | 150 | 150 | 150 |
| 610839 E02960 | 2011812880849 | 0 | 60 | 60 | 60 |
| 610839 E02960 | 2011812880856 | 0 | 60 | 60 | 60 |
| 610839 E02960 | 2011812880863 | 0 | 30 | 30 | 30 |
| 610839 E02960 | 2011813194563 | 0 | 60 | 60 | 60 |
| 610839 E02960 | 2011813194587 | 0 | 45 | 45 | 45 |
| 610840 E02961 | 2011812880924 | 0 | 75 | 75 | 75 |
| 610840 E02961 | 2011812880931 | 0 | 90 | 90 | 90 |
| 610840 E02961 | 2011812880955 | 0 | 30 | 30 | 30 |
| 610840 E02961 | 2011812880962 | 0 | 15 | 15 | 15 |
| 610840 E02961 | 2011812881020 | 0 | 30 | 30 | 30 |
| 610840 E02961 | 2011812881037 | 0 | 30 | 30 | 30 |
| 610840 E02961 | 2011812881051 | 0 | 30 | 30 | 30 |
| 610840 E02961 | 2011812881068 | 0 | 15 | 15 | 15 |
| 610840 E02961 | 2011812881075 | 0 | 30 | 30 | 30 |
| 610840 E02961 | 2011812881082 | 0 | 45 | 45 | 45 |
| 610840 E02961 | 2011812881105 | 0 | 15 | 15 | 15 |
| 610840 E02961 | 2011812881112 | 0 | 15 | 15 | 15 |
| 610841 E02963 | 2011812881327 | 0 | 45 | 45 | 45 |
| 610841 E02963 | 2011812881334 | 0 | 45 | 45 | 45 |
| 610841 E02963 | 2011812881358 | 0 | 15 | 15 | 15 |
| 610841 E02963 | 2011812881365 | 0 | 15 | 15 | 15 |
| 610841 E02963 | 2011812881426 | 0 | 60 | 60 | 60 |
| 610841 E02963 | 2011812881433 | 0 | 60 | 60 | 60 |

*FIG. 29.10A*

Customer : NEWGERM
Module : MULTI
Description : MULTI CURRENCY FORMAT
File Name : GM19005
Date/Time : 06/11/98 / 4:22:07 PM

<< ESPRIT GERMANY PP REPORT FOR SERVICE BUREAU >>

| | | | | |
|---|---|---|---|---|
| 610841 E02963 2011812881457 | 0 | 15 | 15 | 15 |
| 610841 E02963 2011812881464 | 0 | 15 | 15 | 15 |
| 610841 E02963 2011812881471 | 0 | 45 | 45 | 45 |
| 610841 E02963 2011812881488 | 0 | 60 | 60 | 60 |
| 610841 E02963 2011812881501 | 0 | 15 | 15 | 15 |
| 610841 E02963 2011812881518 | 0 | 15 | 15 | 15 |
| 610841 E02963 2011812881525 | 0 | 90 | 90 | 90 |
| 610841 E02963 2011812881532 | 0 | 105 | 105 | 105 |
| 610841 E02963 2011812881556 | 0 | 30 | 30 | 30 |
| 610841 E02963 2011812881563 | 0 | 15 | 15 | 15 |
| 610841 E02963 2011813194709 | 0 | 60 | 60 | 60 |
| 610841 E02963 2011813194723 | 0 | 75 | 75 | 75 |
| 610843 E02967 2011812881976 | 0 | 60 | 60 | 60 |
| 610843 E02967 2011812881983 | 0 | 60 | 60 | 60 |
| 610843 E02967 2011812882072 | 0 | 120 | 120 | 120 |
| 610843 E02967 2011812882089 | 0 | 135 | 135 | 135 |
| 610843 E02967 2011812882102 | 0 | 45 | 45 | 45 |
| 610843 E02967 2011812882119 | 0 | 30 | 30 | 30 |
| 610843 E02967 2011812882126 | 0 | 45 | 45 | 45 |
| 610843 E02967 2011812882133 | 0 | 45 | 45 | 45 |
| 610843 E02967 2011812882157 | 0 | 15 | 15 | 15 |
| 610843 E02967 2011812882171 | 0 | 120 | 120 | 120 |
| 610843 E02967 2011812882188 | 0 | 135 | 135 | 135 |
| 610843 E02967 2011812882201 | 0 | 15 | 15 | 15 |
| 610843 E02967 2011812882218 | 0 | 15 | 15 | 15 |
| 610848 E02970 2011812934825 | 0 | 210 | 210 | 210 |
| 610848 E02970 2011812934832 | 0 | 240 | 240 | 240 |
| 610848 E02970 2011812934856 | 0 | 15 | 15 | 15 |
| 610848 E02970 2011812934863 | 0 | 75 | 75 | 75 |
| 610848 E02970 2011812934870 | 0 | 75 | 75 | 75 |
| 610848 E02970 2011812934894 | 0 | 15 | 15 | 15 |
| 610848 E02970 2011812934900 | 0 | 45 | 45 | 45 |

*FIG. 29.10B*

Customer     : NEWGERM
Module       : MULTI
Description  : MULTI CURRENCY FORMAT
File Name    : GM19005
Date/Time    : 06/11/98 / 4:22:07 PM

<< ESPRIT  GERMANY  PP REPORT FOR SERVICE BUREAU >>

| | | | | | |
|---|---|---|---|---|---|
| 610848 | E02970 | 2011812934917 | 0 | 45 | 45 | 45 |
| 610848 | E02970 | 2011812934931 | 0 | 15 | 15 | 15 |
| 610848 | E02970 | 2011812934948 | 0 | 45 | 45 | 45 |
| 610848 | E02970 | 2011812934955 | 0 | 45 | 45 | 45 |
| 610848 | E02970 | 2011812934979 | 0 | 15 | 15 | 15 |
| 610848 | E02970 | 2011812935020 | 0 | 15 | 15 | 15 |
| 610848 | E02970 | 2011812935037 | 0 | 15 | 15 | 15 |
| 610848 | E02970 | 2011812977525 | 0 | 30 | 30 | 30 |
| 610848 | E02970 | 2011812977532 | 0 | 15 | 15 | 15 |
| 610848 | E02970 | 2011812977549 | 0 | 15 | 15 | 15 |
| 610848 | E02970 | 2011812977556 | 0 | 15 | 15 | 15 |
| 610848 | E02970 | 2011812977570 | 0 | 15 | 15 | 15 |
| 610848 | E02970 | 2011813196840 | 0 | 90 | 90 | 90 |
| 610848 | E02970 | 2011813196864 | 0 | 45 | 45 | 45 |
| 610850 | E02971 | 2011812935068 | 0 | 15 | 15 | 15 |
| 610850 | E02971 | 2011812935075 | 0 | 15 | 15 | 15 |
| 610850 | E02971 | 2011812935099 | 0 | 15 | 15 | 15 |
| 610850 | E02971 | 2011812935105 | 0 | 45 | 45 | 45 |
| 610850 | E02971 | 2011812935112 | 0 | 30 | 30 | 30 |
| 610850 | E02971 | 2011812935181 | 0 | 30 | 30 | 30 |
| 610850 | E02971 | 2011812935198 | 0 | 30 | 30 | 30 |
| 610850 | E02971 | 2011812935211 | 0 | 15 | 15 | 15 |
| 610850 | E02971 | 2011812977839 | 0 | 15 | 15 | 15 |
| 610850 | E02971 | 2011812977860 | 0 | 15 | 15 | 15 |
| 610850 | E02971 | 2011813196871 | 0 | 60 | 60 | 60 |
| 610851 | E02973 | 2011812935754 | 0 | 225 | 225 | 225 |
| 610851 | E02973 | 2011812935761 | 0 | 270 | 270 | 270 |
| 610851 | E02973 | 2011812935785 | 0 | 90 | 90 | 90 |
| 610851 | E02973 | 2011812935792 | 0 | 60 | 60 | 60 |
| 610851 | E02973 | 2011812935808 | 0 | 345 | 345 | 345 |
| 610851 | E02973 | 2011812935815 | 0 | 510 | 510 | 510 |
| 610851 | E02973 | 2011812935839 | 0 | 120 | 120 | 120 |
| 610851 | E02973 | 2011812935846 | 0 | 165 | 165 | 165 |

*FIG. 29.11A*

| Customer | : NEWGERM |
|---|---|
| Module | : MULTI |
| Description | : MULTI CURRENCY FORMAT |
| File Name | : GM19005 |
| Date/Time | : 06/11/98 / 4:22:07 PM |

<< ESPRIT GERMANY PP REPORT FOR SERVICE BUREAU>>

| | | | | | |
|---|---|---|---|---|---|
| 610851 E02973 | 2011812935853 | 0 | 30 | 30 | 30 |
| 610851 E02973 | 2011812935860 | 0 | 30 | 30 | 30 |
| 610851 E02973 | 2011812935884 | 0 | 15 | 15 | 15 |
| 610851 E02973 | 2011813193122 | 0 | 105 | 105 | 105 |
| 610851 E02973 | 2011813193139 | 0 | 75 | 75 | 75 |
| 610853 E02980 | 2011813029285 | 0 | 105 | 105 | 105 |
| 610853 E02980 | 2011813029292 | 0 | 105 | 105 | 105 |
| 610853 E02980 | 2011813029315 | 0 | 45 | 45 | 45 |
| 610853 E02980 | 2011813029322 | 0 | 30 | 30 | 30 |
| 610853 E02980 | 2011813029339 | 0 | 45 | 45 | 45 |
| 610853 E02980 | 2011813029346 | 0 | 45 | 45 | 45 |
| 610853 E02980 | 2011813029360 | 0 | 30 | 30 | 30 |
| 610853 E02980 | 2011813029377 | 0 | 15 | 15 | 15 |
| 610854 E02990 | 2011813197007 | 0 | 75 | 75 | 75 |
| 610854 E02990 | 2011813197014 | 0 | 75 | 75 | 75 |
| 610854 E02990 | 2011813197038 | 0 | 60 | 60 | 60 |
| 610854 E02990 | 2011813197045 | 0 | 45 | 45 | 45 |
| 610855 E02991 | 2011813197151 | 0 | 60 | 60 | 60 |
| 610855 E02991 | 2011813197168 | 0 | 60 | 60 | 60 |
| 610855 E02991 | 2011813197182 | 0 | 30 | 30 | 30 |
| 610855 E02991 | 2011813197199 | 0 | 30 | 30 | 30 |
| 610857 E02999 | 2011813180351 | 0 | 60 | 60 | 60 |
| 610857 E02999 | 2011813182577 | 0 | 45 | 45 | 45 |
| 610857 E02999 | 2011813182584 | 0 | 60 | 60 | 60 |
| 610857 E02999 | 2011813182591 | 0 | 15 | 15 | 15 |
| 610871 E06928 | 2011812882799 | 0 | 90 | 90 | 90 |
| 610781 E06928 | 2011812882805 | 0 | 15 | 15 | 15 |
| 610871 E06928 | 2011812882812 | 0 | 15 | 15 | 15 |
| 610871 E06928 | 2011812882829 | 0 | 255 | 255 | 255 |
| 610871 E06928 | 2011812882836 | 0 | 15 | 15 | 15 |
| 610871 E06928 | 2011812882843 | 0 | 15 | 15 | 15 |
| 610871 E06928 | 2011812882881 | 0 | 45 | 45 | 45 |

*FIG. 29.11B*

Customer    : NEWGERM
Module      : MULTI
Description : MULTI CURRENCY FORMAT
File Name   : GM19005
Date/Time   : 06/11/98 / 4:22:07 PM

<< ESPRIT GERMANY PP REPORT FOR SERVICE BUREAU >>

| | | | | |
|---|---|---|---|---|
| 610871 E06928 2011812882898 | 0 | 15 | 15 | 15 |
| 610871 E06928 2011812882911 | 0 | 345 | 345 | 345 |
| 610871 E06928 2011812882928 | 0 | 45 | 45 | 45 |
| 610871 E06928 2011812882935 | 0 | 75 | 75 | 75 |
| 610872 E06930 2011812883321 | 0 | 60 | 60 | 60 |
| 610872 E06930 2011812883338 | 0 | 15 | 15 | 15 |
| 610872 E06930 2011812883345 | 0 | 15 | 15 | 15 |
| 610872 E06930 2011812883352 | 0 | 360 | 360 | 360 |
| 610872 E06930 2011812883369 | 0 | 15 | 15 | 15 |
| 610872 E06930 2011812883376 | 0 | 105 | 105 | 105 |
| 610872 E06930 2011812883413 | 0 | 75 | 75 | 75 |
| 610872 E06930 2011812883420 | 0 | 15 | 15 | 15 |
| 610872 E06930 2011812883437 | 0 | 15 | 15 | 15 |
| 610872 E06930 2011812883444 | 0 | 480 | 480 | 480 |
| 610872 E06930 2011812883451 | 0 | 45 | 45 | 45 |
| 610872 E06930 2011812883468 | 0 | 150 | 150 | 150 |
| 610872 E06930 2011812979536 | 0 | 30 | 30 | 30 |
| 610872 E06930 2011812979543 | 0 | 75 | 75 | 75 |
| 610872 E06930 2011812979567 | 0 | 15 | 15 | 15 |
| 610872 E06930 2011812979574 | 0 | 135 | 135 | 135 |
| 610873 E06931 2011812883482 | 0 | 75 | 75 | 75 |
| 610873 E06931 2011812883499 | 0 | 15 | 15 | 15 |
| 610873 E06931 2011812883505 | 0 | 15 | 15 | 15 |
| 610873 E06931 2011812883512 | 0 | 735 | 735 | 735 |
| 610873 E06931 2011812883529 | 0 | 60 | 60 | 60 |
| 610873 E06931 2011812883536 | 0 | 285 | 285 | 285 |
| 610874 E06933 2011812883604 | 0 | 45 | 45 | 45 |
| 610874 E06933 2011812883611 | 0 | 15 | 15 | 15 |
| 610874 E06933 2011812883628 | 0 | 15 | 15 | 15 |
| 610874 E06933 2011812883635 | 0 | 30 | 30 | 30 |
| 610874 E06933 2011812883642 | 0 | 15 | 15 | 15 |
| 610874 E06933 2011812883697 | 0 | 210 | 210 | 210 |
| 610874 E06933 2011812883703 | 0 | 15 | 15 | 15 |

*FIG. 29.12A*

Customer : NEWGERM
Module : MULTI
Description : MULTI CURRENCY FORMAT
File Name : GM19005
Date/Time : 06/11/98 / 4:22:07 PM

<< ESPRIT GERMANY PP REPORT FOR SERVICE BUREAU >>

| | | | | | |
|---|---|---|---|---|---|
| 610874 E06933 | 2011812883710 | 0 | 135 | 135 | 135 |
| 610874 E06933 | 2011812979918 | 0 | 15 | 15 | 15 |
| 610874 E06933 | 2011812979925 | 0 | 15 | 15 | 15 |
| 610874 E06933 | 2011812979949 | 0 | 60 | 60 | 60 |
| 610876 E06936 | 2011812883840 | 0 | 60 | 60 | 60 |
| 610876 E06936 | 2011812883857 | 0 | 15 | 15 | 15 |
| 610876 E06936 | 2011812883864 | 0 | 15 | 15 | 15 |
| 610876 E06936 | 2011812883901 | 0 | 120 | 120 | 120 |
| 610876 E06936 | 2011812883918 | 0 | 15 | 15 | 15 |
| 610876 E06936 | 2011812883925 | 0 | 15 | 15 | 15 |
| 610876 E06936 | 2011812883932 | 0 | 255 | 255 | 255 |
| 610876 E06936 | 2011812883949 | 0 | 15 | 15 | 15 |
| 610876 E06936 | 2011812883956 | 0 | 30 | 30 | 30 |
| 610876 E06936 | 2011812883963 | 0 | 180 | 180 | 180 |
| 610876 E06936 | 2011812883970 | 0 | 15 | 15 | 15 |
| 610876 E06936 | 2011812883987 | 0 | 45 | 45 | 45 |
| 610876 E06936 | 2011812883994 | 0 | 645 | 645 | 645 |
| 610876 E06936 | 2011812884007 | 0 | 15 | 15 | 15 |
| 610876 E06936 | 2011812884014 | 0 | 195 | 195 | 195 |
| 610876 E06936 | 2011812884021 | 0 | 765 | 765 | 765 |
| 610876 E06936 | 2011812884038 | 0 | 45 | 45 | 45 |
| 610876 E06936 | 2011812884045 | 0 | 330 | 330 | 330 |
| 610876 E06936 | 2011813026840 | 0 | 30 | 30 | 30 |
| 610876 E06936 | 2011813026864 | 0 | 60 | 60 | 60 |
| 610876 E06936 | 2011813026871 | 0 | 75 | 75 | 75 |
| 610876 E06936 | 2011813026888 | 0 | 60 | 60 | 60 |
| 610876 E06936 | 2011813026895 | 0 | 165 | 165 | 165 |
| 610876 E06936 | 2011813026901 | 0 | 225 | 225 | 225 |
| 610882 E06941 | 2011812884410 | 0 | 150 | 150 | 150 |
| 610882 E06941 | 2011812884427 | 0 | 15 | 15 | 15 |
| 610882 E06941 | 2011812884434 | 0 | 15 | 15 | 15 |
| 610882 E06941 | 2011812884472 | 0 | 75 | 75 | 75 |

*FIG. 29.12B*

Customer : NEWGERM
Module : MULTI
Description : MULTI CURRENCY FORMAT
File Name : GM19005
Date/Time : 06/11/98 / 4:22:07 PM

<<ESPRIT GERMANY PP REPORT FOR SERVICE BUREAU>>

| | | | | | |
|---|---|---|---|---|---|
| 610882 E06941 | 2011812884489 | 0 | 15 | 15 | 15 |
| 610882 E06941 | 2011812884496 | 0 | 30 | 30 | 30 |
| 610884 E06945 | 2011812885417 | 0 | 45 | 45 | 45 |
| 610884 E06945 | 2011812885424 | 0 | 15 | 15 | 15 |
| 610884 E06945 | 2011812885431 | 0 | 15 | 15 | 15 |
| 610884 E06945 | 2011812885479 | 0 | 150 | 150 | 150 |
| 610884 E06945 | 2011812885486 | 0 | 15 | 15 | 15 |
| 610884 E06945 | 2011812885509 | 0 | 75 | 75 | 75 |
| 610884 E06945 | 2011812885516 | 0 | 15 | 15 | 15 |
| 610884 E06945 | 2011812885523 | 0 | 15 | 15 | 15 |
| 610885 E06947 | 2011812886223 | 0 | 180 | 180 | 180 |
| 610885 E06947 | 2011812886230 | 0 | 15 | 15 | 15 |
| 610885 E06947 | 2011812886241 | 0 | 15 | 15 | 15 |
| 610885 E06947 | 2011812886254 | 0 | 90 | 90 | 90 |
| 610885 E06947 | 2011812886261 | 0 | 15 | 15 | 15 |
| 610885 E06947 | 2011812886278 | 0 | 15 | 15 | 15 |
| 610885 E06947 | 2011812886285 | 0 | 645 | 645 | 645 |
| 610885 E06947 | 2011812886292 | 0 | 30 | 30 | 30 |
| 610885 E06947 | 2011812886308 | 0 | 150 | 150 | 150 |
| 610885 E06947 | 2011812886315 | 0 | 540 | 540 | 540 |
| 610885 E06947 | 2011812886322 | 0 | 30 | 30 | 30 |
| 610885 E06947 | 2011812886339 | 0 | 165 | 165 | 165 |
| 610885 E06947 | 2011813026574 | 0 | 45 | 45 | 45 |
| 610885 E06947 | 2011813026581 | 0 | 30 | 30 | 30 |
| 610885 E06947 | 2011813026598 | 0 | 105 | 105 | 105 |
| 610885 E06947 | 2011813026604 | 0 | 150 | 150 | 150 |
| 610886 E06948 | 2011812886377 | 0 | 120 | 120 | 120 |
| 610886 E06948 | 2011812886384 | 0 | 15 | 15 | 15 |
| 610886 E06948 | 2011812886391 | 0 | 15 | 15 | 15 |
| 610886 E06948 | 2011812886407 | 0 | 75 | 75 | 75 |
| 610886 E06948 | 2011812886414 | 0 | 15 | 15 | 15 |
| 610886 E06948 | 2011812886421 | 0 | 15 | 15 | 15 |
| 610886 E06948 | 2011812886438 | 0 | 435 | 435 | 435 |

*FIG. 29.13A*

| Customer | : NEWGERM |
|---|---|
| Module | : MULTI |
| Description | : MULTI CURRENCY FORMAT |
| File Name | : GM19005 |
| Date/Time | : 06/11/98 / 4:22:07 PM |

<< ESPRIT GERMANY PP REPORT FOR SERVICE BUREAU >>

| | | | | | |
|---|---|---|---|---|---|
| 610886 E06948 | 2011812886445 | 0 | 30 | 30 | 30 |
| 610886 E06948 | 2011812886452 | 0 | 180 | 180 | 180 |
| 610886 E06948 | 2011812886469 | 0 | 810 | 810 | 810 |
| 610886 E06948 | 2011812886476 | 0 | 60 | 60 | 60 |
| 610886 E06948 | 2011812886483 | 0 | 210 | 210 | 210 |
| 610902 E06958 | 2011812888180 | 0 | 105 | 105 | 105 |
| 610902 E06958 | 2011812888197 | 0 | 15 | 15 | 15 |
| 610902 E06958 | 2011812888210 | 0 | 345 | 345 | 345 |
| 610902 E06958 | 2011812888227 | 0 | 30 | 30 | 30 |
| 610902 E06958 | 2011812888234 | 0 | 135 | 135 | 135 |
| 610902 E06958 | 2011812888241 | 0 | 405 | 405 | 405 |
| 610902 E06958 | 2011812888265 | 0 | 165 | 165 | 165 |
| 610902 E06958 | 2011812888272 | 0 | 90 | 90 | 90 |
| 610902 E06958 | 2011812888289 | 0 | 15 | 15 | 15 |
| 610906 E06963 | 2011812888876 | 0 | 150 | 150 | 150 |
| 610906 E06963 | 2011812888883 | 0 | 15 | 15 | 15 |
| 610906 E06963 | 2011812888906 | 0 | 165 | 165 | 165 |
| 610906 E06963 | 2011812888920 | 0 | 60 | 60 | 60 |
| 610906 E06963 | 2011812888937 | 0 | 180 | 180 | 180 |
| 610906 E06963 | 2011812888944 | 0 | 15 | 15 | 15 |
| 610906 E06963 | 2011812888951 | 0 | 15 | 15 | 15 |
| 610907 E06970 | 2011812935488 | 0 | 135 | 135 | 135 |
| 610907 E06970 | 2011812935501 | 0 | 60 | 60 | 60 |
| 610907 E06970 | 2011812935549 | 0 | 90 | 90 | 90 |
| 610907 E06970 | 2011812935563 | 0 | 45 | 45 | 45 |
| 610907 E06970 | 2011812935570 | 0 | 165 | 165 | 165 |
| 610907 E06970 | 2011812935631 | 0 | 75 | 75 | 75 |
| 610914 E07925 | 2011812889590 | 0 | 180 | 180 | 180 |
| 610914 E07925 | 2011812889606 | 0 | 60 | 60 | 60 |
| 610914 E07925 | 2011812889613 | 0 | 30 | 30 | 30 |
| 610914 E07925 | 2011812889620 | 0 | 660 | 660 | 660 |
| 610914 E07925 | 2011812889637 | 0 | 45 | 45 | 45 |

*FIG. 29.13B*

Customer : NEWGERM
Module : MULTI
Description : MULTI CURRENCY FORMAT
File Name : GM19005
Date/Time : 06/11/98 / 4:22:08PM

<< ESPRIT GERMANY PP REPORT FOR SERVICE BUREAU>>

| | | | | | |
|---|---|---|---|---|---|
| 610914 E07925 | 2011812889644 | 0 | 210 | 210 | 210 |
| 610914 E07925 | 2011812889651 | 0 | 45 | 45 | 45 |
| 610914 E07925 | 2011812889712 | 0 | 585 | 585 | 585 |
| 610914 E07925 | 2011812889729 | 0 | 30 | 30 | 30 |
| 610914 E07925 | 2011812889736 | 0 | 90 | 90 | 90 |
| 610916 E07927 | 2011812889958 | 0 | 135 | 135 | 135 |
| 610916 E07927 | 2011812889965 | 0 | 30 | 30 | 30 |
| 610916 E07927 | 2011812889989 | 0 | 645 | 645 | 645 |
| 610916 E07927 | 2011812889996 | 0 | 75 | 75 | 75 |
| 610916 E07927 | 2011812890008 | 0 | 105 | 105 | 105 |
| 610921 E07934 | 2011812980815 | 0 | 75 | 75 | 75 |
| 610921 E07934 | 2011812980822 | 0 | 15 | 15 | 15 |
| 610921 E07934 | 2011812980877 | 0 | 120 | 120 | 120 |
| 610921 E07934 | 2011812980884 | 0 | 15 | 15 | 15 |
| 610921 E07934 | 2011812980891 | 0 | 45 | 45 | 45 |
| 610921 E07934 | 2011812980907 | 0 | 210 | 210 | 210 |
| 610921 E07934 | 2011812980914 | 0 | 30 | 30 | 30 |
| 610921 E07934 | 2011812980921 | 0 | 60 | 60 | 60 |
| 610921 E07934 | 2011812980938 | 0 | 45 | 45 | 45 |
| 610921 E07934 | 2011812980945 | 0 | 15 | 15 | 15 |
| 610922 E07935 | 2011812890251 | 0 | 90 | 90 | 90 |
| 610922 E07935 | 2011812890282 | 0 | 150 | 150 | 150 |
| 610922 E07935 | 2011812890305 | 0 | 30 | 30 | 30 |
| 610922 E07935 | 2011812890312 | 0 | 90 | 90 | 90 |
| 610926 E07940 | 2011812890886 | 0 | 45 | 45 | 45 |
| 610926 E07940 | 2011812890916 | 0 | 60 | 60 | 60 |
| 610926 E07940 | 2011812890947 | 0 | 135 | 135 | 135 |
| 610926 E07940 | 2011812890954 | 0 | 15 | 15 | 15 |
| 610926 E07940 | 2011812890961 | 0 | 15 | 15 | 15 |
| 610927 E07942 | 2011812980990 | 0 | 90 | 90 | 90 |
| 610927 E07942 | 2011812981003 | 0 | 15 | 15 | 15 |
| 610927 E07942 | 2011812981027 | 0 | 75 | 75 | 75 |
| 610927 E07942 | 2011812981034 | 0 | 30 | 30 | 30 |

*FIG. 29.14A*

Customer : NEWGERM
Module : MULTI
Description : MULTI CURRENCY FORMAT
File Name : GM19005
Date/Time : 06/11/98 / 4:22:08 PM

<< ESPRIT GERMANY PP REPORT FOR SERVICE BUREAU >>

| | | | | | |
|---|---|---|---|---|---|
| 610927 E07942 | 2011812981058 | 0 | 300 | 300 | 300 |
| 610927 E07942 | 2011812981065 | 0 | 30 | 30 | 30 |
| 610927 E07942 | 2011812981072 | 0 | 60 | 60 | 60 |
| 610927 E07942 | 2011812981089 | 0 | 405 | 405 | 405 |
| 610927 E07942 | 2011812981096 | 0 | 45 | 45 | 45 |
| 610927 E07942 | 2011812981102 | 0 | 30 | 30 | 30 |
| 610927 E07942 | 2011812981119 | 0 | 225 | 225 | 225 |
| 610927 E07942 | 2011812981126 | 0 | 30 | 30 | 30 |
| 610927 E07942 | 2011812981133 | 0 | 135 | 135 | 135 |
| 610928 E08926 | 2011812892064 | 0 | 45 | 45 | 45 |
| 610928 E08926 | 2011812892071 | 0 | 45 | 45 | 45 |
| 610928 E08926 | 2011812892095 | 0 | 30 | 30 | 30 |
| 610928 E08926 | 2011812892101 | 0 | 15 | 15 | 15 |
| 610928 E08926 | 2011812892163 | 0 | 135 | 135 | 135 |
| 610928 E08926 | 2011812892170 | 0 | 165 | 165 | 165 |
| 610928 E08926 | 2011812892194 | 0 | 45 | 45 | 45 |
| 610928 E08926 | 2011812892200 | 0 | 30 | 30 | 30 |
| 610928 E08926 | 2011812892316 | 0 | 165 | 165 | 165 |
| 610928 E08926 | 2011812892323 | 0 | 180 | 180 | 180 |
| 610928 E08926 | 2011812892347 | 0 | 60 | 60 | 60 |
| 610928 E08926 | 2011812892354 | 0 | 30 | 30 | 30 |
| 610931 E08927 | 2011812892361 | 0 | 120 | 120 | 120 |
| 610931 E08927 | 2011812892378 | 0 | 165 | 165 | 165 |
| 610931 E08927 | 2011812892392 | 0 | 75 | 75 | 75 |
| 610931 E08927 | 2011812892408 | 0 | 45 | 45 | 45 |
| 610931 E08927 | 2011812892460 | 0 | 135 | 135 | 135 |
| 610931 E08927 | 2011812892477 | 0 | 165 | 165 | 165 |
| 610931 E08927 | 2011812892491 | 0 | 75 | 75 | 75 |
| 610931 E08927 | 2011812892507 | 0 | 30 | 30 | 30 |
| 610931 E08927 | 2011812892613 | 0 | 45 | 45 | 45 |
| 610931 E08927 | 2011812892620 | 0 | 60 | 60 | 60 |
| 610931 E08927 | 2011812892644 | 0 | 30 | 30 | 30 |
| 610931 E08927 | 2011813071383 | 0 | 15 | 15 | 15 |

*FIG. 29.14B*

Customer : NEWGERM
Module : MULTI
Description : MULTI CURRENCY FORMAT
File Name : GM19005
Date/Time : 06/11/98 / 4:22:08 PM

<< ESPRIT GERMANY PP REPORT FOR SERVICE BUREAU >>

| | | | | | | |
|---|---|---|---|---|---|---|
| 610933 | E08928 | 2011812892668 | 0 | 120 | 120 | 120 |
| 610933 | E08928 | 2011812892675 | 0 | 135 | 135 | 135 |
| 610933 | E08928 | 2011812892699 | 0 | 30 | 30 | 30 |
| 610933 | E08928 | 2011812892767 | 0 | 135 | 135 | 135 |
| 610933 | E08928 | 2011812892774 | 0 | 150 | 150 | 150 |
| 610933 | E08928 | 2011812892798 | 0 | 60 | 60 | 60 |
| 610933 | E08928 | 2011812892910 | 0 | 45 | 45 | 45 |
| 610933 | E08928 | 2011812892927 | 0 | 45 | 45 | 45 |
| 610933 | E08928 | 2011812892941 | 0 | 30 | 30 | 30 |
| 610933 | E08928 | 2011813071444 | 0 | 30 | 30 | 30 |
| 610938 | E08935 | 2011812893368 | 0 | 105 | 105 | 105 |
| 610938 | E08935 | 2011812893375 | 0 | 105 | 105 | 105 |
| 610938 | E08935 | 2011812893399 | 0 | 30 | 30 | 30 |
| 610938 | E08935 | 2011812893412 | 0 | 60 | 60 | 60 |
| 610938 | E08935 | 2011812893429 | 0 | 45 | 45 | 45 |
| 610938 | E08935 | 2011812893443 | 0 | 45 | 45 | 45 |
| 610938 | E08935 | 2011812893467 | 0 | 30 | 30 | 30 |
| 610938 | E08935 | 2011812893474 | 0 | 30 | 30 | 30 |
| 610938 | E08935 | 2011812893498 | 0 | 15 | 15 | 15 |
| 610940 | E08940 | 2011812894013 | 0 | 45 | 45 | 45 |
| 610940 | E08940 | 2011812894020 | 0 | 45 | 45 | 45 |
| 610940 | E08940 | 2011812894044 | 0 | 15 | 15 | 15 |
| 610940 | E08940 | 2011812894068 | 0 | 45 | 45 | 45 |
| 610940 | E08940 | 2011812894075 | 0 | 60 | 60 | 60 |
| 610940 | E08940 | 2011812894099 | 0 | 15 | 15 | 15 |
| 610940 | E08940 | 2011812894112 | 0 | 105 | 105 | 105 |
| 610940 | E08940 | 2011812894129 | 0 | 120 | 120 | 120 |
| 610940 | E08940 | 2011812894143 | 0 | 30 | 30 | 30 |
| 610940 | E08940 | 2011812894150 | 0 | 30 | 30 | 30 |
| 610941 | E08941 | 2011812894211 | 0 | 45 | 45 | 45 |
| 610941 | E08941 | 2011812894228 | 0 | 45 | 45 | 45 |
| 610941 | E08941 | 2011812894242 | 0 | 30 | 30 | 30 |
| 610941 | E08941 | 2011812894310 | 0 | 45 | 45 | 45 |

*FIG. 29.15A*

Customer    : NEWGERM
Module      : MULTI
Description : MULTI CURRENCY FORMAT
File Name   : GM19005
Date/Time   : 06/11/98 / 4:22:08 PM

<< ESPRIT GERMANY PP REPORT FOR SERVICE BUREAU >>

| | | | | | |
|---|---|---|---|---|---|
| 610941 E08941 | 2011812894327 | 0 | 45 | 45 | 45 |
| 610941 E08941 | 2011812894341 | 0 | 15 | 15 | 15 |
| 610941 E08941 | 2011812894365 | 0 | 90 | 90 | 90 |
| 610941 E08941 | 2011812894372 | 0 | 90 | 90 | 90 |
| 610941 E08941 | 2011812894396 | 0 | 75 | 75 | 75 |
| 610941 E08941 | 2011812894419 | 0 | 60 | 60 | 60 |
| 610941 E08941 | 2011812894426 | 0 | 60 | 60 | 60 |
| 610941 E08941 | 2011812894440 | 0 | 30 | 30 | 30 |
| 610941 E08941 | 2011813087261 | 0 | 90 | 90 | 90 |
| 610941 E08941 | 2011813087285 | 0 | 30 | 30 | 30 |
| 610941 E08941 | 2011813087308 | 0 | 60 | 60 | 60 |
| | | | | 46380 | 46380 |

SEASON: E    HT_REF: PP

| SPO | STYLE | CODE | OLD_QTY | NEW_QTY | QTY | RQTY |
|---|---|---|---|---|---|---|
| 609534 | E26000 | 2011812974883 | 0 | 75 | 75 | 75 |
| 609534 | E26000 | 2011812974890 | 0 | 30 | 30 | 30 |
| 609535 | E26003 | 2011812974944 | 0 | 60 | 60 | 60 |
| 609535 | E26003 | 2011812974951 | 0 | 30 | 30 | 30 |
| 609536 | E26004 | 2011812974968 | 0 | 60 | 60 | 60 |
| 609536 | E26004 | 2011812974975 | 0 | 30 | 30 | 30 |
| 609537 | E26009 | 2011812975354 | 0 | 75 | 75 | 75 |
| 609537 | E26009 | 2011812975361 | 0 | 30 | 30 | 30 |
| 609539 | E26023 | 2011812976443 | 0 | 45 | 45 | 45 |
| 609540 | E26024 | 2011812976467 | 0 | 60 | 60 | 60 |
| 609541 | E26026 | 2011812976504 | 0 | 60 | 60 | 60 |
| 609542 | E26027 | 2011813114721 | 0 | 30 | 30 | 30 |
| 609543 | E26028 | 2011812976542 | 0 | 120 | 120 | 120 |
| 609546 | E26453 | 2011812976689 | 0 | 15 | 15 | 15 |
| | | | | | 720 | 720 |

*FIG. 29.15B*

Customer : NEWGERM
Module : MULTI
Description : MULTI CURRENCY FORMAT
Date/Time : 06/11/98 / 4:24:29 PM

<< ESPRIT GERMANY C4 & PP ORDER DETAIL >>

FILENAME: G9819005  HT_REF: EU  SEASON: D  DIV: 21

| HANGTAGTYP | SPO | STYLE | COUNTRY | FACTORY | CODE | CLRCODE | SIZE |
|---|---|---|---|---|---|---|---|
| C4 | 609096 | D21521 | T | MISIR | 2700006090965 | | |
| C4 | 609097 | D21522 | T | MISIR | 2700006090972 | | |
| PP | 609096 | D21521 | T | MISIR | 2011813174329 | 543 | SORT#26 |
| PP | 609097 | D21522 | T | MISIR | 2011813174336 | 543 | SORT#26 |

FIG. 30.1A

| DISTRI | RETAILCODE | RETAIL DIV | QTY | RQTY |
|---|---|---|---|---|
| UKI | & | 21 | 20 | 80 |
| UKI | & | 21 | 20 | 80 |
| UKI | & | 21 | 135 | 135 |
| UKI | & | 21 | 135 | 135 |

*FIG. 30.1B*

Customer : NEWGERM
Module : MULTI
Description : MULTI CURRENCY FORMAT
Date/Time : 06/11/98 / 4:24:29 PM

<< ESPRIT GERMANY C4 & PP ORDER DETAIL >>

FILENAME: G9819005   HT_REF: EU   SEASON: N   DIV: 29

| HANGTAGTYP | SPO | STYLE | COUNTRY | FACTORY | CODE | CLRCODE | SIZE |
|---|---|---|---|---|---|---|---|
| C4 | 610645 | N29510 | HKG | WGF | 2700006106451 | | |

FIG. 30.2A

| DISTRI | RETAILCODE | RETAIL | DIV | QTY | RQTY |
|---|---|---|---|---|---|
| UKI | £ | | 29 | 25 | 100 |

FIG. 30.2B

Structure : EDCGM-MULTI
Product : EU
Date/Time : 06/12/98 / 4:05:26 PM

<< PLATE LAYOUT DETAIL LIST >>

| REC_ID | PLATENO | SPO | STYLE | CLRCODE | STYLEDESC | CODE | DISTRI | SIZE | CTY_SZ1 | SIZE1 |
|---|---|---|---|---|---|---|---|---|---|---|
| 1 | 1 | 609097 | D21522 | 543 | ESPRIT PANTY | 4011815904236 | UKI | S | D | S |
| 2 | 1 | 609096 | D21521 | 543 | ESPRIT BUSTIER | 4011815904229 | UKI | L | D | L |
| 3 | 2 | 609096 | D21521 | 543 | ESPRIT BUSTIER | 4011815904205 | UKI | S | D | S |
| 4 | 3 | 609097 | D21522 | 543 | ESPRIT PANTY | 4011815904243 | UKI | M | D | M |
| 5 | 3 | 609096 | D21521 | 543 | ESPRIT BUSTIER | 4011815904212 | UKI | M | D | M |

*FIG. 31A*

| CTY_SZ2 | SIZE2 | CTY_SZ3 | SIZE3 | CTY_SZ4 | SIZE4 | CTY_SZ5 | SIZE5 | RETAILCODE |
|---|---|---|---|---|---|---|---|---|
| F | M | – | M | UK | S | USA | S | £ |
| F | XL | – | XL | UK | L | USA |  | £ |
| F | M | – | M | UK | S | USA | S | £ |
| F | L | – | L | UK | M | USA | M | £ |
| F | L | – | L | UK | M | USA | M | £ |

*FIG. 31B*

File Name : EUW589
Structure : EDCGM-MULTI
Product : EU
Date/Time : 02/10/98 / 11:36:25 AM

<< PLATE LAYOUT SUMMARY LIST >>

| PLATENO | QTY | SHPQTY | PLATEQTY |
|---:|---:|---:|---:|
| 1 | 250 | 400 | 40 |
| 2 | 250 | 400 | 40 |
| 3 | 450 | 600 | 60 |
| 4 | 875 | 1000 | 100 |
| 5 | 625 | 800 | 80 |
| 6 | 650 | 800 | 80 |
| 7 | 775 | 1000 | 100 |
| 8 | 375 | 400 | 40 |
| 9 | 200 | 200 | 20 |
| 10 | 700 | 800 | 80 |
| 11 | 250 | 250 | 25 |
| 12 | 700 | 800 | 80 |
| | 6100 | 7450 | 745 |

*FIG. 32*

| EDCGM-MULTI: EG-128-EU | EDCGM-MULTI: EG-128-EU |
| --- | --- |
| AW JOB#: 146589 | AW JOB#: 146589 |
| PLATE #: 1 | PLATE #: 3 |
| PRINT QTY: 40 | PRINT QTY: 60 |
| EDCGM-MULTI: EG-128-EU | EDCGM-MULTI: EG-128-EU |
| AW JOB#: 146589 | AW JOB#: 146589 |
| PLATE #: 5 | PLATE #: 7 |
| PRINT QTY: 80 | PRINT QTY: 100 |
| EDCGM-MULTI: EG-128-EU | EDCGM-MULTI: EG-128-EU |
| AW JOB#: 146589 | AW JOB#: 146589 |
| PLATE #: 9 | PLATE #: 11 |
| PRINT QTY: 20 | PRINT QTY: 25 |

*FIG. 33*

File Name     : EUW456
Structure     : EDCGM-MULTI
Product       : EU
Date/Time     : 06/12/98 / 3:28:13 PM

<< PLATE ANALYSIS REPORT >>

SUMMARY

| | |
|---|---|
| AW JOB NO | = 123456 |
| INPUT FILE PATH | = C:\BILL\ORDER |
| INPUT FILE NAME | = EU456.DBF |
| WORKING FILE NAME | = EUW456.DBF |
| PACKING TEMP FILE NAME | = PKEU56.DBF |
| BOX CHECKING FILE NAME | = 123456.EU |
| ARTWORK CHECKING FILE NAME | = EUA456.DBF |
| ARTWORK FILE NAME | = EUW456.ART |
| CUTTING LABEL FILE NAME | = EUW456.CUT |
| BOX LABEL FILE NAME | = EUW456.BOX |
| CARTON LABEL FILE NAME | = EUW456.CAR |
| BOX CAPACITY | = 1500 |
| CARTON CAPACITY | = 9000 |
| MARK UP% | = 0.00 |
| NEAR UP | = 25 |
| UP PER PLATE | = 10 |
| WASTE IMPORTANCE (PAPER/PLATE) | = 90 : 10 |
| MAXIMUM PAPER WASTE PER PLATE | = 100 |
| TOTAL NO OF RECORDS | = 5 |
| TOTAL ROUND QTY | = 1500 |
| TOTAL SHIP QTY | = 1500 |
| TOTAL NO OF PLATE | = 3 |
| TOTAL PAPER WASTE | = |
| MIN NO OF PLATE | = 1 |
| PAPER WASTE % | = 0.00 |
| PLATE WASTE % | = 200.00 |
| TOTAL PROCESSING TIME | = 2.00 |

*FIG. 34*

File Name : EUW456
Structure : EDCGM-MULTI
Product : EU
Date/Time : 06/12/98 / 3:28:17 PM

AWJOBNO: 123456   HANGTAGTYP: EU   COUNTRY: T   CARTON# 1 OF 1

| FACTORY | SPO | PKG# | STYLE | CLRCODE | SIZE | CODE | RETAILCODE | RETAIL | QTY |
|---------|-----|------|-------|---------|------|------|------------|--------|-----|
| MISIR | 609096 | 1 | D21521 | 543 | L | 4011815904229 | £ | | 250 |
| | | 1 | D21521 | 543 | M | 4011815904212 | £ | | 375 |
| | | 1 | D21521 | 543 | S | 4011815904205 | £ | | 250 |
| | | | | | | | | | 875 |
| | | | | | | | | | ===== |

| FACTORY | SPO | PKG# | STYLE | CLRCODE | SIZE | CODE | RETAILCODE | RETAIL | QTY |
|---------|-----|------|-------|---------|------|------|------------|--------|-----|
| MISIR | 609097 | 2 | D21522 | 543 | M | 4011815904243 | £ | | 375 |
| | | 2 | D21522 | 543 | S | 4011815904236 | £ | | 250 |
| | | | | | | | | | 625 |
| | | | | | | | | | ===== |

FIG. 35.1

File Name : EUW456
Structure : EDCGM-MULTI
Product : EU
Date/Time : 06/12/98 / 3:28:18 PM

AWJOBNO: 123456  HANGTAGTYP: EU  COUNTRY: T  CARTON # 1 OF 1

| FACTORY | SPO | PKG# | STYLE | CLRCODE | SIZE | CODE | RETAILCODE | RETAIL | QTY |
|---|---|---|---|---|---|---|---|---|---|
| MISIR | 609096 | 1 | D21521 | 543 | L | 4011815904229 | £ | | 250 |
| | | 1 | D21521 | 543 | M | 4011815904212 | £ | | 375 |
| | | 1 | D21521 | 543 | S | 4011815904205 | £ | | 250 |
| | | | | | | | | | 875 |

| FACTORY | SPO | PKG# | STYLE | CLRCODE | SIZE | CODE | RETAILCODE | RETAIL | QTY |
|---|---|---|---|---|---|---|---|---|---|
| MISIR | 609097 | 2 | D21522 | 543 | M | 4011815904243 | £ | | 375 |
| | | 2 | D21522 | 543 | S | 4011815904236 | £ | | 250 |
| | | | | | | | | | 625 |

*FIG. 35.2*

File Name  : EUW456
Structure  : EDCGM-MULTI
Product    : EU
Date/Time  : 06/12/98 / 3:28:18 PM

AWJOBNO: 123456    HANGTAGTYP: EU    COUNTRY: T    CARTON# 1 OF 1

| FACTORY | SPO | PKG# | STYLE | CLRCODE | SIZE | CODE | RETAILCODE | RETAIL | QTY |
|---------|-----|------|-------|---------|------|------|------------|--------|-----|
| MISIR   | 609096 | 1 | D21521 | 543 | L | 4011815904229 | £ | | 250 |
|         |        | 1 | D21521 | 543 | M | 4011815904212 | £ | | 375 |
|         |        | 1 | D21521 | 543 | S | 4011815904205 | £ | | 250 |
|         |        |   |        |     |   |               |   | | 875 |
|         |        |   |        |     |   |               |   | | ==== |

| FACTORY | SPO | PKG# | STYLE | CLRCODE | SIZE | CODE | RETAILCODE | RETAIL | QTY |
|---------|-----|------|-------|---------|------|------|------------|--------|-----|
| MISIR   | 609097 | 2 | D21522 | 543 | M | 4011815904243 | £ | | 375 |
|         |        | 2 | D21522 | 543 | S | 4011815904236 | £ | | 250 |
|         |        |   |        |     |   |               |   | | 625 |
|         |        |   |        |     |   |               |   | | ==== |

FIG. 35.3

BOX: 1  SORT: S0001  TOT. QTY: 1000
COUNTRY: HKG  FACTORY: AWIC
SPO: 605420  JOB: 146589-EU

| STYLE  | CLRCODE | SIZE | CODE          | RETAIL | QTY |
|--------|---------|------|---------------|--------|-----|
| C21165 | 071     | 34   | 4011817902537 |        | 75  |
| C21165 | 071     | 34   | 4011817902537 |        | 75  |
| C21165 | 071     | 36   | 4011817902544 |        | 125 |
| C21165 | 071     | 36   | 4011817902544 |        | 125 |
| C21165 | 071     | 38   | 4011817902551 |        | 175 |
| C21165 | 071     | 38   | 4011817902551 |        | 175 |
| C21165 | 071     | 40   | 4011817902568 |        | 125 |
| C21165 | 071     | 40   | 4011817902568 |        | 125 |

*FIG. 36.1*

BOX: 2  SORT: S0002  TOT. QTY: 1500
COUNTRY: HKG  FACTORY: AWIC
SPO: 605420  JOB: 146589-EU

| STYLE  | CLRCODE | SIZE | CODE          | RETAIL | QTY |
|--------|---------|------|---------------|--------|-----|
| C21165 | 071     | 42   | 4011817902575 |        | 75  |
| C21165 | 071     | 42   | 4011817902575 |        | 75  |
| C21165 | 141     | 34   | 4011817902599 |        | 125 |
| C21165 | 141     | 34   | 4011817902599 |        | 125 |
| C21165 | 141     | 36   | 4011817902605 |        | 225 |
| C21165 | 141     | 36   | 4011817902605 |        | 225 |
| C21165 | 141     | 38   | 4011817902612 |        | 350 |
| C21165 | 141     | 38   | 4011817902612 |        | 300 |

*FIG. 36.2*

BOX: 3  SORT: S0003  TOT. QTY: 950
COUNTRY: HKG  FACTORY: AWIC
SPO: 605420  JOB: 146589-EU

| STYLE  | CLRCODE | SIZE | CODE          | RETAIL | QTY |
|--------|---------|------|---------------|--------|-----|
| C21165 | 141     | 38   | 4011817902612 |        | 50  |
| C21165 | 141     | 40   | 4011817902629 |        | 250 |
| C21165 | 141     | 40   | 4011817902629 |        | 250 |
| C21165 | 141     | 42   | 4011817902636 |        | 150 |
| C21165 | 141     | 42   | 4011817902636 |        | 150 |
| C21165 | 141     | 44   | 4011817902643 |        | 50  |
| C21165 | 141     | 44   | 4011817902643 |        | 50  |

*FIG. 36.3*

BOX: 1  SORT: S0004  TOT. QTY: 400
COUNTRY: HKG  FACTORY: FMRK
SPO: 605879  JOB: 146589-EU

| STYLE  | CLRCODE | SIZE | CODE          | RETAIL | QTY |
|--------|---------|------|---------------|--------|-----|
| C21232 | 041     | 34   | 4011817896416 |        | 25  |
| C21232 | 041     | 36   | 4011817896423 |        | 25  |
| C21232 | 041     | 38   | 4011817896430 |        | 25  |
| C21232 | 041     | 40   | 4011817896447 |        | 25  |
| C21232 | 041     | 42   | 4011817896454 |        | 25  |
| C21232 | 543     | 34   | 4011817896775 |        | 50  |
| C21232 | 543     | 36   | 4011817896782 |        | 100 |
| C21232 | 543     | 38   | 4011817896799 |        | 125 |

*FIG. 36.4*

BOX: 2  SORT: S0005  TOT. QTY: 175
COUNTRY: HKG  FACTORY: FMRK
SPO: 605879  JOB: 146589-EU

| STYLE | CLRCODE | SIZE | CODE | RETAIL | QTY |
|-------|---------|------|------|--------|-----|
| C21232 | 543 | 40 | 4011817896805 | | 100 |
| C21232 | 543 | 42 | 4011817896812 | | 50 |
| C21232 | 543 | 44 | 4011817896829 | | 25 |

*FIG. 36.5*

BOX: 1  SORT: S0006  TOT. QTY: 400
COUNTRY: HKG  FACTORY: PAKA
SPO: 605900  JOB: 146589-EU

| STYLE | CLRCODE | SIZE | CODE | RETAIL | QTY |
|-------|---------|------|------|--------|-----|
| C21228 | 041 | 34 | 4011817894733 | | 25 |
| C21228 | 041 | 36 | 4011817894740 | | 50 |
| C21228 | 041 | 38 | 4011817894757 | | 50 |
| C21228 | 041 | 40 | 4011817894764 | | 75 |
| C21228 | 041 | 42 | 4011817894771 | | 50 |
| C21228 | 041 | 44 | 4011817894788 | | 25 |
| C21228 | 543 | 34 | 4011817894856 | | 50 |
| C21228 | 543 | 36 | 4011817894863 | | 75 |

*FIG. 36.6*

BOX: 2  SORT: S0007  TOT. QTY: 275
COUNTRY: HKG  FACTORY: PAKA
SPO: 605900  JOB: 146589-EU

| STYLE  | CLRCODE | SIZE | CODE          | RETAIL | QTY |
|--------|---------|------|---------------|--------|-----|
| C21228 | 543     | 38   | 4011817894870 |        | 100 |
| C21228 | 543     | 40   | 4011817894887 |        | 100 |
| C21228 | 543     | 42   | 4011817894894 |        | 50  |
| C21228 | 543     | 44   | 4011817894900 |        | 25  |

*FIG. 36.7*

BOX: 3  SORT: S0008  TOT. QTY: 975
COUNTRY: HKG  FACTORY: PAKA
SPO: 605903  JOB: 146589-EU

| STYLE  | CLRCODE | SIZE | CODE          | RETAIL | QTY |
|--------|---------|------|---------------|--------|-----|
| C21230 | 041     | 34   | 4011817895211 |        | 50  |
| C21230 | 041     | 36   | 4011817895228 |        | 150 |
| C21230 | 041     | 38   | 4011817895235 |        | 200 |
| C21230 | 041     | 40   | 4011817895242 |        | 200 |
| C21230 | 041     | 42   | 4011817895259 |        | 150 |
| C21230 | 041     | 44   | 4011817895266 |        | 75  |
| C21230 | 543     | 34   | 4011817895334 |        | 25  |
| C21230 | 543     | 36   | 4011817895341 |        | 125 |

*FIG. 36.8*

BOX: 4  SORT: S0009  TOT. QTY: 425
COUNTRY: HKG  FACTORY: PAKA
SPO: 605903  JOB: 146589-EU

| STYLE | CLRCODE | SIZE | CODE | RETAIL | QTY |
|---|---|---|---|---|---|
| C21230 | 543 | 38 | 4011817895358 | | 150 |
| C21230 | 543 | 40 | 4011817895365 | | 125 |
| C21230 | 543 | 42 | 4011817895372 | | 100 |
| C21230 | 543 | 44 | 4011817895389 | | 50 |

*FIG. 36.9*

File Name : EUW456
Structure : EDCGM-MULTI
Product : EU
Date/Time : 06/12/98 / 3:28:19 PM EDCGM-MULTI
Packing Summary

AWJOBNO: 123456    HANGTAGTYP: EU

| COUNTRY | FACTORY | SPO | STYLE | CARTON NO. | SWRAP | QTY |
|---------|---------|--------|--------|------------|-------|------|
| T | MISIR | 609096 | D21521 | 1-1 | 1-1 | 875 |
|   |       | 609097 | D21522 | 1-1 | 2-2 | 625 |
|   |       |        |        |     |     | 1500 |

FIG. 37.1

File Name : EUW456
Structure : EDCGM-MULTI
Product : EU
Date/Time : 06/12/98 / 3:28:19 PM EDCGM-MULTI
Packing Summary

AWJOBNO: 123456  HANGTAGTYP: EU

| COUNTRY | FACTORY | SPO | STYLE | CARTON NO. | SWRAP | QTY |
|---|---|---|---|---|---|---|
| T | MISIR | 609096 | D21521 | 1-1 | 1-1 | 875 |
|   |   | 609097 | D21522 | 1-1 | 2-2 | 625 |
|   |   |   |   |   |   | 1500 |

FIG. 37.2

File Name : EUW456
Structure : EDCGM-MULTI
Product : EU
Date/Time : 06/12/98 / 3:28:20 PM

EDCGM-MULTI
Packing Summary

AWJOBNO: 123456   HANGTAGTYP: EU

| COUNTRY | FACTORY | SPO | STYLE | CARTON NO. | SWRAP | QTY |
|---------|---------|--------|--------|------------|-------|------|
| T | MISIR | 609096 | D21521 | 1-1 | 1-1 | 875 |
|   |       | 609097 | D21522 | 1-1 | 2-2 | 625 |
|   |       |        |        |     |     | 1500 |

FIG. 37.3

File Name    : EUW456
Structure    : EDCGM-MULTI
Product      : EU
Date/Time    : 06/12/98 / 3:28:18 PM

COUNTRY: T   FACTORY: MISIR

| CARTON# | SP-CODE | NO. OF BOX | QTY |
|---------|---------|------------|------|
| 1       | 1       | 2          | 1500 |

*FIG. 38*

Customer    : NEWGERM
Module      : MULTI
Description : MULTI CURRENCY FORMAT
File Name   : GM19005
Date/Time   : 06/11/98 / 4:25:52 PM

<< C4 PACKING LIST >>

FILENAME: G9819005  HT_REF: AA  SEASON: E  COUNTRY: CHN  FACTORY: MGR

| SPO | STYLE | CODE | DISTRI | DISTNAME | FCARNO | LCARNO | QTY |
|---|---|---|---|---|---|---|---|
| 850770 | E15203 | 2700008507706 | T | TURKEY | 1 | 10 | 40 |
| | | | | | | | 40 |

FIG. 39.1

Customer    : NEWGERM
Module      : MULTI
Description : MULTI CURRENCY FORMAT
Date/Time   : 06/11/98 / 4:25:52 PM

<< C4 PACKING LIST >>

FILENAME: G9819005  HT_REF: AA  SEASON: E  COUNTRY: CHN  FACTORY: UNN

| SPO | STYLE | CODE | DISTRI | DISTNAME | FCARNO | LCARNO | QTY |
|---|---|---|---|---|---|---|---|
| 850772 | E15204 | 2700008507720 | T | TURKEY | 1 | 10 | 40 |
| 850773 | E15206 | 2700008507737 | T | TURKEY | 1 | 10 | 40 |
| 850774 | E15192 | 2700008507744 | T | TURKEY | 1 | 10 | 40 |
| | | | | | | | 120 |
| | | | | | | | ===== |

FIG. 39.2

Customer : NEWGERM
Module : MULTI
Description : MULTI CURRENCY FORMAT
Date/Time : 06/11/98 / 4:25:52 PM

<< C4 PACKING LIST >>

FILENAME: G9819005  HT_REF: AU  SEASON: E  COUNTRY: CHN  FACTORY: HD

| SPO | STYLE | CODE | DISTRI | DISTNAME | FCARNO | LCARNO | QTY |
|-----|-------|------|--------|----------|--------|--------|-----|
| 611046 | E26290 | 2700006110465 | UKI | GERMANY | 1 | 110 | 440 |
|  |  |  |  |  |  |  | 440 |

FIG. 39.3

Customer : NEWGERM
Module : MULTI
Description : MULTI CURRENCY FORMAT
Date/Time : 06/11/98 / 4:25:53 PM

<< C4 PACKING LIST >>

FILENAME: G9819005  HT_REF: AU  SEASON: E  COUNTRY: CHN  FACTORY: HTU2

| SPO | STYLE | CODE | DISTRI | DISTNAME | FCARNO | LCARNO | QTY |
|---|---|---|---|---|---|---|---|
| 609525 | E15361 | 2700006095250 | UKI | GERMANY | 1 | 55 | 220 |
| 609526 | E15362 | 2700006095267 | UKI | GERMANY | 1 | 40 | 160 |
| 609527 | E15363 | 2700006095274 | UKI | GERMANY | 1 | 105 | 420 |
| 609529 | E15364 | 2700006095298 | UKI | GERMANY | 1 | 80 | 320 |
| 611036 | E15361 | 2700006110366 | UKI | GERMANY | 1 | 55 | 220 |
| 611043 | E15362 | 2700006110434 | UKI | GERMANY | 1 | 10 | 40 |
| 611044 | E15363 | 2700006110441 | UKI | GERMANY | 1 | 70 | 280 |
| 611045 | E15364 | 2700006110458 | UKI | GERMANY | 1 | 20 | 80 |
|  |  |  |  |  |  |  | 1740 |

FIG. 39.4

Customer    : NEWGERM
Module      : MULTI
Description : MULTI CURRENCY FORMAT
Date/Time   : 06/11/98 / 4:25:53 PM

<< C4 PACKING LIST >>

FILENAME: G9819005  HT_REF: AU  SEASON: E  COUNTRY: CHN  FACTORY: JF2

| SPO | STYLE | CODE | DISTRI | DISTNAME | FCARNO | LCARNO | QTY |
|---|---|---|---|---|---|---|---|
| 610042 | E26022 | 2700006100428 | UKI | GERMANY | 1 | 70 | 280 |
| 610048 | E26023 | 2700006100480 | UKI | GERMANY | 1 | 60 | 240 |
| 610057 | E26024 | 2700006100572 | UKI | GERMANY | 1 | 80 | 640 |
| 610067 | E26026 | 2700006100671 | UKI | GERMANY | 1 | 25 | 200 |
|  |  |  |  |  |  |  | 1360 |
|  |  |  |  |  |  |  | ===== |

*FIG. 39.5*

Customer : NEWGERM
Module : MULTI
Description : MULTI CURRENCY FORMAT
Date/Time : 06/11/98 / 4:25:53 PM

<< C4 PACKING LIST >>

FILENAME: G9819005  HT_REF: AU  SEASON: E  COUNTRY: CHN  FACTORY: JF4

| SPO | STYLE | CODE | DISTRI | DISTNAME | FCARNO | LCARNO | QTY |
|---|---|---|---|---|---|---|---|
| 610094 | E26027 | 2700006100947 | UKI | GERMANY | 1 | 30 | 120 |
| 610099 | E26028 | 2700006100992 | UKI | GERMANY | 1 | 40 | 160 |
| | | | | | | | 280 |

FIG. 39.6

Customer    : NEWGERM
Module      : MULTI
Description : MULTI CURRENCY FORMAT
Date/Time   : 06/11/98 / 4:25:53 PM

<< C4 PACKING LIST >>

FILENAME: G9819005  HT_REF: AU  SEASON: E  COUNTRY: CHN  FACTORY: MAXY

| SPO | STYLE | CODE | DISTRI | DISTNAME | FCARNO | LCARNO | QTY |
|---|---|---|---|---|---|---|---|
| 609981 | E26453 | 2700060099814 | UKI | GERMANY | 1 | 10 | 40 |
| | | | | | | | 40 |
| | | | | | | | === |

*FIG. 39.7*

Customer    : NEWGERM
Module      : MULTI
Description : MULTI CURRENCY FORMAT
Date/Time   : 06/11/98 / 4:25:53 PM

<< C4 PACKING LIST >>

FILENAME: G9819005  HT_REF: AU  SEASON: E  COUNTRY: CHN  FACTORY: MGR

| SPO | STYLE | CODE | DISTRI | DISTNAME | FCARNO | LCARNO | QTY |
|---|---|---|---|---|---|---|---|
| 609686 | E15200 | 2700006096868 | UKI | GERMANY | 1 | 15 | 60 |
| 609716 | E15259 | 2700006097162 | UKI | GERMANY | 1 | 160 | 640 |
| 609719 | E15262 | 2700006097193 | UKI | GERMANY | 1 | 45 | 180 |
| 610292 | E15203 | 2700006102927 | UKI | GERMANY | 1 | 125 | 500 |
| 611028 | E15259 | 2700006110281 | UKI | GERMANY | 1 | 170 | 680 |
| 611030 | E15262 | 2700006110304 | UKI | GERMANY | 1 | 10 | 40 |
| | | | | | | | 2100 |

FIG. 39.8

Customer : NEWGERM
Module : MULTI
Description : MULTI CURRENCY FORMAT
Date/Time : 06/11/98 / 4:25:53 PM

<< C4 PACKING LIST >>

FILENAME: G9819005  HT_REF: AU  SEASON: E  COUNTRY: CHN  FACTORY: MWH

| SPO | STYLE | CODE | DISTRI | DISTNAME | FCARNO | LCARNO | QTY |
|---|---|---|---|---|---|---|---|
| 609264 | E15295 | 270000609264B | UKI | GERMANY | 1 | 30 | 120 |
| 609265 | E15297 | 270000609265S | UKI | GERMANY | 1 | 10 | 40 |
| 609270 | E15300 | 270000609270P | UKI | GERMANY | 1 | 15 | 60 |
| 609592 | E15295 | 270000609592 | UKI | GERMANY | 1 | 140 | 560 |
| 609593 | E15295 | 270000609593 | UKI | GERMANY | 1 | 200 | 800 |
| 609595 | E15297 | 270000609595 | UKI | GERMANY | 1 | 20 | 80 |
| 609596 | E15297 | 270000609596 | UKI | GERMANY | 1 | 95 | 380 |
| 609598 | E15300 | 270000609598 | UKI | GERMANY | 1 | 180 | 720 |
| 609599 | E15300 | 270000609599 | UKI | GERMANY | 1 | 125 | 500 |
| 611047 | E26293 | 270000611047Z | UKI | GERMANY | 1 | 10 | 40 |
| 611048 | E26293 | 270000611048P | UKI | GERMANY | 1 | 65 | 260 |
| | | | | | | | 3560 |

FIG. 39.9

Customer     : NEWGERM
Module       : MULTI
Description  : MULTI CURRENCY FORMAT
Date/Time    : 06/11/98 / 4:25:54 PM

<< C4 PACKING LIST >>

FILENAME: G9819005   HT_REF: AU   SEASON: E   COUNTRY: CHN   FACTORY: SFL2

| SPO | STYLE | CODE | DISTRI | DISTNAME | FCARNO | LCARNO | QTY |
|---|---|---|---|---|---|---|---|
| 609779 | E26003 | 2700006097797 | UKI | GERMANY | 1 | 95 | 380 |
| 609781 | E26004 | 2700006097810 | UKI | GERMANY | 1 | 85 | 340 |
| 609782 | E26005 | 2700006097827 | UKI | GERMANY | 1 | 65 | 260 |
| 609784 | E26009 | 2700006097841 | UKI | GERMANY | 1 | 25 | 100 |
| | | | | | | | 1080 |

FIG. 39.10

Customer    : NEWGERM
Module      : MULTI
Description : MULTI CURRENCY FORMAT
Date/Time   : 06/11/98 / 4:25:54 PM

<< C4 PACKING LIST >>

FILENAME: G9819005  HT_REF: AU  SEASON: E  COUNTRY: CHN  FACTORY: UNN

| SPO | STYLE | CODE | DISTRI | DISTNAME | FCARNO | LCARNO | QTY |
|---|---|---|---|---|---|---|---|
| 609688 | E15204 | 270000609688 | UKI | GERMANY | 1 | 310 | 1240 |
| 609718 | E15261 | 270000609718 | UKI | GERMANY | 1 | 145 | 580 |
| 610294 | E15205 | 270000610294 | UKI | GERMANY | 1 | 160 | 640 |
| 610296 | E15206 | 270000610296 | UKI | GERMANY | 1 | 15 | 60 |
| 610395 | E15192 | 270000610395 | UKI | GERMANY | 1 | 150 | 600 |
| 610396 | E15192 | 270000610396 | UKI | GERMANY | 1 | 20 | 80 |
| 611015 | E15204 | 270000611015 | UKI | GERMANY | 1 | 65 | 260 |
| 611029 | E15261 | 270000611029 | UKI | GERMANY | 1 | 55 | 220 |
| | | | | | | | 3680 |

*FIG. 39.11*

Customer : NEWGERM
Module : MULTI
Description : MULTI CURRENCY FORMAT
Date/Time : 06/11/98 / 4:25:54 PM

<< C4 PACKING LIST >>

FILENAME: G9819005  HT_REF: AU  SEASON: E  COUNTRY: CHN  FACTORY: YTX

| SPO | STYLE | CODE | DISTRI | DISTNAME | FCARNO | LCARNO | QTY |
|---|---|---|---|---|---|---|---|
| 609261 | E15251 | 270006092617 | UKI | GERMANY | 1 | 60 | 240 |
| 609262 | E15291 | 270006092624 | UKI | GERMANY | 1 | 95 | 380 |
| 609271 | E15321 | 270006092716 | UKI | GERMANY | 1 | 30 | 120 |
| 609273 | E15359 | 270006092730 | UKI | GERMANY | 1 | 20 | 80 |
| 611019 | E15251 | 270006110199 | UKI | GERMANY | 1 | 315 | 1260 |
| 611031 | E15291 | 270006110311 | UKI | GERMANY | 1 | 330 | 1320 |
| 611033 | E15321 | 270006110335 | UKI | GERMANY | 1 | 105 | 420 |
| 611035 | E15359 | 270006110359 | UKI | GERMANY | 1 | 100 | 400 |
| | | | | | | | 4220 |
| | | | | | | | ===== |

FIG. 39.12

Customer : NEWGERM
Module : MULTI
Description : MULTI CURRENCY FORMAT
Date/Time : 06/11/98 / 4:25:54 PM

<< C4 PACKING LIST >>

FILENAME: G9819005  HT_REF: AU  SEASON: E  COUNTRY: I  FACTORY: ITALC

| SPO | STYLE | CODE | DISTRI | DISTNAME | FCARNO | LCARNO | QTY |
|---|---|---|---|---|---|---|---|
| 610017 | E15196 | 2700006100176 | UKI | GERMANY | 1 | 235 | 940 |
|  |  |  |  |  |  |  | 940 |

FIG. 39.13

Customer : NEWGERM
Module : MULTI
Description : MULTI CURRENCY FORMAT
Date/Time : 06/11/98 / 4:25:54 PM

<< C4 PACKING LIST >>

FILENAME: G9819005  HT_REF: AU  SEASON: E  COUNTRY: I  FACTORY: MASET

| SPO | STYLE | CODE | DISTRI | DISTNAME | FCARNO | LCARNO | QTY |
|---|---|---|---|---|---|---|---|
| 610021 | E15197 | 2700006100213 | UKI | GERMANY | 1 | 30 | 120 |
| | | | | | | | 120 |

FIG. 39.14

Customer : NEWGERM
Module : MULTI
Description : MULTI CURRENCY FORMAT
Date/Time : 06/11/98 / 4:25:54 PM

<< C4 PACKING LIST >>

FILENAME: G9819005  HT_REF: BE  SEASON: E  COUNTRY: P  FACTORY: FIL0B

| SPO | STYLE | CODE | DISTRI | DISTNAME | FCARNO | LCARNO | QTY |
|---|---|---|---|---|---|---|---|
| 610951 | E20953 | 2700006109513 | UKI | GERMANY | 1 | 90 | 360 |
| 610952 | E20954 | 2700006109520 | UKI | GERMANY | 1 | 60 | 240 |
| 610953 | E20955 | 2700006109537 | UKI | GERMANY | 1 | 45 | 180 |
| 610956 | E20956 | 2700006109568 | UKI | GERMANY | 1 | 25 | 100 |
| 610967 | E20967 | 2700006109674 | UKI | GERMANY | 1 | 80 | 320 |
| | | | | | | | 1200 |
| | | | | | | | ====== |

FIG. 39.15

Customer : NEWGERM
Module : MULTI
Description : MULTI CURRENCY FORMAT
Date/Time : 06/11/98 / 4:25:09 PM

<< C4 SUMMARY LIST >>

FILENAME: G9819005  HT_REF: AA  SEASON: E

| COUNTRY | FACTORY | SPO | STYLE | DISTRI | DISTNAME | QTY |
|---|---|---|---|---|---|---|
| CHN | MGR | 850770 | E15203 | T | TURKEY | 40 |
| CHN | UNN | 850772 | E15204 | T | TURKEY | 40 |
| CHN | UNN | 850773 | E15206 | T | TURKEY | 40 |
| CHN | UNN | 850774 | E15192 | T | TURKEY | 40 |
| | | | | | | 160 |

FIG. 40.1

Customer : NEWGERM
Module : MULTI
Description : MULTI CURRENCY FORMAT
Date/Time : 06/11/98 / 4:25:10 PM

<< C4 SUMMARY LIST >>

FILENAME: G9819005  HT_REF: AU  SEASON: E

| COUNTRY | FACTORY | SPO | STYLE | DISTRI | DISTNAME | QTY |
|---------|---------|--------|--------|--------|----------|-----|
| CHN | HD | 611046 | E26290 | UKI | GERMANY | 440 |
| CHN | HTU2 | 609525 | E15361 | UKI | GERMANY | 220 |
| CHN | HTU2 | 609526 | E15362 | UKI | GERMANY | 160 |
| CHN | HTU2 | 609527 | E15363 | UKI | GERMANY | 420 |
| CHN | HTU2 | 609529 | E15364 | UKI | GERMANY | 320 |
| CHN | HTU2 | 611036 | E15361 | UKI | GERMANY | 220 |
| CHN | HTU2 | 611043 | E15362 | UKI | GERMANY | 40 |
| CHN | HTU2 | 611044 | E15363 | UKI | GERMANY | 280 |
| CHN | HTU2 | 611045 | E15364 | UKI | GERMANY | 80 |
| CHN | JF2 | 610042 | E26022 | UKI | GERMANY | 280 |
| CHN | JF2 | 610048 | E26023 | UKI | GERMANY | 240 |
| CHN | JF2 | 610057 | E26024 | UKI | GERMANY | 340 |
| CHN | JF2 | 610067 | E26026 | UKI | GERMANY | 200 |
| CHN | JF4 | 610094 | E26027 | UKI | GERMANY | 120 |
| CHN | JF4 | 610099 | E26028 | UKI | GERMANY | 160 |

*FIG. 40.2A*

| | | | | | |
|---|---|---|---|---|---|
| CHN | MAXY | 609981 | E26453 | UKI | 40 |
| CHN | MGR | 609686 | E15200 | UKI | 60 |
| CHN | MGR | 609716 | E15259 | UKI | 640 |
| CHN | MGR | 609719 | E15262 | UKI | 180 |
| CHN | MGR | 610292 | E15203 | UKI | 500 |
| CHN | MGR | 611028 | E15259 | UKI | 680 |
| CHN | MGR | 611030 | E15262 | UKI | 40 |
| CHN | MWH | 609264 | E15295 | UKI | 120 |
| CHN | MWH | 609265 | E15297 | UKI | 40 |
| CHN | MWH | 609270 | E15300 | UKI | 60 |
| CHN | MWH | 609592 | E15295 | UKI | 560 |
| CHN | MWH | 609593 | E15295 | UKI | 800 |
| CHN | MWH | 609595 | E15297 | UKI | 80 |
| CHN | MWH | 609596 | E15297 | UKI | 380 |
| CHN | MWH | 609598 | E15300 | UKI | 720 |
| CHN | MWH | 609599 | E15300 | UKI | 500 |
| CHN | MWH | 611047 | E26293 | UKI | 40 |
| CHN | MWH | 611048 | E26293 | UKI | 260 |
| CHN | SFL2 | 609779 | E26003 | UKI | 380 |
| CHN | SFL2 | 609781 | E26004 | UKI | 340 |
| CHN | SFL2 | 609782 | E26005 | UKI | 260 |
| CHN | SFL2 | 609784 | E26009 | UKI | 100 |
| CHN | UNN | 609688 | E15204 | UKI | 1240 |
| CHN | UNN | 609718 | E15261 | UKI | 580 |
| CHN | UNN | 610294 | E15205 | UKI | 640 |
| CHN | UNN | 610296 | E15206 | UKI | 60 |

All entries with country GERMANY.

FIG. 40.2B

| | | | | | |
|---|---|---|---|---|---|
| CHN | UNN | 610395 | E15192 | UKI | GERMANY | 600 |
| CHN | UNN | 610396 | E15192 | UKI | GERMANY | 80 |
| CHN | UNN | 611015 | E15204 | UKI | GERMANY | 260 |
| CHN | UNN | 611029 | E15261 | UKI | GERMANY | 220 |
| CHN | YTX | 609261 | E15251 | UKI | GERMANY | 240 |
| CHN | YTX | 609262 | E15291 | UKI | GERMANY | 380 |
| CHN | YTX | 609271 | E15321 | UKI | GERMANY | 120 |
| CHN | YTX | 609273 | E15359 | UKI | GERMANY | 80 |
| CHN | YTX | 611019 | E15251 | UKI | GERMANY | 1260 |
| CHN | YTX | 611031 | E15291 | UKI | GERMANY | 1320 |
| CHN | YTX | 611033 | E15321 | UKI | GERMANY | 420 |
| CHN | YTX | 611035 | E15359 | UKI | GERMANY | 400 |
| — | ITALC | 610017 | E15196 | UKI | GERMANY | 940 |
| — | MASET | 610021 | E15197 | UKI | GERMANY | 120 |
| | | | | | | ------- |
| | | | | | | 19560 |
| | | | | | | ======= |

*FIG. 40.2C*

Customer : NEWGERM
Module : MULTI
Description : MULTI CURRENCY FORMAT
Date/Time : 06/11/98 / 4:25:10 PM

<< C4 SUMMARY LIST >>

FILENAME: G9819005  HT_REF: BE  SEASON: E

| COUNTRY | FACTORY | SPO | STYLE | DISTRI | DISTNAME | QTY |
|---------|---------|--------|--------|--------|----------|-----|
| P | FILOB | 610951 | E20953 | UKI | GERMANY | 360 |
| P | FILOB | 610952 | E20954 | UKI | GERMANY | 240 |
| P | FILOB | 610953 | E20955 | UKI | GERMANY | 180 |
| P | FILOB | 610956 | E20956 | UKI | GERMANY | 100 |
| P | FILOB | 610967 | E20967 | UKI | GERMANY | 320 |
| P | M&O | 610957 | E20957 | UKI | GERMANY | 280 |
| P | M&O | 610958 | E20958 | UKI | GERMANY | 380 |
| P | M&O | 610959 | E20959 | UKI | GERMANY | 300 |
| P | M&O | 610963 | E20962 | UKI | GERMANY | 320 |
| P | M&O | 610976 | E20998 | UKI | GERMANY | 120 |
|   |   |   |   |   |   | 2600 |

FIG. 40.3

Customer : NEWGERM
Module : MULTI
Description : MULTI CURRENCY FORMAT
Date/Time : 06/11/98 / 4:25:10 PM

<< C4 SUMMARY LIST >>

FILENAME: G9819005  HT_REF: EU  SEASON: D

| COUNTRY | FACTORY | SPO | STYLE | DISTRI | DISTNAME | QTY |
|---|---|---|---|---|---|---|
| T | MISIR | 609096 | D21521 | UKI | GERMANY | 80 |
| T | MISIR | 609097 | D21522 | UKI | GERMANY | 80 |
| | | | | | | 160 |

FIG. 40.4

Customer : NEWGERM
Module : MULTI
Description : MULTI CURRENCY FORMAT
Date/Time : 06/11/98 / 4:25:10 PM

<< C4 SUMMARY LIST >>

FILENAME: G9819005 HT_REF: EU SEASON: N

| COUNTRY | FACTORY | SPO | STYLE | DISTRI | DISTNAME | QTY |
|---------|---------|--------|--------|--------|----------|-----|
| HKG | WGF | 610645 | N29510 | UKI | GERMANY | 100 |
| | | | | | | 100 |

*FIG. 40.5*

Customer : NEWGERM
Module : MULTI
Description : MULTI CURRENCY FORMAT
Date/Time : 06/11/98 / 4:25:11 PM

<< C4 SUMMARY LIST >>

FILENAME: G9819005  HT_REF: KG  SEASON: E

| COUNTRY | FACTORY | SPO | STYLE | DISTRI | DISTNAME | QTY |
|---|---|---|---|---|---|---|
| HKG | DRGT | 610059 | E02132 | UKI | GERMANY | 80 |
| P | CANDI | 610822 | E02945 | UKI | GERMANY | 280 |
| P | CANDI | 610824 | E02946 | UKI | GERMANY | 220 |
| P | CANDI | 610841 | E02963 | UKI | GERMANY | 280 |
| P | CANDI | 610843 | E02967 | UKI | GERMANY | 240 |
| P | CANDI | 610848 | E02970 | UKI | GERMANY | 340 |
| P | CANDI | 610850 | E02971 | UKI | GERMANY | 80 |
| P | CANDI | 610884 | E06945 | UKI | GERMANY | 80 |
| P | CANDI | 610906 | E06963 | UKI | GERMANY | 140 |
| P | CANDI | 610907 | E06970 | UKI | GERMANY | 140 |
| P | CANDI | 610922 | E07935 | UKI | GERMANY | 80 |
| P | CANDI | 610926 | E07940 | UKI | GERMANY | 60 |
| P | CANDI | 610938 | E08935 | UKI | GERMANY | 160 |
| P | CANDI | 610940 | E08940 | UKI | GERMANY | 160 |
| P | FILOB | 610807 | E02930 | UKI | GERMANY | 380 |
| P | FILOB | 610808 | E02931 | UKI | GERMANY | 260 |

*FIG. 40.6A*

Customer : NEWGERM
Module : MULTI
Description : MULTI CURRENCY FORMAT
Date/Time : 06/11/98 / 4:25:11 PM

<< C4 SUMMARY LIST >>

FILENAME: G9819005  HT_REF: KG  SEASON: E

| COUNTRY | FACTORY | SPO | STYLE | DISTRI | DISTNAME | QTY |
|---------|---------|--------|--------|--------|----------|-----|
| HKG | DRGT | 610059 | E02132 | UKI | GERMANY | 80 |
| P | CANDI | 610822 | E02945 | UKI | GERMANY | 280 |
| P | CANDI | 610824 | E02946 | UKI | GERMANY | 220 |
| P | CANDI | 610841 | E02963 | UKI | GERMANY | 280 |
| P | CANDI | 610843 | E02967 | UKI | GERMANY | 240 |
| P | CANDI | 610848 | E02970 | UKI | GERMANY | 340 |
| P | CANDI | 610850 | E02971 | UKI | GERMANY | 80 |
| P | CANDI | 610884 | E06945 | UKI | GERMANY | 80 |
| P | CANDI | 610906 | E06963 | UKI | GERMANY | 140 |
| P | CANDI | 610907 | E06970 | UKI | GERMANY | 140 |
| P | CANDI | 610922 | E07935 | UKI | GERMANY | 80 |
| P | CANDI | 610926 | E07940 | UKI | GERMANY | 60 |
| P | CANDI | 610938 | E08935 | UKI | GERMANY | 160 |
| P | CANDI | 610940 | E08940 | UKI | GERMANY | 160 |
| P | FILOB | 610807 | E02930 | UKI | GERMANY | 380 |
| P | FILOB | 610808 | E02931 | UKI | GERMANY | 260 |

FIG. 40.6A

| | | | | | |
|---|---|---|---|---|---|
| P | FILOB | 610825 | E02948 | UKI | GERMANY | 400 |
| P | FILOB | 610827 | E02949 | UKI | GERMANY | 160 |
| P | FILOB | 610851 | E02973 | UKI | GERMANY | 620 |
| P | FILOB | 610857 | E02999 | UKI | GERMANY | 80 |
| P | FILOB | 610876 | E06936 | UKI | GERMANY | 740 |
| P | FILOB | 610885 | E06947 | UKI | GERMANY | 500 |
| P | FILOB | 610886 | E06948 | UKI | GERMANY | 460 |
| P | FILOB | 610914 | E07925 | UKI | GERMANY | 460 |
| P | FILOB | 610916 | E07927 | UKI | GERMANY | 240 |
| P | FILOB | 610921 | E07934 | UKI | GERMANY | 140 |
| P | FILOB | 610927 | E07942 | UKI | GERMANY | 340 |
| P | FILOB | 610928 | E08926 | UKI | GERMANY | 280 |
| P | FILOB | 610931 | E08927 | UKI | GERMANY | 280 |
| P | FILOB | 610933 | E08928 | UKI | GERMANY | 280 |
| P | FILOB | 610941 | E08941 | UKI | GERMANY | 320 |
| P | M&O | 610809 | E02932 | UKI | GERMANY | 420 |
| P | M&O | 610810 | E02933 | UKI | GERMANY | 920 |
| P | M&O | 610811 | E02934 | UKI | GERMANY | 60 |
| P | M&O | 610812 | E02936 | UKI | GERMANY | 80 |
| P | M&O | 610813 | E02937 | UKI | GERMANY | 480 |
| P | M&O | 610835 | E02957 | UKI | GERMANY | 80 |
| P | M&O | 610839 | E02960 | UKI | GERMANY | 440 |
| P | M&O | 610840 | E02961 | UKI | GERMANY | 80 |
| P | M&O | 610853 | E02980 | UKI | GERMANY | 80 |
| P | M&O | 610854 | E02990 | UKI | GERMANY | 60 |
| P | M&O | 610855 | E02991 | UKI | GERMANY | 40 |

*FIG. 40.6B*

| P | M&O | 610871 | E06928 | UKI | GERMANY | 220 |
| P | M&O | 610872 | E06930 | UKI | GERMANY | 360 |
| P | M&O | 610873 | E06931 | UKI | GERMANY | 280 |
| P | M&O | 610874 | E06933 | UKI | GERMANY | 120 |
| P | M&O | 610882 | E06941 | UKI | GERMANY | 60 |
| P | M&O | 610902 | E06958 | UKI | GERMANY | 300 |
| | | | | | | ----- |
| | | | | | | 12360 |
| | | | | | | ===== |

FIG. 40.6C

File Name    : EUW456
Structure    : EDCGM-MULTI
Product      : EU
Date/Time    : 06/12/98 / 3:28:20 PM

EDCGM-MULTI
Shipping Summary List

AWJOBNO: 123456    HANGTAGTYP: EU

| CARTON# | COUNTRY | FACTORY | SP-CODE | QTY | WEIGHT | BOX CODE |
|---------|---------|---------|---------|------|--------|----------|
| 1 | T | MISIR | 1 - 2 | 1500 | | |

FIG. 41

| STRUCTURE MAINTENANCE | | | | | | |
|---|---|---|---|---|---|---|
| CUSTOMER STRUCTURE | ESPRIT - GERMANY | | CLEAR STRUCTURE | | | |
| STRUCTURE CODE | | FIELD NAME | FIELD TYPE | FIELD LENGTH | FIELD DECIMAL | INPUT LENGTH |
| ESPRIT - GERMANY | 1 | AWJOBNO | C | 6 | 0 | 6 |
| | 2 | CLRCODE | C | 3 | 0 | 3 |
| | 3 | CLRNAME | C | 3 | 0 | 3 |
| | 4 | CODE | C | 13 | 0 | 13 |
| | 5 | COLORHEAD | C | 15 | 0 | 15 |
| | 6 | COUNTRY | C | 3 | 0 | 3 |
| | 7 | DISTNAME | C | 15 | 0 | 15 |
| | 8 | DISTRI | C | 3 | 0 | 3 |
| | 9 | DIV | C | 2 | 0 | 2 |
| | 10 | FACTORY | C | 5 | 0 | 5 |
| | 11 | FILE NAME | C | 8 | 0 | 8 |
| | 12 | HANGTAGTYP | C | 2 | 0 | 2 |
| | 13 | HT_REF | C | 2 | 0 | 2 |
| | 14 | ORDERDATE | N | 6 | 0 | 6 |

| DELETE STRUCTURE | SAVE STRUCTURE | IMPORT STRUCTURE | INSERT ROW | DELETE ROW | EXIT |

*FIG. 42*

| ORDER ANALYSIS CONFIGURATION | | | | | |
|---|---|---|---|---|---|
| DATA ENTRY | COPY TO DBF | SELF LOOKUP TABLES | RUN TIME OPTIONS | AW JOB# ASSIGN | |
| CHECK CRITERIA | CONTROL TABLES | REPORTS | ORDER STRUCTURE | BARCODE CHECK | |
| MAIN MENU | DUPLICATE | CONTROL FIELDS | REPLACE FIELDS | LOOK UP TABLES | |

| | OA MODULE # | DESCRIPTION | |
|---|---|---|---|
| | EMAIL | EMAIL FILE TRANSFER | CUSTOMER FIELD LIST |
| DETAIL EDC_SFO | NOOS | NEVER OUT OF STOCK ORDERS (NOOS) | |
| GERMANY | | | |
| PATAGON | | | |
| SF_SHOE | | | |

| ADD MODULE | DELETE MODULE | COPY MODULE SETTINGS |
|---|---|---|
| CLEAR LOCK | SAVE MODULE | EXIT |

*FIG. 43*

| ORDER ANALYSIS CONFIGURATION | | | | | |
|---|---|---|---|---|---|
| DATA ENTRY | COPY TO DBF | SELF LOOKUP TABLES | RUN TIME OPTIONS | AW JOB# ASSIGN | |
| CHECK CRITERIA | CONTROL TABLES | REPORTS | ORDER ST | CUSTOMER FIELD LIST | |
| MAIN MENU | DUPLICATE | CONTROL FIELDS | REPLACE FIELDS | LOOK UP TABLES | |

| DUPLICATE FIELD | |
|---|---|
| SPO | |
| CODE | |

CLEAR DUPLICATE FIELD

*FIG. 44*

| ORDER ANALYSIS CONFIGURATION | | | | | |
|---|---|---|---|---|---|
| DATA ENTRY | COPY TO DBF | SELF LOOKUP TABLES | RUN TIME OPTIONS | AW JOB# ASSIGN | |
| CHECK CRITERIA | CONTROL TABLES | REPORTS | ORDER ST | CUSTOMER FIELD LIST | |
| MAIN MENU | DUPLICATE | CONTROL FIELDS | REPLACE FIELDS | LOOK UP TABLES | |

| | FIELD NAME | FIELD TYPE | FIELD LENGTH | FIELD DECIMAL | REPLACE VALUE EXPRESSION |
|---|---|---|---|---|---|
| 1 | HT_REF | C | 2 | 0 | |
| 2 | DISTNAME | C | 15 | 0 | |
| 3 | SIZEHEAD | C | 10 | 0 | |
| 4 | ERR_HTG | C | 1 | 0 | |
| 5 | RQTY | C | 7 | 0 | |
| 6 | ERR_RET | C | 1 | 0 | |
| 7 | ERR_FTY | C | 1 | 0 | |
| 8 | LENGTH | C | 10 | 0 | |
| 9 | AWJOBNO | C | 6 | 0 | |
| 10 | CODE1 | C | 13 | 0 | |
| 11 | ERR_CODE | C | 1 | 0 | |
| 12 | SHPQTY | C | 7 | 0 | |

INSERT ROW    DELETE ROW    CLEAR STRUCTURE

*FIG. 45*

USER ADMINISTRATION MAINTENANCE

ORDER ANALYSIS CONFIGURATION

| DATA ENTRY | COPY TO DBF | SELF LOOKUP TABLES | RUN TIME OPTIONS | BARCODE CHECK |
| CHECK CRITERIA | CONTROL TABLES | REPORTS | ORDER ST | CUSTOMER FIELD LIST |
| MAIN MENU | DUPLICATE | CONTROL FIELDS | REPLACE FIELDS | LOOK UP TABLES |

| TABLE | LOOKUP KEY EXPRESSION | STRUCTURE | INDEX TAG | INDEX KEY EXPRESSION |
|---|---|---|---|---|
| HTDIV | HANGTAGTYP + DIV | EXIST | DIV | HANGTAGTYP + DIV |
| COD1 | SPO + CLRCODE | EXIST | SPO | SPO + CLRCODE |
| DIST | DISTRI | EXIST | DISTRI | DISTRI |
| MULTI | HANGTAGTYP | EXIST | HANGTG | HANGTAGTYP |
| MCCTY | CTY_M1 | EXIST | CTYM1 | CTY_M1 |
| INVOICE | COUNTRY | EXIST | COUNTRY | COUNTRY |
| GRAPHIC | STYLE | EXIST | GRAPHIC | STYLE |

| REPLACE FIELD | REPLACE VALUE EXPRESSION | DEFAULT VALUE EXPRESSION |
|---|---|---|
| ERR_HTG | "N" | "Y" |

EDIT LOOKUP TABLE
CLEAR TABLE ROW
CLEAR REPLACE ROW

FIG. 48

ORDER ANALYSIS CONFIGURATION

| MAIN MENU | DUPLICATE | CONTROL FIELDS | REPLACE FIELDS | LOOK UP TABLES |
| DATA ENTRY | COPY TO DBF | SELF LOOKUP TABLES | RUN TIME OPTIONS | AW JOB# ASSIGN |
| CHECK CRITERIA | CONTROL TABLES | REPORTS | ORDER STRUCTURE | BARCODE CHECK |

CUSTOMER FIELD LIST

| | CHECKING DESCRIPTION | CHECKING CONDITION |
|---|---|---|
| 1 | DUPLICATE CHECKING | DEFAULT |
| 2 | BARCODE CHECKING | DEFAULT |
| 3 | ZERO QUANTITY | QTY <= 0 |
| 4 | ERROR FLAG | ERR_FTY='Y'.OR.ERR_RET='Y'.OR.ERR_HTG='Y'.OR.E |
| 5 | | |
| 6 | | |
| 7 | | |
| 8 | | |
| 9 | | |
| 10 | | |
| 11 | | |
| 12 | | |
| 13 | | |

INSERT ROW | DELETE ROW | CLEAR ALL CHECKING

FIG. 49

USER ADMINISTRATION MAINTENANCE

ORDER ANALYSIS CONFIGURATION

| MAIN MENU | DUPLICATE | CONTROL FIELDS | REPLACE FIELDS | LOOK UP TABLES |
|---|---|---|---|---|
| DATA ENTRY | COPY TO DBF | SELF LOOKUP TABLES | RUN T... | CUSTOMER FIELD LIST |
| CHECK CRITERIA | CONTROL TABLES | REPORTS | ORDER STRUCTURE | BARCODE CHECK |

| | FIELD NAME | FIELD TYPE | FIELD LENGTH | FIELD DECIMAL |
|---|---|---|---|---|
| 1 | ORDERDATE | N | 6 | 0 |
| 2 | YEAR1 | C | 4 | 0 |
| 3 | DISTRI | C | 3 | 0 |
| 4 | COUNTRY | C | 3 | 0 |
| 5 | CHG_CNTRY | C | 1 | 0 |
| 6 | CNTYNAME | C | 25 | 0 |
| 7 | SEASON | C | 1 | 0 |
| 8 | DIV | C | 2 | 0 |
| 9 | STYLEHEAD | C | 15 | 0 |
| 10 | STYLE | C | 6 | 0 |
| 11 | STYLEDESC | C | 15 | 0 |
| 12 | COLORHEAD | C | 15 | 0 |

INPUT FILE TYPE
6 - DBASE III AND FOXPRO
ASCII SEPARATOR 44 ,
ASCII QUOTE 34 "

[INSERT ROW] [DELETE ROW] [IMPORT STRUCTURE] [CLEAR STRUCTURE]

FIG. 52

ORDER ANALYSIS CONFIGURATION

| MAIN MENU | DUPLICATE | CONTROL FIELDS | REPLACE FIELDS | LOOK UP TABLES |
|---|---|---|---|---|
| DATA ENTRY | COPY TO DBF | SELF LOOKUP TABLES | RUN TIME OPTIONS | AW JOB# ASSIGN |
| CHECK CRITERIA | CONTROL TABLES | REPORTS | ORDER STRUCTURE | BARCODE CHECK |

| FIELD NAME | BARCODE |
|---|---|
| CODE | EAN-13 |

| BARCODE TYPE |
|---|
| UPC |
| EAN-13 |

[CLEAR BARCODE ROW]

FIG. 53

| ORDER ANALYSIS CONFIGURATION | | | | | | | | | ☒ |
|---|---|---|---|---|---|---|---|---|---|
| CHECK CRITERIA | | CONTROL TABLES | | REPORTS | | ORDER STRUCTURE | | BARCODE CHECK | |
| MAIN MENU | | DUPLICATE | | CONTROL FIELDS | | REPLACE FIELDS | | LOOK UP TABLES | |
| DATA ENTRY | | COPY TO DBF | | SELF LOOKUP TABLES | | RUN TIME OPTIONS | | AW JOB# ASSIGN | |
| FIELD NAME | TYPE | LEN | DEC | TABLE | LOOKUP KEY EXPRESSION | | INDEX TAG | INDEX KEY EXPRESSION | |
| | | | | | | | | | |

CLEAR DATA ENTRY ROW

FIG. 54

| ORDER ANALYSIS CONFIGURATION | | | | | ☒ |
|---|---|---|---|---|---|
| CHECK CRITERIA | CONTROL TABLES | REPORTS | | ORDER STRUCTURE | BARCODE CHECK |
| MAIN MENU | DUPLICATE | CONTROL FIELDS | | REPLACE FIELDS | AW JOB# ASSIGN |
| DATA ENTRY | COPY TO DBF | SELF LOOKUP TABLES | RUN TI | CUSTOMER FIELD LIST | ⇩ |
| COPY NAME EXPRESSION | COPY SORT EXPRESSION | COPY FOR EXPRESSION | REPEAT FIELD | | |
| "GM" + RIGHT (FILENAME,5) | HANGTAGTYP | QTY > 0 | | | |
| "PP" + RIGHT (FILENAME,5) | COUNTRY + FACTORY + SPO | QTY > 0 .AND. HANGTAGTYP | | | |
| "C4" + HT_REF + SEASON | SEASON + HT_REF + | HANGTAGTYP = 'C4' .AND. | QTY | | |

| FIELD NAME | FIELD TYPE | FIELD LEN | FIELD DEC | INSERT BLANK | |
|---|---|---|---|---|---|
| AWJOBNO | C | 6 | 0 | | |
| CLRCODE | C | 3 | 0 | | |
| CLRNAME | C | 3 | 0 | | |
| CODE | C | 13 | 0 | | |
| CODE1 | C | 13 | 0 | | |
| COLORHEAD | C | 15 | 0 | | |

CLEAR COPY FILE ROW

CLEAR COPY SYRUCTURE ROW

ORDER ANALYSIS CONFIGURATION

Tabs: CHECK CRITERIA | CONTROL TABLES | REPORTS | ORDER STRUCTURE | BARCODE CHECK | MAIN MENU | DUPLICATE | CONTROL FIELDS | REPLACE FIELDS | LOOK UP TABLES | DATA ENTRY | COPY TO DBF | SELF LOOKUP TABLES | RUN TI | CUSTOMER FIELD LIST

| TABLE | LOOKUP KEY EXPRESSION | STRUCTURE | INDEX TAG | INDEX KEY EXPRESSION | FOR EXPRESSION |
|---|---|---|---|---|---|
| SPOPP | SPO | EXIST | SPO | SPO | HANGTAGTYP # |

| REPLACE FIELD | REPLACE VALUE EXPRESSION | DEFAULT VALUE EXPRESSION |
|---|---|---|
| HT_REF | HANGTAGTYP | |

CLEAR TABLE ROW
CLEAR REPLACE ROW

FIG. 57

ORDER ANALYSIS CONFIGURATION

Tabs: CHECK CRITERIA | CONTROL TABLES | REPORTS | ORDER STRUCTURE | BARCODE CHECK | MAIN MENU | DUPLICATE | CONTROL FIELDS | REPLACE FIELDS | LOOK UP TABLES | DATA ENTRY | COPY TO DBF | SELF LOOKUP TABLES | RUN TIME OPTIONS | AW JOB# ASSIGN

| FILE PROCESS OPTION | FIRST RUN | RE-RUN |
|---|---|---|
| CHECK DUPLICATE RECORDS | ☐ | ☐ |
| LOOKUP AND REPLACE FIELD VALUES | ☐ | ☐ |
| REPLACE CONTROL FIELD VALUES | ☐ | ☐ |
| REPLACE FIELD VALUES WITH CONDITIONS | ☑ | ☐ |
| CHECK BARCODE VALIDATION | ☑ | ☐ |
| CHECK CUSTOM CRITERIA | ☐ | ☐ |
| SELF LOOKUP AND REPLACE FIELD VALUES | ☐ | ☐ |
| UPDATE CONTROL TABLES | ☐ | ☐ |
| COPY TO DBF BY CONDITIONS | ☐ | ☐ |
| SPLIT FILES BY CONDITIONS | ☐ | ☐ |
| PRINT CONTROL TABLES FOR NEW INFO | ☐ | ☐ |

☐ SKIP SYSTEM FIELDS

SELECT ALL FIRST RUN PROCESS | DESELECT ALL FIRST RUN PROCESS
SELECT ALL RE-RUN PROCESS | DESELECT ALL RE-RUN PROCESS

| USER ADMINISTRATION MAINTENANCE | | | | ☒ |
|---|---|---|---|---|
| 🖥 ORDER ANALYSIS RUN TIME | | | | |
| MAIN MENU | RUN TIME OPTIONS | VIEW WORKING FILE | VIEW RECORD ERROR | |

| FILE PROCESS OPTION | | REPORT OPTION | |
|---|---|---|---|
| CHECK DUPLICATE RECORDS | ☐ | ESPRIT GERMANY HANGTAG/SUMMARY | ☑ |
| LOOKUP AND REPLACE FIELD VALUES | ☐ | ESPRIT GERMANY HANGTAG/DIV SUMMARY | ☑ |
| REPLACE CONTROL FIELD VALUES | ☐ | ZERO QUANTITY REPORT | ☑ |
| REPLACE FIELD VALUES WITH CONDITIONS | ☑ | DUPLICATE ORDERS | ☑ |
| CHECK BARCODE VALIDATION | ☐ | ESPRIT GERMANY ERROR REPORT | ☑ |
| CHECK CUSTOM CRITERIA | ☑ | ESPRIT GERMANY C4 REPORT FOR THERMALPRINTING | ☑ |
| SELF LOOKUP AND REPLACE FIELD VALUES | ☑ | ESPRIT GERMANY PP REPORT FOR SERVICE BUREAU | ☑ |
| UPDATE CONTROL TABLES | ☐ | ESPRIT GERMANY HANGTAG ORDER DETAIL REPORT | ☑ |
| COPY TO DBF BY CONDITIONS | ☑ | ESPRIT GERMANY HANGTAG (A2 & S2) ORDER DETAIL | ☑ |
| SPLIT FILES BY CONDITIONS | ☐ | ESPRIT GERMANY C4 & PP ORDER DETAIL | ☑ |
| PRINT CONTROL TABLES FOR NEW INFO | ☐ | C4 SUMMARY LIST | ☑ |

[SELECT PROCESS] [DESELECT ALL PROCESS]　　[SELECT ALL REPORT] [DESELECT ALL REPORT]

INPUT FILE PATH:
INPUT FILE NAME:
WORK FILE NAME: [      ] .DBF [BROWSE]

[CONVERT INPUT FILE] [EXECUTE ALL PROCESS]

FIG. 60

| USER ADMINISTRATION MAINTENANCE | | | | ☒ |
|---|---|---|---|---|
| 🖥 ORDER ANALYSIS RUN TIME | | | | |
| MAIN MENU | RUN TIME OPTIONS | VIEW WORKING FILE | VIEW RECORD ERROR | |

| | YEAR1 | DISTRI | COUNTRY | CHG_CNTRY | CNTYNAME | SEASON | DIV | STYLEHEAD | STYL | ERROR ROW # |
|---|---|---|---|---|---|---|---|---|---|---|
| 1 | 1998 | UKI | SIN | N | SINGAPORE | D | 50 | | D5L628 | |
| 2 | 1998 | UKI | SIN | N | SINGAPORE | D | 50 | | D5L630 | |
| 3 | 1998 | UKI | SIN | N | SINGAPORE | D | 50 | | D5L620 | |
| 4 | 1998 | UKI | SIN | N | SINGAPORE | D | 50 | | D5L613 | |
| 5 | 1998 | UKI | SIN | N | SINGAPORE | D | 50 | | D5L630 | |
| 6 | 1998 | UKI | SIN | N | SINGAPORE | D | 50 | | D5L620 | |

[DELETE ROW] [START ANALYSIS]　TOTAL NUMBER OF ROWS RETRIEVED : 6

[INVALID DATE] [INVALID NUMBER]
[INVALID LENGTH] [INVALID NUMBER & LENGTH]

FIG. 61

| USER ADMINISTRATION MAINTENANCE | | | | | | | | |
|---|---|---|---|---|---|---|---|---|
| ⛶ ORDER ANALYSIS RUN TIME ☒ | | | | | | | | |
| MAIN MENU | | RUN TIME OPTIONS | | VIEW WORKING FILE | | | VIEW RECORD ERROR | |
| DISTRI | COUNTRY | CHG_COUNTRY | CNTYNAME | SEASON | DIV | STYLEHEAD | STYLE | STY |
| UKI | SIN | N | SINGAPORE | D | 50 | | D5L628 | |
| UKI | SIN | N | SINGAPORE | D | 50 | | D5L630 | |
| UKI | SIN | N | SINGAPORE | D | 50 | | D5L620 | |
| UKI | SIN | N | SINGAPORE | D | 50 | | D5L613 | |
| UKI | SIN | N | SINGAPORE | D | 50 | | D5L630 | |
| UKI | SIN | N | SINGAPORE | D | 50 | | D5L620 | |

| SET FILTER | | PRINT ALL REPORTS | FILL COLUMN |
|---|---|---|---|

*FIG. 62*

| USER ADMINISTRATION MAINTENANCE | | | |
|---|---|---|---|
| ⧉ ORDER ANALYSIS RE-RUN | | | ☒ |

| MAIN MENU | RUN TIME OPTIONS | ASSIGN JOB NUMBER | VIEW RECORD ERROR |
|---|---|---|---|
| AUSTRAL | MODULE # | DESCRIPTION | |
| NEWGERM | DISK | DISK FILE TRANSFER | |
| | | | |
| | | | EXIT |

FIG. 63

| MAIN MENU | RUN TIME OPTIONS | ASSIGN JOB NUMBER | VIEW RECORD ERROR |
|---|---|---|---|

| FILE PROCESS OPTION | ▲ | REPORT OPTION | ▲ |
|---|---|---|---|
| CHECK DUPLICATE RECORDS | ☐ | DUPLICATE ORDERS | ☐ |
| LOOKUP AND REPLACE FIELD VALUES | ☐ | ZERO QTY REPORT | ☐ |
| REPLACE CONTROL FIELD VALUES | ☐ | ESPRIT AUSTRALIA ORDER DETAIL | ☐ |
| REPLACE FIELD VALUES WITH CONDITIONS | ☑ | | |
| CHECK BARCODE VALIDATION | ☐ | | |
| CHECK CUSTOM CRITERIA | ☑ | | |
| SELF LOOKUP AND REPLACE FIELD VALUES | ☑ | | |
| UPDATE CONTROL TABLES | ☐ | | |
| COPY TO DBF BY CONDITIONS | ☑ | | |
| SPLIT FILES BY CONDITIONS | ☐ | | |
| PRINT CONTROL TABLES FOR NEW INFO | ☐ ▼ | | ▼ |

[SELECT ALL PROCESS] [DESELECT ALL PROCESS] [SELECT ALL REPORT] [DESELECT ALL REPORT]

WORK FILE PATH:
WORK FILE NAME: [        ] .DBF [BROWSE]

[START] [EXECUTE ALL PROCESS]   ☑ ASSIGN AW JOB NUMBER

FIG. 64

| USER ADMINISTRATION MAINTENANCE | | | | |
|---|---|---|---|---|
| ORDER ANALYSIS RE-RUN | | | | ☒ |
| MAIN MENU | RUN TIME OPTIONS | ASSIGN JOB NUMBER | VIEW RECORD ERROR | |
| | SEASON | HANGTAGTYP | DIV | AW JOB# |
| 1 | D | C4 | 50 | |

ORDER ANALYSIS RUN TIME

FIG. 66

STRUCTURE MAINTENANCE

CUSTOMER STRUCTURE [        ]   [CLEAR STRUCTURE]

STRUCTURE CODE:
- BANANA REPUBLIC
- BASS OUTLET
- COLUMBIA SPORT
- DATA
- EB-SOCK RIDER
- EDCSFO-SHOES
- EDDIE BAUER
- ESPRIT AUST
- ESPRIT-GERMANY
- ESPRIT-SFO
- ESPRIT-TAIWAN
- GAP ADDRESS LAB
- GAP OLD NAVY
- GAP-MADISON AVE
- JOB PLANNING
- LANE BRYANT
- MONTGOMERY WARD

| # | FIELD NAME | FIELD TYPE | FIELD LENGTH | FIELD DECIMAL | INPUT LENGTH |
|---|---|---|---|---|---|
| 1 | | | | | |
| 2 | | | | | |
| 3 | | | | | |
| 4 | | | | | |
| 5 | | | | | |
| 6 | | | | | |
| 7 | | | | | |
| 8 | | | | | |
| 9 | | | | | |
| 10 | | | | | |
| 11 | | | | | |
| 12 | | | | | |
| 13 | | | | | |
| 14 | | | | | |

[DELETE STRUCTURE] [SAVE STRUCTURE] [IMPORT STRUCTURE] [INSERT ROW] [DELETE ROW] [EXIT]

FIG. 67

CONTROL FIELDS LIST

| | CONTROL FIELD | DESCRIPTION |
|---|---|---|
| 1 | PACKID | UNIQUE PACKING ID FOR EACH ORDER RECORD |
| 2 | BOXNUM | BOX REFERENCE NUMBER IN BOX LABEL ABOVE LEVEL ONE |
| 3 | FIRST | FIRST PACK ID IN LEVEL ONE OR FIRST BOX NUMBER IN OTHER LEVEL |
| 4 | LAST | LAST PACK ID IN LEVEL ONE OR LAST BOX NUMBER IN OTHER LEVEL |
| 5 | LABELNO | LABEL NUMBER + " OF " + TOTAL LABEL NUMBER OF ONE BOX LIKE "1 OF 2" |
| 6 | PLATENO | PLATE NUMBER IN A PLATE OR CUTTING LABEL |
| 7 | PLATEQTY | PLATE QUANTITY IN A PLATE OR CUTTING LABEL |
| 8 | QTY | ORDER QUANTITY |
| 9 | SHIPQTY | SHIPPING QUANTITY |
| 10 | RQTY | ROUND AND NEAR UP QUANTITY |
| 11 | CODEASC | BARCODE FIELD FOR ARTWORK OR CUTTING LABEL |
| 12 | STRUCODE | STRUCTURE CODE |
| 13 | PRODCODE | PRODUCT CODE |
| 14 | AWJOBNO | AW PRINTING JOB NUMBER |
| 15 | BOXQTY | BOX LABEL QUANTITY IN ANY BOX LEVEL |
| 16 | WTUNIT | UNIT WEIGHT OF THAT PRODUCT TYPE |
| 17 | WEIGHT | TOTAL WEIGHT OF BOX IN ANY LEVEL OR CUTTING LABEL |
| 18 | BOXCODE | BOX LABEL BARCODE |
| 19 | MAXBOXNUM | MAXIMUM BOX REFERENCE NUMBER IN BOX LABEL ABOVE LEVEL ONE |

DOUBLE CLICK TO SELECT     [OK]

| | FIELD NAME | FIELD TYPE | FIELD LENGTH | FIELD DECIMAL | INPUT LENGTH |
|---|---|---|---|---|---|
| 1 | AWJOBNO | C | 6 | 0 | 6 |
| 2 | CLRCODE | C | 3 | 0 | 3 |
| 3 | CLRNAME | C | 3 | 0 | 3 |
| 4 | CODE | C | 13 | 0 | 13 |
| 5 | COLORHEAD | C | 15 | 0 | 15 |
| 6 | COUNTRY | C | 3 | 0 | 3 |
| 7 | DISTNAME | C | 15 | 0 | 15 |
| 8 | DISTRI | C | 3 | 0 | 3 |
| 9 | DIV | C | 2 | 0 | 2 |
| 10 | FACTORY | C | 5 | 0 | 5 |
| 11 | FILE NAME | C | 8 | 0 | 8 |
| 12 | HANGTAGTYP | C | 2 | 0 | 2 |
| 13 | HT_REF | C | 2 | 0 | 2 |
| 14 | ORDERDATE | N | 6 | 0 | 6 |

RETRIEVE FILE STRUCTURE

FIG. 72

Configuration — PLATE tab

ALL FIELDS:
AWJOBNO, CLRCODE, CLRNAME, CODE, COLORHEAD, COUNTRY, DISTNAME, DISTRI, DIV, FACTORY, FILENAME, HANGTAGTYP, HT_REF, ORDERDATE, QTY, RETAIL, RETAIL CODE, RETAIL TEXT, RQTY

PACKING SUMMARY LIST GROUP HEADER FIELDS

| | FIELD NAME |
|---|---|
| 1 | AWJOBNO |
| 2 | DIV |
| 3 | SEASON |

| | NO. OF COPIES |
|---|---|
| NO. OF COPIES FOR PACKING DETAIL LIST | 3 |
| NO. OF COPIES FOR PACKING SUMMARY LIST | 3 |
| NO. OF COPIES FOR SHIPPING SUMMARY LIST | 3 |
| NO. OF COPIES FOR DELIVERY NOTES | 3 |

PACKING SUMMARY LIST GROUP HEADER FIELDS

| | FIELD NAME | PRINT REPEAT FIELD | FIELD HEADER |
|---|---|---|---|
| 1 | COUNTRY | ☐ | |
| 2 | FACTORY | ☐ | |
| 3 | SPO | ☑ | |
| 4 | STYLE | ☑ | |

FILE  CONFIG  CONTROL FIELDS  DATABASE FIELDS  STRUCTURE MAINTENANCE  INDEX MAINTENANCE

CONFIGURATION

Tabs: PRODUCT | PLATE | INPUT FILE | QTY DISTRIBUTION | PACKING
BOX LABEL | ARTWORK | CUTTING LABEL | SKU LABEL | BARCODE Rows 1-9 (empty)

Buttons: DELETE TAG ROW, INSERT TAG ROW, DELETE FOOT ROW, INSERT FOOT ROW

FOOTER FIELDS
Rows 1-5 (empty)

Buttons: COPY FROM TAG, COPY FROM FOOTER, PASTE TO TAG, PASTE TO FOOTER

FIG. 78

CONFIGURATION

Tabs: PRODUCT | PLATE | INPUT FILE | QTY DISTRIBUTION | PACKING
BOX LABEL | ARTWORK | CUTTING LABEL | SKU LABEL | BARCODE ALL FIELDS:
- AWJOBNO
- CLRCODE
- CLRNAME
- CODE
- COLORHEAD
- COUNTRY
- DISTNAME
- DISTRI
- DIV
- FACTORY
- FILENAME
- HANGTAGTYP
- HT_REF
- ORDERDATE
- QTY
- RETAIL
- RETAIL CODE
- RETAIL TEXT
- RQTY Buttons: ADD, DELETE (x2)

ARTWORK BARCODE FIELDS
CODE

CUTTING BARCODE FIELDS
CODE

EAN 13

BARCODE 128B
UPC A
EAN 13
EAN 8

| | |
|---|---|
| 🗀 USER JOB CONTROL PANEL | _ □ ☒ |

| STRUCTURE CODE ▲ | HT CODE | HANG TAG DESCRIPTION |
|---|---|---|
| | BR-079 | BR OUTLET BELT BARCODE LABEL (BR-079) |
| BANANA REPUBLIC | SF178 | BR-063-SF178 (BELT BARCODE LABEL) |
| BASS OUTLET | SF300 | BR-059-SF300 BELT BARCODE |
| COLUMBIA SPORT | | |
| DATA | | |
| EB-SOCK RIDER ▼ | | |

| OPEN INPUT FILE | WORKING DIRECTORY INPUT FILE NAME | | AWJOBNO | |
| | WORKING FILE | | MANUAL PLATE ARRANGEMENT ☐ |

PRINT OPTION
- ☑ PRINT QTY DISTRIBUTION LIST     ☑ PRINT PACKING LIST
- ☐ PRINT SUMMARY DISTRIB LIST      ☑ PRINT PACKING SUMMARY LIST
- ☑ PRINT PLATE DETAIL LIST         ☑ PRINT OVERALL PACKING SUMMARY LIST
- ☑ PRINT PLATE LAYOUT LIST         ☑ PRINT BOX LABEL
- ☑ PRINT PLATE LABEL               ☑ PRINT CARTON LABEL
- ☑ PRINT PLATE SUMMARY LIST        ☐ PRINT BOX LABEL REPORT
- ☑ CREATE ARTWORK ASCII FILE       ☑ PRINT SHIPPING SUMMARY LIST
- ☑ CREATE CUTTING LABEL ASCII FILE ☐ PRINT DELIVERY NOTE
- ☑ CREATE ARTWORK CHECKING FILE    ☑ CREATE BOX CHECKING FILE

GENERATE
EXIT
USE LEGAL PAPER ☐
SKIP CHECKING HT ☐

CHECK BOX OUTPUT FILE EXTENSION [    ]
CHECK ARTWORK FILE NAME [         ]

PLATE OPTION
NO. OF UP PER PLATE [ 24 ]
WASTE IMPORTANCE (PAPER/PLATE) % [ 30 ] / [ 70 ]
MAX PAPER WASTE PER PLATE [ 100 ]

*FIG. 79*

| MANUAL PLATE ARRANGEMENT (10 PER PLATE) | | | | | | | | | |
|---|---|---|---|---|---|---|---|---|---|

ALL CHARACTER FIELDS: AWJOBNO, YEAR, ORDERDATE, DISTRI, COUNTRY, SEASON, DIV

SORT FIELDS: QTY

REPORT FIELDS: STYLE, CLRCODE, CODE, SIZE, RETAIL CODE, RETAIL, DISTRI

[ADD] [DELETE] [ADD] [DELETE] [CONTINUE] [REFRESH GRID]

| STYLE | CLRCODE | CODE | SIZE | RETAILCO | PLATE# | RQTY | REPEAT | PLATEQTY |
|---|---|---|---|---|---|---|---|---|
| A40411 | 566 | 40118170566 | S | HFL | | 25 | | |
| A40411 | 566 | 40118170566 | XL | HFL | | 25 | | |
| A40380 | 141 | 40118170559 | 36 | HFL | | 50 | | |
| A40381 | 141 | 40118170562 | 42 | HFL | | 50 | | |
| A40381 | 543 | 40118170562 | 34 | HFL | | 50 | | |
| A40381 | 141 | 40118170561 | 34 | HFL | | 50 | | |
| A40380 | 141 | 40118170559 | 34 | HFL | | 50 | | |
| A40380 | 141 | 40118170559 | 40 | HFL | | 50 | | |
| A40380 | 141 | 40118170559 | 42 | HFL | | 50 | | |
| A40380 | 543 | 40118170560 | 34 | HFL | | 50 | | |
| A40380 | 543 | 40118170560 | 36 | HFL | | 50 | | |
| A40380 | 543 | 40118170560 | 40 | HFL | | 50 | | |
| A40380 | 543 | 40118170560 | 42 | HFL | | 50 | | |
| A40411 | 566 | 40118170566 | M | HFL | | 50 | | |
| A40411 | 566 | 40118170566 | L | HFL | | 50 | | |
| A40381 | 543 | 40118170562 | 42 | HFL | | 75 | | |
| A40380 | 543 | 40118170560 | 38 | HFL | | 75 | | |
| A40381 | 543 | 40118170562 | 40 | HFL | | | | |

PLATE#: 1
PLATE QTY
[ASSIGN PLATE]
[CLEAR SELECT]
PLATE TOTAL UP
PLATE WASTE

*FIG. 80*

INTEGRATED HANGTAG PRODUCTION SYSTEM

This application is a continuation in part of application Ser. No. 09/408,740 filed Sep. 29, 1999 now U.S. Pat. No. 6,197,823 which is a C-I-P Ser. No. 09/133,103 filed Aug. 12, 1998.

BACKGROUND OF THE INVENTION

The present invention generally relates to printing and, more particularly, to an integrated system for the production of graphic hangtags.

A hangtag is a strip of material that is suspended from a piece of merchandise in order to provide information about the product to which it is attached. For example, paper, cardboard, leather, plastic, and metal hangtags are commonly used in the fashion retail industry for providing information about the manufacturer, size, price, color, style, and/or stock keeping unit ("SKU") of a particular garment. However, hangtags may also be used in various other industries and/or applications for providing any information about the item to which the tag is attached.

Due to the large amount of information typically contained on each hangtag in a modern inventory control system, and the wide variety of tag styles in use, each hangtag is essentially unique to a single piece of merchandise. Furthermore, since at least some portion of the information on each hangtag is typically printed in a machine-readable "barcode" format, it can be quite difficult to visually confirm that a tag printed with the correct information has been attached to the appropriate merchandise in the field. Consequently, even a minor error in the printing and/or distribution of a hangtag printing order can wreak havoc on the customer's inventory control system. Therefore, printing order can wreak havoc on the customer's inventory control system. Therefore, many purchasers of hangtags hold their hangtag suppliers liable for the substantial cost of re-tagging merchandise in the field whenever a hangtag error is discovered. Moreover, improved inventory management techniques have created tighter production and shipping schedules for delivering larger numbers of hangtags to more distribution points than ever before.

FIG. 1 is a schematic flow diagram depicting several phases of a conventional process for the production of hangtags. The first phase in a typical hangtag production process is usually the data management phase 2 when orders are received from customers in a text format via mail, facsimile, electronic mail ("e-mail"), or other conventional means. The substantial amount of information contained in these customer orders is often incomplete or inaccurate, and can vary significantly in arrangement and content, even between different facilities of the same customer. The orders may also be subject to revision by the customer at any time during the production process. Consequently, during the data management phase 2, this raw customer order data, and any revisions, must be manually decomposed and rearranged into one or more formats which can be used to efficiently coordinate and accurately complete the various other activities that are required to produce the order.

For example, information from the data management stage 2 may be used during the customer service stage 4 for order verification and tracking, follow-up on job due dates, and periodic reporting of a job's status to the customer during various later stages of the production process. Similarly, information from the data management phase 2 is used during the job planning phase 6 to order materials, prepare of "job pockets" and other production instructions, analyze current shop loads, and monitor and schedule activities during later stages in the production process. Activities such as comparing shipping fees and schedules, shipment scheduling, notification and confirmation of shipments, and delivery tracking are then completed during the traffic phase 8.

Information from the job planning phase 6 is used during the pre-press phase 8 to coordinate printing plate preparation, plate inspection, print proofing, and other activities. For example, during the pre-press phase 8, logos, SKUs, and other graphic "art" are laid-out on printing plates which are then transferred to presses, or other printing equipment, during the on press phase 12. Once stock sheets have been printed with multiple hangtag images during the on-press phase 12, the printed sheets are then transferred to the post press phase 12 for die-cutting, folding, drilling, cutting, eyeletting, stringing, laminating, labeling, sorting, taping, stitching, shrink-wrapping, and/or other final preparation and packaging. Finally, the finished hangtags are passed to the delivery phase 14 for final inspection, preparation of packing and shipping documents, and distribution to the appropriate courier for timely delivery to the customer based upon information prepared during the traffic phase 8.

In general terms, hangtag production systems are most efficiently operated when the number of plates, and therefore plate changes, and the number of stock sheets used to complete a job is minimized. Conventional hangtag production runs can require from at least five to ten days to complete and also result in a significant percentage of "make ready" wasted sheet stock material.

SUMMARY OF THE INVENTION

Such conventional hangtag production methods have been found to have significant drawbacks. For example, the manual posting and analysis of the raw customer order data is an expensive, labor-intensive, and error-prone process, even for a highly qualified staff. The manual preparation and tracking of various production and distribution plans also generally lacks the flexibility to accommodate error checking, or revisions to a customer order, once a production run has been initiated. Even when a product defect is identified early in the process, it can be difficult to trace and correct the cause of that defect using conventional production systems. For these reasons, and others, it can be difficult assure the speedy delivery of a low-cost and high-quality finished product using conventional hangtag production techniques.

The invention disclosed below addresses these and other drawbacks associated with conventional hangtag production methods by providing an integrated hangtag production system including an order analysis system and a hangtag production system. The integrated system allows customer orders to be received in a variety of formats through various electronic communication mediums such as e-mail, modem, direct Internet connection, electronic bulletin board posting, or others. The electronic customer order data is then processed by the order analysis system to identify errors, replace missing and/or incorrect data, and generate various data files and customer order reports. The analyzed order data is then used by the hangtag production system to create additional data files, reports, lists, tickets, and labels for use in preparing, printing, packaging, and distributing the hangtags.

More particularly, the present disclosure relates to an integrated hangtag production system, including an order analysis program for receiving an electronic order file from a customer. The order analysis program includes means for outputting an analyzed customer data file, a box label production file, and a carton label production file; and means for generating documents that are useful for evaluating the integrity of the electronic customer order field. These documents include a Hangtag Summary Report, a Hangtag Order Detail Report, a Hangtag/Division Summary Report, an Error Report, a Zero Quantity Report, a Duplicate Order Report, an Invoice Distributors Report, a Rejected SPO's Report, a Missing Multi-Size/Currency Report, a C4 Thermal Printing Report, and a Pre Pack Service Bureau Report. The system also includes a hangtag automation program for receiving the analyzed customer data file and outputting an artwork ASCII file, an artwork checking file, a cutting label file, a box checking file, and a packing temp file; and mean for generating additional documents for coordinating the production of hangtags in the customer order. These additional documents may include a Hangtag Order Detail Report, a Detail Packing List, a Plate Layout Detail List, a Plate Layout Summary List, Plate Ticket Images, Cutting Labels, a Plate Analysis Report, Box and Carton Labels, a Box Carton Summary, a Packing Summary, an In-House Box/Carton Summary, a C4 Summary List, a C4 Packing List, a C4 and PP Order Detail, a Shipping Summary List, and Delivery Notes.

The present disclosure also relates to an integrated process for the production of hangtags including the steps of receiving an electronic order file via e-mail from a customer, processing the electronic customer order file with an order analysis computer program, generating documents from the order analysis program that are useful for evaluating the integrity of the customer order file, modifying the electronic customer order file to produce an analyzed customer data file, processing the analyzed customer data file with a hangtag automation program, and generating additional documents from the analyzed customer data file which are useful for coordinating the production of hangtags. The process may also include the step outputting at least one data file which may be used with another computer program for further coordinating the production of hangtags.

BRIEF DESCRIPTION OF THE DRAWINGS

The embodiments disclosed below will now be described with reference to the following drawings wherein the same reference numerals are used to refer to the same features in each of the drawings.

FIG. 3 is the first thirty-five lines of a typical electronic customer purchase order file for use with the integrated hangtag production system shown in FIG. 2;

FIG. 4 is the first thirty-five lines of a box label production file that was prepared from the customer order file that is partially shown in FIG. 3;

FIG. 6 is the first thirty-five lines of a carton label production file that was prepared from the customer order file that is partially shown in FIG. 3;

FIG. 8 is the first thirty-five lines of an order analysis storage file that was prepared from the customer order file that is partially shown in FIG. 3;

FIG. 9 is an artwork ASCII file that was prepared from the customer order file that is partially shown in FIG. 3;

FIG. 10 is the artwork created from the ASCII artwork file shown in FIG. 9;

FIG. 11 is a QuarkXpress template that was used to create the artwork shown in FIG. 10;

FIG. 12 is an artwork checking file that was prepared from the customer order file that is partially shown in FIG. 3;

FIG. 13 is a box checking file that was prepared from the customer order file that is partially shown in FIG. 3;

FIG. 14 is a cutting label file that was prepared from the customer order file that is partially shown in FIG. 3;

FIG. 15 is the cutting label images that were created from the cutting label file shown in FIG. 14;

FIG. 16 is a packing label temp file that was prepared from the customer order file that is partially shown in FIG. 3;

FIG. 17 is an analyzed customer data file that was prepared from the customer order file that is partially shown in FIG. 3;

FIG. 18 is a hangtag automation storage file that was prepared from the customer order file that is partially shown in FIG. 3;

FIG. 19 is a Hangtag Summary Report that was prepared from the customer order file that is partially shown in FIG. 3;

FIG. 20 is the first fifteen pages of a Hangtag Order Detail Report that was prepared from the customer order file that is partially shown in FIG. 3;

FIG. 21 is a Hangtag/Division Summary Report that was prepared from the customer order file that is partially shown in FIG. 3;

FIG. 22 is an Error Report that was prepared from the customer order file that is partially shown in FIG. 3;

FIG. 23 is a Zero Quantity Report that was prepared from the customer order file that is partially shown in FIG. 3;

FIG. 24 is a Duplicate Orders Report that was prepared from the customer order file that is partially shown in FIG. 3;

FIG. 25 is an Invoice Distributors Report that was prepared from the customer order file that is partially shown in FIG. 3;

FIG. 26 is a Rejected Style Purchase Order Report that was prepared from the customer order file that is partially shown in FIG. 3;

FIG. 27 is a Missing Multi-Size/Currency Data Report that was prepared from the customer order file that is partially shown in FIG. 3;

FIG. 28 is a C4 Thermal Printing Report that was prepared from the customer order file that is partially shown in FIG. 3;

FIG. 29 is a Pre Pack Service Bureau Report that was prepared from the customer order file that is partially shown in FIG. 3;

FIG. 30 is a C4 and PP Order Detail Report that was prepared from the customer order file that is partially shown in FIG. 3;

FIG. 31 is a Plate Layout Detail List that was prepared from the customer order file that is partially shown in FIG. 3;

FIG. 32 is a Plate Layout Summary List that was prepared from the customer order file that is partially shown in FIG. 3;

FIG. 33 are some Plate Ticket Images;

FIG. 34 is a Plate Analysis Report that was prepared from the customer order file that is partially shown in FIG. 3;

FIG. 35 is a Detail Packing List that was prepared from the customer order file that is partially shown in FIG. 3;

FIG. 36 is a Box/Carton Summary List that was prepared from the customer order file that is partially shown in FIG. 3;

FIG. 37 is a Packing Summary that was prepared from the customer order file that is partially shown in FIG. 3;

FIG. 38 is an In-House Box/Carton Summary that was prepared from the customer order file that is partially shown in FIG. 3;

FIG. 39 is the first fifteen pages of a Box Detail List that was prepared from the customer order file that is partially shown in FIG. 3;

FIG. 40 is a Box Summary List that was prepared from the customer order file that is partially shown in FIG. 3;

FIG. 41 is a Shipping Summary List that was prepared from the customer order file that is partially shown in FIG. 3;

FIG. 42 shows the Customer Order Structure Maintenance form in the order analysis program using the customer order file that is partially shown in FIG. 3;

FIG. 43 shows the Main Menu tab of the Order Analysis Configuration form using the customer order file that is partially shown in FIG. 3;

FIG. 44 shows the Duplicate tab of the Order Analysis Configuration form using the customer order file that is partially shown in FIG. 3;

FIG. 45 shows the Control Fields tab in the Order Analysis Configuration form using the customer order file that is partially shown in FIG. 3;

FIG. 48 shows the Lookup Tables tab in the Order Analysis Configuration form using the customer order file that is partially shown in FIG. 3;

FIG. 49 shows the Check Criteria tab in the Order Analysis Configuration form using the customer order file that is partially shown in FIG. 3;

FIG. 52 shows the Order Structure tab in the Order Analysis Configuration form using the customer order file that is partially shown in FIG. 3;

FIG. 53 shows the Barcode Check tab in the Order Analysis Configuration form using the customer order file that is partially shown in FIG. 3;

FIG. 54 shows the Data Entry tab in the Order Analysis Configuration form using the customer order file that is partially shown in FIG. 3;

FIG. 55 shows the Copy to DBF tab in the Order Analysis Configuration form using the customer order file that is partially shown in FIG. 3;

FIG. 56 shows the Self Lookup Tables tab in the Order Analysis Configuration form using the customer order file that is partially shown in FIG. 3;

FIG. 57 shows the Run Time Options tab in the Order Analysis Configuration form using the customer order file that is partially shown in FIG. 3;

FIG. 60 shows the Run Time Options tab in the Order Analysis Run Time form using the customer order file that is partially shown in FIG. 3;

FIG. 61 shows the View Working file tab in the Order Analysis Run Time form using the customer order file that is partially shown in FIG. 3;

FIG. 62 shows the View Record Error tab in the Order Analysis Run Time form using the customer order file that is partially shown in FIG. 3;

FIG. 63 shows the Main Menu tab in the Order Analysis Rerun form using the customer order file that is partially shown in FIG. 3;

FIG. 64 shows the Run Time Options tab in the Order Analysis Rerun form using the customer order file that is partially shown in FIG. 3;

FIG. 65 shows the Assign Job Number tab in the Order Analysis Rerun form using the customer order file that is partially shown in FIG. 3;

FIG. 66 shows the View Record Error tab in the Order Analysis Rerun form using the customer order file that is partially shown in FIG. 3;

FIG. 67 shows the Structure Maintenance form in the hangtag automation program using the customer order file that is partially shown in FIG. 3;

FIG. 68 shows the Control Fields List form in the hangtag automation program using the customer order file that is partially shown in FIG. 3;

FIG. 70 shows the Plate tab in the Configuration form using the customer order file that is partially shown in FIG. 3;

FIG. 71 shows the Input File tab in the Configuration form using the customer order file that is partially shown in FIG. 3;

FIG. 72 shows the Quantity Distribution tab in the Configuration form using the customer order file that is partially shown in FIG. 3;

FIG. 73 shows the Packing tab in the Configuration form using the customer order file that is partially shown in FIG. 3;

FIG. 74 shows the Box Label tab in the Configuration form using the customer order file that is partially shown in FIG. 3;

FIG. 75 shows the Artwork tab in the Configuration form using the customer order file that is partially shown in FIG. 3;

FIG. 76 shows the Cutting Label tab in the Configuration form using the customer order file that is partially shown in FIG. 3;

FIG. 77 shows the SKU label tab in the Configuration form using the customer order file that is partially shown in FIG. 3;

FIG. 78 shows the Barcode tab in the Configuration form using the customer order file that is partially shown in FIG. 3;

FIG. 79 shows the First Level User Job Control panel form in the hangtag automation program;

FIG. 80 shows the Manual Plate Arrangement form in the hangtag automation program.

DESCRIPTION OF THE PREFERRED EMBODIMENTS

Figure 1:
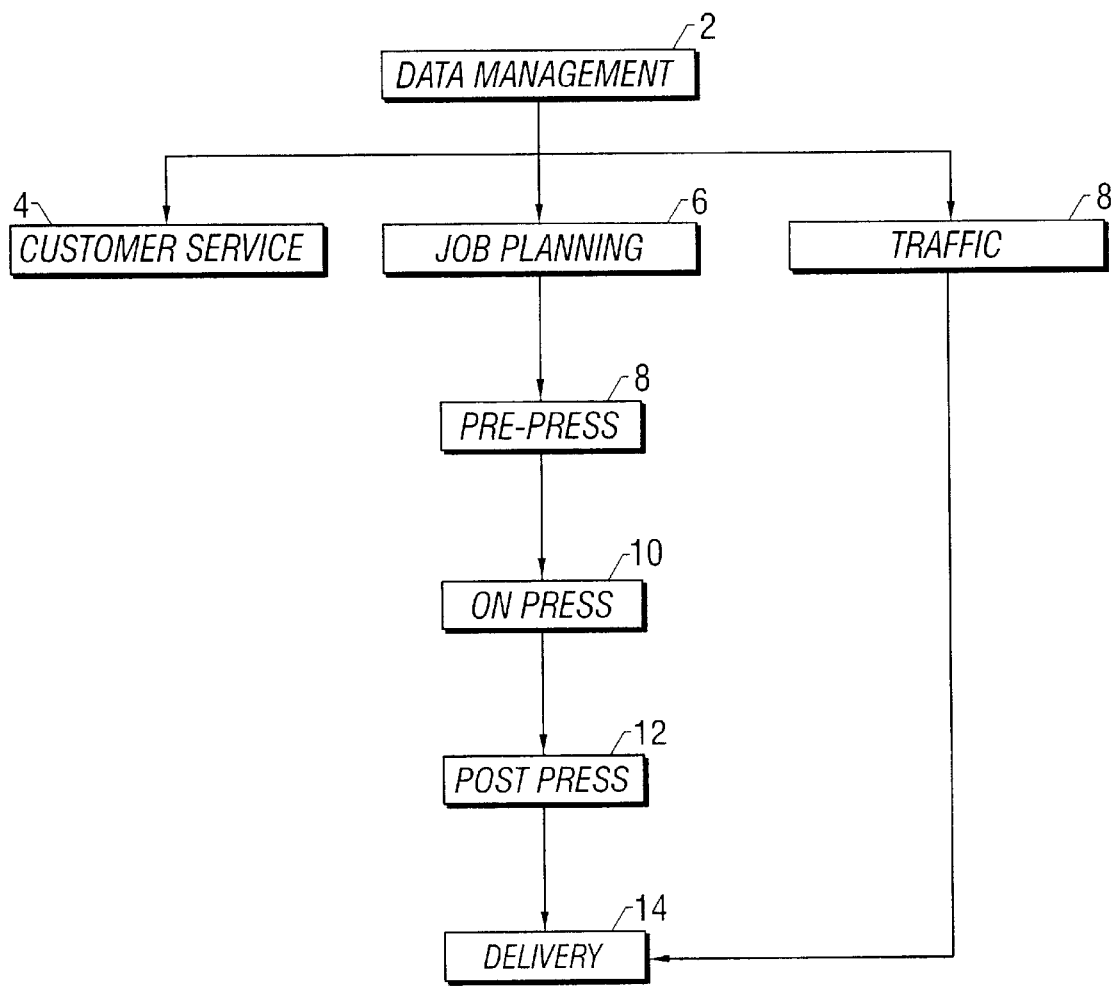
FIG. 1 is a schematic flow diagram depicting several phases of a conventional process for the production of hangtags.

An otherwise conventional process for the production of hangtags may be significantly improved by integrating an order analysis system and a hangtag automation system into the data management phase of the process as discussed in more detail below. Additional systems may also be implemented using data files generated by the order analysis and hangtag automation systems. In a preferred embodiment, these systems include computer software and/or firmware. A copy of an exemplary embodiment of such computer code, written in the Visual Basic (version 3.0) programming language, is attached as an appendix to this disclosure and is discussed in more detail below.

The appended computer program has been found to operate adequately on a personal computer having at least a Pentium 166 MHZ processor, 16 MB of RAM, and a Windows 95 operating system. In a preferred embodiment, the computer is connected via a network adapter card to a Novell 4.0 (or Windows NT) server with a 9 GB hard drive and 130 MB of RAM for storing various data files.

Tables 1 and 2 below list variable names that are used by the software set forth in Appendix A. Each variable listed in Table 1 corresponds to an input data field from a purchase order that is received from a customer. Each variable in Table 2 corresponds to a control data field which is supplied by the printer, or created by the software, in order to supplement the input data received from the customer. Since the variables in Tables 1 and 2 corresponds to a data field, the variable names in these tables are referred to simply as "field names."

For each field name in Tables 1 and 2, the table also lists the data type assigned to that field where "N" stands for a numeric data type, such as decimal, and "C" stands for a character data type, such as string. The number of characters, or length, for each field name is also shown, along with a short description of the data contained in that field.

TABLE 1

Field Names for Customer Order Data

| FIELD NAME | DATA TYPE | LENGTH | DESCRIPTION |
| --- | --- | --- | --- |
| ORDERDATE | N | 6 | Date order was placed by customer |

TABLE 1-continued

Field Names for Customer Order Data

| FIELD NAME | DATA TYPE | LENGTH | DESCRIPTION |
| --- | --- | --- | --- |
| YEAR1 | C | 2 | Season year identifier |
| DISTR1 | C | 3 | Distribution center identifier |
| COUNTRY | C | 3 | Country of factory |
| CHG_CNTRY | C | 1 | Country change indicator ("Y" or "N" depending on whether COUNTRY is changed after the order is placed by the customer) |
| CNTRYNAME | C | 25 | Name of country |
| SEASON | C | 1 | Order Season |
| DIV | C | 2 | Hangtag division product category (e.g., infant or adult) |
| STYLEHEAD | C | 15 | Header printed on tag for identifying style information |
| STYLE | C | 6 | Style number printed under STYLEHEAD |
| STYLEDESC | C | 15 | Style description printed under STYLEHEAD |
| COLORHEAD | C | 15 | Header printed on tag for identifying color information |
| CLRCODE | C | 3 | Color code printed under COLORHEAD |
| CLRNAME | C | 3 | Color name printed under COLORHEAD |
| SIZEHEAD | C | 15 | Header printed on tag for identifying size information |
| SIZE | C | 7 | Garment size information printed under SIZEHEAD |
| RETAILTXT | C | 15 | Header printed on tag for identifying retail information |
| RETAIL | C | 9 | Retail price |
| RETAILCODE | C | 3 | Retail code |
| CODE | C | 13 | U.S. or European barcode data |
| SPO | C | 6 | Style Purchase Order designating a particular garment |
| OLD_QTY | N | 7 | Customer's original order quantity |
| NEW_QTY | N | 7 | Customer's revised order quantity |
| QTY | N | 7 | Production quantity (typically larger than customer's order quantity) |
| CHG_QTY | N | 7 | NEW QTY minus OLD_QTY |
| AGENT | C | 5 | Agent code |
| CHG_AGNT | C | 1 | Agent code change indicator ("Y" or "N" depending on whether AGENT is changed after the order is placed by the customer) |
| AGENTNAME | C | 25 | Agent Name |
| HANGTAGTYP | C | 2 | Hangtag type |
| CHG_HT | C | 1 | Hangtag type change indicator ("Y" or "N" depending on whether HANGTAGTYP is changed after the order is placed by the customer) |
| FACTORY | C | 5 | Factory code |
| SUP_NAME | C | 25 | Factory name |
| SUPP_ADR | C | 25 | Factory shipping address |
| SUPP_ZIP | C | 12 | Factory zipcode |
| SUPP_CNTRY | C | 3 | Country location of factory |
| SUPP_PHONE | C | 20 | Telephone number of factory |
| SUPP_FAX | C | 20 | Facsimile number of factory |
| SUPP_TELEX | C | 20 | Telex address of factory |
| CHG_SUPP | C | 1 | Factory change indicator ("Y" or "N" depending on whether FACTORY is changed after the order is placed by the customer) |
| EX_OR_DATE | N | 6 | Exit date garment is scheduled to leave factory with hangtag attached (i.e., delivery deadline) |

TABLE 1-continued

Field Names for Customer Order Data

| FIELD NAME | DATA TYPE | LENGTH | DESCRIPTION |
|---|---|---|---|
| CHG_EX_OR | C | 1 | Exit date change indicator ("Y" or "N" depending on whether EX_OR_DATE is changed after the order is placed by the customer) |
| CTY_SZ1 | C | 3 | Multi size country code (sort 1) |
| CTY_SZ2 | C | 3 | Multi size country code (sort 2) |
| CTY_SZ3 | C | 3 | Multi size country code (sort 3) |
| CTY_SZ4 | C | 3 | Multi size country code (sort 4) |
| CTY_SZ5 | C | 3 | Multi size country code (sort 5) |
| SIZE1 | C | 7 | Multi size (sort 1) |
| SIZE2 | C | 7 | Multi size (sort 2) |
| SIZE3 | C | 7 | Multi size (sort 3) |
| SIZE4 | C | 7 | Multi size (sort 4) |
| SIZE5 | C | 7 | Multi size (sort 5) |
| CTY_M1 | C | 3 | Multi-currency country code(sort 1) |
| CTY_M2 | C | 3 | Multi-currency country code(sort 2) |
| CTY_M3 | C | 3 | Multi-currency country code(sort 3) |
| CTY_M4 | C | 3 | Multi-currency country code(sort 4) |
| CTY_M5 | C | 3 | Multi-currency country code(sort 5) |
| CTY_M6 | C | 3 | Multi-currency country code(sort 6) |
| CTY_M7 | C | 3 | Multi-currency country code(sort 7) |
| CTY_M8 | C | 3 | Multi-currency country code(sort 8) |
| CTY_M9 | C | 3 | Multi-currency country code(sort 9) |
| RETDESC11 | C | 30 | Multi-currency retail description (sort 1, top line) |
| RETDESC12 | C | 30 | Multi-currency retail description (sort 1, bottom line) |
| RETDESC21 | C | 30 | Multi-currency retail description (sort 2, top line) |
| RETDESC22 | C | 30 | Multi-currency retail description (sort 2, bottom line) |
| RETDESC31 | C | 30 | Multi-currency retail description (sort 3, top line) |
| RETDESC32 | C | 30 | Multi-currency retail description (sort 3, bottom line) |
| RETDESC41 | C | 30 | Multi-currency retail description (sort 4, top line) |
| RETDESC42 | C | 30 | Multi-currency retail description (sort 4, bottom line) |
| RETDESC51 | C | 30 | Multi-currency retail description (sort 5, top line) |
| RETDESC52 | C | 30 | Multi-currency retail description (sort 5, bottom line) |
| RETDESC61 | C | 30 | Multi-currency retail description (sort 6, top line) |
| RETDESC62 | C | 30 | Multi-currency retail description (sort 6, bottom line) |
| RETDESC71 | C | 30 | Multi-currency retail description (sort 7, top fine) |
| RETDESC72 | C | 30 | Multi-currency retail description (sort 7, bottom line) |
| RETDESC81 | C | 30 | Multi-currency retail description (sort 8, top line) |
| RETDESC82 | C | 30 | Multi-currency retail description (sort 8, bottom line) |
| RETDESC91 | C | 30 | Multi-currency retail description (sort 9, top line) |
| RETDESC92 | C | 30 | Multi-currency retail description (sort 9, bottom line) |
| RETCODE1 | C | 3 | Multi-currency retail code (sort 1) |
| RETCODE2 | C | 3 | Multi-currency retail code (sort 2) |
| RETCODE3 | C | 3 | Multi-currency retail code (sort 3) |
| RETCODE4 | C | 3 | Multi-currency retail code (sort 4) |
| RETCODE5 | C | 3 | Multi-currency retail code (sort 5) |
| RETCODE6 | C | 3 | Multi-currency retail code (sort 6) |
| RETCODE7 | C | 3 | Multi-currency retail code (sort 7) |
| RETCODE8 | C | 3 | Multi-currency retail code (sort 8) |
| RETCODE9 | C | 3 | Multi-currency retail code (sort 9) |
| RETAIL1 | C | 9 | Retail price (sort 1) |
| RETAIL2 | C | 9 | Retail price (sort 2) |
| RETAIL3 | C | 9 | Retail price (sort 3) |
| RETAIL4 | C | 9 | Retail price (sort 4) |
| RETAIL5 | C | 9 | Retail price (sort 5) |
| RETAIL6 | C | 9 | Retail price (sort 6) |
| RETAIL7 | C | 9 | Retail price (sort 7) |
| RETAIL8 | C | 9 | Retail price (sort 8) |
| RETAIL9 | C | 9 | Retail price (sort 9) |

Data for the variable names listed in Table 1 is preferably supplied to the order analysis program from an electronic purchase order file which is sent by a customer, such as by an attachment to an e-mail message, each time a new batch of hangtags is ordered. However, electronic order files may also be created by the hangtag printer from customer orders which are not received in an electronic format. Since each customer typically uses its own order format, or several different order formats, any particular order may require only a portion of the data listed above. This subset of the field names from Table 1 which is used for a particular customer order format is referred to as the "customer order structure." As new customers and/or new order formats for existing customers are encountered, additional variables may be added to those listed in Table 1 in order to accommodate each customer's printing needs.

Table 2 lists control field names, their data type, field length, and a short description of the data for field names that are supplied by the printer or created by the order analysis and hangtag automation programs.

TABLE 2

Field Names for Control Data

| FIELD NAME | DATA TYPE | LENGTH | DESCRIPTION |
|---|---|---|---|
| HT_REF | C | 2 | Hangtag refernece for C4 size stickers and prepack labels |
| DISTNAME | C | 15 | Distributor name for C4 size stickers and prepack labels |
| ERR_HTG | C | 1 | HANGTAG error indicator flag |
| RQTY | N | 7 | Production quantity for C4 size stickers and prepack labels |
| ERR_RET | C | 1 | RETAIL error indicator flag |
| ERR_FTY | C | 1 | FACTORY error indicator flag |
| LENGTH | C | 10 | Header for length on show cards (cropped, regular, or long) |
| AWJOBNO | C | 6 | Printer's job number |
| CODE1 | C | 13 | A2 and S2 assigned barcode for new department |

TABLE 2-continued

Field Names for Control Data

| FIELD NAME | DATA TYPE | LENGTH | DESCRIPTION |
|---|---|---|---|
| ERR_CODE | C | 1 | A2 and S2 with missing barcode information |
| SHPQTY | N | 7 | Shipping quantity for prepack labels |
| REPEAT | N | 5 | Control field for prepack label order program |
| CARTON_NO | N | 5 | Carton number for C4 size labels |
| FCARNO | C | 4 | Carton number for C4 size labels (always 1) |
| YEAR | C | 2 | Two-digit field for use in other programs such as traffic optimization for assigning shipper |
| BUCKLE | C | 1 | Flag for special graphic tag |
| MULTI | C | 1 | Multi-/single-currency indicator flag, "M" for multi-currency, "S" for single currency |
| ERR_MC | C | 1 | Missing currency data indicator flag |
| ERR_MS | C | 1 | Missing size data indicator flag |
| SPEED | C | 1 | Flag for rush or regular order delivery |
| DIS_RET | C | 1 | Flag for "00" in RETAIL field |
| VALIDCTY | C | 1 | Indicator for valid multi size/multi-currency country code |
| ERR_MUKI | C | 1 | Flag for UKI distributor group placing and order as a single currency tag |
| REPEAT | N | 6 | Number of times a tag repeats on a plate |
| REC_ID | N | 4 | Unique identifier for a record |
| SORTNUM | C | 5 | Sort number for sorting SKU tags |
| FSORTNUM | N | 5 | First sort number |
| LSORTNUM | N | 5 | Last sort number |
| PLATEUP | N | 4 | Number of ups on a layout (plate) |
| TOTPLATE | N | 4 | Total number of plates produced for one order |
| PACKID | N | 4 | Packing ID number for tags with no barcodes |
| FBOXNO1 | N | 5 | First box number in which SKU is assigned for packing |
| LBOXNO1 | N | 5 | Last box number in which SKU is assigned for packing |
| CCAPACITY1 | N | 8 | Carton packing capacity |
| FBOXNO2 | N | 5 | Duplicate of FBOXNO1 |
| LBOXNO2 | N | 5 | Duplicate of LBOXNO1 |
| CCAPACITY2 | N | 8 | Duplicate of CCAPACITY1 |
| CODETYP | C | 15 | Barcode type |
| REMAINDER | N | 5 | Generated for placement on barcode check digit formula |
| CHKSUM | N | 5 | Formulated check digit for barcode |
| FBOXNO | N | 5 | Duplicate of FBOXNO1 |
| LBOXNO | N | 5 | Duplicate of LBOXNO1 |
| FCARNO | N | 5 | First carton number assigned for packing SKU tags |
| LCARNO | N | 5 | Last carton number assigned for packing SKU tags |
| BCAPACITY | N | 8 | Total inner box (shrink wrap) capacity |
| CCAPACITY | N | 8 | Duplicate of COAPACITY1 |
| INFILE | C | 8 | Input file |
| PLTPAGE | N | 3 | |
| PLTLABEL | N | 3 | |
| C4 | C | 2 | HT reference for C4 sticker |
| PP | C | 2 | HT reference for pre pack sticker |
| THERM | C | 1 | Flag for changing barcodes for SPO and CARTON_NO |
| INVOICE | C | 3 | Invoice identifier |

Figure 2:
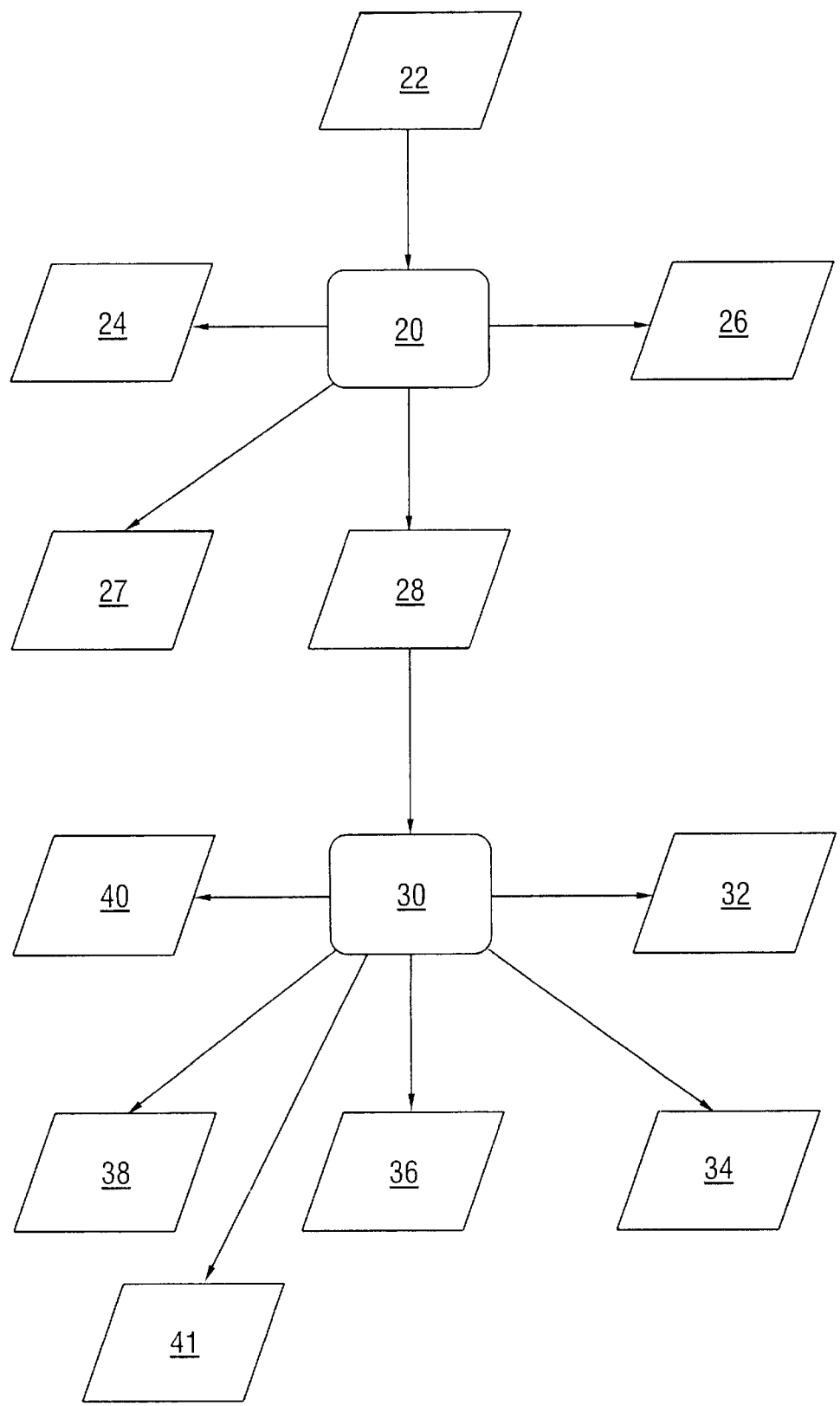
FIG. 2 is a schematic flow diagram depicting the flow of data during at least a portion of the data management stage in an integrated hangtag production system.

FIG. 2 is a schematic flow diagram depicting the flow of data during at least a portion of the date management stage in an integrated hangtag production system including an order analysis program 20 and a hangtag automation program 30 such as the ones disclosed in the attached appendix. In FIG. 2, a raw customer order data file 22 is input to the order analysis program 20 which then outputs a carton label production file 24, a box label production file 26, an order analysis storage file 27, and an analyzed customer data file 28.

FIG. 3 shows the first 35 lines of a typical electronic customer purchase order file 20 for use with the integrated hangtag production system shown in FIG. 2. The remaining lines of data have been deleted from FIG. 3 in order to allow the file to be printed on a single series of pages. As noted above, the customer orders are preferably received via e-mail or other electronic communication medium in an electronic format, such as various conventional database (.dbf), spreadsheet (.wk3 or .wk4), or word processor file formats (.rtf, .doc, or .wpd). The order analysis program 20 may also be configured to accept new input file formats as they are encountered. Of course, an electronic customer purchase order file may also be created by the hangtag manufacturer from a customer order that is received by non-electronic means such as by mail, fax, or voice telephone call.

Figure 5:
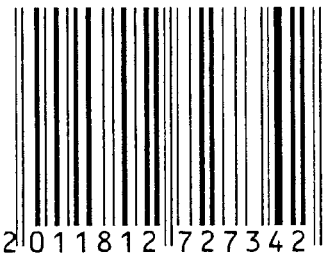
FIG. 5 is a box label that was prepared from the box label production file shown in FIG. 4.

FIG. 4 is the first 35 lines of a box label production file 24 that was prepared from the customer order file 20 that is partially shown in FIG. 3. The remaining lines of data have been deleted from FIG. 4 in order to allow the file to be printed on a single series of pages. The box label file 24 (or "C4 sticker work file" or "C4 production file") is a database file given a ".box" extension and used as input data to a conventional label-making program, such as "IPRINT" version 3.21 from Indigo Software (not shown), to create and print box labels on a conventional sheet-fed laser printer. FIG. 5 shows a "C4 sticker" box label prepared from the box label production file 24 in FIG. 4. The box label SKUs preferably match the SKU information on the cutting labels in order to aide in packing the box.

Figure 7:
FIG. 7 is a carton label that was prepared from the carton label production file shown in FIG. 6.

FIG. 6 is the first 35 lines of a carton label production file 26 that was prepared from the customer order file 20 that is partially shown in FIG. 3. The remaining lines of data have been deleted from FIG. 6 in order to allow the file to be printed on a single series of pages. The carton label production file 26 (or "pre pack work file" or "prepack production file") is a database file that is given a ".car" file extension and used as input data to a conventional label-making program, such as "Label Matrix 4.41 " (not shown), for printing larger carton labels on a suitable printer, such as an Intermec 4400 roll-feed printer. FIG. 7 shows a "pre pack sticker" carton label prepared from the carton label production file 26 in FIG. 6. A carton is typically packed with one or more boxes.

FIG. 8 is the first 35 lines of an order analysis storage file 27 that was prepared from the customer order file 20 that is partially shown in FIG. 3. The remaining lines of data have been deleted from FIG. 8 in order to allow the file to be printed on a single series of pages.

FIG. 17 is an analyzed customer data file 28 that was prepared from the customer order file 20 that is partially shown in FIG. 3. The remaining lines of data have been deleted from FIG. 17 in order to allow the file to be printed on a single series of pages. The analyzed customer data file 28 is input to the hangtag automation program 30 which then outputs an artwork ASCII file 32, an artwork checking file 34, a box checking file 36, a cutting label file 38, a packing temp file 40, and a hangtag automation storage file 41.

FIG. 9 is an artwork ASCII file 32 that was prepared from the customer order file 20 that is partially shown in FIG. 3. The artwork ASCII file 32 (or "artwork file (ASCII)") is a graphics data file that is given a name with a ".art" extension and used as input data to a conventional graphics program, such as "QuarkXpress 3.32" (not shown), for combining data with templates to create completed "art" images that may then be output to a conventional printer or image setter.

The QuarkXpress program preferably runs on a J300 Super Macintosh personal computer with conventional translation software, such as the "Viper" package, for translating files between Apple and PC-based operating systems. An AGFA Accuset 100 image setter preferably receives the translated images files and produces polyester printing plates for use in direct to plate printing of the hangtags. The plates are preferably developed under the AGFA Rapilene 20 process and then cut to size before being mounted on the press. The plate images may also be printed on paper for checking. FIG. 10 shows the artwork created using the ASCII artwork file 32 shown in FIG. 9 and the QuarkXpress template shown in FIG. 11.

FIG. 12 is an artwork checking file 34 that was prepared from the customer order file 20 that is partially shown in FIG. 3. The artwork checking file 34 (or "artwork check file") is a database file that may be used with barcode equipment, such as a "Scanteam 300" (not shown), to confirm that the appropriate barcodes have been laid-out with the artwork in FIG. 10 for each hangtag on a printing plate.

FIG. 13 is a box checking file 36 that was prepared from the customer order file 20 that is partially shown in FIG. 3. The box checking file 36 (or "check file for sorting" or "sorting check file") may also be used with conventional barcode reading software (not shown) to confirm that the appropriate boxes are packed in the correct carton. The box checking file 36 is given the file name "AWJOBNO.hhh" where the file extension ".hhh" refers to the hangtag type or customer.

FIG. 14 is a cutting label file 38 that was prepared from the customer order file 20 that is partially shown in FIG. 3. The cutting label file (or "cutting label ascii file") 37 is given a filename with a ".cut" extension and used by the hangtag automation program 30 to create labels that are used to coordinate the post-press stage. FIG. 15 shows the cutting labels produced using the cutting label file 37 in FIG. 14. The cutting labels are placed on top of a completed stack produced from one printing plate and are used as a reference for packing.

FIG. 16 is a packing temp file 40 that was prepared from the customer order file 20 that is partially shown in FIG. 3. The packing temp file 40 is a temporary database file given the filename "PKHHHJJ.dbf" where "PK" denotes a packing temp file, "HHH" is the hangtag type, "JJ" is the last two digits of AWJOBNO, and ".dbf" refers to the database file-type extension. The packing temp file 40 tabulates artwork identification numbers and packing assignements.

FIG. 18 shows the hangtag automation storage file 41 that was prepared from the customer order file 20 that is partially shown in FIG. 3. This file is used on subsequent reruns of the hangtag automation program 30.

Although the software disclosed in the attached Appendix is written as two distinct computer programs, it is also possible to combine these programs into one larger package.

Besides generating data files 24, 26 and 27, the order analysis program 20 also analyzes the raw customer order data file 22 and generates various reports including a Hangtag Summary Report, Hangtag Order Detail Report, Hangtag/Division Summary Report, Error Report, Zero Quantity Report, Duplicate Order Report, Invoice Distributors Report, Rejected SPO's Report, Missing Multi-Size/Currency Report, C4 Thermal Printing Report, and Pre Pack Service Bureau Report. Although these documents are preferably generated in paper format for manual review, they may also be generated in other formats and/or automaticly reviewed.

FIG. 19 is a Hangtag Summary Report prepared from the customer order 20 that is partially shown in FIG. 3. This report summarizes and sorts the raw customer order data by season by SEASON and HANGTAGTYP, listing QTY and the number of records in the database file for each. This report is used during the customer service stage 4 to review quantities and hangtag types in an order.

FIG. 20 is the first fifteen pages of a Hangtag Order Detail Report prepared from the customer order 20 that is partially shown in FIG. 3. This report lists additional information for a particular SEASON, HANGTAGTYP, and DIV data.

FIG. 21 is a Hangtag/Division Summary Report prepared from the customer order 20 that is partially shown in FIG. 3. This report lists DIV data in addition to the information listed in the Hangtag Summary Report in FIG. 19 and is also used to review the order.

FIG. 22 is an Error Report prepared from the customer order 20 that is partially shown in FIG. 3. As described in more detail below, the criteria for identifying an error in the raw customer order data 20 can be defined and modified by an administartor for the order analysis program 22.

FIG. 23 is a Zero Quantity Report prepared from the customer order 20 that is partially shown in FIG. 3. The Zero Quantity Report identifies records having QTY equal to zero and any corresponding values for OLD_QTY and NEW_QTY.

FIG. 24 is a Duplicate Orders Report prepared from the customer order 20 that is partially shown in FIG. 3. The Duplicate Orders Report identifies records having duplicate information in fields defined by the program administartor as discussed in more detail below.

FIG. 25 is an Invoice Distributors Report prepared from the customer order 20 that is partially shown in FIG. 3. This report lists records by an INVOIC invoice identifier which may be provided by the hangtag printer using a suitable traffic or invoice management system (not shown).

FIG. 26 is a Rejected Style Purchase Order Report prepared from the customer order 20 that is partially shown in FIG. 3. This report list various records that have been flagged (as discussed in more detail below) after the raw customer order data 22 is analyzed by the order analysis program 20.

FIG. 27 is a Missing Multi-Size/Currency Data Report prepared from the customer order 20 that is partially shown in FIG. 3. This report lists details for the multi-size/currency errors identified in the Rejected Style Purchase Order Report in FIG. 26.

FIG. 28 is a C4 Thermal Printing Report prepared from the customer order 20 that is partially shown in FIG. 3. This report identifies, by HT_REF and SEASON, the SPO, CODE, STYLE, hangtag quantities QTY, and number of stickers for groups of hantags in a particular box.

FIG. 29 is a PrePack Service Bureau Report prepared from the customer order that is partially shown in FIG. 3. This report identifies, by SEASON and HT_REF, the SPO and CODE for groups of hantags RQTY production quantity for prepack labels.

Refering to FIG. 2, besides generating production data files 32, 34, 36, 38, 40, and 41, the hangtag automation program 30 also produces various reports, lists, summaries, tickets, labels, and notes including a Hangtag Order Detail Report (or "Quantity Order Report"), Detail Packing List, Plate Layout Detail List, Plate Layout Summary List, Plate Ticket Images, Cutting Labels, Plate Analysis Report, Box and Carton Labels (discussed above), Box Carton Summary, Packing Summary, In-House Box/Carton Summary, C4 Summary List (or "Box Summary List"), C4 Packing List (or "Box Detail List"), C4 and PP Order Detail, Shipping Sumary List, and Delivery Notes. Although these documents are preferably generated in paper format for manual review, they may also be generated in other formats and/or automaticly reviewed, such as by further computer analysis.

As noted above, FIG. 20 is the first fifteen pages of a Hangtag Order Detail Report prepared from the customer order 20 that is partially shown in FIG. 3. This report acts as a back-up hardcopy of the customer order and lists, by SEASON, HANGTAGTYP, and DIV, the QTY production quantity and other information for various SPO style purchase orders in a particular customer order.

FIG. 30 is a C4 and PP Order Detail Report prepared from the customer order 20 that is partially shown in FIG. 3. This report lists, by HT_REF, SEASON, and DIV, the RQTY production quantity for C4 and PP labels for each HANGTATYP and SPO.

FIG. 31 is Plate Layout Detail List prepared from the customer order 20 that is partially shown in FIG. 3. This list provides information about the layout of the printing plate and is used to check the artwork on each plate before a printing run.

FIG. 32 is a Plate Layout Summary List prepared from the customer order 20 that is partially shown in FIG. 3. This list provides a summary of the various quantities to be procuced from each printing plate and may be used to allocate sheets of preprinted stock from inventory to a particular customer order.

FIG. 33 are some Plate Ticket Images. This report produces images for cards, called "plate tickets," that may are used by the pressman to separate groups of printed sheets from a particular plate as they come off of the printer.

FIG. 34 is a Plate Analysis Report that was prepared from the customer order 20 that is partially shown in FIG. 3. This report documents the location of various data files and documents other production information about the order. This report may be stored in the job folder.

FIG. 35 is a Detail Packing List that was prepared from the customer order 20 that is partially shown in FIG. 3. This list provides production quantity information by factory to which a carton is to be delivered and can be used to confirm that there is no more than one factory's hangtags included in each carton. Copies of this report may be placed on the inside and outside of the carton.

FIG. 36 is a Box/Carton Summary List that was prepared from the customer order 20 that is partially shown in FIG. 3. This list provides a record of the box labels so that they can be matched to their boxes if they fall off of their packages.

FIG. 37 is a Packing Summary that was prepared from the customer order 20 that is partially shown in FIG. 3. This summary provides a list of SPO job numbers and packaging information that is useful for notifying a factory as to which hangtags have been sent from the manufacturer.

FIG. 38 is an In-House Box/Carton Summary that was prepared from the customer order 20 that is partially shown in FIG. 3. This summary provides information about the number of hangtags and number of boxes in each carton.

FIG. 39 is the first fifteen pages of a Box Detail List (or "C4 Packing List") that was prepared from the customer order 20 that is partially shown in FIG. 3. The box detail list provides a duplicate box label report for placement inside a box that may be used to check the box contents on arrival at the customer.

FIG. 40 is a Box Summary List (or "C4 Sumary List") that was prepared from the customer order 20 that is partially shown in FIG. 3. This list provides QTY quantity information by country and factory.

FIG. 41 is a Shipping Summary List that was prepared from the customer order 20 that is partially shown in FIG. 3. This list may be used to record weight and box code information prior to shipment.

The order analysis program 20 and hangtag automation program 30 may be operated at two levels of authorization: a higher administrator level, and a lower user level. The form screens shown in FIGS. 42 through 58 are accessed at the administrator level when running the order analysis program 20 contained in the appended computer code.

FIG. 42 shows the customer order Structure Maintenance form using the customer order file 20 which is partially shown in FIG. 3. As noted above, the customer order structure is the subset of field names from Table 1. In this form, the administrator highlights a customer name, such as "ESPRIT-GERMANY," in the left column box (other customer names not shown) and the right box shows the variable names, or "field names," from Table 1 (above) which are then used to analyze orders from the highlighted customer. The Structure Maintenance form shows the type, length, and decimal format (i.e., number of decimal places in the field) for each field name. A drop-down box may be provided in the form for choosing the field type assigned to each field name.

The order structure for each customer may be modified using the command buttons arranged along the bottom of the screen to add and delete customers, save changes to the order structure, maintain the database index, delete and insert rows in an order structure, import a structure from another file, clear the entire order structure, and/or view an order history for the customer.

FIG. 43 shows the Main Menu tab of the Order Analysis Configuration form. As in the customer order structure form shown in FIG. 42, the administrator highlights a customer name from the left column in order to reveal the existing order analysis modules, and their descriptions, for the highlighted customer. Each order analysis module operates on a different order format from that particular customer. In the example illustrated in FIG. 43, electronic customer purchase orders can be received from a customer named "GERMANY" in two formats identified as "e-mail" and "noos" (never out of stock). Order analysis modules are selected for modification by highlighting the module name in the middle column and working with forms under the remaining tabs in the order analysis configuration form, as discussed in more detail below. Order analysis modules may be added, deleted, copied, and saved after modification using the control buttons arranged along the bottom of the screen. A current module user may be knocked-off the system using the "clear lock" button.

FIG. 44 shows the Duplicate tab of the Order Analysis Configuration form. The Duplicate tab portion of the order analysis configuration form allows the administrator to copy field names from the customer field list drop-down box into the "duplicate field" box. Field names which are listed in the duplicate field box are then checked for duplicate entries which are noted on the Error Report. In the example shown in FIG. 44, the order analysis program 20 has been configured to check for the same entries in the purchase order number SPO and barcode CODE fields. The list of fields to be checked for duplicate entries may be cleared using the control button in the lower left corner of FIG. 44.

FIG. 45 shows the Control Fields tab in the Order Analysis Configuration form. The administrator uses this window to select the control fields listed in Table 2 for use with the highlighted order analysis module in FIG. 43. The control fields tab is similar in appearance to the customer order structure maintenance form shown in FIG. 42, except that it uses the field names from Table 2, rather than Table 1. This screen tab allows the administrator to create new field names which are added to the original customer order file and to configure the order analysis module to automatically replace any of those field names with a new value or expression. Rows may be inserted and deleted, and the entire control field structure cleared, using the control buttons arranged at the bottom of the tab.

Figure 46:
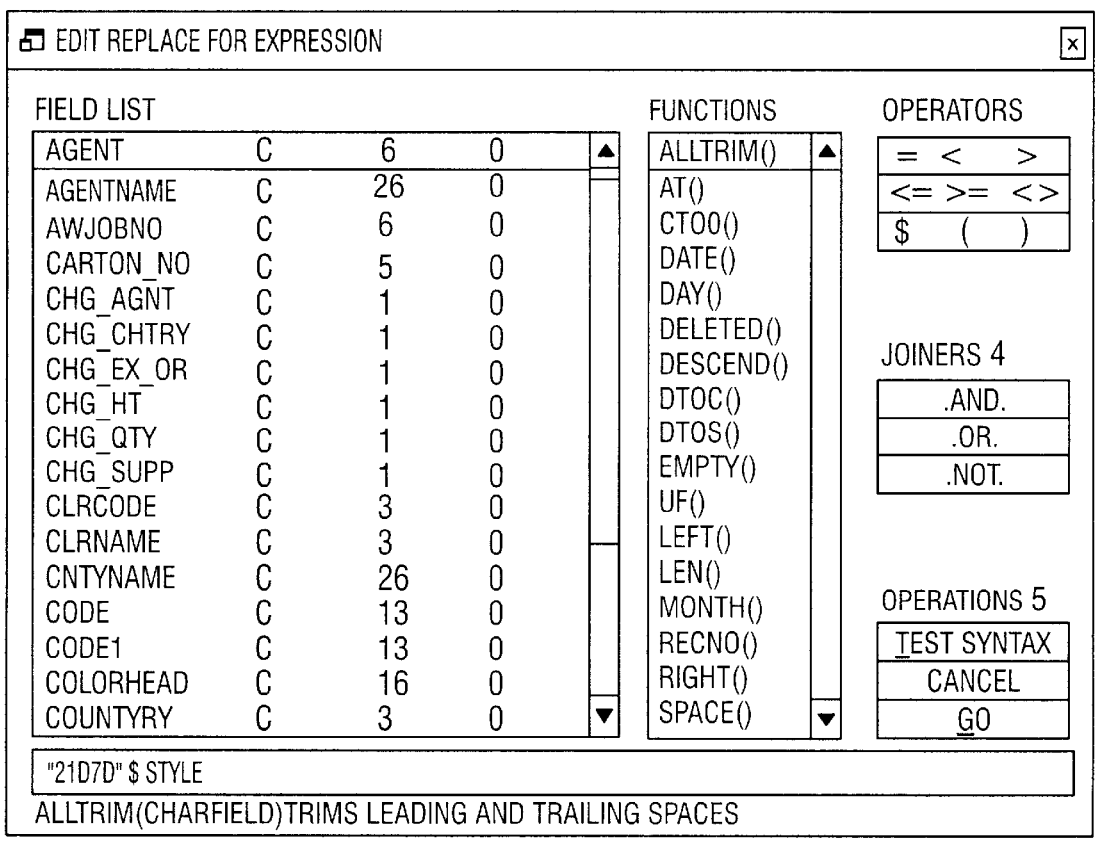
FIG. 46 shows the Edit Expression form in the Order Analysis Configuration form using the customer order file that is partially shown in FIG. 3.

A replacement field name or expression may be added to the right column in various forms by calling up the edit expression form (or "edit replace for expression form") shown in FIG. 46. The edit expression form automatically appears when the administrator attempts to add a replacement value expression to another form. The left box in FIG. 46 shows all field names from Tables 1 and 2. The field names from the left box are selected for use with the functions listed in the right box (and described in the window at the bottom of the screen) and the operators and joiners shown on the control buttons. The lower box shows the expression as it is being created.

Figure 47:
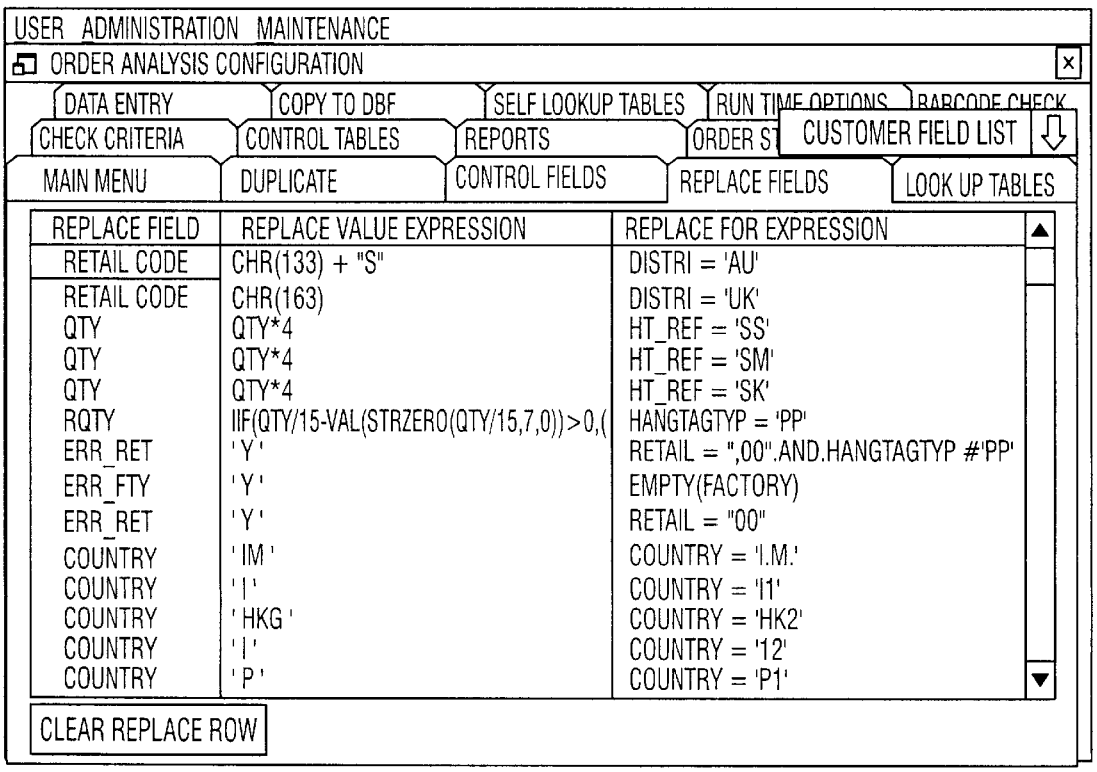
FIG. 47 shows the Replace Fields tab in the Order Analysis Configuration form using the customer order file that is partially shown in FIG. 3.

FIG. 47 shows the Replace Fields tab in the Order Analysis Configuration form. The administrator uses this tab to choose field names from the "replace field" column to be replaced with conventional Visual Basic expressions from the "replace value expression" column when the condition listed in the "replace for expression" column is met. This feature of the order analysis program 20 allows hangtag manufacturers to automatically revise incorrect or inconsistent customer purchase orders.

For example, in the third through fifth rows in FIG. 47, when the hangtag reference field HT_REF contains any of the expressions "SS, SM, or SK" the order analysis module will replace the current order quantity QTY with a new quantity that is four times as large in order to supply additional prepack labels that are required for shoe box stickers. This change implements a customer request to have labels on four sides of the boxes. In the sixth row, the original order quantity RQTY is rounded to the nearest fifteen for prepack label orders only in order to allow for a waste level specified by the customer.

FIG. 48 shows the Lookup Tables tab in the Order Analysis Configuration form. In the example shown, seven lookup tables have been created to compare data from, or add missing data to, the electronic customer purchase order. Although seven lookup tables have been shown in the example, additional lookup tables may also be used.

For example, in the first row of the FIG. 48, the DIV and HANGTAGTYP fields in the customer order are compared against a database file, or "table," named DIVHT.dbf (located in the server at address G:\aw\oatest\newgerm\divht.dbf) which contains all valid hangtag types and divisions for this particular customer. A valid hangtag and/or division results in the ERR_HTG field being set to "N," otherwise the default is set to "Y" in order to indicate that there is no match.

In the third row of FIG. 48, the DISTRI distribution center abbreviation field in the customer order is replaced by the full name of the distributor from the DISTRIB.DBF table (located at the address G:\aw\oatest\newgerm\invoice.dbf) for use on the carton label template. The INVOICE.dbf table (located at G:\aw\oatest\newgerm\invoice.dbf) provides billing address information to an invoice preparation program (not shown). The MULTI.dbf table (located at G:\aw\oatest\newgerm\multi.dbf) provides the MULTI control field (see Table 2) for flagging multi- and single-currency hangtags with "M" and "S," respectively. The CODE!, MCCTV, and GRAPHIC tables provide similar SPO+CLRCODE, CTY_M1, and STYLE information.

FIG. 49 shows the Check Criteria tab in the Order Analysis Configuration form. The check criteria tab allows an administrator to define parameters for checking the customer's order. In the example shown in FIG. 49, the duplicate checking routine and barcode checking routine (not functioning in the appendix) are set to their default checking conditions defined under other tabs. The zero quantity checking routing checks for current order quantities QTY which are less than or equal to zero while the error flag routine checks whether various error flag fields are set to "Y," indicating an error has been found. Once a checking condition has been met, the information is printed in the Error Report.

Figure 50:
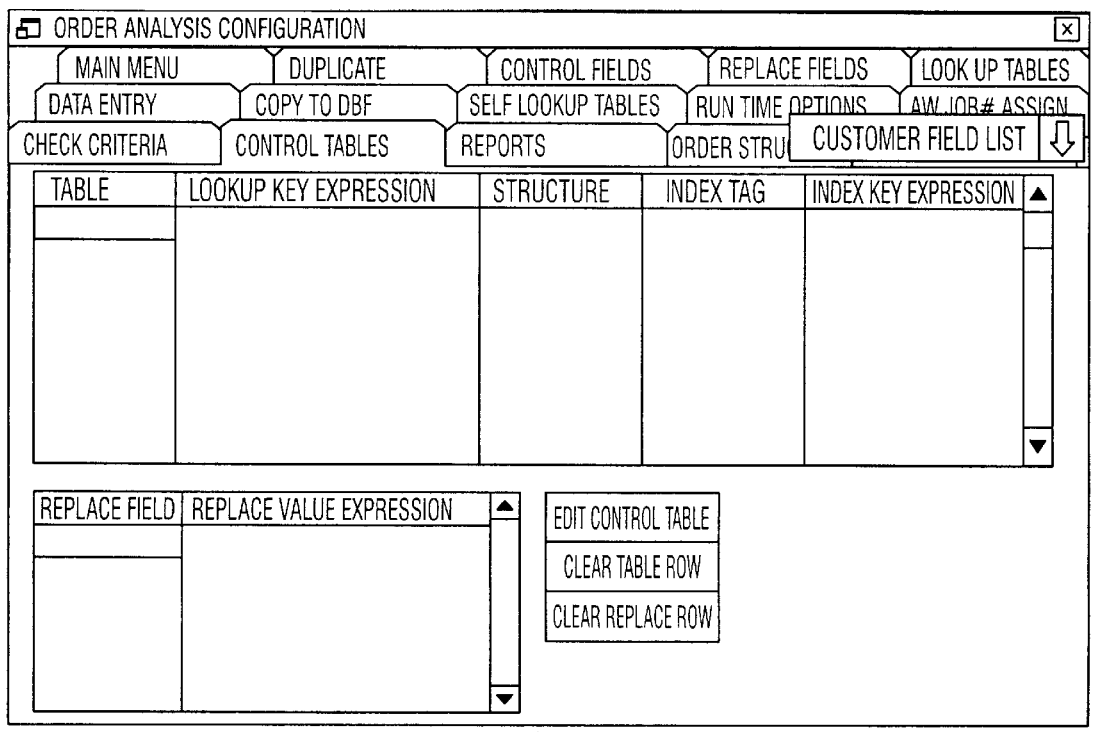
FIG. 50 shows the Control Tables tab in the Order Analysis Configuration form using the customer order file that is partially shown in FIG. 3.

FIG. 50 shows the Control Tables tab in the Order Analysis Configuration form. This form is not functional at this time.

Figure 51:
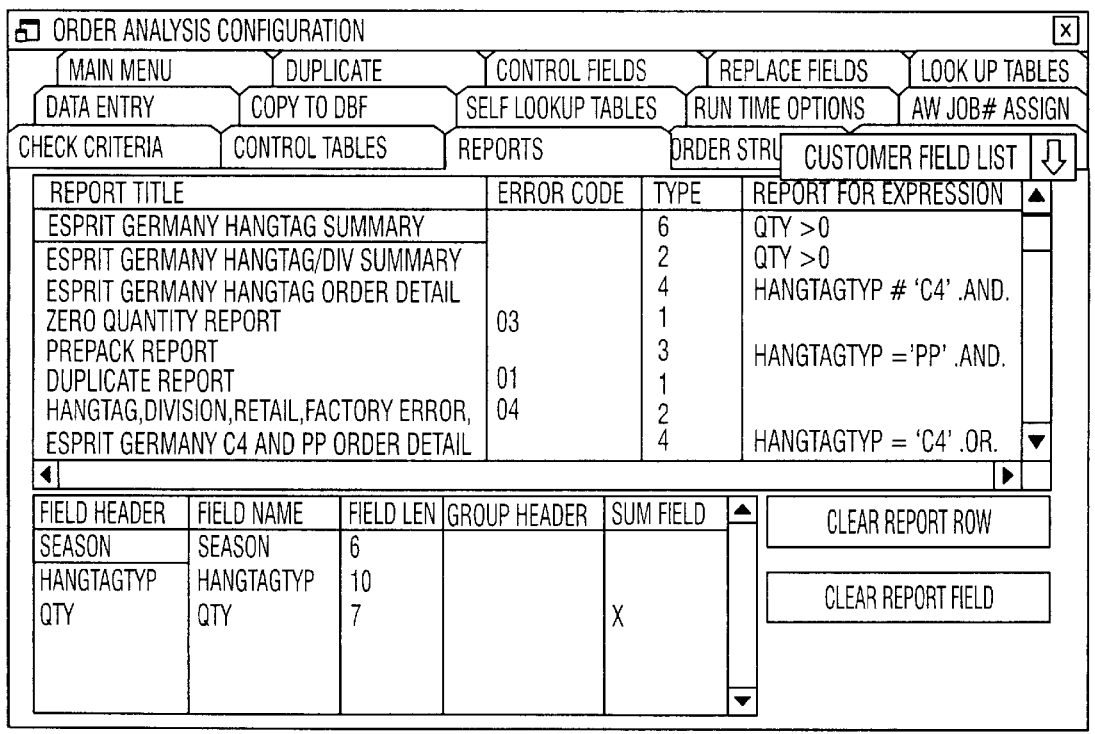
FIG. 51 shows the Reports tab in the Order Analysis Configuration form using the customer order file that is partially shown in FIG. 3.

FIG. 51 shows the Reports Tab in the Order Analysis Configuration form. This tab allows the administrator to define the format of various reports. The various report titles are listed in the left column, followed by the error codes put in the ERR_CODE field when an error is found. There are five report type formats listed in the "type" column: 1-detail, 2-summary, 3-group summary breakdown, 4-group summary breakdown with page breaks, 5-summary with total records. There are also three report layouts in the "Orient" column: 1-portrait, 2-landscape, and 3-legal landscape. In the lower box, the administrator can define the field headers, field names, group headers, and tag fields for summary for the highlighted report title.

FIG. 52 shows the Order Structure tab in the Order Analysis Configuration form which allows the administrator to define the sequence of the original customer order file format. In the illustrated example, the customer order file comes from a database file. Control buttons along the bottom of this tab allow the administrator to insert and delete rows, import existing order structures, and clear the entire structure shown in the box.

FIG. 53 shows the Barcode Check tab in the Order Analysis Configuration form. This form allows the administrator to choose a barcode type (U.S. "U.P.C." or European "EAN-13" formats) from the right window for checking the (check digit) accuracy of the barcode numbers contained in the CODE field using conventional barcode checking routines. The EAN-13 checking routine in the attached appendix is not currently working.

FIG. 54 shows the Data Entry tab in the Order Analysis Configuration form. This form is under construction for allowing the administrator to configure the order analysis module to allow a user to manually enter customer order data.

FIG. 55 shows the Copy to DBF tab in the Order Analysis Configuration form. This form allows the administrator to define selected fields for copying from the original electronic customer order to another database file, such as for box label files and carton label files.

FIG. 56 shows the Self LookUp Tables tab in the Order Analysis Configuration form. A self lookup table is a database that is automatically extracted from a customer order to a current subdirectory for use by other portions of the software. In the illustrated example, the style purchase order SPO and hangtag type HANGTAGTYP field names are used to develop a temporary table which adds a hangtag reference HT_REF to various reports.

FIG. 57 shows the Run Time Options tab in the Order Analysis Configuration form. This tab allows the administrator to check which file process options will be run during a first run (referred to as "runtime") of the program and which file process options will be performed on subsequent reruns. The first run time mode generally assigns additional internal code fields to the original customer order and is executed only once when a new customer order is received, or when the order is changed. The second run time mode operates on the enhanced order file (FIG. 18) created during the first user run time to provide additional copies of various reports and check files.

The file process options listed in FIG. 57 generally correspond to other tabs in the office analysis program 20. For example, the Replace Control Field Values option corresponds to the Control Tables tab and the Spilt files by Conditions option corresponds to the Copy to DBF tab. The Print Control Tables for New Info option is not used at this time.

Figure 58:
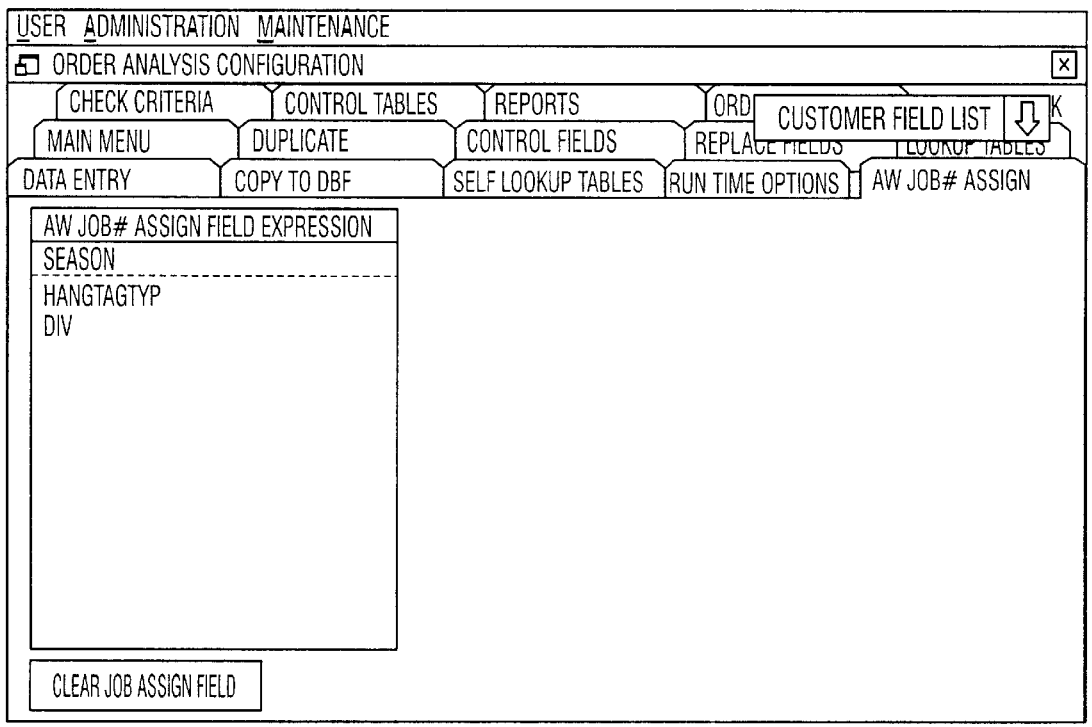
FIG. 58 shows the AW Job# Assign tab in the Order Analysis Configuration form using the customer order file that is partially shown in FIG. 3.

FIG. 58 shows the AW Job# Assign tab in the Order Analysis Configuration form. This tab allows the administrator to provide multiple job numbers for a defined field name. The style purchase order field SPO is typically used.

Figure 59:
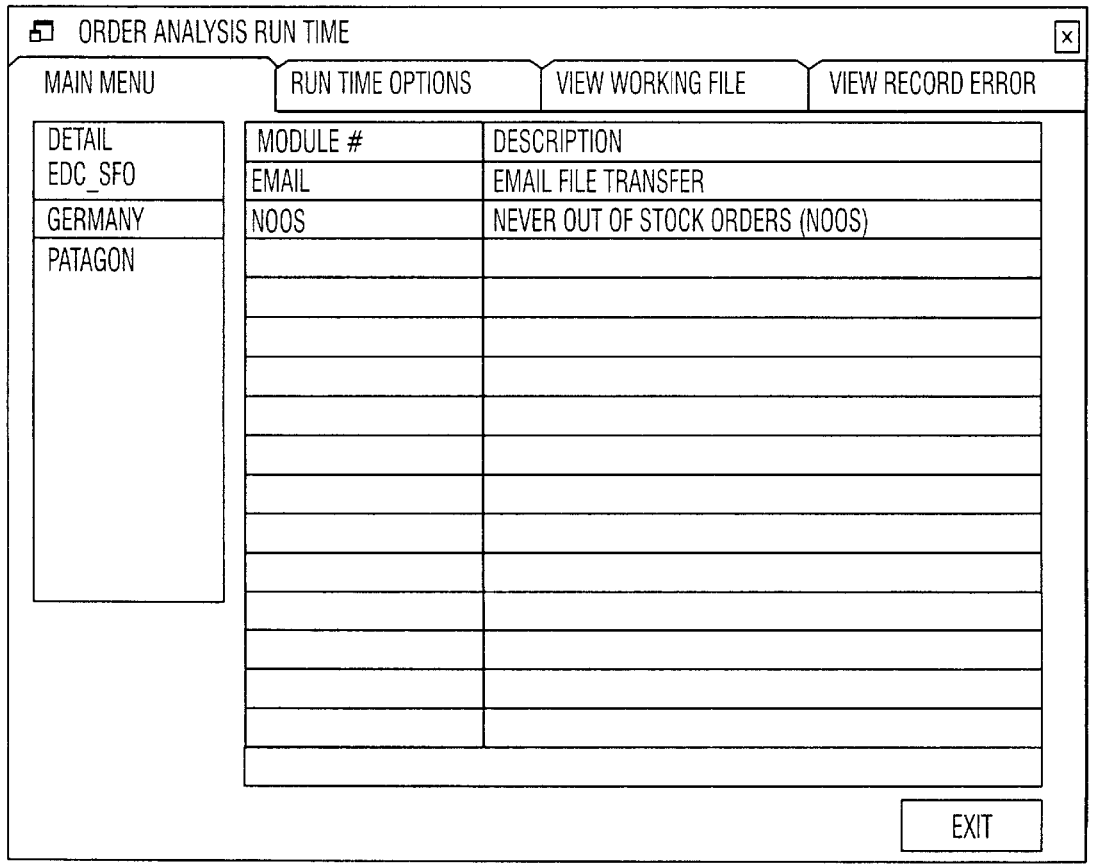
FIG. 59 shows the Main Menu tab in the Order Analysis Run Time form using the customer order file that is partially shown in FIG. 3.

FIGS. 59 through 62 show various tabs in the Order Analysis Run Time form which are accessed at the user level when the order analysis program is run for each customer order. FIG. 59 shows the Main Menu tab in the Order Analysis Run Time form. This form allows a user to choose a customer and module to analyze the original customer order. Once the customer and module have been selected, the user moves to the next tab for further configuration of the program.

FIG. 60 shows the Run Time options tab in the Order Analysis Run Time form. In the lower portion of this form, a user may browse and specify the filename of the original customer order which is to be analyzed by the order analysis program. The file process option and report option choices for the run time are set by the administrator using other tabs. The convert input file button causes the order analysis program to sequence the raw customer order file 22 into the analyzed customer order file 28 (see FIG. 2). The Execute All Process button causes the program to execute the order analysis program 20.

FIG. 61 shows the View Working File tab in the order analysis run time form. This form allows a user to view the analyzed customer order file 28 (see FIG. 2) which is created by the order analysis program from the customer's order. If there are errors in the analyzed order file 28, the row numbers where the errors are located will be displayed in the right column in color-coded format according to the legend in the lower right corner of the form. An invalid number error refers to a field where the data does not match the data type defined for that field while an invalid length indicator occurs when the data is too long for the specified field length. The delete row button allows a user to delete an invalid row. The Start Analysis Button activates the order analysis program 20 to restart the analysis with the edited file.

FIG. 62 shows the View Record Error tab in the Order Analysis Runtime form. This tab appears automatically after the analysis is complete and displays the analyzed customer order data file 28. The set filter button allows the user to search for records which are specified in the view window next to the button. The print all reports button prints the reports specified in the Reports tab. The fill column button allows the user to change all data in a highlighted column.

FIGS. 63 through 66 show various tabs in the Order Analysis Rerun form which allows the user to reprint reports and regenerate working database files. Using the Main Menu tab shown in FIG. 63, a user chooses the customer and module number to rerun. The Run Time Options tab in FIG. 64 allows the user to choose file process and report options for subsequent runs which may be different than those selected by the administrator. The Assign Job Number tab shown in FIG. 65 allows the user to manually assign new job numbers. The View Record Error tab shown in FIG. 66 allows the user to view the work file after subsequent reruns of the Order Analysis module.

FIGS. 67 through 78 are screens from the Order Analysis Run Time forms in the hangtag automation program. These screens allow an administrator to define product specifications, number of ups, artwork merging fields and formats, check file names, packing box label formats, and sorting and packing requirements. The administrator can also fully test these configurations before authorizing access at the user level.

FIG. 67 shows the Structure Maintenance form in the hangtag automation program 30. The table shows the customer order structure for the highlighted customer in the left column.

FIG. 68 shows the Control Fields List form in the hangtag automation program. This form is called up automatically when a control field needs to be inserted into another form in the program.

Figure 69:
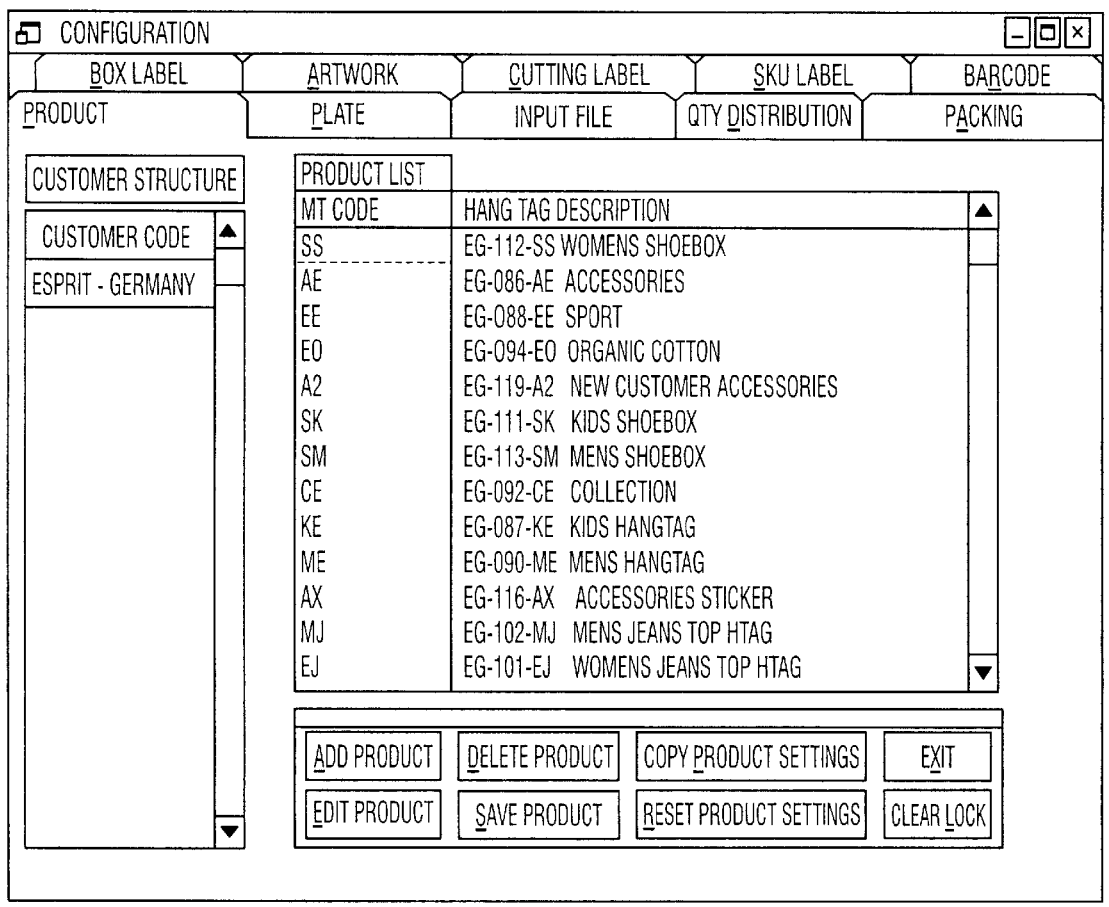
FIG. 69 shows the Product tab in the Configuration form using the customer order file that is partially shown in FIG. 3.

FIGS. 69 through 78 show the various tabs in the Configuration window which are accessible by an administrator in the hangtag automation program 30. FIG. 69 shows the Product tab in the Configuration window. This is tab allows the administrator to choose a customer from the "customer structure" list in the left column and a product configuration from the list of existing configurations for that customer in the right window. The product configuration may be deleted, copied, edited, saved, or reset (not used) using the control buttons at the bottom of the form. New products may also be added using the add product button. The clear lock button allows an administrator to block all users from accessing that setting while it is being configured by the administrator.

FIG. 70 shows the Plate tab in the Configuration window. This tab allows the administrator to set the plate arrangements, layouts, sorting, and tickets; plate and sheet waste; and artwork detail list. The all character fields box displays a list of database fields used by the specified customer. The sort fields box allows an administrator to add sort fields for plate arrangements. The reset plate number field box allows the administrator to add a field from the sort field to restart the numbering for the plate arrangement. The report fields box allows the administrator to add database fields to be listed on the Detail Artwork List. The plate label box is used to set up the plate ticket fields. The option box allows the administrator to define job planning variables such as the mark up percentage, up per plate, near up amount (number for rounding up), speed performance, waste importance, and maximum waste per plate (number of tags per plate).

FIG. 71 shows the Input File tab in the Configuration window. This tab allows the administrator to retrieve and review the structure of the analyzed customer data file 28 for the specified customer.

FIG. 72 shows the Quantity Distribution tab in the Configuration window. This tab is used by the administrator to define various parameters of the Packing Summary List. For example, the group header fields box allows the administrator to chose field names for headers in the list while the body fields box allows the administrator to choose the field names which appear under those headers.

FIG. 73 shows the Packing tab in the Configuration window. This tab is used by the administrator to define various parameters of the Detail Packing List. The "all fields" box provides a list of field names used by the customer. Field names may be added and deleted from the sort fields box as sorting criteria for the list. The group header fields box allows the administrator to define the header fields on the Detail Packing List while the body fields box allows the administrator to define the body of the list.

Checking the use order quantity for calculation box will change the field used for box calculation to QTY from the default SHPQTY. The administrator also defines the extension for the check file for sorting and the complete filename for the artwork database file. The "@" character causes the program to use the default characters for naming.

FIG. 74 shows the Box Label tab of the Configuration window which is used by the administrator to set up the box and carton label images. Header rows are entered in the top box. Field names for data in the body of the labels is entered in the middle section of the tab. The maximum number or rows on a label is entered in the max label rows box. The bottom box shows each of the rows on a label.

FIG. 75 shows the Artwork tab in the Configuration window. The information typed in this tab is used with the ASCII artwork file and QuarkXpress templates to create finished artwork. Fields that appear in the completed artwork are entered in the tag fields box while AWJOBNO, the plate number, and other variables are entered into the footer fields box. Commands from the edit expression form may also be used.

FIG. 76 shows the Cutting Label tab from the Configuration window. The information in this form is also converted to an ASCII file (having a cut extension) which is merged with another QuarkXpress template to produce a cutting label images containing the information used for sorting. The box number, country, factory, print quantity, and plate number are the main data used for the cutting labels.

FIG. 77 shows the SKU Label tab in the configuration window. The information in this form is also converted to an ASCII file (having an art extension) which is merged with another QuarkXpress template to provide the barcode on artwork.

FIG. 78 shows the barcode tab in the configuration window. This form is used by the administrator to convert the data in the CODE field from numerical data to ASCII format barcode images. Each type of barcode has its own conversion table.

FIG. 79 shows the first level user job control panel form which is run only one time per job. The user chooses a customer and module from the upper boxes and uses the form to input various file names and print options. The skip checking hangtag box is checked when more than one hangtag type is chosen. In the plate option box, the user is able to adjust the number of ups per plate and the waste importance. When the form is completed, the user clicks the generate button to execute level one of the hangtag automation program.

FIG. 80 shows the manual plate arrangement form which is displayed when the user has checked the manual plate arrangement box in FIG. 79. Manual plate arrangement is an option that the user can access in order to manually arrange records to fit on a plate. In FIG. 80, the user highlights the rows of records that are to be arranged on one plate. The plate number and number of times the records will be repeated for one hangtag type are entered into the plate # and plate quantity windows, respectively. The user then clicks the assign plate button to make the assignments.

Figure 81:
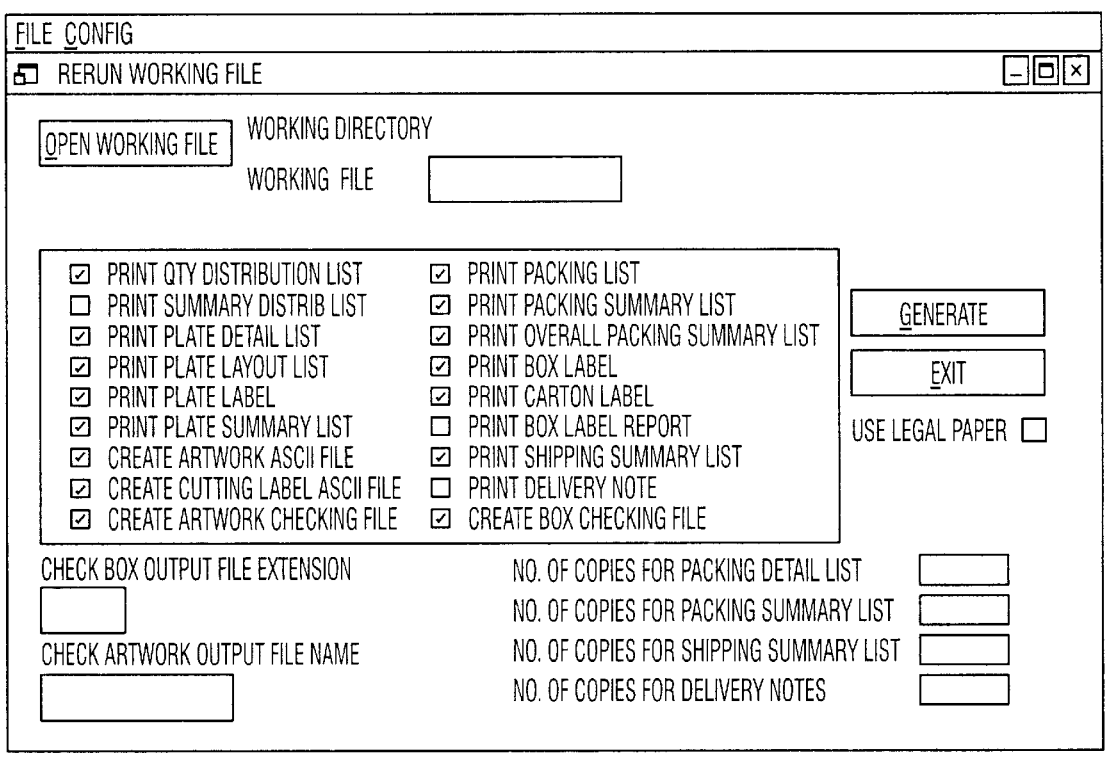
FIG. 81 shows the Rerun Level User Job Control panel form in the hangtag automation program.

FIG. 81 shows the rerun level user job control form which is used to reprint copies of the listed reports.

Although this disclosure has been mainly directed to an integrated system for the production of hangtags, the system may also be used to produce other types printed matter.

While the integrated hangtag production system described above has been discussed with respect to certain computer programs, vendors, products, and preferred configurations, this description is merely illustrative of some of the various useful forms in which the invention might be reduced to practice by one of ordinary skill in the art. The scope of the actual invention, on the other hand, is defined by the subject matter of the following claims.

What is claimed is:

1. A method for producing hangtags comprising:
   (1) receiving an electronic order file from a customer;
   (2) outputting an analyzed customer data file;
   (3) generating a first plurality of documents from said electronic order file which are used to evaluate the integrity of the customer order; and
   (4) generating a second plurality of documents from analyzed customer data file which are used to coordinate the production of hangtags ordered by the customer;
   (5) outputting a data file selected from the group consisting of a box label production file and a carton label production file;
   (6) outputting a data file to an artwork ASCII file;
   (7) outputting of said artwork ASCII file to an artwork checking file; and
   (8) allowing an administrator to define parameters for coordinating the production of hangtags.

2. The method of claim 1, further comprising the step of allowing an administrator to define parameters for evaluating the integrity of the electronic order file.

3. The method of claim 1, further comprising the step of outputting a data file selected from the group consisting of a cutting label file and a box checking file.

4. The method of claim 1, wherein said first plurality of documents includes documents selected from the group consisting of a Hangtag Summary Report, a Hangtag Order Detail Report, a Hangtag/Division Summary Report, an Error Report, a Zero Quantity Report, a Duplicate Order Report, an Invoice Distributors Report, a Rejected SPO's Report, a Missing Multi-Size/Currency Report, a C4 Thermal Printing Report, and a Pre Pack Service Bureau Report.

5. The method of claim 1, wherein said second plurality of documents includes documents selected from the group consisting of a Hangtag Order Detail Report, a Detail Packing List, a Plate Layout Detail List, a Plate Layout Summary List, Plate Ticket Images, Cutting Labels, a Plate Analysis Report, Box and Carton Labels, a Box Carton Summary, a Packing Summary, an in-House Box/Carton Summary, a C4 Summary List, a C4 Packing List, a C4 and PP Order Detail, a Shipping Summary List and Delivery Notes.

6. A method for producing hangtags comprising:

(a) receiving an electronic order file from a customer, (b) outputting an analyzed customer data file, a box label production file, and a carton label production file;

(c) generating first documents that are useful for evaluating the integrity of the electronic customer order file, wherein said first documents are selected from the group consisting of a Hangtag Summary Report, a Hangtag Order Detail Report, a Hangtag/Division Summary Report, an Error Report, a Zero Quantity Report, a Duplicate Order Report, an Invoice Distributors Report, a Rejected SPO's Report, a Missing Multi-Size/Currency Report, a C4 Thermal Printing Report, and a Pre Pack Service Bureau Report;

(d) receiving the analyzed customer data file and outputting an artwork ASCII file, an artwork checking file, a cutting label file, a box checking file, and a packing temp file; and (e) generating second documents for coordinating the production of hangtags in the customer order, said second documents being selected from the group consisting of a Hangtag Order Detail Report, a Detail Packing List, a Plate Layout Detail List, a Plate Layout Summary List, Plate Ticket Images, Cutting Labels, a Plate Analysis Report, Box and Carton Labels, a Box Carton Summary, a Packing Summary, an In-House Box/Carton Summary, a C4 Summary List, a C4 Packing List, a C4 and PP Order Detail, a Shipping Summary List, and Delivery Notes; and (f) optimizing the layout of a printing plate.

7. The method of claim 6, further comprising the step of outputting an order analysis storage file and outputting a hangtag automation storage file.

8. The method of claim 6, optimization step includes means for defining a mark up option, a near up option, an up per plate option, a speed performance option, a waste importance option, and a max paper waste per plate option.

9. The method of claim 6, comprising the steps of:

receiving an electronic order file from a customer;

generating documents from said electronic order file which are useful for evaluating the integrity of the customer order file;

modifying the electronic customer order file to produce a analyzed customer data file;

generating additional documents and data files from said electronic customer order file and said analyzed customer data file which are useful for coordinating the production of hangtags.

10. The method of claim 9, wherein said receiving step includes receiving the electronic customer order file via e-mail.

11. The method of claim 9, wherein said step of generating documents and said step of modifying the electronic customer order file includes processing said electronic order file with an order analysis computer program.

12. The method of claim 9, wherein said step of generating additional documents and data files further includes the steps of:

processing said electronic order file with an order analysis computer program; and processing said analyzed data file with a hangtag automation computer program.

13. The method of claim 6, further comprising the steps of:

receiving an electronic order file via e-mail from a customer;

processing said electronic customer order file with an order analysis computer program;

generating documents from said order analysis program for evaluating the integrity of the customer order file;

modifying the electronic customer order file to produce an analyzed customer data file;

processing said analyzed customer data file with a hangtag automation program; and generating additional documents from said analyzed customer data file which are useful for coordinating the production of hangtags.

14. The method of claim 13, further comprising the step of outputting a data file for further coordinating the production of hangtags.

* * * * *